US010189880B2

(12) United States Patent
Heemskerk et al.

(10) Patent No.: US 10,189,880 B2
(45) Date of Patent: Jan. 29, 2019

(54) T CELL RECEPTORS DIRECTED AGAINST BOB1 AND USES THEREOF

(71) Applicant: LEIDEN UNIVERSITY MEDICAL CENTER, Leiden (NL)

(72) Inventors: Mirjam H. M. Heemskerk, Leiden (NL); J. H. Frederik Falkenburg, Leiden (NL)

(73) Assignee: LEIDEN UNIVERSITY MEDICAL CENTER, Leiden (NL)

( * ) Notice: Subject to any disclaimer, the term of this patent is extended or adjusted under 35 U.S.C. 154(b) by 0 days.

(21) Appl. No.: 14/930,572

(22) Filed: Nov. 2, 2015

(65) Prior Publication Data

US 2016/0129094 A1 May 12, 2016

Related U.S. Application Data

(60) Provisional application No. 62/115,737, filed on Feb. 13, 2015, provisional application No. 62/074,534, filed on Nov. 3, 2014.

(51) Int. Cl.

| | |
|---|---|
| *C12N 9/64* | (2006.01) |
| *C12N 9/90* | (2006.01) |
| *A61K 39/00* | (2006.01) |
| *C07K 14/47* | (2006.01) |
| *C07K 14/725* | (2006.01) |
| *C12N 5/0783* | (2010.01) |

(52) U.S. Cl.

CPC ...... *C07K 14/4702* (2013.01); *A61K 39/0011* (2013.01); *C07K 14/7051* (2013.01); *C12N 5/0636* (2013.01); *C12N 9/6472* (2013.01); *C12N 9/90* (2013.01); *C12Y 304/22062* (2013.01); *C12Y 502/01008* (2013.01); *A61K 39/00* (2013.01); *C07K 2319/70* (2013.01); *C12N 2510/00* (2013.01)

(58) Field of Classification Search

CPC .......................... C12N 5/0636; C07K 14/7051

See application file for complete search history.

(56) References Cited

U.S. PATENT DOCUMENTS

| | | | |
|---|---|---|---|
| 4,514,506 | A | 4/1985 | Braatz et al. |
| 5,384,253 | A | 1/1995 | Krzyek et al. |
| 5,538,880 | A | 7/1996 | Lundquist et al. |
| 5,550,214 | A | 8/1996 | Eberlein et al. |
| 5,550,318 | A | 8/1996 | Adams et al. |
| 5,589,343 | A | 12/1996 | Marchand et al. |
| 5,610,042 | A | 3/1997 | Chang et al. |
| 5,645,992 | A | 7/1997 | Lott et al. |
| 5,648,226 | A | 7/1997 | Van Den Eynde et al. |
| 5,709,995 | A | 1/1998 | Chisari et al. |
| 5,719,054 | A | 2/1998 | Boursnell et al. |
| 5,741,899 | A | 4/1998 | Capon et al. |
| 5,750,395 | A | 5/1998 | Fikes et al. |
| 5,780,036 | A | 7/1998 | Chisari |
| 5,830,462 | A | 11/1998 | Crabtree et al. |
| 5,834,266 | A | 11/1998 | Crabtree et al. |
| 5,840,839 | A | 11/1998 | Wang et al. |
| 5,869,337 | A | 2/1999 | Crabtree et al. |
| 5,869,608 | A | 2/1999 | Caldwell et al. |
| 5,871,753 | A | 2/1999 | Crabtree et al. |
| 5,925,565 | A | 7/1999 | Berlioz et al. |
| 5,935,819 | A | 8/1999 | Eichner et al. |
| 5,955,596 | A | 9/1999 | Zagursky et al. |
| 5,965,242 | A | 10/1999 | Patton et al. |
| 5,994,313 | A | 11/1999 | Crabtree et al. |
| 6,010,878 | A | 1/2000 | Dixit et al. |
| 6,011,018 | A | 1/2000 | Crabtree et al. |
| 6,043,082 | A | 3/2000 | Crabtree et al. |
| 6,046,047 | A | 4/2000 | Crabtree et al. |
| 6,046,158 | A | 4/2000 | Ariizumi et al. |
| 6,054,436 | A | 4/2000 | Crabtree et al. |
| 6,403,765 | B1 | 6/2002 | Alnemri |
| 6,497,876 | B1 | 12/2002 | Maraskovsky et al. |
| 6,558,951 | B1 | 5/2003 | Tomai et al. |
| 6,670,186 | B1 | 12/2003 | Nair et al. |
| 6,943,245 | B2 | 9/2005 | Killary et al. |
| 7,404,950 | B2 | 7/2008 | Spencer |
| 9,089,520 | B2 | 7/2015 | Brenner |
| 9,434,935 | B2 | 9/2016 | Spencer et al. |
| 9,913,882 | B2 | 3/2018 | Slawin et al. |
| 2002/0160975 | A1 | 10/2002 | Alnemri et al. |
| 2003/0082163 | A1 | 5/2003 | Shu |
| 2003/0091593 | A1 | 5/2003 | Bachmann et al. |

(Continued)

FOREIGN PATENT DOCUMENTS

| | | |
|---|---|---|
| EP | 0 273 085 | 7/1988 |
| EP | 0 510 691 | 10/1996 |

(Continued)

OTHER PUBLICATIONS

Arstila et al. (Science Oct. 29, 1999 286: 958-961).*
Anderson et al. (PNAS USA May 1988 85: 3551-3554).*
Expression vector—Biology-Online Dictionary (http://www.biology-online.org/dictionary/Expression_vector Jun. 2010).*
Rudikoff et al. (PNAS USA, 1982, 79: 1979-1983).*
Coleman et al. (Research in Immunology, 1994; 145(1): 33-36).*
Ibragimova and Wade (Biophysical Journal, Oct. 1999, vol. 77, pp. 2191-2198).*
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.

(Continued)

*Primary Examiner* — Peter J Reddig

(74) *Attorney, Agent, or Firm* — Grant IP, Inc.

(57) ABSTRACT

The technology relates in part to compositions and methods for inducing an immune response against a Bob1 antigen. Provided are methods for treating hyperproliferative diseases by inducing an immune response against a Bob1 antigen; the immune response may be induced using a Bob1 polypeptide fragment, or by specifically targeting Bob1-expressing cells using T cell receptors directed against Bob1.

14 Claims, 16 Drawing Sheets

Specification includes a Sequence Listing.

(56) References Cited

U.S. PATENT DOCUMENTS

| | | | | |
|---|---|---|---|---|
| 2003/0092132 | A1 | 5/2003 | Williams | |
| 2003/0105000 | A1* | 6/2003 | Pero | A61K 38/06 514/19.3 |
| 2003/0108527 | A1 | 6/2003 | Seya et al. | |
| 2003/0153518 | A1 | 8/2003 | Foxwell et al. | |
| 2003/0206917 | A1 | 11/2003 | Tykocinski et al. | |
| 2003/0232055 | A1 | 12/2003 | Medzhitov | |
| 2004/0019195 | A1 | 1/2004 | Scholm et al. | |
| 2004/0209836 | A1 | 10/2004 | Spencer | |
| 2005/0215472 | A1 | 9/2005 | Schulke et al. | |
| 2006/0263368 | A1 | 11/2006 | Rosenblum et al. | |
| 2007/0081963 | A1 | 4/2007 | Oh et al. | |
| 2007/0161108 | A1* | 7/2007 | Harrer | C07K 14/47 435/372.2 |
| 2008/0269160 | A1 | 10/2008 | Spencer et al. | |
| 2008/0274140 | A1 | 11/2008 | Weiner et al. | |
| 2008/0300202 | A1 | 12/2008 | Kentros | |
| 2009/0175880 | A1 | 7/2009 | Keler et al. | |
| 2009/0191159 | A1 | 7/2009 | Sakurada et al. | |
| 2009/0263852 | A1 | 10/2009 | Sperandio et al. | |
| 2009/0299763 | A1 | 12/2009 | Sakurada | |
| 2009/0311183 | A1 | 12/2009 | Devy et al. | |
| 2010/0196336 | A1 | 8/2010 | Park et al. | |
| 2010/0203067 | A1 | 8/2010 | Spencer et al. | |
| 2011/0023137 | A1 | 1/2011 | Chu et al. | |
| 2011/0033383 | A1 | 2/2011 | Spencer et al. | |
| 2011/0280889 | A1* | 11/2011 | Schendel | C07K 14/7051 424/178.1 |
| 2011/0286980 | A1 | 11/2011 | Brenner | |
| 2011/0287038 | A1 | 11/2011 | Slawin et al. | |
| 2013/0323834 | A1 | 12/2013 | Brenner et al. | |
| 2014/0255360 | A1 | 9/2014 | Spencer et al. | |
| 2015/0328292 | A1 | 11/2015 | Spencer et al. | |
| 2015/0366954 | A1 | 12/2015 | Brenner | |

FOREIGN PATENT DOCUMENTS

| | | |
|---|---|---|
| WO | WO 94/09699 | 5/1994 |
| WO | WO 96/12796 | 5/1996 |
| WO | WO 01/83551 | 11/2001 |
| WO | WO 02/36769 | 5/2002 |
| WO | WO 04/073641 | 9/2004 |
| WO | WO 05/100390 | 10/2005 |
| WO | WO 06/133398 | 12/2006 |
| WO | WO 08/006087 | 1/2008 |
| WO | WO 08/049113 | 4/2008 |
| WO | WO 10/033949 | 3/2010 |
| WO | WO 11/035018 | 3/2011 |
| WO | WO 11/146862 | 11/2011 |
| WO | WO 11/130566 | 12/2011 |
| WO | WO 14/164348 | 10/2014 |
| WO | WO 14/197638 | 12/2014 |
| WO | WO 15/134877 | 9/2015 |
| WO | WO 16/071758 | 5/2016 |

OTHER PUBLICATIONS

Addgene product literature Plasmid #15567, Feb. 22, 2016, pp. 1-4, https://www.addgene.org/15567/.

Adema et al., "A dendritic-cell-deprived C—C chemokine that preferentially attracts naïve T cells." Nature. Jun. 12, 1997;387(6634):713-717.

Adema et al., "Migration of dendritic cell based cancer vaccines: in vivo veritas?" Curr Opin Immunol. Apr. 2005;17(2):170-174.

Albert et al., "Dendritic cell maturation is required for the cross-tolerization of CD8+ T cells." Nat Immunol. Nov. 2001;2(11):1010-1017.

AliPrantis et al., EMBO J. 19(13):3325-3336, 2000.

Amara et al, "A versatile synthetic dimerizer for the regulation of protein-protein interactions." PNAS 1997;94:10618-10623.

Amrolia et al., "Adoptive immunotherapy with allodepleted donor T-cells improves immune reconstitution after haploidentical stem cell transplantation." Blood. Sep. 15, 2006;108(6):1797-808.

Amrolia et al., "Selective depletion of donor alloreactive T cells without loss of antiviral or antileukemic responses." Blood. Sep. 15, 2003;102(6):2292-9.

Anasetti et al., Donor Buffy Coat Cell Infusion After Marrow Transplantation for Aplastic Anemia. Blood, 1988, 72: 1099-1100.

Anderson et al., "A homologue of the TNF receptor and its ligand enhance T-cell growth and dendritic-cell function." Nature. Nov. 13, 1997;390(6656):175-179.

Ando et al., "A Safeguard System for Induced Pluripotent Stem Cell-Derived Rejuvenated T Cell Therapy" Stem Cell Reports (2015) 5(4): 597-608.

Andre-Schmutz et al., "Immune reconstitution without graft-versus-host disease after haemopoietic stem-cell transplantation: a phase 1/2 study." Lancet. Jul. 13, 2002;360(9327):130-7.

Arcone et al., "Identification of sequences responsible for acute-phase induction of human C-reactive protein." Nucleic Acids Res. Apr. 25, 1988;16(8):3195-3207.

Ardeshna et al., "The PI3 kinase, p38 SAP kinase, and NF-kappaB signal transduction pathways are involved in the survival and maturation of lipopolysaccharide-stimulated human monocyte-derived dendritic cells." Blood. Aug. 1, 2000;96(3):1039-1046.

Argent™ Regulated Homodimerization Kit Instructions. Version 2.0 ARIAD Pharmaceuticals, Inc. Cambridge, MA. Sep. 9, 2002, p. 1-15.

ARIAD Pharmaceuticals, Inc., "ARGENT Regulated Homodimerization Kit" Version 2.0, product brochure, Sep. 9, 2002.

Aversa et al., "Full haplotype-mismatched hematopoietic stem-cell transplantation: a phase II study in patients with acute leukemia at high risk of relapse." J Clin Oncol. May 20, 2005;23(15):3447-54.

Aversa et al., "Treatment of high-risk acute leukemia with T-cell-depleted stem cells from related donors with one fully mismatched HLA haplotype." N Engl J Med. Oct. 22, 1998;339(17):1186-93.

Banchereau et al., "Dendritic cells and the control of immunity." Nature. Mar. 19, 1998;392(6673):245-252.

Banchereau et al., "Dendritic cells as therapeutic vaccines against cancer." Nat Rev Immunol. Apr. 2005;5(4):296-306.

Banchereau et al., "Dendritic cells: controllers of the immune system and a new promise for immunotherapy." Ann NY Acad Sci. Apr. 2003;987:180-187.

Banchereau et al., "Immunobiology of dendritic cells." Annu Rev Immunol. 2000; 18:767-811.

Bander et al., "Phase I trial of 177lutetium-labeled J591, a monoclonal antibody to prostate-specific membrane antigen, in patients with androgen-independent prostate cancer." J Clin Oncol. Jul. 20, 2005;23(21):4591-601.

Belshaw et al. (Sep. 1996). "Controlling programmed cell death with a cyclophilin-cyclosporin-based chemical inducer of dimerization." Chemistry & Biology. 3(9): pp. 731-738.

Bennett et al., "Apoptosis of rat vascular smooth muscle cells is regulated by p53-dependent and -independent pathways." Circ Res. Aug. 1995;77(2):266-273.

Bennett et al., "Help for cytotoxic-T-cell response is mediated by CD40 signaling." Nature. Jun. 4, 1998;393(6684):478-480.

Berger et al., "Pharmacologically regulated Fas-mediated death of adoptively transferred T cells in a nonhuman primate model." Blood. Feb. 15, 2004;103(4):1261-9.

Bernard et al., "HIV-specific cytotoxic T-lymphocyte activity in immunologically normal HIV-infected persons." AIDS. Nov. 12, 1998;12(16):2125-2139.

Beutler B., "Inferences, questions and possibilities in Toll-like receptor signaling." Nature. Jul. 8, 2004;430(6996):257-263.

Bianco FJ, et al., "Natural History of Biochemically-Recurrent Castrate-Resistant Disease in Men treated with maximal androgen blockage for a Rising PSA after Radical Prostatectomy," Cancer Symposium: Abstract 278, 2005.

Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.

Blau et al., "A proliferation switch for genetically modified cells." Proc Natl Acad Sci USA. Apr. 1, 1997;94(7):3076-3081.

(56) References Cited

OTHER PUBLICATIONS

Bleakley M, Riddell SR., "Molecules and mechanisms of the graft-versus-leukemia effect." Nat Rev Cancer. May 2004;4(5):371-80.
Bloom, J.D. and F.H. Arnold, In the light of directed evolution: pathways of adaptive protein evolution. Proc Natl Acad Sci U S A, 2009. 106 Suppl 1: p. 9995-10000.
Boatright, K.M. and G.S. Salvesen, Mechanisms of Caspase activation. Curr Opin Cell Biol, 2003. 15(6): p. 725-31.
Boatright, K.M., et al., A unified model for apical Caspase activation. Mol Cell, 2003. 11(2): p. 529-41.
Bojak et al., "Muscle specific versus ubiquitous expression of Gag based HIV-1 DNA vaccines: a comparative analysis." Vaccine. May 6, 2002;20(15):1975-1979.
Boldin et al., "Involvement of MACH, a Novel MORT1/FADD-Interacting Protease, in Fas/APO-1- and TNF Receptor-Induced Cell Death," Cell vol. 85, 803-815, Jun. 14, 1996.
Bollard CM, et al., Blood. 2002, 99:3179-3187.
Bollard et al., "Cytotoxic T lymphocyte therapy for Epstein-Barr virus+ Hodgkin's disease." J Exp Med. Dec. 20, 2004;200(12):1623-33.
Bonini et al., "HSV-TK gene transfer into donor lymphocytes for control of allogeneic graft-versus-leukemia." Science. Jun. 13, 1997;276(5319):1719-24.
Bonnert et al., GeneBank: AAC50954.1; GI: 1814020; Feb. 2, 1997.
Boss, W.F., et al., Basal signaling regulates plant growth and development. Plant Physiol, 2010. 154(2): p. 439-43.
Bowie et al, "Deciphering the message in protein sequences: tolerance to amino acid substitutions." Science Mar. 1990; 247:1306-1310.
Brady, S.C., L.A. Allan, and P.R. Clarke, Regulation of caspase-9 through phosphorylation by protein kinase C zeta in response to hyperosmotic stress. Mol Cell Biol, 2005. 25(23): p. 10543-55.
Breitbach et al., "Potential risks of bone marrow cell transplantation into infarcted hearts." Blood. Aug. 15, 2007;110(4):1362-9.
Brentjens RJ, Davila ML, Riviere I, et al: CD19-targeted T cells rapidly induce molecular remissions in adults with chemotherapy-refractory acute lymphoblastic leukemia. Sci Transl Med 5:177ra38, 2013.
Burns et al., J. Exp. Med 197(2):263-268, 2003.
Cardone, M.H., et al., Regulation of cell death protease caspase-9 by phosphorylation. Science, 1998. 282(5392): p. 1318-21.
Carpenito C, Milone MC, Hassan R, et al: Control of large, established tumor xenografts with genetically retargeted human T cells containing CD28 and CD137 domains. Proc Natl Acad Sci U S A 106:3360-5, 2009.
Carter et al., "Prostate-specific membrane antigen is a hydrolase with substrate and pharmacologic characteristics of a neuropeptidase." Proc Natl Acad Sci U S A. Jan. 23, 1996;93(2):749-53.
Caux et al., "CD34+ hematopoietic progenitors from human cord blood differentiate along two independent dendritic cell pathways in response to GM-CSF+TNF alpha." Adv Exp Med Biol. 1997;417:21-25.
Caux et al., "In vitro regulation of development and function of dendritic cells." Hematol Cell Ther. Oct. 1996;38(5):463.
Cazeaux et al., "Comparative study of immune responses induced after immunization with plasmids encoding the HIV-1 Nef protein under the control of the CMV-IE or the muscle-specific desmin promoter." Vaccine. Sep. 10, 2002;20(27-28):3322-31.
Chamberlain et al., "Concise review: mesenchymal stem cells: their phenotype, differentiation capacity, immunological features, and potential for homing." Stem Cells. Nov. 2007;25(11):2739-49.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang et al., "Metastatic renal cell carcinoma neovasculature expresses prostate-specific membrane antigen." Urology. Apr. 2001;57(4):801-5.
Chang et al., "Proarrhythmic potential of mesenchymal stem cell transplantation revealed in an in vitro coculture model." Circulation. Apr. 18, 2006;113(15):1832-41.
Chang et al., "Prostate-specific membrane antigen is produced in tumor-associated neovasculature." Clin Cancer Res. Oct. 1999;5(10):2674-81.
Chang, W.C., et al., Modifying ligand-induced and constitutive signaling of the human 5-HT4 receptor. PLoS One, 2007. 2(12): p. e1317.
Chao, Y., et al., Engineering a dimeric Caspase-9: a re-evaluation of the induced proximity model for Caspase activation. PLoS Biol, 2005. 3(6): p. e183. 1079-1087.
Chatterjee et al., "Strategies for efficient gene transfer into hematopoietic cells. The use of adeno-associated virus vectors in gene therapy." Ann NY Acad Sci. Dec. 29, 1995;770:79-90.
Chen C, Okayama H., "High-efficiency transformation of mammalian cells by plasmid DNA." Mol Cell Biol. Aug. 1987;7(8):2745-2752.
Chen et al., "A testicular antigen aberrantly expressed in human cancers detected by autologous antibody screening." Proc Natl Acad Sci USA. Mar. 4, 1997;94(5):1914-1918.
Cheung et al., "Plasmid encoding papillomavirus Type 16 (HPV16) DNA constructed with codon optimization improved the immunogenicity against HPV infection." Vaccine. Dec. 16, 2004;23(5):629-638.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo- genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain" Science. Jul. 22, 2005;309(5734):581-585.
Christiansen et al., "N-glycosylation and microtubule integrity are involved in apical targeting of prostate-specific membrane antigen: implications for immunotherapy." Mol Cancer Ther. May 2005;4(5):704-14.
Ciceri, F., et al., "Infusion of suicide-gene-engineered donor lymphocytes after family haploidentical haemopoietic stem-cell transplantation for leukemia (the TK007 trial): a non-randomized phase I-II study," Lancet Oncol. 2009, vol. 10, No. 5, pp. 489-500.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T., "Dissecting the functions of proteins and pathways using chemically induced dimerization." Chem Biol Drug Des. Jun. 2006;67(6):440-442.
Clackson, T., "Controlling Protein-Protein interactions Using Chemical inducers and Disrupters of Dimerization" Chapter 4.2, pp. 227-249 in Chemical Biology: From Small Molecules to Systems Biology and Drug Design (Schreiber, s., et al., eds., Wiley, 2007)).
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke SR., "The critical role of CD40/CD40L in the CD4-dependent generation of CD8+ T cell immunity." J Leukoc Biol. May 2000;67(5):607-614.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Cohen et al., "Nucleotide sequence of the cDNA encoding human tyrosinase-related protein." Nucleic Acids Res. May 11, 1990;18(9):2807-2808.

(56) References Cited

OTHER PUBLICATIONS

Contin et al., "Membrane-anchored CD40 is processed by the tumor necrosis factor-alpha-converting enzyme. Implications for CD40 signaling." J Biol Chem. Aug. 29, 2003;278(35):32801-32809.
Coupar et al., "A general methods for the construction of recombinant vaccinia viruses expressing multiple foreign genes." Gene. Aug. 15, 1988;68(1):1-10.
Cranmer et al., "Clinical applications of dendritic cell vaccination in the treatment of cancer." Cancer Immunol Immunother. Apr. 2004;54(4):275-306.
Crawford et al., "A controlled trial of leuprolide with and without flutamide in prostatic carcinoma." N Engl J Med. Aug. 17, 1989;321(7):419-424, w/, erratum N Engl J Med Nov. 16, 1989;321(20):1420.
Cremer et al., "Long-lived immature dendritic cells mediated by TRANCE-RANK interaction." Blood. Nov. 15, 2002;100(10):3646-3655.
Cristofanilli et al., "Circulating tumor cells, disease progression, and survival in metastatic breast cancer." N Engl J Med. Aug. 19, 2004;351(8):781-91.
Cyster JG., "Chemokines and cell migration in secondary lymphoid organs." Science. Dec. 10, 1999;286(5447):2098-2102.
Dallal RM, Lotze MT., "The dendritic cell and human cancer vaccines." Curr Opin Immunol. Oct. 2000;12(5):583-588.
Davis et al., "Crystal structure of prostate-specific membrane antigen, a tumor marker and peptidase." Proc Natl Acad Sci USA. Apr. 26, 2005;102(17):5981-5986.
De Becker et al., "The adjuvant monophosphoryl lipid A increases the function of antigen-presenting cells." Int Immunol. Jun. 2000;12(6):807-815.
de Gruijl et al, "Prolonged Maturation and Enhanced Transduction of Dendritic Cells Migrated from Human Skin Explants After In Situ Delivery of CD40-Targeted Adenoviral Vectors," The Joumal of Immunology vol. 169,2002 PQS 5322-5331.
de la Thille et al., "Detection of prostate-specific membrane antigen expressing cells in blood obtained from renal cancer patients: a potential biomarker of vascular invasion." Cancer Detect Prev. 2000;24(6):579-88.
De Vries et al., "Effective migration of antigen-pulsed dendritic cells to lymph nodes in melanoma patients is determined by their maturation state." Cancer Res. Jan. 1, 2003;63(1):12-17.
de Witte et al., "An inducible caspase 9 safety switch can halt cell therapy-induced autoimmune disease." J Immunol. May 1, 2008;180(9):6365-73.
Deml et al. "Multiple effects of codon usage optimization on expression and immunogenicity of DNA candidate vaccines encoding the human immunodeficiency virus type 1 Gag protein," 2001. J. Virol. 75:10991-11001.
Denault et al., "Caspase 3 attenuates XIAP(X-linked inhibitor of apoptosis protein)-mediated inhibition of Caspase 9" Biochem. J. (2007) 11-19.
Deonarain, "Ligand-targeted receptor-mediated vectors for gene delivery," 1998, Expert Opin. Ther. Pat., vol. 8, pp. 53-69.
Dey BR, Spitzer TR., "Current status of haploidentical stem cell transplantation." Br J Haematol. Nov. 2006;135(4):423-37.
Di Stasi, A., et al., Inducible apoptosis as a safety switch for adoptive cell therapy. N Engl J Med, 2011. 365(18): p. 1673-83.
Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.
Dominici et al., "Minimal criteria for defining multipotent mesenchymal stromal cells. The International Society for Cellular Therapy position statement." Cytotherapy. 2006;8(4):315-7.
Donnelly et al., "DNA vaccines." Annu Rev Immunol. 1997;15:617-48.
Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.
Dudley et al., "Cancer regression and autoimmunity in patients after clonal repopulation with antitumor lymphocytes." Science. Oct. 25, 2002;298(5594):850-4.
Elgueta et al., "Molecular mechanism and function of CD40/CD40L engagement in the immune system," Immunological Reviews, 229, (2009) 152-172.
Evel-Kabler et al., "SOCS1 restricts dendritic cells' ability to break self tolerance and induce antitumor immunity by regulating IL-12 production and signaling." J Clin Invest. Jan. 2006;116(1):90-100.
Fan et al., "Improved artificial death switches based on caspases and FADD." Hum Gene Ther. Sep. 20, 1999;10(14):2273-2285.
Farrar et al., "Activation of the Raf-1 kinase cascade by coumermycin-induced dimerization," Nature, Sep. 12, 1996;383(6596):178-181.
Fearon et al., "The instructive role of innate immunity in the acquired immune response," Science, Apr. 5, 1996;272(5258):50-53.
Fechheimer et al., "Transfection of mammalian cells with plasmid DNA by scrape loading and sonication loading." Proc Natl Acad Sci USA. Dec. 1987;84(23):8463-8467.
Fernandez et al., "Dendritic cells directly trigger NK cell functions: cross-talk relevant in innate anti-tumor immune responses in vivo." Nat Med. Apr. 1999;5(4):405-411.
Ferrari et al., "Second-strand synthesis is a rate-limiting step for efficient transduction by recombinant adeno-associated virus vectors." J Virol. May 1996;70(5):3227-3234.
Ferraro, B. et al., Human Vaccines 7:120-127 (2011).
Finney HM, Akbar AN, Lawson AD: Activation of resting human primary T cells with chimeric receptors: costimulation from CD28, inducible costimulator, CD134, and CD137 in series with signals from the TCR zeta chain. J Immunol 172:104-13, 2004.
Fisher et al., "Transduction with recombinant adeno-associated virus for gene therapy is limited by leading-strand synthesis." J Virol. Jan. 1996;70(1):520-532.
Flotte et al., "Stable in vivo expression of the cystic fibrosis transmembrane conductance regulator with an adeno-associated virus vector." Proc Natl Acad Sci USA. Nov. 15, 1993;90(22):10613-10617.
Flotte TR, Carter BJ. "Adeno-associated virus vectors for gene therapy." Gene Ther. Aug. 1995;2(6):357-362.
Flotte, "Prospects for Virus-Based Gene Therapy for Cystic Fibrosis," Journal of Bioenergetics and Bioinformatics, vol. 25, No. 1, 1993.
Freeman et al., "The role of (111)In Capromab Pendetide (ProstaScintR) immunoscintigraphy in the management of prostate cancer." Q J Nucl Med. Jun. 2002;46(2):131-7.
Freytag et al., "Phase I study of replication-competent adenovirus-mediated double suicide gene therapy for the treatment of locally recurrent prostate cancer." Cancer Res. Sep. 1, 2002;62(17):4968-76.
Fujio Y, Walsh K., "Akt mediates cytoprotection of endothelial cells by vascular endothelial growth factor in an anchorage-dependent manner." J Biol Chem. Jun. 4, 1999;274(23):16349-16354.
Galbiati et al., "N-terminal fatty acylation of the alpha-subunit of the G-protein Gi1: only the myristoylated protein is a substrate for palmitoylation." Biochem J. Nov. 1, 1994;303(Pt 3):697-700.
Gauthier-Campbell et al., "Regulation of dendritic branching and pilopodia formation in hippocampal neurons by specific acylated protein motifs." Mol Biol Cell. May 2004;15(5):2205-2217.
Gefter et al., "A simple method for polyethylene glycol-promoted hybridization of mouse myeloma cells." Somatic Cell Genet. Mar. 1977;3(2):231-236.
GenBank Accession No. M29540, Nov. 1, 1994.
Gestwicki JE, Marinec PS., Chemical control over protein-protein interactions: beyond inhibitors. Comb Chem High Throughput Screen. Sep. 2007;10(8):667-675.
Ghetie et al., "The GLP large scale preparation of immunotoxins containing deglycosylated ricin A chain and a hindered disulfide bond." J Immunol Methods. Sep. 13, 1991;142(2):223-30.
Gilboa E, Vieweg J., "Cancer immunotherapy with mRNA-transfected dendritic cells." Immunol Rev. Jun. 2004;199:251-263.
Gilboa E., "The promise of cancer vaccines." Nat Rev Cancer. May 2004;4(5):401-411.

(56) References Cited

OTHER PUBLICATIONS

Gittes RF., "Carcinoma of the prostate." N Engl J Med. Jan. 24, 1991;324(4):236-245.
Goodman et al., "Recombinant adeno-associated virus-mediated gene transfer into hematopoietic progenitor cells." Blood. Sep. 1, 1994;84(5):1492-1500.
Goodwin et al., "Suppression of human T-cell mitogenesis by prostaglandin. Existence of a prostaglandin-producing suppressor cell." J Exp Med. Dec. 1, 1977;146(6):1719-1734.
Goodwin JS., "Immunomodulation by eicosanoids and anti-inflammatory drugs." Curr Opin Immunol. Dec. 1989;2(2):264-268.
Gopal TV., "Gene transfer method for transient gene expression, stable transformation, and cotransformation of suspension cell cultures." Mol Cell Biol. May 1985;5(5):1188-1190.
Gossen et al., "Transcriptional activation by tetracyclines in mammalian cells." Science. Jun. 23, 1995;268(5218):1766-1769.
Gossen M, Bujard H., "Tight control of gene expression in mammalian cells by tetracycline-responsive promoters." Proc Natil Acad Sci USA. Jun. 15, 1992;89(12):5547-5551.
Gottschalk et al., "Post-transplant lymphoproliferative disorders." Annu Rev Med. 2005;56:29-44.
Graham FL, van der Eb AJ., "A new technique for the assay of infectivity of human adenovirus 5 DNA." Virology. Apr. 1973;52(2):456-467.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Gross, G., and Eshar, Z., FASEB Journal 6:3370-3378 (1992).
Guedan S, Chen X, Madar A, et al: ICOS-based chimeric antigen receptors program bipolar TH17/TH1 cells. Blood, 2014.
Haase et al., "Generation of induced pluripotent stem cells from human cord blood" Cell Stem Cell (2009) 5:434-441.
Hall et al., "Mesenchymal stem cells in cancer: tumor-associated fibroblasts and cell-based delivery vehicles." Int J Hematol. Jul. 2007;86(1):8-16.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.
Hanks B.A., et al.. "Re-engineered CD40 receptor enables potent pharmacological activation of dendritic-cell cancer vaccines in vivo" Nature Medicine, vol. 11, No. 2. 2005 pp. 130-137.
Harbury et al., "Crystal structure of an isoleucine-zipper trimer," Nature, vol. 371, Sep. 1, 1994, 80-83.
Hauer et al., "TNF receptor (TNFR)-associated factor (TRAF) 3 serves as an Inhibitor of TRAF2 5-mediated activation of the noncanonical NF-B pathway by TRAF-binding TNFRs." PNAS, vol. 102, No. 8, Feb. 22, 2005; pp. 2874-2879.
Hay et al., "Replication of Adenovirus Mini-Chromosomes," J. Mol. Biol. (1984) 175, 493-510.
Haynes, N.M., et al. J. Immunol. 166:182-7 (2001).
He et al., "A simplified system for generating recombinant adenoviruses." Proc Natl Acad Sci USA. Mar. 3, 1998;95(5):2509-2514.
Hearing et al., "Identification of a repeated sequence element required for efficient encapsidation of the adenovirus type 5 chromosome." J Virol. Aug. 1987;61(8):2555-2558.
Hearing P, Shenk T., "Functional analysis of the nucleotide sequence surrounding the cap site for adenovirus type 5 region E1A messenger RNAs." J Mol Biol. Jul. 15, 1983;167(4):809-822.
Hermans et al., "CD8+ T cell-dependent elimination of dendritic cells in vivo limits the induction of antitumor immunity." J Immunol. Mar. 15, 2000;164(6):3095-3101.
Heslop, H.E., Blood 122:853-854 (2013).
Ho et al., "Dimeric ligands define a role for transcriptional activation domains in reinitiation." Nature. Aug. 29, 1996;382(6594):822-826.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunologial Methods 237(2000) 159-173.
Hollstein et al., "Database of p53 gene somatic mutations in human tumors and cell lines." Nucleic Acids Ress. Sep. 1994;22(17):3551-3555.
Holsinger et al., "Signal transduction in T lymphocytes using a conditional allele of Sos." Proc Natl Acad Sci USA. Oct. 10, 1995;92(21):9810-9814.
Hong, T., et al., A simple theoretical framework for understanding heterogeneous differentiation of CD4+ T cells. BMC Syst Biol, 2012. 6: p. 66.
Horng et al., PNAS 98(22):12654-12658, 2001.
Horwitz et al., "Fludarabine-based nonmyeloablative stem cell transplantation for sickle cell disease with and without renal failure: clinical outcome and pharmacokinetics." Biol Blood Marrow Transplant. Dec. 2007;13(12):1422-6.
Horwitz et al., "Isolated allogeneic bone marrow-derived mesenchymal cells engraft and stimulate growth in children with osteogenesis imperfecta: Implications for cell therapy of bone." Proc Natl Acad Sci U S A. Jun. 25, 2002;99(13):8932-7.
Horwitz et al., "Transplantability and therapeutic effects of bone marrow-derived mesenchymal cells in children with osteogenesis imperfecta." Nat Med. Mar. 1999;5(3):309-13.
Horwitz, E. M., et al., (2007). Biol Blood Marrow Transplant 13: 53-57.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hostager et al., J. Immunol. 157:1047-1053 1996.
Hou WS, Van Parijs L., "A Bcl-2-dependent molecular timer regulates the lifespan and immunogenicity of dendritic cells." Nat Immunol. Jun. 2004;5(6):583-589.
Hsiao, E.C., et al., Constitutive Gs activation using a single-construct tetracycline-inducible expression system in embryonic stem cells and mice. Stem Cell Res Ther, 2011. 2(2): p. 11.
Huang et al., "Donor lymphocyte infusion for the treatment of leukemia relapse after HLA-mismatched/haploidentical T-cell-replete hematopoietic stem cell transplantation." Haematologica. Mar. 2007;92(3):414-7.
Huang et al., "Modified donor lymphocyte infusion after HLA-mismatched/haploidentical T cell-replete hematopoietic stem cell transplantation for prophylaxis of relapse of leukemia in patients with advanced leukemia." J Clin Immunol. May 2008;28(3):276-83.
Hurley et al., "National Marrow Donor Program HLA-matching guidelines for unrelated marrow transplants." Biol Blood Marrow Transplant. Oct. 2003;9(10):610-5.
Introna et al., "Genetic modification of human T cells with CD20: a strategy to purify and lyse transduced cells with anti-CD20 antibodies." Hum Gene Ther. Mar. 1, 2000;11(4):611-20.
Ismaili et al., "Monophosphoryl lipid A activates both human dendritic cells and T cells." J Immunol. Jan. 15, 2002;168(2):926-932.
Israeli et al., "Expression of the prostate-specific membrane antigen." Cancer Res. Apr. 1, 1994;54(7):1807-11.
Israeli et al., "Sensitive nested reverse transcription polymerase chain reaction detection of circulating prostatic tumor cells: comparison of prostate-specific membrane antigen and prostate-specific antigen-based assays." Cancer Res. Dec. 15, 1994;54(24):6306-10.
Israeli et al., Molecular cloning of a complementary DNA encoding a prostate-specific membrane antigen. Cancer Res. Jan. 15, 1993;53(2):227-230.
Iuliucci et al., "Intravenous safety and pharmacokinetics of a novel dimerizer drug, AP1903, in healthy volunteers." J Clin Pharmacol. Aug. 2001;41(8):870-9.

(56) References Cited

OTHER PUBLICATIONS

Jackson et al., "A second tyrosinase-related protein, TRP-2, maps to and is mutated at the mouse slaty locus." EMBO J. Feb. 1992;11(2):527-535.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Janeway et al., "Approaching the asymptote? Evolution and revolution in immunology." Cold Spring Harb Symp Quant Biol. 1989;54 Pt 1:1-13.
Jemal et al., "Cancer statistics, 2008." CA Cancer J Clin. Mar.-Apr. 2008;58(2):71-96.
Jonuleit et al., Eur. J. Immunol 27:3135-3142, 1997.
Josien et al., "TRANCE, a tumor necrosis factor family member, enhances the longevity and adjuvant properties of dendritic cells in vivo." J Exp Med. Feb. 7, 2000;191(3):495-502.
Junker et al., "Kinetics of cell death in T lymphocytes genetically modified with two novel suicide fusion genes." Gene Ther. Jul. 2003;10(14):1189-97.
Kadowaki N. et al., "Subsets of human dendritic cell precursors express different toll-like receptors and respond to different microbial antigens," J Exp Med. 2001, vol. 194, pp. 863-869.
Kagan JC, Medzhitov R., "Phosphoinositide-mediated adaptor recruitment controls Toll-like receptor signaling." Cell. Jun. 2, 2006;125(5):943-955.
Kageyama et al., "Differing utilization of homologous transcription initiation sites of rat K and T kininogen genes under inflammation condition." J Biol Chem. Feb. 15, 1987;262(5):2345-2351.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kalinski et al., "Prostaglandin E(2) is a selective inducer of interleukin-12 p40 (IL-12p40) production and an inhibitor of bioactive IL-12p70 heterodimer." Blood. Jun. 1, 2001;97(11):3466-3469.
Kalos M, Levine BL, Porter DL, et al: T cells with chimeric antigen receptors have potent antitumor effects and can establish memory in patients with advanced leukemia. Sci Transl Med 3:95ra73, 2011.
Kandel ES, Hay N., "The regulation and activities of the multifunctional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7):1099-105.
Kantoff et al., "Sipuleucel-T immunotherapy for castration-resistant prostate cancer." N Engl J Med. Jul. 29, 2010;363(5):411-22.
Kaplitt et al., "Long-term gene expression and phenotypic correction using adeno-associated virus vectors in the mammalian brain." Nat Genet. Oct. 1994;8(2):148-154.
Kaplitt et al., "Long-term gene transfer in porcine myocardium after coronary infusion of an adeno-associated virus vector." Ann Thorac Surg. Dec. 1996;62(6):1669-76.
Kawakami et al., "Identification of a human melanoma antigen recognized by tumor-infiltrating lymphocytes associated with in vivo tumor rejection." Proc Natl Acad Sci USA. Jul. 5, 1994;91(14):6458-6462.
Kawakami et al., "Identification of the immunodominant peptides of the MART-1 human melanoma antigen recognized by the majority of HLA-A2-restricted tumor infiltrating lymphocytes." J Exp Med. Jul. 1, 1994;180(1):347-352.
Kehry, Marilyn R., "CD40-Mediated Signaling in B Cells, Balancing Cell Survival, Growth and Death," The American Association of Immunologists, 1996, 2345-2348.
Kelly WK, Slovin SF., "Chemotherapy for androgen- independent prostate cancer: myth or reality." Curr Oncol Rep. Sep. 2000;2(5):394-401.
Kempf et al, "Improved stimulation of human dendritic cells by receptor engagement with surface-modified microparticles," J Drug Target vol. 11 No. 1, Jan. 2003 pp. 11-18.
Kershaw MH, Westwood JA, Parker LL, et al: A phase I study on adoptive immunotherapy using gene-modified T cells for ovarian cancer. Clin Cancer Res 12:6106-15, 2006.
Kessler et al., "Gene delivery to skeletal muscle results in sustained expression and systemic delivery of a therapeutic protein." Proc Natl Acad Sci USA. Nov. 26, 1996;93(24):14082-14087.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Kiuru et al., "Genetic control of wayward pluripotent stem cells and their progeny after transplantation" Cell Stem Cell (2009) 4(4):289-300.
Klein et al., "High-velocity microprojectiles for delivering nucleic acids into living cells," (1987) Nature, 327,70-73.
Kobayashi et al., "IRAK-M is a negative regulator of Toll-like receptor signaling." Cell. Jul. 26, 2002;110(2):191-202.
Koeberl et al., "Persistent expression of human clotting factor IX from mouse liver after intravenous injection of adeno-associated virus vectors." Proc Natl Acad Sci USA. Feb. 18, 1997;94(4):1426-1431.
Kohler G, Milstein C., "Continuous cultures of fused cells secreting antibody of predefined specificity." Nature. Aug. 7, 1975;256(5517):495-497.
Kohler G, Milstein C., "Derivation of specific antibody-producing tissue culture and tumor lines by cell fusion." Eur J Immunol. Jul. 1976;6(7):511-519.
Kolb et al., "Graft-versus-leukemia reactions in allogeneic chimeras." Blood. Feb. 1, 2004;103(3):767-76.
Kopytek et al., "Chemically induced dimerization of dihydrofolate reductase by a homobifunctional dimer of methotrexate." Chem Biol. May 2000;7(5):313-321.
Korst et al., "Effect of adenovirus gene transfer vectors on the immunologic functions of mouse dendritic cells." Mol Ther. Mar. 2002;5(3):307-315.
Kouskoff, V., et al., B cell receptor expression level determines the fate of developing B lymphocytes: receptor editing versus selection. Proc Natl Acad Sci U S A, 2000. 97(13): p. 7435-9.
Kraaij et al., "Prostate specific membrane antigen (PSMA) is a tissue-specific target for adenoviral transduction of prostate cancer in vitro." Prostate. Feb. 15, 2005;62(3):253-9.
Kumar et al., "Immunogenicity testing of a novel engineered HIV-1 envelope gp140 DNA vaccine construct." DNA Cell Biol. Jul. 2006;25(7):383-392.
Kutzler et al., "Coimmunization with an optimized IL-15 plasmid results in enhanced function and longevity of CD8 T cells that are partially independent of CD4 T cell help." J Immunol. Jul. 1, 2005;175(1):112-123.
Kutzler MA, Weiner DB., "DNA vaccines: ready for prime time?" Nat Rev Genet. Oct. 2008;9(10):776-788.
Kwon et al., "Isolation and sequence of a cDNA clone for human tyrosinase that maps at the mouse c-albino locus." Proc Natl Acad Sci USA. Nov. 1987;84(21):7473-7477.
Labeur et al., "Generation of tumor immunity by bone marrow-derived dendritic cells correlates with dendritic cell maturation stage." J Immunol. Jan. 1, 1999;162(1):168-175.
Laddy et al., "Heterosubtypic protection against pathogenic human and avian influenza viruses via in vivo electroporation of synthetic consensus DNA antigens." PLoS One. Jun. 25, 2008;3(6):e2517.
Lang et al., "Long-term outcome after haploidentical stem cell transplantation in children." Blood Cells Mol Dis. Nov.-Dec. 2004;33(3):281-7.
Langenkamp et al., "Kinetics of dendritic cell activation: impact on priming of TH1, TH1 and nonpolarized T cells." Nat Immunol. Oct. 2000;1(4):311-316.
Lanzavecchia A, Sallusto F., "Regulation of T cell immunity by dendritic cells." Cell. Aug. 10, 2001;106(3):263-266.

(56) References Cited

OTHER PUBLICATIONS

Lanzavecchia et al., "Dynamics of T lymphocyte responses: intermediates, effectors, and memory cells." Science. Oct. 6, 2000;290(5489):92-97.
Lapointe et al., "Human dendritic cells require multiple activation signals for the efficient generation of tumor antigen-specific T lymphocytes." Eur J Immunol. Nov. 2000;30(11):3291-3298.
Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.
Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.
Le Blanc et al., "Mesenchymal stem cells for treatment of steroid-resistant, severe, acute graft-versus-host disease: a phase II study." Lancet. May 10, 2008;371(9624):1579-86.
Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.
Lee et al., "Cytoplasmic domain-mediated dimerizations of toll-like receptor 4 observed by beta-lactamase enzyme fragment complementation." J Biol Chem. Mar. 12, 2004;279(11):10564-10574.
Lee et al., "Multipotent stromal cells from human marrow home to and promote repair of pancreatic islets and renal glomeruli in diabetic NOD/scid mice." Proc Natl Acad Sci U S A. Nov. 14, 2006;103(46):17438-43.
Leo et al., "Partition coefficients and their uses." Chem Rev. Dec. 1971;71(6):525-616.
Levrero et al., "Defective and nondefective adenovirus vectors for expressing foreign genes in vitro and in vivo." Gene. May 30, 1991;101(2):195-202.
Li et al., "A novel conditional Akt 'survival+A185 switch' reversibly protects cells from apoptosis." Gene Ther. Feb. 2002;9(4):233-244.
Li et al., "The HIV-1 Env protein signal sequence retards its cleavage and down-regulates the glycoprotein folding." Virology. Jul. 5, 2000;272(2):417-428.
Lim et al., "Lentiviral vector mediated thymidine kinase expression in pluripotent stem cells enables removal of tumorigenic cells" PLoS One (2013) 8(7):e70543.
Liu et al., "Constitutive and antibody-induced internalization of prostate-specific membrane antigen." Cancer Res. Sep. 15, 1998;58(18):4055-60.
Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.
Liu et al., "Monoclonal antibodies to the extracellular domain of prostate-specific membrane antigen also react with tumor vascular endothelium." Cancer Res. Sep. 1, 1997;57(17):3629-34.
Livak et al., "Analysis of relative gene expression data using real-time quantitative PCR and the 2(-Delta Delta C(T)) Method." Methods. Dec. 2001;25(4):402-408.
Lodge et al., Dendridic Cell-based Immunotherapy of Prostate Cancer: Immune Monitoring of a Phase II Clincal Trial, Cancer Res. 60:829-833, 2000.
Loiarro et al., "Peptide-mediated interference of TIR domain dimerization in MyD88 inhibits interleukin-1-dependent activation of NF-{kappa}B." J Biol. Chem. Apr. 22, 2005;280(16):15809-15814.
Luft et al., "Functionally distinct dendritic cell (DC) populations induced by physiologic stimuli: prostaglandin E(2) regulates the migratory capacity of specific DC subsets." Blood. Aug. 15, 2002;100(4):1362-1372.
Luning Prak, E.T., M. Monestier, and R.A. Eisenberg, B cell receptor editing in tolerance and autoimmunity. Ann NY Acad Sci, 2011. 1217: p. 96-121.
Luo et al., "Oligomerization activates c-RAF-1 through a Ras-dependent mechanism." Nature. Sep. 12, 1996;383(6596):181-185.
MacCorkle et al., "Synthetic activation of caspases: artificial death switches." Proc Natl Acad Sci USA. Mar. 31, 1998;95(7):3655-3660.
Macejak DG, Sarnow P., "Internal initiation of translation mediated by the 5' leader of a cellular mRNA." Nature. Sep. 5, 1991;353(6339):90-94.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.
Malin et al., "Vaccinia expression of *Mycobacterium tuberculosis*-secreted proteins: tissue plasminogen activator signal sequence enhances expression and immunogenicity of *M. tuberculosis* Ag85." Microbes Infect. Nov. 2000;2(14):1677-1685.
Malissen B, Ewbank JJ., "'TaiLoRing' the response of dendritic cells to pathogens." Nat Immunol. Aug. 2005;6(8):750-769.
Mann et al., "Construction of a retrovirus packaging mutant and its use to produce helper-free defective retrovirus." Cell. May 1983;33(1):153-159.
Marijt et al., "Hematopoiesis-restricted minor histocompatibility antigens HA-1- or HA-2-specific T cells can induce complete remissions of relapsed leukemia." Proc Natl Acad Sci U S A. Mar. 4, 2003;100(5):2742-7.
Marsland et al., "CCL19 and CCL21 induce a potent proinflammatory differentiation program in licensed dendritic cells." Immunity. Apr. 2005;22(4):493-505.
Martin, M.C., et al., Protein kinase A regulates Caspase-9 activation by Apaf-1 downstream of cytochrome c. J Biol Chem, 2005. 280(15): p. 15449-55.
MartIn-Fontecha et al., "Regulation of dendritic cell migration to the draining lymph node: impact on T lymphocyte traffic and priming." J Exp Med. Aug. 18, 2003;198(4):615-621.
Mazouz et al., "CD40 triggering increases the efficiency of dendritic cells for antitumoral immunization." Cancer Immun. Mar. 27, 2002;2:2.
McCown et al., "Differential and persistent expression patterns of CNS gene transfer by an adeno-associated virus (AAV) vector." Brain Res. Mar. 25, 1996;713(1-2):99-107.
McIlroy et al., "Histamine and prostaglandin E up-regulate the production of Th2-attracting chemokines (CCL17 and CCL22) and down-regulate Ifn-gamma-induced CXCL10 production by immature human dendritic cells." Immunology. Apr. 2006;117(4):507-516.
McWhirter et al., "Crystallographic analysis of CD40 recognition and signaling by human TRAF2." Proc Natl Acad Sci USA. Jul. 20, 1999;96(15):8408-8413.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the *Drosophila* Toll protein signals activation of adaptive immunity." Nature. Jul. 24, 1997;388(6640):394-397.
Medzhitov et al., Molecular Cell, 2:253-258, 1998.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on precision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Meylan et al., "Intracellular pattern recognition receptors in the host response." Nature. Jul. 6, 2006;442(7098):39-44.
Miga et al., "Dendritic cell longevity and T cell persistence is controlled by CD154-CD40 interactions." Eur J Immunol. Mar. 2001;31(3):959-965.
Milone, M.C., et al., (2009) Mol. Ther. 17:1453-1464.
Mizukami et al., "Adeno-associated virus type 2 binds to a 150-kilodalton cell membrane glycoprotein." Virology. Mar. 1, 1996;217(1):124-130.

(56) References Cited

OTHER PUBLICATIONS

Mochizuki et al., "Akt protein kinase inhibits non-apoptotic programmed cell death induced by ceramide." J Biol Chem. Jan. 25, 2002;277(4):2790-2797.
Molldrem et al., "A PR1-human leukocyte antigen-A2 tetramer can be used to isolate low-frequency cytotoxic T lymphocytes from healthy donors that selectively lyse chronic myelogenous leukemia." Cancer Res. Jun. 1, 1999;59(11):2675-81.
Montgomery et al., "Heterologous and homologous protection against influenza A by DNA vaccination: optimization of DNA vectors." DNA Cell Biol. Nov. 1993;12(9):777-783.
Morgan et al., "Cancer regression in patients after transfer of genetically engineered lymphocytes." Science. Oct. 6, 2006;314(5796):126-129.
Morgan et al., "Case report of a serious adverse event following the administration of T cells transduced with a chimeric antigen receptor recognizing ERBB2." Mol Ther. Apr. 2010;18(4):843-51.
Morse et al., "Migration of human dendritic cells after injection in patients with metastatic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., "Recombinant gene expression in vivo within endothelial cells of the arterial wall." Science. Jun. 16, 1989;244(4910):1342-1344.
Nakagami et al., "Safety and efficacy of docetaxel, estramustine phosphate and hydrocortisone in hormone-refractory prostate cancer patients." Int J Urol. Jul. 2010;17(7):629-34.
Napolitanl et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1529.
Narum et al., "Codon optimization of gene fragments encoding Plasmodium falciparum merzoite proteins enhances DNA vaccine protein expression and immunogenicity in mice." Infect Immun. Dec. 2001;69(12):7250-7253.
Nauta AJ, Fibbe WE., "Immunomodulatory properties of mesenchymal stromal cells." Blood. Nov. 15, 2007;110(10):3499-506.
Nestle et al., "Dendritic cells: On the move from bench to bedside." Nat Med. Jul. 2001;7(7):761-765.
Ni et al., "Molecular basis for CD40 signaling mediated by TRAF3." Proc Natl Acad Sci USA. Sep. 12, 2000;97(19):10395-10399.
Nicolau et al., "Liposomes as carriers for in vivo gene transfer and expression." Methods Enzymol. 1987;149:157-176.
Nikitina, E., et al, Cancer Res 65: 4309-4319 (2005).
Nociari et al., "A novel one-step, highly sensitive fluorometric assay to evaluate cell-mediated cytotoxicity." J Immunol Methods. Apr. 15, 1998;213(2):157-167.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen*," The Journal of Biological Chemistry, vol. 267, No. 15, May 25, 1992 10709-10715.
Ohshima et al., "Expression and function of OX40 ligand on human dendritic cells." J Immunol. Oct. 15, 1997;159(8):3838-3848.
Oliviero et al., "The human haptoglobin gene: transcriptional regulation during development and acute phase induction." EMBO J. Jul. 1987;6(7):1905-1912.
O'Neill et al., "Manipulating dendritic cell biology for the active immunotherapy of cancer." Blood. Oct. 15, 2004;104(8):2235-2246.
O'Sullivan B, Thomas R., "CD40 and dendritic cell function." Crit Rev Immunol. 2003;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Page et al., "A nonisotopic method for the measurement of cell membrane integrity." Anticancer Res. Jul.-Aug. 1998;18(4A):2313-2316.
Palecek et al., "Integrin-ligand binding properties govern cell migration speed through cell-substratum adhesiveness." Nature. Feb. 6, 1997;385(6616):537-540.
Papworth, C., Bauer, J. C., Braman, J. and Wright, D. A. , Site-directed mutagenesis in one day with >80% efficiency. Strategies, 1996. 9(3): p. 3-4.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Pasare C, Medzhitov R., "Toll pathway-dependent blockade of CD4+CD25+ T cell-mediated suppression by dendritic cells." Science. Feb. 14, 2003;299(5609):1033-1036.
Paskind et al., "Dependence of Moloney murine leukemia virus production on cell growth." Virology. Sep. 1975;67(1):242-248.
Pelletier J, Sonenberg N., "Internal initiation of translation of eukaryotic mRNA directed by a sequence derived from poliovirus RNA." Nature. Jul. 28, 1988;334(6180):320-325.
Perales et al., "Gene transfer in vivo: sustained expression and regulation of genes introduced into the liver by receptor-targeted uptake." Proc Natl Acad Sci USA. Apr. 26, 1994;91(9):4086-4090.
Phinney DG, Prockop DJ., "Concise review: mesenchymal stem/multipotent stromal cells: the state of transdifferentiation and modes of tissue repair—current views." Stem Cells. Nov. 2007;25(11):2896-902.
Ping et al., "Altered beta-adrenergic receptor signaling in heart failure, in vivo gene transfer via adeno and adeno-associated virus." Microcirculation. Jun. 1996;3(2):225-228.
Pinto et al., "Prostate-specific membrane antigen: a novel folate hydrolase in human prostatic carcinoma cells." Clin Cancer Res. Sep. 1996;2(9):1445-51.
Pittenger et al., "Multilineage potential of adult human mesenchymal stem cells." Science. Apr. 2, 1999;284(5411):143-7.
Poli V, Cortese R., "Interleukin 6 induces a liver-specific nuclear protein that binds to the promoter of acute-phase genes." Proc Natl Acad Sci USA. Nov. 1989;86(21):8202-8206.
Porter DL, Levine BL, Kalos M, et al: Chimeric antigen receptor-modified T cells in chronic lymphoid leukemia. N Engl J Med 365:725-33, 2011.
Potter et al., "Enhancer-dependent expression of human kappa immunoglobulin genes introduced into mouse pre-B lymphocytes by electroporation." Proc Natl Acad Sci USA. Nov. 1984;81(22):7161-7165.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.
Prockop DJ., "Marrow stromal cells as stem cells for nonhematopoietic tissues." Science. Apr. 4, 1997;276(5309):71-4.
Prowse KR, Baumann H., "Hepatocyte-stimulating factor, beta 2 interferon, and interleukin-1 enhance expresson of the rat alpha 1-acid glycoprotein gene via a distal upstream regulatory region." Mol Cell Biol. Jan. 1988;8(1):42-51.
Pruschy et al., "Mechanistic Sutdies of a Signaling Pathway Activated by the Organic Dimerizer FK1012," Chemistry and biology 1994 vol. 1, No. 3, 164-172.
Przepiorka et al., "1994 Consensus Conference on Acute GVHD Grading." Bone Marrow Transplant. Jun. 1995;15(6):825-8.
Puccetti et al., "Effects of IL-12 and IL-23 on antigen-presenting cells at the interface between innate and adaptive immunity." Crit Rev Immunol. 2002;22(5-6):373-390.
Pule et al., "Artificial T-cell receptors." Cytotherapy. 2003;5(3):211-26.

(56) References Cited

OTHER PUBLICATIONS

Pule MA, Savoldo B, Myers GD, et al: Virus-specific T cells engineered to coexpress tumor-specific receptors: persistence and antitumor activity in individuals with neuroblastoma. Nat Med 14:1264-70, 2008.
Pullen et al., "CD40 signaling through tumor necrosis factor receptor-associated factors (TRAFs). Binding site specificity and activation of downstream pathways by distinct TRAFs." J Biol Chem. May 14, 1999;274(20):14246-14254.
Quintarelli et al., "Co-expression of cytokine and suicide genes to enhance the activity and safety of tumor-specific cytotoxic T lymphocytes" Blood (2007) 110:2793-2802.
Raina, D., et al., c-Abl tyrosine kinase regulates caspase-9 autocleavage in the apoptotic response to DNA damage. J Biol Chem, 2005. 280(12): p. 11147-51.
Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.
Randall, K.L., et al., Dock8 mutations cripple B cell immunological synapses, germinal centers and long-lived antibody production. Nat Immunol, 2009. 10(12): p. 1283-91.
Re F, Strominger JL., "Toll-Ike receptor 2(TLR2) and TLR4 differentially activate human dendritic cells." J Biol Chem. Oct. 5, 2001;276(40):37692-37699.
Reis e Sousa C., "Dendritic cells as sensors of infection." Immunity. May 2001;14(5):495-498.
Renan MJ., "Cancer genes: current status, future prospects, and applications in radiotherapy/oncology." Radiother Oncol. Nov. 1990;19(3):197-218.
Renatus, M., et al., Dimer formation drives the activation of the cell death protease Caspase-9. Proc Natl Acad Sci U S A, 2001. 98(25): p. 14250-5.
Rescigno et al., "Dendritic cell survival and maturation are regulated by different signaling pathways." J Exp Med. Dec. 7, 1998;188(11):2175-2180.
Rezvani et al., "Functional leukemia-associated antigen-specific memory CD8+ T cells exist in healthy individuals and in patients with chronic myelogenous leukemia before and after stem cell transplantation." Blood. Oct. 15, 2003;102(8):2892-900.
Rezvani et al., "T-cell responses directed against multiple HLA-A*0201-restricted epitopes derived from Wilms' tumor 1 protein in patients with leukemia and healthy donors: identification, quantification, and characterization." Clin Cancer Res. Dec. 15, 2005;11(24 Pt 1):8799-807.
Richard et al, "Expansion of Genetically modified Primary Human HemopOietic cells Using Chemical Inducers of Dimerization," Blood vol. 95, 2000 pp. 430-436.
Riddell et al., "T-cell mediated rejection of gene-modified HIV-specific cytotoxic T lymphocytes in HIV-infected patients." Nat Med. Feb. 1996;2(2):216-23.
Ridge et al., "A conditioned dendritic cell can be a temporal bridge between a CD4+ T-helper and a T-Killer cell." Nature. Jun. 4, 1998;393(6684):474-478.
Ridgway D., "The first 1000 dendritic cell vaccinees." Cancer Invest. 2003;21(6):873-886.
Riol-Blanco et al., "The chemokine receptor CCR7 activates in dendritic cells two signaling modules that independently regulate chemotaxis and migratory speed." J Immunol. Apr. 1, 2005;174(7):4070-4080.
Rippe et al., "DNA-mediated gene transfer into adult rat hepatocytes in primary culture." Mol Cell Biol. Feb. 1990;10(2):689-695.
Rivera et al., "A humanized system for pharmacologic control of gene expression." Nat Med. Sep. 1996;2(9):1028-1032.
Rivera, V.M., "Controlling Gene Expression Using Synthetic Ligands," Methods: A companion to Methods in Enzymology vol. 14,1998 pp. 421-429.
Ron et al., "Angiotensinogen gene-inducible enhancer-binding protein 1, a member of a new family of large nuclear proteins that recognize nuclear factor kappa B-binding sites through a zinc finger motif." Mol Cell Biol. May 1991;11(5):2887-2895.
Rooney et al., "Infusion of cytotoxic T cells for the prevention and treatment of Epstein-Barr virus-induced lymphoma in allogeneic transplant recipients." Blood. Sep. 1, 1998;92(5):1549-55.
Roose, J.P., et al., T cell receptor-independent basal signaling via Erk and Abl kinases suppresses RAG gene expression. PLoS Biol, 2003. 1(2): p. E53.
Rosenberg SA., "A new era for cancer immunotherapy based on the genes that encode cancer antigens." Immunity. Mar. 1999;10(3):281-287.
Roux et al., "A versatile and potentially general approach to the targeting of specific cell types by retrovirus: application to the infection of human cells by means of major histocompatibility complex class I and class II antigens by mouse ecotropic murine leukemia virus-derived viruses." Proc Natl Acad Sci USA. Dec. 1989;86(23):9079-9083.
Rudd, M.L., A. Tua-Smith, and D.B. Straus, Lck SH3 domain function is required for T-cell receptor signals regulating thymocyte development. Mol Cell Biol, 2006. 26(21): p. 7892-900.
Rudinger, Peptide Hormones 1976; June; pp. 1-7.
Sale GE, Storb R., "Bilateral diffuse pulmonary ectopic ossification after marrow allograft in a dog. Evidence for allotransplantation of hemopoietic and mesenchymal stem cells." Exp Hematol. Nov. 1983;11(10):961-6.
Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.
Sallusto et al., "Rapid and coordinated switch in chemokine receptor expression during dendritic cell maturation." Eur J Immunol. Sep. 1998;28(9):2760-2769.
Samulski et al., "A recombinant plasmid from which an infectious adeno-associated virus genome can be excised in vitro and its use to study viral replication." J Virol. Oct. 1987;61(10):3096-3101.
Sanchez-Sanchez et al., "The multiple personalities of the chemokine receptor CCR7 in dendritic cells." J Immunol. May 1, 2006;176(9):5153-5159.
Sardesai, N.Y., and Weiner, D.B., Current Opinion in Immunotherapy 23:421-9 (2011).
Sato et al., "Combination of monocyte-derived dendrinic cells and activated T cells which express CD40 ligand an new approach to cancer Immunotherapy," Cancer Imminol Immunther, vol. 53, No. 1, Jan. 2004, pp. 53-61.
Scandella et al., "CCL19/CCL21-triggered signal transduction and migration of dendritic cells requires prostaglandin E2." Blood. Mar. 1, 2004;103(5):1595-1601.
Scandella et al., "Prostaglandin E2 is a key factor for CCR7 surface expression and migration of monocyte-derved dendritic cells." Blood. Aug. 15, 2002;100(4):1354-1361.
Schellhammer et al., "Prostate specific antigen decreases after withdrawal of antiandrogen therapy with bicalutamide or flutamide in patients receiving combined androgen blockade." J Urol. May 1997;157(5):1731-1735.
Scher et al., "Clinical trials in relapsed prostate cancer: defining the target." J Natl Cancer Inst. Nov. 20, 1996;88(22):1623-1634.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7):1148-59.
Scher Hi, Kelly WK., "Flutamide withdrawal syndrome: its impact on clinical trials in hormone-refractory prostate cancer." J Clin Oncol. Aug. 1993;11(8):1566-1572.
Schneider et al., "Inactivation of the human immunodeficiency virus type 1 inhibitory elements allows Rev-independent expression of Gag and Gag/protease and particle formation." J Virol. Jul. 1997;71(7):4892-4903.
Schoenberger et al., "T-cell help for cytotoxic T lymphocytes is mediated by CD40-CD40L interactions." Nature. Jun. 4, 1998;393(6684):480-483.
Schram, B.R., et al., B cell receptor basal signaling regulates antigen-induced Ig light chain rearrangements. J Immunol, 2008. 180(7): p. 4728-41.
Schuler et al., "The use of dendritic cells in cancer immunotherapy." Curr Opin Immunol. Apr. 2003; 15(2):138-147.

(56) References Cited

OTHER PUBLICATIONS

Schumacher TN., “T-cell-receptor gene therapy.” Nat Rev Immunol. Jul. 2002;2(7):512-9.
Schuster, et al., “ALD518, a humanized anti-IL-6 antibody, treats anemia in patients with advanced non-small cell lung cancer (NSCLC): Results of a phase II, randomized, double-blind, placebo-controlled trial,” 2010, J. Clin. Oncol. 28-7s (suppl.; abstr. 7631).
Schweitzer BA, Kool ET., “Aromatic Nonpolar Nucleosides as Hydrophobic Isosteres of Pyrimidine and Purine Nucleosides.” J Org Chem. Dec. 1, 1994;59(24):7238-7242.
Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
Shaffer et al., “Circulating tumor cell analysis in patients with progressive castration-resistant prostate cancer.” Clin Cancer Res. Apr. 1, 2007;13(7):2023-9.
Shen et al., “Silencing of SOCS1 enhances antigen presentation by dendritic cells and antigen-specific anti-tumor immunity.” Nat Biotechnol. Dec. 2004;22(12):1546-1553.
Shi, Y., Mechanisms of Caspase activation and inhibition during apoptosis. Mol Cell, 2002. 9(3): p. 459-70.
Shiozaki, E.N., et al., Mechanism of XIAP-mediated inhibition of caspase-9. Mol Cell, 2003. 11(2): p. 519-27.
Shiozaki, E.N., J. Chai, and Y. Shi, Oligomerization and activation of caspase-9, induced by Apaf-1 CARD. Proc Natl Acad Sci U S A, 2002. 99(7): p. 4197-202.
Silver et al., “Prostate-specific membrane antigen expression in normal and malignant human tissues.” Clin Cancer Res. Jan. 1997;3(1):81-5.
Simpson et al., “Consequences of Fas-ligand and perforin expression by colon T cells in a mouse model of inflammatory bowel disease.” Gastroenterology. Oct. 1998; 115(4):849-855.
Small EJ, Srinivas S., “The antiandrogen withdrawal syndrome. Experience in a large cohort of unselected patients with advanced prostate cancer.” Cancer. Oct. 15, 1995;76(8):1428-1434.
Small EJ, Vogelzang NJ., “Second-line hormonal therapy for advanced prostate cancer: a shifting paradigm.” J Clin Oncol. Jan. 1997;15(1):382-388.
Smith et al., “Cognate CD4(+) T cell licensing of dendritic cells in CD8(+) T cell immunity.” Nat Immunol. Nov. 2004;5(11):1142-1148.
Smith et al., “DNA/MVA vaccine for HIV type 1:effects of codon-optimization and the expression of aggregates or virus-like particles on the immunogenicity of the DNA prime.” AIDS Res Hum Retroviruses. Dec. 2004;20(12):1335-1347.
Snyder et al., “Prostaglandins modulate macrophage la expression.” Nature. Sep. 9, 1982;299(5879):163-165.
Solomon et al., “Selective depletion of alloreactive donor lymphocytes: a novel method to reduce the severity of graft-versus-host disease in older patients undergoing matched sibling donor stem cell transplantation.” Blood. Aug. 1, 2005;106(3):1123-9.
Song DG, Ye Q, Poussin M, et al: CD27 costimulation augments the survival and antitumor activity of redirected human T cells in vivo. Blood 119:696-706, 2012.
Sorensen et al., “Endostatin reduces cascularization, blood flow, and growth in a rat gliosarcoma.” Neuro Oncol. Jan. 2002;4(1):1-8.
Sorkin, A. and M. von Zastrow, Endocytosis and signalling: intertwining molecular networks. Nat Rev Mol Cell Biol, 2009. 10(9): p. 609-22.
Spencer et al., “A general strategy for producing conditional alleles of Src-like tyrosine kinases.” Proc Natl Acad Sci USA Oct. 10, 1995;92(21):9805-9809.
Spencer et al., “Controlling signal transduction with synthetic ligands.” Science. Nov. 12, 1993;262(5136):1019-1024.
Spencer et al., “Functional analysis of Fas signaling in vivo using synthetic inducers of dimerization.” Curr Biol. Jul. 1, 1996;6(7):839-847.
Spiegel, A.M., Defects in G protein-coupled signal transduction in human disease. Annu Rev Physiol, 1996. 58: p. 143-70.
Spitzer, TM. “Haploidentical Stem Cell Transplantation: The Always Present but overlooked Donor,” Hematology, 2005, 1:390-395.
Sporri R, Reis e Sousa C., “Inflammatory mediators are insufficient for full dendritic cell activation and promote expansion of CD4+ T cell populations lacking helper function.” Nat Immunol. Feb. 2005;6(2):163-170.
Srinivasula et al., “A conserved XIAP-interaction motif in caspase-9 and Smac/DIABLO regulates caspase activity and apoptosis,” Nature 410, 112-116.
Steinman et al., “Tolerogenic dendritic cells.” Annu Rev Immunol. 2003;21:685-711.
Steinman RM, Pope M., “Exploiting dendritic cells to improve vaccine efficacy.” J Clin Invest. Jun. 2002:109(12):1519-1526.
Stennicke, H.R., et al., Caspase-9 can be activated without proteolytic processing. J Biol Chem, 1999. 274(13): p. 8359-62.
Straathof et al., “An inducible caspase 9 safety switch for T-cell therapy.” Blood. Jun. 1, 2005;105(11):4247-54.
Strasser et al., “Integrin Activation by Regulated Dimerization and Oligomerization of Platelet Endothelial Cell Adhesion Molecule (PECAM)-1 from Within the Cell,” Immunity Review 30, Feb. 20, 2009, 180-192.
Strober et al., “Signaling pathways and molecular interactions of NOD1 and NOD2.” Nat Rev Immunol. Jan. 2006;6(1):9-20.
Studeny et al., “Bone marrow-derived mesenchymal stem cells as vehicles for interferon-beta delivery into tumors.” Cancer Res. Jul. 1, 2002;62(13):3603-8.
Studeny et al., “Mesenchymal stem cells: potential precursors for tumor stroma and targeted-delivery vehicles for anticancer agents.” J Natl Cancer Inst. Nov. 3, 2004;96(21):1593-603.
Su et al., “Alternatively spliced variants of prostate-specific membrane antigen RNA: ratio of expression as a potential measurement of progression.” Cancer Res. Apr. 1, 1995;55(7):1441-1443.
Su et al., “Telomerase mRNA-transfected dendritic cells stimulate antigen-specific CD8+ and CD4+ T cell responses in patients with metastatic prostate cancer.” J Immunol. Mar. 15, 2005;174(6):3798-3807.
Suarez-Alvarez et al, Epigenetic Mechanisms Regulate MHC and Antigen Processing Molecules in Human Embryonic and Induced Pluripotent Stem Cells. PLoS ONE (April) 5(4):e10192, 2010, pp. 1-12.
Suda et al., “Molecular Cloning and Expression of the Fas Ligand, a Novel Member of the Tumor Necrosis Factor Family,” Cell vol. 75, 1169-1176 Dec. 17, 1993.
Tai et al., “Mechanisms by which SGN-40, a Humanized Anti-CD40 Antibody, Induces Cytotoxicity in Human Multiple Myeloma Celis: Clinical Implications,” Cancer Research, Apr. 15, 2004, vol. 64, pp. 2846-2852.
Tao, Y.X., Constitutive activation of G protein-coupled receptors and diseases: insights into mechanisms of activation and therapeutics. Pharmacol Ther, 2008. 120(2): p. 129-48.
ten Klooster JP, Hordijk PL., “Targeting and localized signaling by small GTPases.” Biol Cell. Jan. 2007;99(1):1-12.
Tepler et al., “The gene for the rat mast cell high affinity IgE receptor alpha chain. Structure and alternative mRNA splicing patterns.” J Biol Chem. Apr. 5, 1989;264(10):5912-5915.
Termeer et al., “Oligosaccharides of hyaluronan are potent activators of dendritic cells.” J Immunol. Aug. 15, 2000;165(4):1863-1870.
Tey et al., Inducible Caspase 9 Suicide Gene to Improve the Safety of Allodepleted T Cells after Haploidentical Stem Cell Transplantation. Bio Blood & Marrow Transplant. 13:913-924 (2007).
Thomis et al., “A Fas-based suicide switch in human T cells for the treatment of graft-versus-host disease.” Blood. Mar. 1, 2001;97(5):1249-57.
Thompson et al., “The low-toxicity versions of LPS, MPL adjuvant and RC529, are efficient adjuvants for CD4+ T Cells.” J Leukoc Biol. Dec. 2005;78(6):1273-1280.
Tibbetts C., “Viral DNA sequence from incomplete particles of human adenovirus type 7.” Cell. Sep. 1977;12(1):243-249.
Tiberghien et al., “Administration of herpes simplex-thymidine kinase-expressing donor T cells with a T-cell-depleted allogeneic marrow graft.” Blood. Jan. 1, 2001;97(1):63-72.

(56) References Cited

OTHER PUBLICATIONS

Till BG, Jensen MC, Wang J, et al: CD20-specific adoptive immunotherapy for lymphoma using a chimeric antigen receptor with both CD28 and 4-1BB domains: pilot clinical trial results. Blood 119:3940-50, 2012.
Tolar et al., "Sarcoma derived from cultured mesenchymal stem cells." Stem Cells. Feb. 2007;25(2):371-9.
Tone M . et al., "Regulation of CD40 function by its isoforms generated through alternative splicing," PNAS. Feb. 13, 2001, vol. 98, No. 4, pp. 1751-1756.
Tong et al, "Prospects for CD40-directed Experimental Therapy of Human Cancer," Cancer Gene Therapy vol. 10, 2003,pp. 1-13.
Troyer et al., "Detection and characterization of the prostate-specific membrane antigen (PSMA) in tissue extracts and body fluids." Int J Cancer. Sep. 4, 1995;62(5):552-8.
Tur-Kaspa et al., "Use of electroporation to introduce biologically active foreign genes into primary rat hepatocytes." Mol Cell Biol. Feb. 1986;6(2):716-718.
Tyndall A, Uccelli A., "Multipotent mesenchymal stromal cells for autoimmune diseases: teaching new dogs old tricks." Bone Marrow Transplant. Jun. 2009;43(11):821-8.
Tze, L.E., et al., Basal immunoglobulin signaling actively maintains developmental stage in immature B cells. PLoS Biol, 2005. 3(3): p. e82.
van der Pouw Krann T.C., et al., "Prostaglandin E2 is a potent inhibitor of human interleukin12 production," J Exp Med., 1995, vol. 181, pp. 775-779.
Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg J, Jackson A., "Modulation of antitumor responses by dendritic cells." Springer Semin Immunopathol. Jan. 2005;26(3):329-341.
Vincent et al., "Targeting of proteins to membranes through hedgehog auto-processing." Nat Biotechnol. Aug. 2003;21(8):936-940.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "A strategy for treatment of Epstein-Barr virus-positive Hodgkin's disease by targeting interleukin 12 to the tumor environment using tumor antigen-specific T cells." Cancer Gene Ther. Feb. 2004;11(2):81-91.
Wagner et al., "Transferrin-polycation conjugates as carriers for DNA uptake into cells." Proc Natl Acad Sci USA. May 1990;87(9):3410-3414.
Waldner, C., et al., Double conditional human embryonic kidney cell line based on FLP and PhiC31 mediated transgene integration. BMC Res Notes, 2011. 4: p. 420.
Walter et al., "Reconstitution of cellular immunity against cytomegalovirus in recipients of allogeneic bone marrow by transfer of T-cell clones from the donor." N Engl J Med. Oct. 19, 1995;333(16):1038-44.
Wang et al., "Relative contributions of codon usage, promoter efficiency and leader sequence to the antigen expression and immunogenicity of HIV-1 Env DNA vaccine." Vaccine. May 22, 2006;24(21):4531-4540.
Werneburg et al., "Molecular Characterization of CD40 Signaling Intermediates," The Journal of Biological Chemistry, vol. 276, Nov. 16, 2001, 43334-43342.
Werts et al., "TIR, CARD and PYRIN: three domains for an antimicrobial triad." Cell Death Differ. May 2006;14(5):798-815.
Wesemann et al., "Suppressor of cytokine signaling 1 inhibits cytokine induction of CD40 expression in macrophages." J Immunol. Sep. 1, 2002;169(5):2354-2360.
Wilson et al., "A 58-base-par region of the human C3 gene confers synergistic inducibility by interleukin-1 and interleukin-6." Mol Cell Biol. Dec. 1990;10(12):6181-6191.
Wilson et al., "Implantation of vascular grafts lined with genetically modified endothelial cells." Science. Jun. 16, 1989;244(4910):1344-1346.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright et al., "Upregulation of prostate-specific membrane antigen after androgen-deprivation therapy." Urology. Aug. 1996;48(2):326-34.
Wu and Wu, "Liver-directed gene delivery," Adv Drug Delivery Rev, 1993;12:159-167.
Wu et al., "Codon optimization reveals critical factors for high level expression of two rare codon genes in *Escherichia coli*: RNA stability and secondary structure but not tRNA abundance." Biochem Biophys Res Commun. Jan. 2, 2004;313(1):89-96.
Wu et al., "Development of an inducible caspase-9 safety switch for pluripotent stem cell-based therapies" Molecular Therapy—Methods Clinical Development 1:14053.
Wu GY, Wu CH., "Receptor-mediated in vitro gene transformation by a soluble DNA carrier system." J Biol Chem. Apr. 5, 1987;262(10):4429-32.
Xiao et al., "Efficient long-term gene transfer into muscle tissue of immunocompetent mice by adeno-associated virus vector." J Virol. Nov. 1996;70(11):8098-8108.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61 (18):6795-6804.
Xu et al., "Optimization of transcriptional regulatory elements for constructing plasmid vectors." Gene. Jul. 11, 2001;272(1-2):149-156.
Yadava A, Ockenhouse CF., "Effect of codon optimization on expression levels of a functionally folded malaria vaccine candidate in prokaryotic and eukaryotic expression systems." Infect Immun. Sep. 2003;71(9):4961-4969.
Yan et al., "Enhanced cellular immune responses elicited by an engineered HIV-1 subtype B consensus-based envelope DNA vaccine." Mol Ther. Feb. 2007;15(2):411-421.
Yanagawa Y, Onoe K., "CCL19 induces rapid dendritic extension of murine dendritic cells." Blood. Sep. 15, 2002;100(6):1948-1956.
Yang et al., "In vivo and in vitro gene transfer to mammalian somatic cells by particle bombardment." Proc Natl Acad Sci USA. Dec. 1990;87(24):9568-9572.
Yang et al., "Induction of inflammation by West Nile virus capsid through the caspase-9 apoptotic pathway." Emerg Infect Dis. Dec. 2002;8(12):1379-1384.
Yoon et al., "Unexpected severe calcification after transplantation of bone marrow cells in acute myocardial infarction." Circulation. Jun. 29, 2004;109(25):3154-7.
Zechner et al., "Recombinant human cachectin/tumor necrosis factor by not interleukin-1 alpha downregulates lipoprotein lipase gene expression at the transcriptional level in mouse 3T3-L1 adipocytes." Mol Cell Biol. Jun. 1988;8(6):2394-2401.
Zhai et al., "Vaccinia virus protein F1L is a caspase-9 inhibitor" J. Biol. Chem. (2010) 285(8):5569-80.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "mRNA secondary structure at start AUG codon is a key limiting factor for human protein expression in *Escherichia coli*." Biochem Biophys Res Commun. Oct. 13, 2006;349(1):69-78.
Zhang, Y., et al., PLOS Pathogens 6:1-13 (2010).

(56) References Cited

OTHER PUBLICATIONS

Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zhong et al., "Chimeric antigen receptors combining 4-1BB and CD28 signaling domains augment PI3kinase/AKT/Bcl-XL activation and CD8+ T cell-mediated tumor eradication." Mol Ther. Feb. 2010;18(2):413-20.
Zhong et al., "Safeguarding nonhuman primate iPS cells with suicide genes" Molecular Therapy (2011) 19(9):1667-1675.
Zhou et al., "Multiple RNA splicing and the presence of cryptic RNA splice donor and acceptor sites may contribute to low expression levels and poor immunogenicity of potential DNA vaccines containing the env gene of equine infectious anemia virus (EIAV)." Vet Microbiol. Aug. 25, 2002;88(2):127-151.
Zitvogel et al., "Therapy of murine tumors with tumor peptide-pulsed dendritic cells: dependence on T cells, B7 costimulation, and T helper cell 1-associated cytokines." J Exp Med. Jan. 1, 1996;183(1):87-97.
Zlatkine et al., "Retargeting of cytosolic proteins to the plasma membrane by the Lck protein tyrosine kinase dual acylation motif." J Cell Sci. Mar. 1997;110(Pt5):673-679.
Zou et al., "Regulation of the Apaf-1/Caspase-9 Apoptosome b y Caspase-3 and XIAP," The Journal of Biological Chemistry, vol. 278, No. 10, Mar. 7, 2003, pp. 8091-8098.
zur Medege et al., "Expression and immunogenicity of sequence-modified human immunodeficiency virus type 1 subtype B pol and gagpol DNA vaccines." J Virol. Jun. 2003;77(11):6197-6207.
zur Megede, J., et al., "Increased expression and immunogenicity of sequence-modified human immunodeficiency virus type 1 gag gene," 2000. J. Virol. 74:2628-2635.
International Search Report and Written Opinion dated Apr. 21, 2016, in International Application No. PCT/IB2015/002191 filed Nov. 2, 2015 and published as: WO/2016/071758 on: May 12, 2016.
Browne et al., "The B-Cell Transcription Factors BSAP, OCT-2 and BOB.1 and the PAN-B-Cell markers CD20, CD22, and CD79a are useful in the differential diagnosis of classic Hodgkin Lymphoma," American Society for Clinical Pathology, US, vol. 120, No. 5, Nov. 1, 2003, pp. 767-777.
Chang et al., "Proteases for cell suicide: functions and regulation of caspases", Microbiology and Molecular Biology Reviews, American Society for Microbiology US, vol. 64, No. 4, Dec. 1, 2008, pp. 821-846.
Heckman et al., "Oct transcription factors mediate t(14;18) lymphoma cell survival by directly regulating bcl-2 expression", Oncology, Nature Publishing Group, GB, vol. 25, No. 6, Feb. 1, 2006, pp. 888-898.
Hermann Steller "Artificial death switches: Induction of apoptosis by chemically induced caspase multimerization", PNAS, USA, vol. 95, May 1, 1998, pp. 5421-5422.
Jahn et al., "T Cell Receptors specific for the Intracellular Transcription Factor Bob1 Allow Efficient Targeting of Human B Cell Leukemia and Multiple Myeloma", Blood, vol. 124, No. 21, Dec. 6, 2014, p. 3832.
Stauss, "No hiding place for BOB inside myeloma" Blood (2017) 129(10):1236-1237.
International Preliminary Report on Patentability dated May 18, 2017 in International Application No. PCT/IB2015/002191 filed Nov. 2, 2015 and published as: WO/2016/071758 on: May 12, 2016.
Amir, et al. 2011. PRAME-specific Allo-HLA-restricted T cells with potent antitumor reactivity useful for therapeutic T-cell receptor gene transfer. Clin.Cancer Res. 17:5615-5625.
Anurathapan et al: Kinetics of tumor destruction by chimeric antigen receptor-modified T cells. Mol Ther 22:623-33, 2014.
Becker et al: Expression of a hybrid immunoglobulin-T cell receptor protein in transgenic mice. Cell 58:911-21, 1989.
Leo et al., "Partition Coefficients and their Uses," Chemical Reviews, vol. 71, Issue 6, 526-616, Dec. 1971, p. 599, where entry 4493 shows lauric acid having a log p value of 4.2.
Craddock. et al: Enhanced tumor trafficking of GD2 chimeric antigen receptor T cells by expression of the chemokine receptor CCR2b. J Immunother 33:780-8, 2010.
Deml, L.A., et al., 2001. J. Virol. 75:1099-11001.
Donnelly, ML 2001, J. Gen. Virol. 82:1013-25.
Finney et al: Chimeric receptors providing both primary and costimulatory signaling in T cells from a single gene product. J Immunol 161:2791-7, 1998.
Gaubert, G.; Wengel, J. Tetrahedron Letters 2004, 45, 5629.
GenBank Accession No. AH002818 Feb. 12, 2001.
GenBank Accession No. NM 001229 Oct. 31, 2000.
GenBank Accession No. NM 001770 Oct. 31, 2000.
Galbiati et al., Biochem. J. 303: 697-700 (1994).
Goodman et al. (1994), Blood, 84,1492-1500.
Goverman, et al: Chimeric immunoglobulin-T cell receptor proteins form functional receptors: implications for T cell receptor complex formation and activation. Cell 60:929-39, 1990.
Gross et al., Expression of immunoglobulin-T-cell receptor chimeric molecules as functional receptors with antibody-type specificity. Proc Natl Acad Sci U S A 86:10024-8, 1989.
Heemskerk et al., 2001. Dual HLA class I and class II restricted recognition of alloreactive T lymphocytes mediated by a single T cell receptor complex. Proc.Natl.Acad.Sci.U.S.A 98:6806-6811.
Hombach, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
Hombrink,et al., 2013. Discovery of T cell epitopes implementing HLA-peptidomics into a reverse immunology approach. J.Immunol. 190:3869-3877.
Imai, et al: Chimeric receptors with 4-1BB signaling capacity provoke potent cytotoxicity against acute lymphoblastic leukemia. Leukemia 18:676-84, 2004.
Iuliucci JD, et al., J Clin Pharmacol. 41: 870-9, 2001.
Jensen, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
Kalinski P, Hilkens CM, Wierenga EA, et al: T-cell priming by type-1 and type-2 polarized dendritic cells: the concept of a third signal. Immunol Today 20:561-7, 1999.
Kemnade JO, Seethammagari M, Narayanan P, et al: Off-the-shelf Adenoviral-mediated Immunotherapy via Bicistronic Expression of Tumor Antigen and iMyD88/CD40 Adjuvant. Mol Ther, 2012.
Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
Lee DW, Gardner R, Porter DL, et al: Current concepts in the diagnosis and management of cytokine release syndrome. Blood 124:188-95, 2014.
Maher J, Brentjens RJ, Gunset G, et al: Human T-lymphocyte cytotoxicity and proliferation directed by a single chimeric TCRzeta /CD28 receptor. Nat Biotechnol 20:70-5, 2002.
Martin S, Pahari S, Sudan R, et al: CD40 signaling in CD8+CD40+ T cells turns on contra-T regulatory cell functions. J Immunol 184:5510-8, 2010.
Park, et al: Adoptive transfer of chimeric antigen receptor re-directed cytolytic T lymphocyte clones in patients with neuroblastoma. Mol Ther 15:825-33, 2007.
Pule MA, Straathof KC, Dotti G, et al: A chimeric T cell antigen receptor that augments cytokine release and supports clonal expansion of primary human T cells. Mol Ther 12:933-41, 2005.
Ramos CA, Dotti G: Chimeric antigen receptor (CAR)-engineered lymphocytes for cancer therapy. Expert Opin Biol Ther 11:855-73, 2011.
Sato, M., et al., "A combination of targeted toxin technology and the piggyBac-mediated gene transfer system enables efficient isolation of stable transfectants in nonhuman mammalian cells," Biotechnol J. Jan. 2015;10(1):143-53. doi: 10.1002/biot.201400283. Epub Dec. 5, 2014.

(56) References Cited

OTHER PUBLICATIONS

Savoldo B, Ramos CA, Liu E, et al: CD28 costimulation improves expansion and persistence of chimeric antigen receptor-modified T cells in lymphoma patients. J Clin Invest 121:1822-6, 2011.
Schenten D, Nish SA, Yu S, et al: Signaling through the adaptor molecule MyD88 in CD4+ T cells is required to overcome suppression by regulatory T cells. Immunity 40:78-90, 2014.
Tibbetts et. al. (1977) Cell, 12,243-249.
van Loenen,M.M., B.R.de, L.E.van, P.Meij, I.Jedema, J.H. Falkenburg, and M.H.Heemskerk. 2014. A Good Manufacturing Practice procedure to engineer donor virus-specific T cells into potent anti-leukemic effector cells. Haematologica 99:759-768.
Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
Yan, J. et al., 2007. Mol. Ther. 15:411-21.
Yvon, et al: Immunotherapy of metastatic melanoma using genetically engineered GD2-specific T cells. Clin Cancer Res 15:5852-60, 2009.
Zhao Y, Wang QJ, Yang S, et al: A herceptin-based chimeric antigen receptor with modified signaling domains leads to enhanced survival of transduced T lymphocytes and antitumor activity. J Immunol 183:5563-74, 2009.

* cited by examiner

Amino Acid Seq POU2AF1/BOB1 clone 3C10 pept in A2 (AV13-1*01, BV12-4*01)

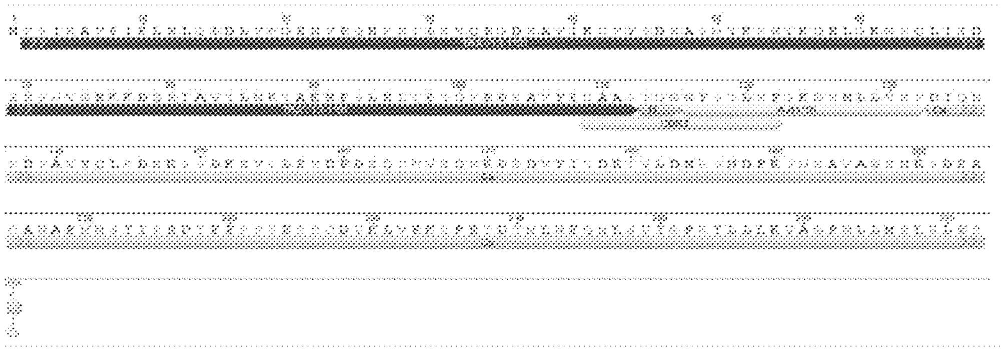

MTSIRAVFIFLWLQLDLVNGENVEQHPSTLSVQEGDSAVIKCTYSDSASNYFPWYKQELGKGPQLIIDIRSNVGEKKDQRIAVTL
NKTAKHFSLHITETQPEDSAVYFCAASTGGGYSTLTFGKGTMLLVSPDIQNPDPAVYQLRDSKSSDKSVCLFTDFDSQTNVSQS
KDSDVYITDKTVLDMRSMDFKSNSAVAWSNKSDFACANAFNNSIIPEDTFFPSPESSCDVKLVEKSFETDTNLNFQNLSVIGFRI
LLLKVAGFNLLMTLRLWSS

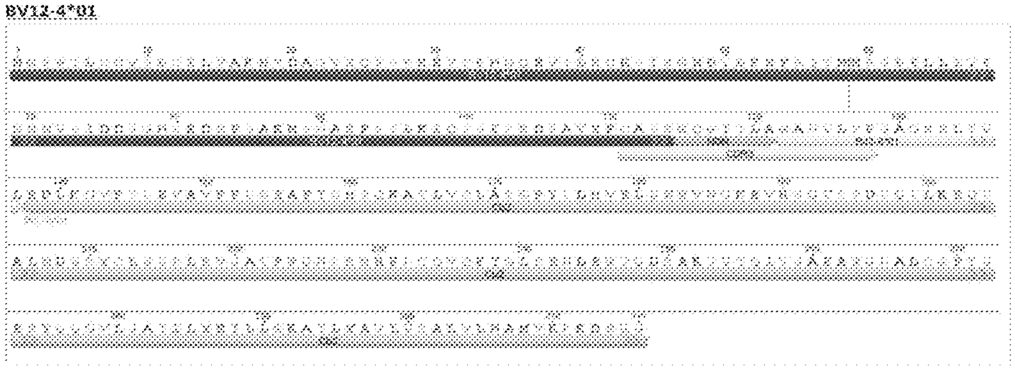

MGSWTLCCVSLCILVAKHTDAGVIQSPRHEVTEMGQEVTLRCKPISGHDYLFWYRQTMMRGLELLIYFNNNVPIDDSGMPED
RFSAKMPNASFSTLKIQPSEPRDSAVYFCASSGQGITLAGANVLTFGAGSRLTVLEDLKNVFPPEVAVFEPSEAEISHTQKATLVC
LATGFYPDHVELSWWVNGKEVHSGVSTDPQPLKEQPALNDSRYCLSSRLRVSATFWQNPRNHFRCQVQFYGLSENDEWTQ
DRAKPVTQIVSAEAWGRADCGFTSESYQQGVLSATILYEILLGKATLYAVLVSALVLMAMVKRKDSRG

Fig. 9A

Amino Acid Seq POU2AF1/BOB1 clone 4G11 pept in B7 (AV13-1*01, TRBV4-1*01)

TRAV13-1*01

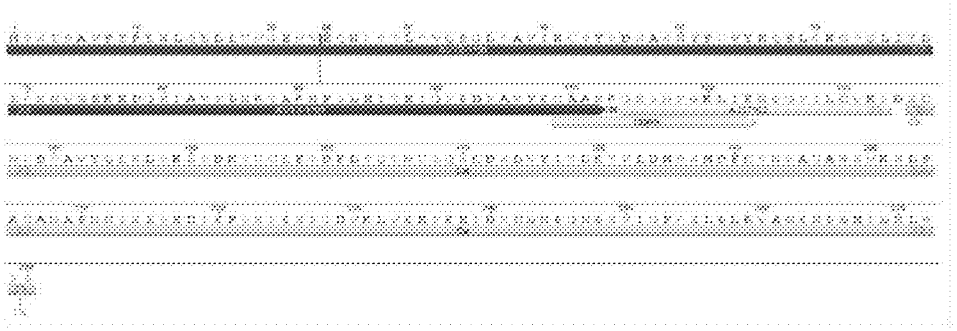

MTSIRAVFIFLWLQLDLVNGENVEQHPSTLSVQEGDSAVIKCTYSDSASNYFPWYKQELGKGPQLIIDIRSNVGEKKDQRIAVTL
NKTAKHFSLHITETQPEDSAVYFCAASKGSSNTGKLIFGQGTTLQVKPDIQNPDPAVYQLRDSKSSDKSVCLFTDFDSQTNVSQS
KDSDVYITDKTVLDMRSMDFKSNSAVAWSNKSDFACANAFNNSIIPEDTFFPSPESSCDVKLVEKSFETDTNLNFQNLSVIGFRI
LLLKVAGFNLLMTLRLWSS

Fig. 9B

TRBV4-1*01

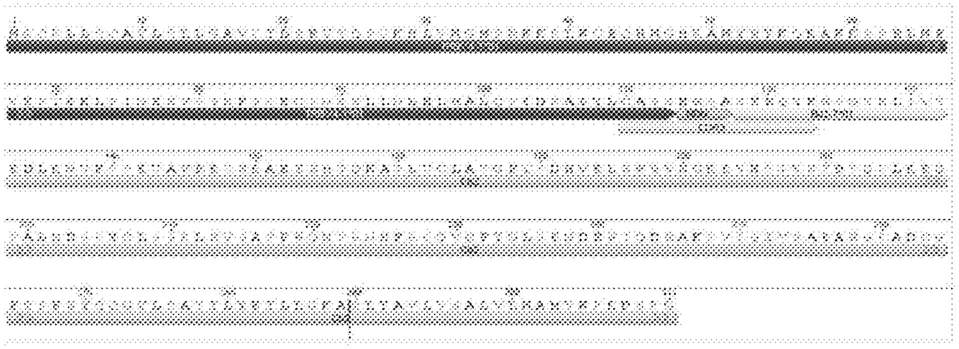

MGCRLLCCAVLCLLGAVPIDTEVTQTPKHLVMGMTNKKSLKCEQHMGHRAMYWYKQKAKKPPELMFVYSYEKLSINESVPSR
FSPECPNSSLLNLHLHALQPEDSALYLCASSHGPASYEQYFGPGTRLTVTEDLKNVFPPEVAVFEPSEAEISHTQKATLVCLATGF
YPDHVELSWWVNGKEVHSGVSTDPQPLKEQPALNDSRYCLSSRLRVSATFWQNPRNHFRCQVQFYGLSENDEWTQDRAKP
VTQIVSAEAWGRADCGFTSESYQQGVLSATILYEILLGKATLYAVLVSALVLMAMVKRKDSRG

Sequence of MP71 Retroviral Multiple Cloning Site

| | | | | | | |
|---|---|---|---|---|---|---|
| 1 | TAGCTTAAGT | AACCCATTTT | GCAAGGCATG | GAAAATACAT | AACTGAGAAT | AGAGAAGTTC |
| 61 | AGATCAAGGT | TAGGAACAGA | GAGACAGCAG | AATATGGGCC | AAACAGGATA | TCTGTGGTAA |
| 121 | GCAGTTCCTG | CCCCGGCTCA | GGGCCAAGAA | CAGTTGGAAC | AGCAGAATAT | GGGCCAAACA |
| 181 | GGATATCTGT | GGTAAGCAGT | TCCTGCCCCG | GCTCAGGGCC | AAGAACAGAT | GGTCCCCAGA |
| 241 | TGCGGTCCCG | CCCTCAGCAG | TTTCTAGAGA | ACCATCAGAT | GTTTCCAGGG | TGCCCCAAGG |
| 301 | ACCTGAAATG | ACCCTGTGCC | TTATTTGAAC | TAACCAATCA | GTTCGCTTCT | CGCTTCTGTT |
| 361 | CGCGCGCTTC | TGCTCCCCGA | GCTCAATAAA | AGAGCCCACA | ACCCCTCACT | CGGCGCGCCA |
| 421 | GTCCTCCGAT | AGACTGCGTC | GCCCGGGTAC | CCGTATTCCC | AATAAAGCCT | CTTGCTGTTT |
| 481 | GCATCCGAAT | CGTGGACTCG | CTGATCCTTG | GGAGGGTCTC | CTCAGATTGA | TTGACTGCCC |
| 541 | ACCTCGGGGG | TCTTTCATTT | GGAGGTTCCA | CCGAGATTTG | GAGACCCCTG | CCCAGGGACC |
| 601 | ACCGACCCCC | CCGCCGGGAG | GTAAGCTGGC | CAGCGGTCGT | TTCGTGTCTG | TCTCTGTCTT |
| 661 | TGTGCGTGTT | TGTGCCGGCA | TCTAATGTTT | GCGCCTGCGT | CTGTACTAGT | TGGCTAACTA |
| 721 | GATCTGTATC | TGGCGGTCCC | GCGGAAGAAC | TGACGAGTTC | GTATTCCCGG | CCGCAGCCCC |
| 781 | TGGGAGACGT | CCCAGCGGCC | TCGGGGGCCC | GTTTTGTGGC | CCATTCTGTA | TCAGTTAACC |
| 841 | TACCCGAGTC | GGACTTTTTG | GAGCTCCGCC | ACTGTCCGAG | GGGTACGTGG | CTTTGTTGGG |
| 901 | GGACGAGAGA | CAGAGACACT | TCCCGCCCCC | GTCTGAATTT | TTGCTTTCGG | TTTTACGCCG |
| 961 | AAACCGCGCC | GCGCGTCTTG | TCTGCTGCAG | CATCGTTCTG | TGTTGTCTCT | GTCTGACTGT |
| 1021 | GTTTCTGTAT | TTGTCTGAAA | ATTAGCTCGA | CAAAGTTAAG | TAATAGTCCC | TCTCTCCAAG |
| 1081 | CTCACTTACA | GGCGGCCACG | CGTGGATCCG | AATTCCTCGA | GATCGATAAG | CTT |
| 2941 | AACACGAGC | CATAGATAGA | ATAAAAGATT | TTATTTAGTC | TCCAGAAAAA | GGGGGGAATG |
| 3001 | AAAGACCCCA | CCTGTAGGTT | TGGCAAGCTA | GCTTAAGTAA | CGCCATTTTG | CAAGGCATGG |
| 3061 | AAAATACATA | ACTGAGAATA | GAGAAGTTCA | GATCAAGGTT | AGGAACAGAG | AGACAGCAGA |
| 3121 | ATATGGGCCA | AACAGGATAT | CTGTGGTAAG | CAGTTCCTGC | CCCGGCTCAG | GGCCAAGAAC |
| 3181 | AGTTGGAACA | GCAGAATATG | GGCCAAACAG | GATATCTGTG | GTAAGCAGTT | CCTGCCCCGG |
| 3241 | CTCAGGGCCA | AGAACAGATG | GTCCCCAGAT | GCGGTCCCGC | CCTCAGCAGT | TTCTAGAGAA |
| 3301 | CCATCAGATG | TTTCCAGGGT | GCCCCAAGGA | CCTGAAATGA | CCCTGTGCCT | TATTTGAACT |
| 3361 | AACCAATCAG | TTCGCTTCTC | GCTTCTGTTC | GCGCGCTTCT | GCTCCCCGAG | CTCAATAAAA |
| 3421 | GAGCCCACAA | CCCCTCACTC | GGCGCGCCAG | TCCTCCGATA | GACTGCGTCG | CCCGGGTACC |
| 3481 | CGTGTTCTCA | ATAAACCCTC | TTGCAGTTGC | ATCCGACTCG | TGGTCTCGCT | GTTCCTTGGG |
| 3541 | AGGGTCTCCT | CTGAGTGATT | GACTGCCCAC | CTCGGGGGTC | TTTCATTCTC | GATCGAGCAG |
| 3601 | CTTGGCGTAA | TCATGGTCAT | AGCTGTTTCC | TGTGTGAAAT | TGTTATCCGC | TCACAATTCC |
| 3661 | ACACAACATA | CGAGCCGGAA | GCATAAAGTG | TAAAGCCTGG | GGTGCCTAAT | GAGTGAGCTA |
| 3721 | ACTCACATTA | ATTGCGTTGC | GCTCACTGCC | CGCTTTCCAG | TCGGGAAACC | TGTCGTGCCA |
| 3781 | GCTGCATTAA | TGAATCGGCC | AACGCGCGGG | GAGAGGCGGT | TTGCGTATTG | GGCGCTCTTC |
| 3841 | CGCTTCCTCG | CTCACTGACT | CGCTGCGCTC | GGTCGTTCGG | CTGCGGCGAG | CGGTATCAGC |
| 3901 | TCACTCAAAG | GCGGTAATAC | GGTTATCCAC | AGAATCAGGG | GATAACGCAG | GAAAGAACAT |
| 3961 | GTGAGCAAAA | GGCCAGCAAA | AGGCCAGGAA | CCGTAAAAAG | GCCGCGTTGC | TGGCGTTTTT |
| 4021 | CCATAGGCTC | CGCCCCCCTG | ACGAGCATCA | CAAAAATCGA | CGCTCAAGTC | AGAGGTGGCG |
| 4081 | AAACCCGACA | GGACTATAAA | GATACCAGGC | GTTTCCCCCT | GGAAGCTCCC | TCGTGCGCTC |
| 4141 | TCCTGTTCCG | ACCCTGCCGC | TTACCGGATA | CCTGTCCGCC | TTTCTCCCTT | CGGGAAGCGT |
| 4201 | GGCGCTTTCT | CATAGCTCAC | GCTGTAGGTA | TCTCAGTTCG | GTGTAGGTCG | TTCGCTCCAA |
| 4261 | GCTGGGCTGT | GTGCACGAAC | CCCCCGTTCA | GCCCGACCGC | TGCGCCTTAT | CCGGTAACTA |
| 4321 | TCGTCTTGAG | TCCAACCCGG | TAAGACACGA | CTTATCGCCA | CTGGCAGCAG | CCACTGGTAA |
| 4381 | CAGGATTAGC | AGAGCGAGGT | ATGTAGGCGG | TGCTACAGAG | TTCTTGAAGT | GGTGGCCTAA |
| 4441 | CTACGGCTAC | ACTAGAAGAA | CAGTATTTGG | TATCTGCGCT | CTGCTGAAGC | CAGTTACCTT |
| 4501 | CGGAAAAAGA | GTTGGTAGCT | CTTGATCCGG | CAAACAAACC | ACCGCTGGTA | GCGGTGGTTT |
| 4561 | TTTTGTTTGC | AAGCAGCAGA | TTACGCGCAG | AAAAAAAGGA | TCTCAAGAAG | ATCCTTTGAT |
| 4621 | CTTTTCTACG | GGGTCTGACG | CTCAGTGGAA | CGAAAACTCA | CGTTAAGGGA | TTTTGGTCAT |
| 4681 | GAGATTATCA | AAAAGGATCT | TCACCTAGAT | CCTTTTAAAT | TAAAAATGAA | GTTTTAAATC |

Fig.11A

```
4741   AATCTAAAGT ATATATGAGT AAACTTGGTC TGACAGTTAC CAATGCTTAA TCAGTGAGGC
4801   ACCTATCTCA GCGATCTGTC TATTTCGTTC ATCCATAGTT GCCTGACTCC CCGTCGTGTA
4861   GATAACTACG ATACGGGAGG GCTTACCATC TGGCCCCAGT GCTGCAATGA TACCGCGAGA
4921   CCCACGCTCA CCGGCTCCAG ATTTATCAGC AATAAACCAG CCAGCCGGAA GGGCCGAGCG

4981   CAGAAGTGGT CCTGCAACTT TATCCGCCTC CATCCAGTCT ATTAATTGTT GCCGGGAAGC
5041   TAGAGTAAGT AGTTCGCCAG TTAATAGTTT GCGCAACGTT GTTGCCATTG CTACAGGCAT
5101   CGTGGTGTCA CGCTCGTCGT TTGGTATGGC TTCATTCAGC TCCGGTTCCC AACGATCAAG
5161   GCGAGTTACA TGATCCCCCA TGTTGTGCAA AAAAGCGGTT AGCTCCTTCG GTCCTCCGAT
5221   CGTTGTCAGA AGTAAGTTGG CCGCAGTGTT ATCACTCATG GTTATGGCAG CACTGCATAA
5281   TTCTCTTACT GTCATGCCAT CCGTAAGATG CTTTTCTGTG ACTGGTGAGT ACTCAACCAA
5341   GTCATTCTGA GAATAGTGTA TGCGGCGACC GAGTTGCTCT TGCCCGGCGT CAATACGGGA
5401   TAATACCGCG CCACATAGCA GAACTTTAAA AGTGCTCATC ATTGGAAAAC GTTCTTCGGG
5461   GCGAAAACTC TCAAGGATCT TACCGCTGTT GAGATCCAGT TCGATGTAAC CCACTCGTGC
5521   ACCCAACTGA TCTTCAGCAT CTTTTACTTT CACCAGCGTT TCTGGGTGAG CAAAAACAGG
5581   AAGGCAAAAT GCCGCAAAAA AGGGAATAAG GGCGACACGG AAATGTTGAA TACTCATACT
5641   CTTCCTTTTT CAATATTATT GAAGCATTTA TCAGGGTTAT TGTCTCATGA GCGGATACAT
5701   ATTTGAATGT ATTTAGAAAA ATAAACAAAT AGGGGTTCCG CGCACATTTC CCCGAAAAGT
5761   GCCACCTGAC GTCTAAGAAA CCATTATTAT CATGACATTA ACCTATAAAA ATAGGCGTAT
5821   CACGAGGCCC TTTCGTCTCG CGCGTTTCGG TGATGACGGT GAAAACCTCT GACACATGCA
5881   GCTCCCGGAG ACGGTCACAG CTTGTCTGTA AGCGGATGCC GGGAGCAGAC AAGCCCGTCA
5941   GGGCGCGTCA GCGGGTGTTG GCGGGTGTCG GGGCTGGCTT AATATGCGGC ATCAGAGCAG
6001   ATTGTACTGA GAGTGCACCA TATGCGGTGT GAAATACCGC ACAGATGCGT AAGGAGAAAA
6061   TACCGCATCA GGCGCCATTC GCCATTCAGG CTGCGCAACT GTTGGGAAGG GCGATCGGTG
6121   CGGGCCTCTT CGCTATTACG CCAGCTGGCG AAAGGGGGAT GTGCTGCAAG GCGATTAAGT
6181   TGGGTAACGC CAGGGTTTTC CCAGTCACGA CGTTGTAAAA CGACGGCCAG TGAATTAGTA
6241   CTC
```

LTR

MPSV leader
MPSV LTR
MPSV LTR
MCS
Amp resistance gene

Fig. 11B

T CELL RECEPTORS DIRECTED AGAINST BOB1 AND USES THEREOF

RELATED APPLICATIONS

Priority is claimed to U.S. Provisional Patent Application Ser. No. 62/074,534, filed Nov. 3, 2014, entitled "T Cell Receptors Directed Against Bob1 and Uses Thereof," naming Mirjam H. M. Heemskerk as an inventor, and to U.S. Provisional Patent Application Ser. No. 62/115,737, filed Feb. 13, 2015, entitled "T Cell Receptors Directed Against Bob1 and Uses Thereof," naming Mirjam H. M. Heemskerk as an inventor, which are all referred to and incorporated by reference thereof, in their entireties.

SEQUENCE LISTING

The instant application contains a Sequence Listing which has been submitted electronically in ASCII format and is hereby incorporated by reference in its entirety. Said ASCII copy, created on Dec. 18, 2015, is named BEL-2018-UT_SL.txt and is 141,686 bytes in size.

FIELD

The technology relates in part to compositions and methods for inducing an immune response against a Bob1 antigen. Provided are methods for treating hyperproliferative diseases by inducing an immune response against a Bob1 antigen; the immune response may be induced using a Bob1 polypeptide fragment, or by specifically targeting Bob1-expressing cells using T cell receptors directed against Bob1.

BACKGROUND

T cell activation is an important step in the protective immunity against pathogenic microorganisms (e.g., viruses, bacteria, and parasites), foreign proteins, and harmful chemicals in the environment, and also as immunity against cancer and other hyperproliferative diseases. T cells express receptors on their surfaces (i.e., T cell receptors) that recognize antigens presented on the surface of cells. During a normal immune response, binding of these antigens to the T cell receptor, in the context of MHC antigen presentation, initiates intracellular changes leading to T cell activation.

Adoptive T cell therapy has been used to treat hyperproliferative diseases, including tumors, by providing an antigen-specific immune response. One method involves the use of genetically modified T cells that express an antigen-specific protein having an extracellular domain that binds to an antigen.

SUMMARY

The intracellular transcription factor B cell Oct binding protein 1 (Bob1) encoded by gene POU2AF1 was identified as a suitable target for TCR-based immunotherapies of B cell malignancies and multiple myeloma. The Bob1 polypeptides may be used as immunogens, or targets for immunotherapy. Bob1 specific T cell clones were identified that recognized primary B cell malignancies and multiple myeloma. TCR gene transfer approaches using Bob1-specific TCRs can bring novel treatment modalities for patients with B cell malignancies or multiple myeloma, among other diseases Provided herein are compositions and methods comprising T cell receptors, nucleic acids coding for T cell receptors, and cells expressing T cell receptors that recognize a Bob1 antigen. The cells may also express an additional polypeptide adding a safety mechanism, such as, for example, an inducible Caspase-9 polypeptide.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 7 A is a bar graph.

FIG. 8A provides a schematic including an amino acid sequence of the POU2AF1/Bob1 clone 3C10 AV13-1*01 TCRα polypeptide (SEQ ID NOS 37 and 37, respectively, in order of appearance). FIG. 8B provides a schematic including an amino acid sequence of the POU2AF1/Bob1 clone 3C10 BV12-4*01 TCRβ polypeptide (SEQ ID NOS 43 and 43, respectively, in order of appearance).

FIG. 9A provides a schematic including an amino acid sequences of POU2AF1/Bob1 clone 4G11 TRAV13-1*01 TCRα polypeptide (SEQ ID NOS 141 and 141, respectively, in order of appearance). FIG. 9B provides a schematic including an amino acid sequences of POU2AF1/Bob1 clone 4G11 TRBV4-1*-1 TCRβ polypeptide (SEQ ID NOS 142 and 142, respectively, in order of appearance).

FIGS. 11A and 11B provide the sequence of an example of a retroviral vector that may be used to express Bob1-TCR (SEQ ID NO: 49).

DETAILED DESCRIPTION

Figure 1A:
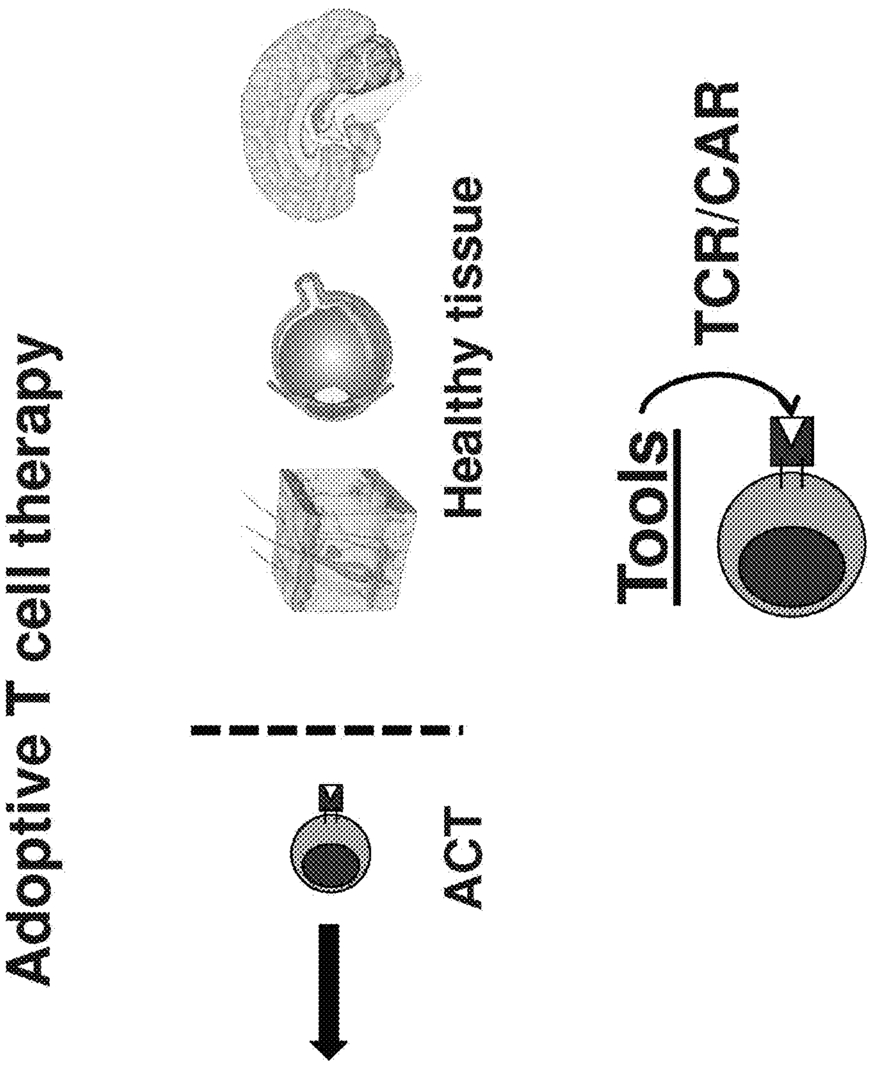
FIG. 1A provides a schematic of adoptive T cell therapy, FIG. 1B provides a schematic of a graph of an example of adoptive T cell therapy directed against a tumor.
Figure 1B:
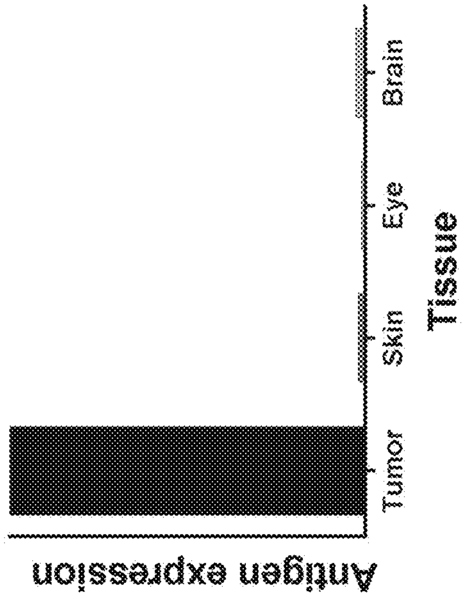

Adoptive T cell therapy has been used to treat hyperproliferative diseases, including tumors, by providing an antigen-specific immune response. One method involves the use of genetically modified T cells that express an antigen-specific protein having an extracellular domain that binds to an antigen. Recombinant T cell receptors have been used to provide specificity to T cells. In other methods, heterologous T cell receptors, specific for a particular antigen, have been expressed in T cells to provide an antigen-specific immune response. Methods of adoptive T cell therapy are provided as a schematic in FIG. 1.

Methods of adoptive T cell therapy have often targeted extracellular antigens. For example, CD19, an extracellular antigen on the surface of B cell malignancies, has been a target for T cell therapy. This adoptive T cell therapy often provided using a CD19-specific antigen receptor-transduced T cell may not be as effective when the B cell malignancy loses expression of the CD19 antigen. Thus, where, for example, T cells are engineered to recognize CD20, or CD19, the loss of CD20 and CD19 expression or absence of these molecules on other malignancies such as multiple myeloma restricts their application.

An intracellular transcription factor Bob1, encoded by gene POU2AF1, is now found to be a suitable target for immunotherapy. Bob1 is highly expressed in $CD19^+$ B cells, acute lymphoblastic leukemia (ALL), chronic lymphocytic leukemia (CLL), mantle cell lymphoma (MCL), follicular lymphoma, large B cell lymphoma, and multiple myeloma (MM) and is absent in the non-B lineages including $CD34^+$ hematopoietic progenitor cells (H PCs), T cells, fibroblasts, keratinocytes and gastrointestinal tract.

Figure 2:
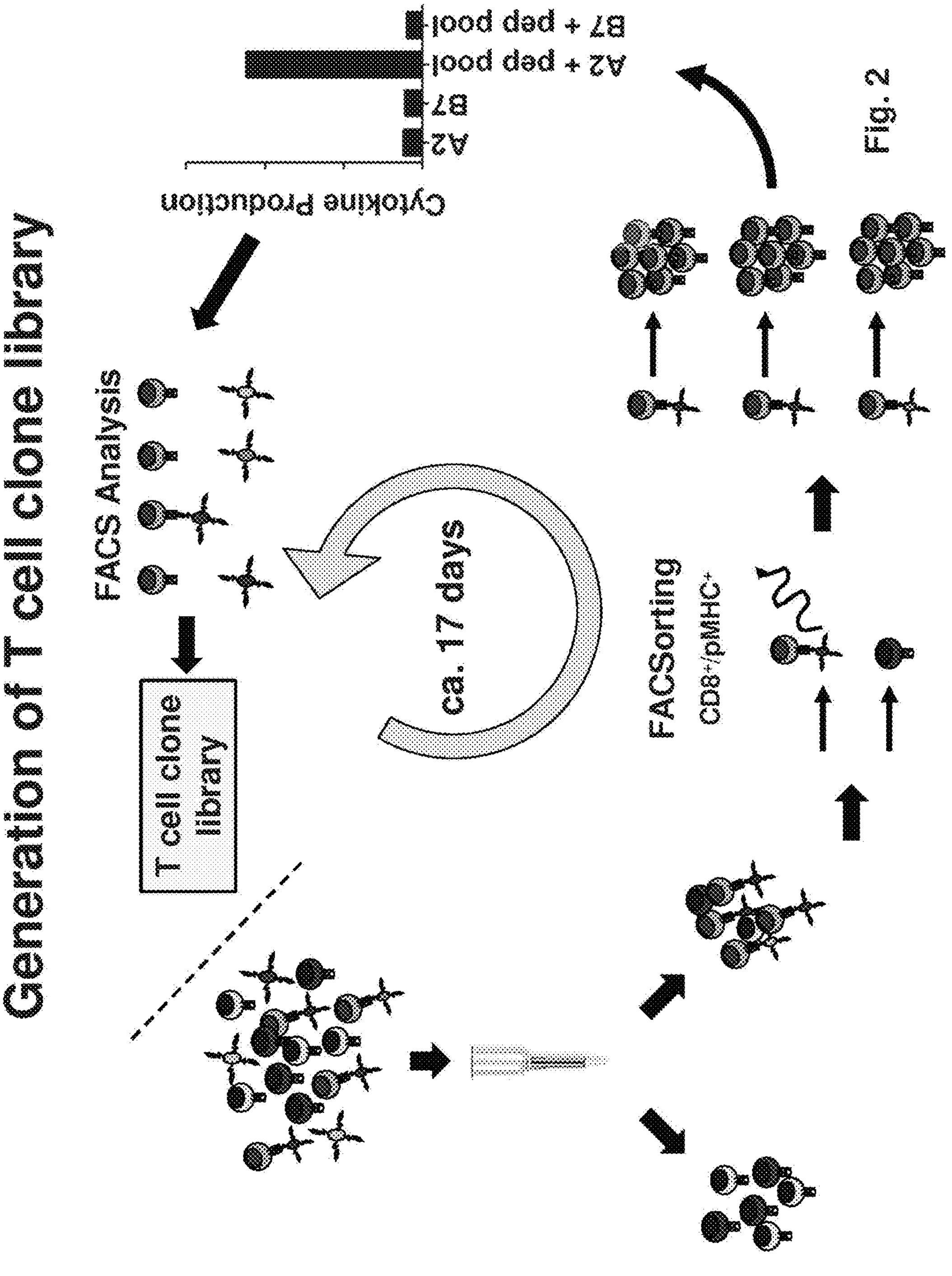
FIG. 2 provides a schematic illustrating and example of a method used to generate a T cell clone library.

Bob1 is localized intracellularly, but HLA-presented Bob1-derived polypeptides are accessible on the cell surface to T cell receptors (TCRs) and can thus be recognized by T cells. From the HLA-presented ligandome (Mol Cell Proteomics, 2013; 12:1829) naturally processed Bob1-derived polypeptides have been identified that are displayed in HLA-A*0201 (HLA-A2), HLA-B*0702 (HLA-B7), and other HLA class I molecules (Tables 1 and 2). Since autoreactivity toward self-antigens such as Bob1 is prevented by depleting high-avidity T cells recognizing self-antigens in self-HLA, the immunogenicity of these polypeptides presented in allogeneic HLA was exploited. From a total of $3\times10^9$ peripheral blood mononuclear cells from 6 different HLA-A2/B7-negative healthy donors, more than 1000 $CD8^+$ T cells binding to polypeptide-MHC-tetramers composed of the Bob1-derived polypeptides bound to HLA-A2 or HLA-B7 were isolated and clonally expanded. (FIG. 2) The T cell clones were tested for stringent polypeptide-specificity by stimulation with Bob1-negative K562 cells expressing either HLA-A2 or B7 unloaded or pulsed with Bob1-derived polypeptides. This resulted in the selection of 15 T cell clones highly specific for Bob1. To identify the T cell clones of highest avidity, T cell clones were compared for polypeptide-sensitivity by testing the recognition of stimulator cells loaded with titrated amounts of Bob1-derived polypeptides and of Bob1-expressing HLA-A2/B7-positive EBV-transformed B cells.

T cell clone 4G11 was selected because of high sensitivity and specificity for Bob1-derived polypeptide Bob144 presented in HLA-B7 and T cell clone 3C10 specifically recognized polypeptide Bob1245 bound to HLA-A2. Bob1-dependent recognition was demonstrated by transduction of Bob1 into cell lines that otherwise lack Bob1 expression. To investigate whether harmful toxicities could be caused by these T cell clones, their reactivity was tested against a wide panel of Bob1-negative stimulator cells demonstrating absence of recognition of HLA-B7-positive $CD34^+$ HPCs, T cells, monocytes, immature and mature dendritic cells, and fibroblasts even under simulated inflamed conditions. Stringent HLA-B7-restricted recognition was observed for clone 4G11 when tested against a stimulator panel expressing a wide range of common and rare HLA class I and II molecules. These data illustrate a safe reactivity profile with little chance of off-target toxicity. To test their clinical applicability, clone 4G11 and 3C10 were tested for recognition of various primary B cell malignancies. Clone 4G11 efficiently recognized HLA-B7-positive primary ALL, CLL and mantle cell lymphoma while clone 3C10 recognized HLA-A2-positive primary B cell malignancies albeit to a lesser degree. Furthermore, reproducible strong recognition of purified primary HLA-B7-positive multiple myeloma could be demonstrated for clone 4G11. Therefore, T cell clone 4G11's TCR may be used for immunotherapy by administering TCR-transduced T cells to multiple myeloma patients. To test whether introduction of 4G11's TCR confers Bob1-reactivity onto recipient cells; the TCR was cloned into a retroviral vector. Highly specific reactivity against HLA-B7-positive Bob1-expressing target cells could be installed to TCR-transduced recipient T cells.

In summary, the intracellular transcription factor Bob1 encoded by gene POU2AF1 was identified as a suitable target for TCR-based immunotherapies of B cell malignancies and multiple myeloma. Bob1-specific T cell clone 4G11 efficiently recognized primary B cell leukemia and multiple myeloma. TCR gene transfer approaches using Bob1-specific TCRs can bring novel treatment modalities for patients with B cell malignancies or multiple myeloma.

Thus provided in some embodiments is a nucleic acid molecule comprising a promoter operatively linked to a polynucleotide that encodes the CDR3 region of a T cell receptor that specifically binds to Bob1, comprising a first polynucleotide that encodes a first polypeptide comprising the CDR3 region of a TCR$\alpha$ polypeptide; and a second polynucleotide that encodes a second polypeptide comprising the CDR3 region of a TCR$\beta$ polypeptide, wherein the CDR3 region of the TCR$\alpha$ polypeptide and TCR $\beta$ polypeptide together specifically bind to Bob1. In some embodiments, the CDR3 region of the T cell receptor specifically binds to a Bob1 polypeptide comprising the amino acid sequence APAPTAVVL (SEQ ID NO: 118) or the amino acid sequence YALNHTLSV (SEQ ID NO: 119). In some embodiments, the first polypeptide comprises the amino acid sequence of SEQ ID NO: 1, or SEQ ID NO: 25 and the second polypeptide comprises the amino acid sequence of SEQ ID NO: 4 or SEQ ID NO: 28. In some embodiments, the first polynucleotide comprises the nucleotide sequence of SEQ ID NO: 2 or SEQ ID NO: 3, or a derivative thereof and the second polynucleotide comprises the nucleotide sequence of SEQ ID NO: 5 or SEQ ID NO: 6, or a derivative thereof; or the first polynucleotide comprises the nucleotide sequence of SEQ ID NO: 26 or SEQ ID NO: 27, or a derivative thereof and the second polynucleotide comprises the nucleotide sequence of SEQ ID NO: 29 or SEQ ID NO: 30, or a derivative thereof.

In some embodiments, the nucleic acid molecule comprising the polynucleotide that encodes the CDR3 region of the T cell receptor that specifically binds to Bob1 comprises a first polynucleotide encodes a first polypeptide comprising the VJ regions of a TCRα polypeptide; and a second polynucleotide encodes a second polypeptide comprising the VDJ regions of a TCRβ polypeptide. In some embodiments, the first polypeptide further comprises the constant region of the TCRα polypeptide and the second polypeptide further comprises the constant region of the TCRβ polypeptide. In some embodiments, the nucleic acid molecule encodes a T cell receptor. In some embodiments, the CDR3 region of the T cell receptor specifically binds to a Bob1 polypeptide comprising the amino acid sequence APAPTAVVL (SEQ ID NO: 118). In some embodiments, the constant region of the first or second polypeptide is a heterologous constant region. In some embodiments, the constant regions of the first and second polypeptides are derived from murine TCR constant regions. In some embodiments, the first polypeptide comprises the amino acid sequence of SEQ ID NO: 1. In some embodiments, the first polynucleotide comprises the nucleotide sequence of SEQ ID NO: 2 or SEQ ID NO: 3, or a derivative thereof. In some embodiments, wherein the second polypeptide comprises the amino acid sequence of SEQ ID NO: 4. In some embodiments, the second polynucleotide comprises the nucleotide sequence of SEQ ID NO: 5 or SEQ ID NO: 6, or a derivative thereof. In some embodiments, the first polypeptide comprises the amino acid sequence of SEQ ID NO: 7. In some embodiments, the first polynucleotide comprises the nucleotide sequence of SEQ ID NO: 8 or SEQ ID NO: 9, or a derivative thereof. In some embodiments, the second polypeptide comprises the amino acid sequence of SEQ ID NO: 10. In some embodiments, the second polynucleotide comprises the nucleotide sequence of SEQ ID NO: 11 or SEQ ID NO: 12, or a derivative thereof. In some embodiments, the first polypeptide comprises the amino acid sequence of SEQ ID NOs: 13 or 14. In some embodiments, the first polynucleotide comprises the nucleotide sequence of SEQ ID NOs: 15, 16, or 18. In some embodiments, wherein the second polypeptide comprises the amino acid sequence of SEQ ID NOs: 19 or 20. In some embodiments, the second polynucleotide comprises the nucleotide sequence of SEQ ID NOs: 21, 22, or 24.

In some embodiments, the CDR3 region of the T cell receptor specifically binds to a Bob1 polypeptide comprising the amino acid sequence YALNHTLSV (SEQ ID NO: 119). In some embodiments, the first polypeptide comprises the amino acid sequence of SEQ ID NO: 25. In some embodiments, the first polynucleotide comprises the nucleotide sequence of SEQ ID NO: 26 or SEQ ID NO: 27, or a derivative thereof. In some embodiments, the second polypeptide comprises the amino acid sequence of SEQ ID NO: 28. In some embodiments, the second polynucleotide comprises the nucleotide sequence of SEQ ID NO: 29 or SEQ ID NO: 30, or a derivative thereof. In some embodiments, the first polypeptide comprises the amino acid sequence of SEQ ID NO: 31. In some embodiments, the first polynucleotide comprises the nucleotide sequence of SEQ ID NO: 32 or SEQ ID NO: 33, or a derivative thereof. In some embodiments, the second polypeptide comprises the amino acid sequence of SEQ ID NO: 34. In some embodiments, the second polynucleotide comprises the nucleotide sequence of SEQ ID NO: 35 or SEQ ID NO: 36, or a derivative thereof. In some embodiments, the first polypeptide comprises the amino acid sequence of SEQ ID NOs: 37 or 38. In some embodiments, the first polynucleotide comprises the nucleotide sequence of SEQ ID NOs: 39, 40, 41, or 42. In some embodiments, the second polypeptide comprises the amino acid sequence of SEQ ID NOs: 43 or 44. In some embodiments, the second polynucleotide comprises the nucleotide sequence of SEQ ID NOs: 45, 46, 47, or 48.

In some embodiments, the nucleic acid molecule further comprises a polynucleotide encoding a chimeric Caspase-9 polypeptide comprising a multimeric ligand binding region and a Caspase-9 polypeptide. In some embodiments, a plasmid or viral vector comprising the nucleic acid molecule is provided.

In some embodiments, a modified cell transfected or transduced with the nucleic acid molecule, the plasmid, or the viral vector, is provided. In some embodiments, the cell further comprises a nucleic acid molecule comprising a polynucleotide encoding a chimeric Caspase-9 polypeptide comprising a multimeric ligand binding region and a Caspase-9 polypeptide. Also provided are pharmaceutical compositions comprising the modified cell and a pharmaceutically acceptable carrier. Also provided are pharmaceutical compositions comprising the nucleic acid and a pharmaceutically acceptable carrier. In some embodiments, methods are provided of enhancing an immune response in a subject diagnosed with a hyperproliferative disease or condition, comprising administering a therapeutically effective amount of the modified cells to the subject. In some embodiments, methods are provided for stimulating a cell mediated immune response to a target cell population or tissue in a subject, comprising administering the modified cells to the subject. In some embodiments, wherein the number or concentration of target cells in the subject is reduced following administration of the modified cell. In some embodiments, the modified cell comprises a nucleic acid comprising a polynucleotide encoding a chimeric Caspase-9 polypeptide comprising a multimeric ligand binding region and a Caspase-9 polypeptide. In some embodiments, the method further comprises administering a multimeric ligand that binds to the multimeric ligand binding region to the subject following administration of the modified cells to the subject. In some embodiments, after administration of the multimeric ligand, the number or concentration of modified cells comprising the chimeric Caspase-9 polypeptide is reduced in a sample obtained from the subject after administering the multimeric ligand compared to the number or concentration of modified cells comprising the chimeric Caspase-9 polypeptide in a sample obtained from the subject before administering the multimeric ligand.

Also provided are methods for expressing a T cell receptor that specifically binds to Bob1 in a cell, comprising contacting the nucleic acid of with a cell under conditions in which the nucleic acid is incorporated into the cell, whereby the cell expresses the T cell receptor from the incorporated nucleic acid.

Also provided are immunogenic peptide epitopes of Bob1. In some embodiments, the immunogenic peptide epitope comprises a polypeptide selected from the group consisting of the Bob1 polypeptides of Table 1. In some embodiments, the immunogenic peptide epitope comprises a polypeptide having the amino acid sequence APAPTAVVL (SEQ ID NO: 118) or having the amino acid sequence YALNHTLS (SEQ ID NO: 120). In some embodiments, a modified cell is provided that is transduced or transfected with a nucleic acid comprising a polynucleotide coding for the immunogenic peptide epitope. Also provided are methods for expressing a Bob1 immunogenic peptide epitope in a cell, comprising contacting the nucleic acid of with a cell under conditions in which the nucleic acid is incorporated into the cell, whereby the cell expresses Bob1 immunogenic epitope from the incorporated nucleic acid.

In some embodiments, a method is provided of enhancing an immune response in a subject diagnosed with a hyperproliferative disease or condition, comprising administering a therapeutically effective amount of the immunogenic peptide epitope to the subject. In some embodiments, a method is provided for stimulating a cell mediated immune response to a target cell population or tissue in a subject, comprising administering a therapeutically effective amount of the immunogenic peptide epitope to the subject. In some embodiments, a method is provided for providing anti-tumor immunity to a subject, comprising administering to the subject an effective amount of the immunogenic peptide epitope to the subject.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct between the host and donor cells.

Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorferi, Plasmodium*, herpes simplex viruses, human immunodeficiency virus, papillomavirus, *Vibrio cholera, E. coli*, measles virus, rotavirus, *shigella, Salmonella typhi, Neisseria* gonorrhea. Therefore, any macromolecules, including virtually all proteins or peptides, can serve as antigens. Furthermore, antigens can be derived from recombinant or genomic DNA. Any DNA that contains nucleotide sequences or partial nucleotide sequences of a pathogenic genome or a gene or a fragment of a gene for a protein that elicits an immune response results in synthesis of an antigen. Furthermore, the present methods are not limited to the use of the entire nucleic acid sequence of a gene or genome. The present compositions and methods include, but are not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "cell" can be any cell that accomplishes the goal of aiding the enhancement of an immune response (i.e., from the T-cell or -B-cell arms of the immune system) against an antigen or antigenic composition. As discussed in Kuby, 2000, Immunology, supp. 4th edition, W.H. Freeman and company, for example, (incorporated herein by reference), and used herein in certain embodiments, a cell that displays or presents an antigen normally or with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fusion of two or more cells are discussed in, for example, Goding, J. W., Monoclonal Antibodies: Principles and Practice, pp. 65-66, 71-74 (Academic Press, 1986); Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Kohler & Milstein, Nature, 256:495-497, 1975; Kohler & Milstein, Eur. J. Immunol., 6:511-519, 1976, Gefter et al., Somatic Cell Genet., 3:231-236, 1977, each incorporated herein by reference. In some cases, the immune cell to which a cell displays or presents an antigen to is a $CD4^+$ TH cell. Additional molecules expressed on the APC or other immune cells may aid or improve the enhancement of an immune response. Secreted or soluble molecules, such as for example, cytokines and adjuvants, may also aid or enhance the immune response against an antigen. Various examples are discussed herein.

An "antigen recognition moiety" may be any polypeptide or fragment thereof, such as, for example, an antibody fragment variable domain, either naturally derived, or synthetic, which binds to an antigen. Examples of antigen recognition moieties include, but are not limited to, polypeptides derived from antibodies, such as, for example, single chain variable fragments (scFv), Fab, Fab', $F(ab')_2$, and Fv fragments; polypeptides derived from T Cell receptors, such as, for example, TCR variable domains; secreted factors (e.g., cytokines, growth factors) that can be artificially fused to signaling domains (e.g., "zytokines"), and any ligand or receptor fragment (e.g., CD27, NKG2D) that binds to the extracellular cognate protein. Combinatorial libraries could also be used to identify peptides binding with high affinity to tumor-associated targets.

The term "autologous" means a cell, nucleic acid, protein, polypeptide, or the like derived from the same individual to which it is later administered. The modified cells of the present methods may, for example, be autologous cells, such as, for example, autologous T cells.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "cDNA" is intended to refer to DNA prepared using messenger RNA (mRNA) as template. The advantage of using a cDNA, as opposed to genomic DNA or DNA polymerized from a genomic, non- or partially processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

As used herein, the term "ex vivo" refers to "outside" the body. The terms "ex vivo" and "in vitro" can be used interchangeably herein.

T cell receptors (TCRs) are immune proteins that specifically bind to antigenic molecules. TCRs are composed of two different polypeptides that are on the surface of T cells. They recognize, or specifically bind to, antigens bound to major histocompatibility complex molecules; upon binding to the antigen, the T cell is activated. TCRs may comprise α and β polypeptides, or chains. The α and β polypeptides include two extracellular domains, the variable and the constant domains. The variable domain of the α and β polypeptides has three complementarity determining regions (CDRs); CDR3 is considered to be the main CDR responsible for recognizing the epitope. The α polypeptide includes the V and J regions, generated by VJ recombination, and the β polypeptide includes the V, D, and J regions, generated by VDJ recombination. The intersection of the VJ regions and VDJ regions corresponds to the CDR3 region. TCRs are often named using the International Immunogenetics (IMGT) TCR nomenclature (IMGT Database, www.IMGT.org; Giudicelli, V., et al., IMGT/LIGM-DB, the IMGT® comprehensive database of immunoglobulin and T cell receptor nucleotide sequences, Nucl. Acids Res., 34, D781-D784 (2006). PMID: 16381979; T Cell Receptor Factsbook, LeFranc and LeFranc, Academic Press ISBN 0-12-441352-8).

By "specifically bind(s) to" as it relates to a T cell receptor, or as it refers to a recombinant T cell receptor, nucleic acid fragment, variant, or analog, or a modified cell, such as, for example, the Bob1 T cell receptors, and Bob1-expressing modified cells herein, is meant that the T cell receptor, or fragment thereof, recognizes, or binds selectively to the Bob1 antigen. Under certain conditions, for example, in an immunoassay, for example an immunoassay discussed herein, the T cell receptor binds to Bob1 and does not bind in a significant amount to other polypeptides. Thus the T cell receptor binds to Bob 1 with at least 5, 10, 20, 30, 40, 50, or 100 fold more affinity than to a control antigenic polypeptide. This binding may also be determined indirectly in the context of a modified T cell that expresses a Bob1 TCR. In assays such as, for example, an assay discussed herein, the modified T cell is specifically reactive against a multiple myeloma cell line and at least one malignant B cell lines such as, for example, ALL, CLL and mantle cell lymphoma cell lines. Thus, the modified Bob1-expressing T cell binds to a multiple myeloma cell line or a malignant B cell line with at least 5, 10, 20, 30, 40, 50, or 100 fold more reactivity when compared to its reactivity against a control cell line that is not a multiple myeloma cell line or a malignant B cell line.

As used herein, the term "functionally equivalent," as it relates to a T cell receptor, for example, or as it refers to a T cell receptor nucleic acid fragment, variant, or analog, refers to a nucleic acid that codes for a T cell receptor or T cell receptor polypeptide, that stimulates an immune response against an antigen or cell. "Functionally equivalent" or "a functional fragment" of a T cell receptor polypeptide refers, for example, to a T cell receptor that is lacking a T cell receptor domain, such as a constant region, but is capable of stimulating an immune response typical for a T cell. A functionally equivalent T cell receptor fragment, may, for example, specifically bind to, or recognize an antigen, and upon recognition, activate the T lymphocyte. When the term "functionally equivalent" is applied to other nucleic acids or polypeptides, such as, for example, Caspase-9 or truncated Caspase-9, it refers to fragments, variants, and the like that have the same or similar activity as the reference polypeptides of the methods herein. For example, a functional fragment of a tumor antigen polypeptide, such as, for example, PSMA may be antigenic, allowing for antibodies to be produced that recognize the particular tumor antigen. A functional fragment of a ligand binding region, for example, Fvls, would include a sufficient portion of the ligand binding region polypeptide to bind the appropriate ligand. "Functionally equivalent" refers, for example, to a co-stimulatory polypeptide that is lacking the extracellular domain, but is capable of amplifying the T cell-mediated tumor killing response when expressed in T cells.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term “immunocompromised” as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body’s defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term “pharmaceutically or pharmacologically acceptable” refers to molecular entities and compositions that do not produce adverse, allergic, or other untoward reactions when administered to an animal or a human.

As used herein, “pharmaceutically acceptable carrier” includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions. In some embodiments, the subject is a mammal. In some embodiments, the subject is a human.

As used herein, the term “polynucleotide” is defined as a chain of nucleotides. Furthermore, nucleic acids are polymers of nucleotides. Thus, nucleic acids and polynucleotides as used herein are interchangeable. Nucleic acids are polynucleotides, which can be hydrolyzed into the monomeric “nucleotides.” The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR", and the like, and by synthetic means. Furthermore, polynucleotides include mutations of the polynucleotides, include but are not limited to, mutation of the nucleotides, or nucleosides by methods well known in the art. A nucleic acid may comprise one or more polynucleotides.

As used herein, the term “polypeptide” is defined as a chain of amino acid residues, usually having a defined sequence. As used herein the term polypeptide may be interchangeable with the term “proteins”.

As used herein, the term “promoter” is defined as a DNA sequence recognized by the synthetic machinery of the cell, or introduced synthetic machinery, required to initiate the specific transcription of a gene.

As used herein, the terms “regulate an immune response,” “modulate an immune response,” or “control an immune response,” refer to the ability to modify the immune response. For example, the composition is capable of enhancing and/or activating the immune response. Still further, the composition is also capable of inhibiting the immune response. The form of regulation is determined by the ligand that is used with the composition. For example, a dimeric analog of the chemical results in dimerization of the co-stimulating polypeptide leading to activation of the T cell, however, a monomeric analog of the chemical does not result in dimerization of the co-stimulating polypeptide, which would not activate the T cells.

The term “transfection” and “transduction” are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term “syngeneic” refers to cells, tissues or animals that have genotypes that are identical or closely related enough to allow tissue transplant, or are immunologically compatible. For example, identical twins or animals of the same inbred strain. Syngeneic and isogeneic can be used interchangeably.

The term “patient” or “subject” are interchangeable, and, as used herein include, but are not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term “vaccine” refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

As used herein, the term “under transcriptional control” or “operatively linked” is defined as the promoter is in the correct location and orientation in relation to the nucleic acid to control RNA polymerase initiation and expression of the gene.

As used herein, the terms “treatment”, “treat”, “treated”, or “treating” refer to prophylaxis and/or therapy. When used with respect to a solid tumor, such as a cancerous solid tumor, for example, the term refers to prevention by prophylactic treatment, which increases the subject’s resistance to solid tumors or cancer. In some examples, the subject may be treated to prevent cancer, where the cancer is familial, or is genetically associated. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, for example, reduce or eliminate the infection or prevent it from becoming worse.

The methods provided herein may be used, for example, to treat a disease, disorder, or condition wherein there is an elevated expression of a tumor antigen.

As used herein, the term “vaccine” refers to a formulation which contains a composition presented herein which is in a form that is capable of being administered to an animal.

Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

Blood disease: The terms “blood disease”, “blood disease” and/or “diseases of the blood” as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

Bone marrow disease: The term “bone marrow disease” as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnocytopenia, anemia, multiple myeloma and the like.

T cells and Activated T cells: $CD3^+$ T cells (also referred to as T lymphocytes) belong to a group of white blood cells referred to as lymphocytes. Lymphocytes generally are involved in cell-mediated immunity. The “T” in “T cells” refers to cells derived from or whose maturation is influenced by the thymus. T cells can be distinguished from other lymphocytes types such as B cells and Natural Killer (NK) cells by the presence of cell surface proteins known as T cell receptors. The term “activated T cells” as used herein, refers to T cells that have been stimulated to produce an immune response (e.g., clonal expansion of activated T cells) by recognition of an antigenic determinant presented in the context of a Class I and II major histo-compatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be “positive” for expression of that protein on the surface of T-cells (e.g., cells positive for CD3 or CD4 expression are referred to as $CD3^+$ or $CD4^+$). CD3, CD4, and CD8 proteins are cell surface receptors or co-receptors that may be directly and/or indirectly involved in signal transduction in T cells.

Peripheral blood: The term “peripheral blood” as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms “umbilical cord blood”, “umbilical blood” or “cord blood”, which can be used interchangeably, refers to blood that remains in the placenta and in the attached umbilical cord after child birth. Cord blood often contains stem cells including hematopoietic cells.

By “obtained or prepared” as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

By “kill” or “killing” as in a percent of cells killed, is meant the death of a cell through apoptosis, as measured using any method known for measuring apoptosis. The term may also refer to cell ablation.

Donor T cell: The term “donor T cell” as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GvHD). Certain activated donor T cells can cause a higher or lower GvHD response than other activated T cells. Donor T cells may also be reactive against recipient tumor cells, causing a beneficial graft vs. tumor effect.

Function-conservative variants are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, “sequence similarity” means the extent to which nucleotide or protein sequences are related. The extent of similarity between two sequences can be based on percent sequence identity and/or conservation. “Sequence identity” herein means the extent to which two nucleotide or amino acid sequences are invariant. “Sequence alignment” means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the preferred settings are those that results in the highest sequence similarity.

Mesenchymal stromal cell: The terms “mesenchymal stromal cell” or “bone marrow derived mesenchymal stromal cell” as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

Embryonic stem cell: The term “embryonic stem cell” as used herein, refers to pluripotent stem cells derived from the inner cell mass of the blastocyst, an early stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from multipotent in that pluripotent cells can generate all cell types, while multipotent cells (e.g., adult stem cells) can only produce a limited number of cell types.

Inducible pluripotent stem cell: The terms “inducible pluripotent stem cell” or “induced pluripotent stem cell” as used herein refers to adult, or differentiated cells, that are “reprogrammed” or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells.

$CD34^+$ cell: The term “$CD34^+$ cell” as used herein refers to a cell expressing the CD34 protein on its cell surface. “CD34” as used herein refers to a cell surface glycoprotein (e.g., sialomucin protein) that often acts as a cell-cell adhesion factor and is involved in T cell entrance into lymph nodes, and is a member of the “cluster of differentiation” gene family. CD34 also may mediate the attachment of stem cells to bone marrow, extracellular matrix or directly to stromal cells. $CD34^+$ cells often are found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population of dendritic cells (which are factor XIIIa negative) in the interstitium and around the adnexa of dermis of skin, as well as cells in certain soft tissue tumors (e.g., alveolar soft part sarcoma, pre-B acute lymphoblastic leukemia (Pre-B-ALL), acute myelogenous leukemia (AML), AML-M7, dermatofibrosarcoma protuberans, gastrointestinal stromal tumors, giant cell fibroblastoma, granulocytic sarcoma, Kaposi’s sarcoma, liposarcoma, malignant fibrous histiocytoma, malignant peripheral nerve sheath tumors, mengingeal hemangiopericytomas, meningiomas, neurofibromas, schwannomas, and papillary thyroid carcinoma).

Tumor infiltrating lymphocytes (TILs) refer to T cells having various receptors which infiltrate tumors and kill tumor cells in a targeted manor. Regulating the activity of the TILs using the methods of the present application would allow for more direct control of the elimination of tumor cells.

Gene expression vector: The terms “gene expression vector”, “nucleic acid expression vector”, or “expression vector” as used herein, which can be used interchangeably throughout the document, generally refers to a nucleic acid molecule (e.g., a plasmid, phage, autonomously replicating sequence (ARS), artificial chromosome, yeast artificial chromosome (e.g., YAC)) that can be replicated in a host cell and be utilized to introduce a gene or genes into a host cell. The genes introduced on the expression vector can be endogenous genes (e.g., a gene normally found in the host cell or organism) or heterologous genes (e.g., genes not normally found in the genome or on extra-chromosomal nucleic acids of the host cell or organism). The genes introduced into a cell by an expression vector can be native genes or genes that have been modified or engineered. The gene expression vector also can be engineered to contain 5' and 3' untranslated regulatory sequences that sometimes can function as enhancer sequences, promoter regions and/or terminator sequences that can facilitate or enhance efficient transcription of the gene or genes carried on the expression vector. A gene expression vector sometimes also is engineered for replication and/or expression functionality (e.g., transcription and translation) in a particular cell type, cell location, or tissue type. Expression vectors sometimes include a selectable marker for maintenance of the vector in the host or recipient cell.

Developmentally regulated promoter: The term “developmentally regulated promoter” as used herein refers to a promoter that acts as the initial binding site for RNA polymerase to transcribe a gene which is expressed under certain conditions that are controlled, initiated by or influenced by a developmental program or pathway. Developmentally regulated promoters often have additional control regions at or near the promoter region for binding activators or repressors of transcription that can influence transcription of a gene that is part of a development program or pathway. Developmentally regulated promoters sometimes are involved in transcribing genes whose gene products influence the developmental differentiation of cells.

Developmentally differentiated cells: The term “developmentally differentiated cells”, as used herein refers to cells that have undergone a process, often involving expression of specific developmentally regulated genes, by which the cell evolves from a less specialized form to a more specialized form in order to perform a specific function. Non-limiting examples of developmentally differentiated cells are liver cells, lung cells, skin cells, nerve cells, blood cells, and the like. Changes in developmental differentiation generally involve changes in gene expression (e.g., changes in patterns of gene expression), genetic re-organization (e.g., remodeling or chromatin to hide or expose genes that will be silenced or expressed, respectively), and occasionally involve changes in DNA sequences (e.g., immune diversity differentiation). Cellular differentiation during development can be understood as the result of a gene regulatory network. A regulatory gene and its cis-regulatory modules are nodes in a gene regulatory network that receive input (e.g., protein expressed upstream in a development pathway or program) and create output elsewhere in the network (e.g., the expressed gene product acts on other genes downstream in the developmental pathway or program).

In some embodiments, the nucleic acid is contained within a viral vector. In certain embodiments, the viral vector is an adenoviral vector, or a retroviral or lentiviral vector. It is understood that in some embodiments, the cell is contacted with the viral vector ex vivo, and in some embodiments, the cell is contacted with the viral vector in vivo.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

The cell in some embodiments is contacted with an antigen, sometimes ex vivo. In certain embodiments the cell is in a subject and an immune response is generated against the antigen, such as a cytotoxic T-lymphocyte (CTL) immune response. In certain embodiments, an immune response is generated against a tumor antigen (e.g., PSMA). In some embodiments, the nucleic acid is prepared ex vivo and administered to the subject by intradermal administration or by subcutaneous administration, for example. Sometimes the cell is transduced or transfected with the nucleic acid ex vivo or in vivo.

In some embodiments, the nucleic acid comprises a promoter sequence operably linked to the polynucleotide sequence. Alternatively, the nucleic acid comprises an ex vivo-transcribed RNA, containing the protein-coding region of the chimeric protein.

By "reducing tumor size" or "inhibiting tumor growth" of a solid tumor is meant a response to treatment, or stabilization of disease, according to standard guidelines, such as, for example, the Response Evaluation Criteria in Solid Tumors (RECIST) criteria. For example, this may include a reduction in the diameter of a solid tumor of about 5%, 10%, 20%, 30%, 40%, 50%, 60%, 70%, 80%, 90%, or 100%, or the reduction in the number of tumors, circulating tumor cells, or tumor markers, of about 5%, 10%, 20%, 30%, 40%, 50%, 60%, 70%, 80%, 90%, or 100%. The size of tumors may be analyzed by any method, including, for example, CT scan, MRI, for example, CT-MRI, chest X-ray (for tumors of the lung), or molecular imaging, for example, PET scan, such as, for example, a PET scan after administering an iodine 123-labelled PSA, for example, PSMA ligand, such as, for example, where the inhibitor is TROFEX™/MIP-1072/1095, or molecular imaging, for example, SPECT, or a PET scan using PSA, for example, PSMA antibody, such as, for example, capromad pendetide (Prostascint), a 111-iridium labeled PSMA antibody.

By "reducing, slowing, or inhibiting tumor vascularization" is meant a reduction in tumor vascularization of about 5%, 10%, 20%, 30%, 40%, 50%, 60%, 70%, 80%, 90%, or 100%, or a reduction in the appearance of new vasculature of about 5%, 10%, 20%, 30%, 40%, 50%, 60%, 70%, 80%, 90%, or 100%, when compared to the amount of tumor vascularization before treatment. The reduction may refer to one tumor, or may be a sum or an average of the vascularization in more than one tumor. Methods of measuring tumor vascularization include, for example, CAT scan, MRI, for example, CT-MRI, or molecular imaging, for example, SPECT, or a PET scan, such as, for example, a PET scan after administering an iodine 123-labelled PSA, for example, PSMA ligand, such as, for example, where the inhibitor is TROFEX™/MIP-1072/1095, or a PET scan using PSA, for example, PSMA antibody, such as, for example, capromad pendetide (Prostascint), a 111-iridium labeled PSMA antibody.

A tumor is classified, or named as part of an organ, such as a prostate cancer tumor when, for example, the tumor is present in the prostate gland, or has derived from or metastasized from a tumor in the prostate gland, or produces PSA. A tumor has metastasized from a tumor in the prostate gland, when, for example, it is determined that the tumor has chromosomal breakpoints that are the same as, or similar to, a tumor in the prostate gland of the subject.

For hematological malignancies, by "reducing, slowing, or inhibiting a hematological malignancy" is meant a reduction, slowing or inhibition of the amount or concentration of malignant cells, for example as measured in a sample obtained from the subject, of about 5%, 10%, 20%, 30%, 40%, 50%, 60%, 70%, 80%, 90%, or 100%, when compared to the amount or concentration of malignant cells before treatment. Methods for measuring the amount or concentration of malignant cells, or the tumor load include, for example, qRT-PCR and genome wide sequencing.

For hematological tumors, by "reducing, slowing, or inhibiting a tumor load" is meant a reduction, slowing or inhibition of the amount or concentration of tumor cells, for example as measured in a sample obtained from the subject, of about 5%, 10%, 20%, 30%, 40%, 50%, 60%, 70%, 80%, 90%, or 100%, when compared to the amount or concentration of tumor cells before treatment. Methods for measuring the amount or concentration of tumor cells, for example, qRT-PCR and genome wide sequencing.

Engineering Expression Constructs

Expression constructs that express the present TCRs or chimeric polypeptides comprise the TCR or polypeptide coding region and a promoter sequence, all operatively linked. In general, the term "operably linked" is meant to indicate that the promoter sequence is functionally linked to a second sequence, wherein the promoter sequence initiates and mediates transcription of the DNA corresponding to the second sequence.

In certain examples, the polynucleotide coding for the TCR or other polypeptide is included in the same vector, such as, for example, a viral or plasmid vector, as a polynucleotide coding for the second polypeptide. This second polypeptide may be, for example, a caspase polypeptide, as discussed herein, or a marker polypeptide. In these examples, the construct may be designed with one promoter operably linked to a nucleic acid comprising a polynucleotide coding for the two polypeptides, linked by a cleavable 2A polypeptide. In this example, the first and second polypeptides are separated during translation, resulting in a TCR and an additional polypeptide. In other examples, the two polypeptides may be expressed separately from the same vector, where each nucleic acid comprising a polynucleotide coding for one of the polypeptides is operably linked to a separate promoter. In yet other examples, one promoter may be operably linked to the two polynucleotides, directing the production of two separate RNA transcripts, and thus two polypeptides; in one example, the promoter may be bidirectional, and the coding regions may be in opposite directions 5'-3'. Therefore, the expression constructs discussed herein may comprise at least one, or at least two promoters.

In yet other examples, two polypeptides, such as, for example, the TCR and a caspase polypeptide may be expressed in the cell using two separate vectors. The cells may be co-transfected or co-transformed with the vectors, or the vectors may be introduced to the cells at different times.

The polypeptides may vary in their order, from the amino terminus to the carboxy terminus. The order of the various domains may be assayed using methods such as, for example, those discussed herein, to obtain the optimal expression and activity.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, β-gal or chloramphenicol acetyltransferase (CAT). In certain embodiments, the marker protein, such as, for example, CD19 is used for selection of the cells for transfusion, such as, for example, in immunomagnetic selection. As discussed herein, a CD19 marker is distinguished from an anti-CD19 antibody, or, for example, an scFv, TCR, or other antigen recognition moiety that binds to CD19.

In certain embodiments, the marker polypeptide is linked to the inducible chimeric signaling molecule. For example, the marker polypeptide may be linked to the inducible chimeric signaling molecule via a polypeptide sequence, such as, for example, a cleavable 2A-like sequence. The marker polypeptide may be, for example, CD19, ΔCD19, or may be, for example, a heterologous protein, selected to not affect the activity of the inducible chimeric signaling molecule. 2A-like sequences, or "peptide bond-skipping" 2A sequences, are derived from, for example, many different viruses, including, for example, from Thosea asigna. These sequences are sometimes also known as "peptide skipping sequences." When this type of sequence is placed within a cistron, between two peptides that are intended to be separated, the ribosome appears to skip a peptide bond, in the case of Thosea asigna sequence; the bond between the Gly and Pro amino acids at the carboxy terminal "P-G-P" is omitted. When this sequence is used, the peptide that is encoded 5' of the 2A sequence may end up with additional amino acids at the carboxy terminus, including the Gly residue and any upstream residues in the 2A sequence. The peptide that is encoded 3' of the 2A sequence may end up with additional amino acids at the amino terminus, including the Pro residue and any downstream residues following the 2A sequence.

In some embodiments, a polypeptide may be included in the expression vector to aid in sorting cells. For example, the CD34 minimal epitope may be incorporated into the vector. In some embodiments, the expression vectors used to express the TCRs provided herein further comprise a polynucleotide that encodes the 16 amino acid CD34 minimal epitope. In some embodiments, such as certain embodiments provided in the examples herein, the CD34 minimal epitope is incorporated at the amino terminal position of the CD8 stalk.

Ligand-Binding Regions

Ligand binding regions may be included in the chimeric polypeptides discussed herein, for example, as part of the inducible caspase polypeptides. The ligand-binding ("dimerization") domain of the expression construct can be any convenient domain that will allow for induction using a natural or unnatural ligand, for example, an unnatural synthetic ligand. The multimerizing region or ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises an $F_vF_{vls}$ sequence. Sometimes, the $F_vF_{vls}$ sequence further comprises an additional Fv' sequence. Examples include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology: From Small Molecules to Systems Biology and Drug Design (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric, nonimmunogenic, have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen). Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the Caspase-9 polypeptide, the ligand for the ligand-binding domains/receptor domains of the chimeric inducible Caspase-9 polypeptides will usually be multimeric in the sense that it will have at least two binding sites, with each of the binding sites capable of binding to the ligand receptor domain. By “multimeric ligand binding region” is meant a ligand binding region that binds to a multimeric ligand. The term “multimeric ligands” include dimeric ligands. A dimeric ligand will have two binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker domain, or modified receptors, and mutated sequences thereof, and the like, any of a large variety of compounds can be used. A significant characteristic of these ligand units is that each binding site is able to bind the receptor with high affinity and they are able to be dimerized chemically. Also, methods are available to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. FKBP12 variants having amino acid substitutions and deletions, such as $FKBP12_{v}36$, that bind to a dimerizer drug, may also be used. In addition, the synthetic ligands are resistant to protease degradation, making them more efficient at activating receptors in vivo than most delivered protein agents.

The ligands used are capable of binding to two or more of the ligand-binding domains. The chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug AP1903 (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by AP1903.

F36V'-FKBP: F36V'-FKBP is a codon-wobbled version of F36V-FKBP. It encodes the identical polypeptide sequence as F36V-FKPB but has only 62% homology at the nucleotide level. F36V'-FKBP was designed to reduce recombination in retroviral vectors (Schellhammer, P. F. et al., J. Urol. 157, 1731-5 (1997)). F36V'-FKBP was constructed by a PCR assembly procedure. The transgene contains one copy of F36V'-FKBP linked directly to one copy of F36V-FKBP.

In some embodiments, the ligand is a small molecule. The appropriate ligand for the selected ligand-binding region may be selected. Often, the ligand is dimeric, sometimes, the ligand is a dimeric FK506 or a dimeric FK506 analog. In certain embodiments, the ligand is AP1903 (CAS Index Name: 2-Piperidinecarboxylic acid, 1-[(2S)-1-oxo-2-(3,4,5-trimethoxyphenyl)butyl]-, 1,2-ethanediylbis[imino(2-oxo-2,1-ethanediyl)oxy-3,1-phenylene[(1R)-3-(3,4-dimethoxyphenyl)propylidene]]ester, [2S-[1(R*),2R*[S[S*[1(R*),2R*]]]]]-(9Cl) CAS Registry Number: 195514-63-7; Molecular Formula: C78H98N4020 Molecular Weight: 1411.65). In certain embodiments, the ligand is AP20187. In certain embodiments, the ligand is an AP20187 analog, such as, for example, AP1510. In some embodiments, certain analogs will be appropriate for the FKBP12, and certain analogs appropriate for the mutant (V36) version of FKBP12. In certain embodiments, one ligand binding region is included in the chimeric protein. In other embodiments, two or more ligand binding regions are included. Where, for example, the ligand binding region is FKBP12, where two of these regions are included, one may, for example, be the wobbled version.

Other dimerization systems contemplated include the coumermycin/DNA gyrase B system. Coumermycin-induced dimerization activates a modified Raf protein and stimulates the MAP kinase cascade. See Farrar et al., 1996.

AP1903 API is manufactured by Alphora Research Inc. and AP1903 Drug Product for Injection is made by AAI Pharma Services Corp. It is formulated as a 5 mg/mL solution of AP1903 in a 25% solution of the non-ionic solubilizer Solutol HS 15 (250 mg/mL, BASF). At room temperature, this formulation is a clear solution. Upon refrigeration, this formulation undergoes a reversible phase transition on extended storage, resulting in a milky solution. This phase transition is reversed upon re-warming to room temperature. The fill is 8 mL in a 10 mL glass vial (~40 mg AP1903 for Injection total per vial).

For use, the AP1903 will be warmed to room temperature and diluted prior to administration. Upon determining a need to administer AP1903 and activate Caspase-9 in order to induce apoptosis of the engineered TCR-expressing T cells, patients may be, for example, administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by ≥10%. The calculated dose is diluted in 100 mL in 0.9% normal saline before infusion.

All study medication is maintained at a temperature between 2 degrees C. and 8 degrees C., protected from excessive light and heat, and stored in a locked area with restricted access.

In a previous Phase I study of AP1903, 24 healthy volunteers were treated with single doses of AP1903 for Injection at dose levels of 0.01, 0.05, 0.1, 0.5 and 1.0 mg/kg infused IV over 2 hours. AP1903 plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 for injection used, for example, may be 0.4 mg/kg intravenously infused over 2 hours. The amount of AP1903 needed in vitro for effective signaling of cells is about 10-100 nM (MW: 1412 Da). This equates to 14-140 μg/L or ~0.014-0.14 mg/kg (1.4-140 μg/kg). The dosage may vary according to the application, and may, in certain examples, be more in the range of 0.1-10 nM, or in the range of 50-150 nM, 10-200 nM, 75-125 nM, 100-500 nM, 100-600 nM, 100-700 nM, 100-800 nM, or 100-900 nM. Doses up to 1 mg/kg were well-tolerated in the Phase I study of AP1903 described above.

Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S-N-K-S-K-P-K-D-A-S-Q-R-R-R (SEQ ID NO: 121)) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 122), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or 010 isoprenyl moieties, from the C-terminus of G-protein gamma subunits and other proteins (e.g., World Wide Web address ebi.ac.uk/interpro/DisplayIproEntry?ac=IPR001230) also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition discussed above and tested for antimicrobial activity using known methods and those discussed hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (010), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association region. Any membrane-targeting sequence can be employed that is functional in the host and may, or may not, be associated with one of the other domains of the chimeric protein. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster J P et al, Biology of the Cell (2007) 99, 1-12, Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-P3, PI (3,4)-P2, PI (4,5)-P2) and thus play a key role in recruiting proteins to different membrane or cellular compartments. Often the phosphorylation state of PI lipids is regulated, such as by PI-3 kinase or PTEN, and thus, interaction of membranes with PH domains are not as stable as by acyl lipids.

Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that may be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity. (Bojak, A., et al., 2002. Vaccine. 20:1975-79; Cazeaux, N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29/CD79b (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-α, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP α, IL-1, IL-6 (Poli and Cortese, (1989) Proc. Nat'l Acad. Sci. USA, 86, 8202-8206), Complement C3 (Wlson et al., (1990) Mol. Cell. Biol., 6181-6191), IL-8, α-1 acid glycoprotein (Prowse and Baumann, (1988) Mol Cell Biol, 8, 42-51), α-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-α, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), α-2 macroglobulin and α-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole stimulates transcription at a distance and often independent of orientation; this need not be true of a promoter region or its component elements. On the other hand, a promoter has one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers includes locus-control regions (LCRs) that can not only increase transcriptional activity, but (along with insulator elements) can also help to insulate the transcriptional element from adjacent sequences when integrated into the genome. Any promoter/enhancer combination (as per the Eukaryotic Promoter Data Base EPDB) can be used to drive expression of the gene, although many will restrict expression to a particular tissue type or subset of tissues. (Reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Appropriate enhancers may be selected for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. One non-limiting example is the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA. (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. The initiation codon is placed in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been discussed (Pelletier and Sonenberg, 1988), as well an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Sequence Optimization

Protein production may also be increased by optimizing the codons in the transgene. Species specific codon changes may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed. (Kutzler, M. A., and Weiner, D. B., 2008. Nature Rev. Gen. 9:776-88; Yan, J. et al., 2007. Mol. Ther. 15:411-21; Cheung, Y. K., et al., 2004. Vaccine 23:629-38; Narum, D. L., et al., 2001. 69:7250-55; Yadava, A., and Ockenhouse, C. F., 2003. Infect. Immun. 71:4962-69; Smith, J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635).

Leader Sequences

Leader sequences may be added to enhance the stability of mRNA and result in more efficient translation. The leader sequence is usually involved in targeting the mRNA to the endoplasmic reticulum. Examples include the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang, J. S., et al., 2002. Emerg. Infect. Dis. 8:1379-84; Kumar, S., et al., 2006. DNA Cell Biol. 25:383-92; Wang, S., et al, 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression. These methods include, for example, optimizing promoters, delivery methods, and gene sequences, (for example, as presented in Laddy, D. J., et al., 2008. PLoS. ONE 3 e2517; Kutzler, M. A., and Weiner, D. B., 2008. Nature Rev. Gen. 9:776-88).

Nucleic Acids

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Nucleic Acid Modification

Any of the modifications discussed below may be applied to a nucleic acid. Examples of modifications include alterations to the RNA or DNA backbone, sugar or base, and various combinations thereof. Any suitable number of backbone linkages, sugars and/or bases in a nucleic acid can be modified (e.g., independently about 5%, 10%, 15%, 20%, 25%, 30%, 35%, 40%, 45%, 50%, 55%, 60%, 65%, 70%, 75%, 80%, 85%, 90%, 95%, up to 100%). An unmodified nucleoside is any one of the bases adenine, cytosine, guanine, thymine, or uracil joined to the 1' carbon of β-D-ribofuranose.

A modified base is a nucleotide base other than adenine, guanine, cytosine and uracil at a 1' position. Non-limiting examples of modified bases include inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and the like. Other non-limiting examples of modified bases include nitropyrrolyl (e.g., 3-nitropyrrolyl), nitroindolyl (e.g., 4-, 5-, 6-nitroindolyl), hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, difluorotolyl, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl and the like.

In some embodiments, for example, a nucleid acid may comprise modified nucleic acid molecules, with phosphate backbone modifications. Non-limiting examples of backbone modifications include phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl modifications. In certain instances, a ribose sugar moiety that naturally occurs in a nucleoside is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. The hexose may be a D-hexose, glucose, or mannose. In certain instances, the polycyclic heteroalkyl group may be a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane.

Nitropyrrolyl and nitroindolyl nucleobases are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, oligonucleotide duplexes containing 3-nitropyrrolyl nucleobases may be stabilized solely by stacking interactions. The absence of significant hydrogen-bonding interactions with nitropyrrolyl nucleobases obviates the specificity for a specific complementary base. In addition, 4-, 5- and 6-nitroindolyl display very little specificity for the four natural bases. Procedures for the preparation of 1-(2'-O-methyl-.β.-D-ribofuranosyl)-5-nitroindole are discussed in Gaubert, G.; Wengel, J. Tetrahedron Letters 2004, 45, 5629. Other universal bases include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof.

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994);

In addition, chemical substituents, for example cross-linking agents, may be used to add further stability or irreversibility to the reaction. Non-limiting examples of cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

A nucleotide analog may also include a “locked” nucleic acid. Certain compositions can be used to essentially “anchor” or “lock” an endogenous nucleic acid into a particular structure. Anchoring sequences serve to prevent disassociation of a nucleic acid complex, and thus not only can prevent copying but may also enable labeling, modification, and/or cloning of the endogenous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

Nucleic acid molecules need not be limited to those molecules containing only RNA or DNA, but further encompass chemically modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%).

Nucleic Acid Preparation

In some embodiments, a nucleic acid is provided for use as a control or standard in an assay, or therapeutic, for example. A nucleic acid may be made by any technique known in the art, such as for example, chemical synthesis, enzymatic production or biological production. Nucleic acids may be recovered or isolated from a biological sample. The nucleic acid may be recombinant or it may be natural or endogenous to the cell (produced from the cell’s genome). It is contemplated that a biological sample may be treated in a way so as to enhance the recovery of small nucleic acid molecules. Generally, methods may involve lysing cells with a solution having guanidinium and a detergent.

Nucleic acid synthesis may also be performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques or via deoxynucleoside H-phosphonate intermediates. Various different mechanisms of oligonucleotide synthesis have been disclosed elsewhere.

Nucleic acids may be isolated using known techniques. In particular embodiments, methods for isolating small nucleic acid molecules, and/or isolating RNA molecules can be employed. Chromatography is a process used to separate or isolate nucleic acids from protein or from other nucleic acids. Such methods can involve electrophoresis with a gel matrix, filter columns, alcohol precipitation, and/or other chromatography. If a nucleic acid from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column is effective for such isolation procedures.

A nucleic acid isolation processes may sometimes include: a) lysing cells in the sample with a lysing solution comprising guanidinium, where a lysate with a concentration of at least about 1 M guanidinium is produced; b) extracting nucleic acid molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the nucleic acid molecules from the solid support with an ionic solution; and, f) capturing the nucleic acid molecules. The sample may be dried down and resuspended in a liquid and volume appropriate for subsequent manipulation.

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer. A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a T cell, a tumor-infiltrating lymphocyte, a natural killer cell, or a natural killer T cell.

An appropriate host may be determined. Generally this is based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Nucleic acid vaccines may include, for example, non-viral DNA vectors, "naked" DNA and RNA, and viral vectors. Methods of transforming cells with these vaccines, and for optimizing the expression of genes included in these vaccines are known and are also discussed herein.

Examples of Methods of Nucleic Acid or Viral Vector Transfer

Any appropriate method may be used to transfect or transform the cells, for example, the T cells, or to administer the nucleotide sequences or compositions of the present methods. Certain examples are presented herein, and further include methods such as delivery using cationic polymers, lipid like molecules, and certain commercial products such as, for example, IN-VIVO-JET PEI.

1. Ex Vivo Transformation

Various methods are available for transfecting vascular cells and tissues removed from an organism in an ex vivo setting. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism. For example, T cells may be obtained from an animal, the cells transfected or transformed with the expression vector and then administered back to the animal.

2. Injection

In certain embodiments, a cell or a nucleic acid or viral vector may be delivered to an organelle, a cell, a tissue or an organism via one or more injections (i.e., a needle injection), such as, for example, subcutaneous, intradermal, intramuscular, intravenous, intraprotatic, intratumor, intrintraperitoneal, etc. Methods of injection include, for example, injection of a composition comprising a saline solution. Further embodiments include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair is clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human K-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell Biol., 6, 716-718) in this manner.

In vivo electroporation for vaccines, or eVac, is clinically implemented through a simple injection technique. A DNA vector encoding tumor antigen is injected intradermally in a patient. Then electrodes apply electrical pulses to the intradermal space causing the cells localized there, especially resident dermal dendritic cells, to take up the DNA vector and express the encoded tumor antigen. These tumor antigen-expressing dendritic cells activated by local inflammation can then migrate to lymph-nodes, presenting tumor antigens and priming tumor antigen-specific T cells. A nucleic acid is electroporetically administered when it is administered using electroporation, following, for example, but not limited to, injection of the nucleic acid or any other means of administration where the nucleic acid may be delivered to the cells by electroporation Methods of electroporation are discussed in, for example, Sardesai, N. Y., and Weiner, D. B., Current Opinion in Immunotherapy 23:421-9 (2011) and Ferraro, B. et al., Human Vaccines 7:120-127 (2011), which are hereby incorporated by reference herein in their entirety.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52, 456-467) using this technique. Also in this manner, mouse L(A9), mouse C127, CHO, CV-1, BHK, NIH3T3 and HeLa cells were transfected with a neomycin marker gene (Chen and Okayama, Mol. Cell Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7 Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine (Gibco BRL) or Superfect (Qiagen).

8. Receptor-Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity. Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been discussed (Wu and Wu, Adv. Drug Delivery Rev., 12:159-167, 1993; incorporated herein by reference). In certain aspects, a ligand is chosen to correspond to a receptor specifically expressed on the target cell population. In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149, 157-176). It is contemplated that the tissue-specific transforming constructs may be specifically delivered into a target cell in a similar manner.

9. Microprojectile Bombardment

Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods. In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold, including, for example, nanoparticles. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

10. Transposon-mediated Transfer

Transposon-mediated transfer methods may also be employed using, for example, the piggy/Bac gene transfer system. Sato, M., et al., Biotechnol J. 2014 Oct. 24. doi: 10.1002/biot.201400283. [Epub ahead of print].

Examples of Methods of Viral Vector-Mediated Transfer

Any viral vector suitable for administering nucleotide sequences, or compositions comprising nucleotide sequences, to a cell or to a subject, such that the cell or cells in the subject may express the genes encoded by the nucleotide sequences may be employed in the present methods. In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector may permit replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells, such as, for example, T cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990). Thus, for example, the present technology includes, for example, cells whereby the polynucleotide used to transduce the cell is integrated into the genome of the cell.

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248). An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may this be desired.

A different approach to targeting of recombinant retroviruses was designed, which used biotinylated antibodies against a retroviral envelope protein and against a specific cell receptor. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Lentivirus

Lentiviral vectors used in the present methods may be derived from any appropriate lentivirus. Lentiviral vectors are a type of retroviral vector, including both primate and non-primate groups. Examples of lentiviral vectors are discussed in, for example, Coffin et al. (1997) "Retroviruses" Cold Spring Harbor Laboratory Press Eds: J M Coffin, S M Hughes, H E Varmus pp 758-763). Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), caprine arthritis-encephalitis virus (CAEV), equine infectious anaemia virus (EIAV) and feline immunodeficiency virus (FIV) and bovine immunodeficiency virus (BIV). Lentiviruses are capable of infecting both dividing and non-dividing cells (Lewis et al. (1992); Lewis and Emerman (1994)).

A lentiviral vector, as used herein, is a vector which comprises at least one component part, wherein the component part is involved in the biological mechanisms by which the vector infects cells, expresses genes or is replicated, derivable from a lentivirus.

The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components. Lentiviruses also comprise additional features, such as rev and RRE sequences in HIV, which enable the efficient export of RNA transcripts of the integrated provirus from the nucleus to the cytoplasm of an infected target cell.

In the provirus, the viral genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different viruses.

In examples of the lentiviral vectors discussed herein, at least part of one or more protein coding regions essential for replication may be removed from the virus. This makes the viral vector replication-defective. Portions of the viral genome may also be replaced by an NOI in order to generate a vector comprising an NOI which is capable of transducing a target non-dividing host cell and/or integrating its genome into a host genome.

In one embodiment the retroviral vectors are non-integrating vectors as discussed in WO 2007/071994, WO 2007/072056, U.S. Pat. No. 9,169,491, U.S. Pat. No. 8,084, 249, or U.S. Pat. No. 7,531,648. In some examples, the lentiviral vector is a self-inactivating retroviral vector, wherein the transcriptional enhancers, or the enhancers and promoter in the U3 region of the 3' LTR have been deleted (see, for example, Yu et al. (1986) Proc. Natl. Acad. Sci. 83:3194-3198; Dougherty and Temin (1987) Proc. Natl. Acad. Sci. 84:1197-1201; Hawley et al. (1987) Proc. Natl. Acad. Sci. 84:2406-2410; Yee et al. (1987) Proc. Natl. Acad. Sci. 91:9564-9568).

The lentiviral plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter.

4. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

5. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Methods for Engineering T Cells, and Evaluation of the Modified T Cells

Examples of methods for engineering T cells and evaluation of the modified T cells are provided herein. Retroviral and lentiviral constructs Retrovirus Transduction For the transient production of retrovirus, 293T cells are transfected with the chimeric polypeptide constructs, along with plasmids encoding gag-pol and RD 114 envelope using GeneJuice transfection reagent (Novagen, Madison, Wis.). Virus is harvested 48 to 72 hours after transfection, snap frozen, and stored at ~80° C. until use. For the transient production of lentivirus, 293T cells are transfected with the constructs along with the plasmids pLP1 (gag/pol), pLP2 (rev) and pLP/VSVG (VSVG env) using GeneJuice. Virus is harvested 48 to 72 hours after transfection, snap frozen, and stored at ~80° C. until use. For large-scale retrovirus production, a stable FLYRD 18-derived retroviral producer line is generated by multiple transductions with VSV-G pseudotyped transient retroviral supernatant. FLYRD18 cells with highest transgene expression are single-cell sorted, and the clone that produces the highest virus titer is expanded and used to produce virus for lymphocyte transduction. The transgene expression, function, and retroviral titer of this clone is maintained during continuous culture for more than 8 weeks. Non-tissue culture-treated 24-well plates are coated with 7 μg/ml Retronectin (Takara Bio, Otsu, Shiga, Japan) for 1 hour at 37° C. or overnight at 4° C. The wells are washed with phosphate-buffered saline (PBS) then coated with retroviral supernatant by incubating the plate with 1.5 ml of supernatant for 30 minutes at 37° C. Subsequently, T cell blasts are plated at $5\times10^5$ cells per well in viral supernatant supplemented with 100 U/ml IL-2. Transduction is performed over a 60-hour period. Following transduction, cells are harvested and phenotyped for CD19 or GFP expression by flow cytometry.

Cytotoxicity of Transduced T Cells

The cytotoxic activity of each transduced T cell line is evaluated in a standard 4-hour 51Cr release assay, as previously presented. T cells transduced with the retrovirus or lentivirus and compared against Cr51-labeled target cells, including autologous phytohaemagglutinin (PHA) stimulated lymphocytes (PHA blasts), LNCaP, PC3 or DU145 and A549 cancer cell lines, and transgenic A549 expressing human PSMA (A549-PSMA). Target cells incubated in complete medium or 1% Triton X-100 (Sigma, St Louis, Mo.) are used to determine spontaneous and maximum 51Cr release, respectively. The mean percentage of specific lysis of triplicate wells was calculated as 100×(experimental release−spontaneous release)/(maximal release−spontaneous release). In addition to chromium-release assays, co-culture experiments with are performed. Here, the cell lines LNCaP, PC3, DU145, A549 and A549-PSMA are transduced to express fluorescent mOrange and used as target cells. mOrange-expressing tumor cells are co-cultured with non-transduced or modified T cells at a ratio of 1:10 tumor cells to T cells in the presence of IL-2 (50 U/ml) in complete media. After 24 hours, T cells are stimulated with 100 nM AP1903. After 72 hours, cells are collected, counted and labeled with CD3 to detect T cells and percentage of mOrange tumor cells is analyzed by flow cytometry (LSRII; BD).

Phenotyping and Activation Status of Transduced T Cells

Cell surface phenotype of transduced T cells is investigated using the following monoclonal antibodies: CD3, CD4, CD8, CD19, CD25, CD27, CD28, CD44, CD45RA, CD45RO, CD62L, CD80, CD83, CD86, CD95, CD127, CD134, CD137, HLA-ABC and HLA-DR. Phenotyping is performed with and without 100 nM AP1903. Appropriate matched isotype controls are used in each experiment and cells are analyzed with a LSRII flow cytometer (BD). The chimeric polypeptide expression is assessed using anti-F (ab')2 (Jackson ImmunoResearch Laboratories, West Grove, Pa.).

Analysis of Cytokine Production of Transduced T Cells

The concentration of interferon-γ (IFN-γ), IL-2, IL-4, IL-5, IL-10, and tumor necrosis factor-α (TNFα) in T cell culture supernatants before and after (24 hours) 100 nM AP1903 stimulation is measured using the Human Th1/Th2 cytokine cytometric Bead Array (BD Pharmin¬gen). Induced cytokine production in the culture supernatants is validated by enzyme-linked immunosorbent assay (ELISA; R&D Systems, Minneapolis, Minn.) according to the instructions of the manufacturer.

Proliferation of Transduced T Cells

The proliferative effect of AP1903-induced activation is evaluated by measuring cell growth of transduced and non-transduced T cells following exposure to AP1903. T cells are labeled with 10 μM carboxyfluorescein diacetate, succinimidyl ester (CFSE) for 10 minutes at 37° C. After incubation, cells are washed in PBS and then resuspended in Cellgenix DC media. $1\times10^6$ CFSE-labeled modified or non-transduced T cells are subsequently cultured in Cellgenix DC media alone, or stimulated with 100 nM AP1903. After 5 days, cells are harvested and labeled with CD3-PerCP.Cy5.5 and CD19-PE and analyzed by flow cytometry for CFSE dilution.

To evaluate whether soluble immunoglobulins affect the proliferation and expansion of the transduced T lymphocytes, cells are cultured at $1\times10^5$ cells/well either with serial dilution of human plasma obtained from healthy donors or serial dilution of purified human immunoglobulins (Jackson ImmunoResearch) without any addition of exogenous cytokines. After 72 hours, the cells are pulsed with 1 μCi (0.037 MBq) methyl-3[H]thymidine (Amersham Pharmacia Biotech, Piscataway, N.J.) and cultured for additional 15 hours. The cells were then harvested onto filters and dried, and counts per minute are measured in a β-scintillation counter (TriCarb 2500 TR; Packard BioScience, Meridien, Conn.). The experiments are performed in triplicate. In other experiments, control and modified T lymphocytes are cultured either with media alone or with media in which serial dilution of plasma or purified immunoglobulins are added every second day. Cells are then counted every third day using trypan blue exclusion.

Activation of T Cells Ex Vivo and Administration to a Human Subject

Presented in this example are methods of using modified T cells, such as Bob1-modified T cells, which may or may not also comprise polynucleotides encoding additional chimeric polypeptides, such as the chimeric Caspase-9 polypeptides discussed herein, for human therapy.

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at $1\times10^6$ cells/ml and stimulated with 0.2 μg/ml αCD3 and 0.5 μg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Plasmid and Retrovirus

The compositions and methods of the present example may be modified to include Bob1-encoding lentiviral vectors as discussed herein. The SFG plasmid consists of inducible chimeric polypeptide linked, via a cleavable 2A-like sequence, to truncated human CD19. The inducible chimeric polypeptide consists of a human FK506-binding protein (FKBP12; GenBank AH002 818) with an F36V mutation, connected via a Ser-Gly-Gly-Gly-Ser-Gly linker (SEQ ID NO: 54) to human chimeric polypeptide. The F36V mutation increases the binding affinity of FKBP12 to the synthetic homodimerizer, AP20187 or AP1903. The 2A-like sequence, "T2A", encodes an 20 amino acid peptide from Thosea asigna insect virus, which mediates >99% cleavage between a glycine and terminal proline residue, resulting in 19 extra amino acids in the C terminus of the inducible chimeric polypeptide, and one extra proline residue in the N terminus of CD19. CD19 consists of full-length CD19 (GenBank NM 001770) truncated at amino acid 333 (TDPTRRF (SEQ ID NO: 123)), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plamid proviral integrants per cell. Single cell cloning is performed, and the PG13 clone that produced the highest titer is expanded and used for vector production.

Retroviral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 micrograms/ml and anti-CD28 0.2 μg/ml or 10 ml of fibronectin 7 micrograms/ml at 4° C. overnight. Fluorinated ethylene propylene bags corona-treated for increased cell adherence (2PF-0072AC, American Fluoroseal Corporation, Gaithersburg, Md.) are also used. PBMCs are seeded in anti-CD3, anti-CD28-coated flasks at $1\times10^6$ cells/ml in media supplemented with 100 U/ml IL-2. For retroviral transduction, retronectin-coated flasks or bags are loaded once with 10 ml of retrovirus-containing supernatant for 2 to 3 hours. Activated T cells are seeded at $1\times10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about $5\times10^5$ cells/ml to $8\times10^5$ cells/ml.

CD19 Immunomagnetic Selection

In the present example, the modified cells express a CD19 marker protein; it is understood that the modified cells may be selected using markers other than CD19, or by other methods. Immunomagnetic selection for CD19 may be performed, in one example, 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CliniMacs Plus automated selection device in large scale experiments. CD19-selected cells are expanded for a further 4 days and cryopreserved on day 8 post transduction. These cells are referred to as “gene-modified cells”.

Immunophenotyping and Pentamer Analysis

Flow cytometric analysis (FACSCalibur and CellQuest software; Becton Dickinson) is performed using the following antibodies: CD3, CD4, CD8, CD19, CD25, CD27, CD28, CD45RA, CD45RO, CD56 and CD62L. CD19-PE (Clone 4G7; Becton Dickinson) is found to give optimum staining and was used in all subsequent analysis. A non-transduced control is used to set the negative gate for CD19.

Statistical Analysis

Paired, 2-tailed Student’s t test is used to determine the statistical significance of differences between samples. All data are represented as mean±1 standard deviation.

Methods for Treating a Disease

The present methods also encompass methods of treatment or prevention of a disease where administration of cells by, for example, infusion, may be beneficial.

Cells, such as, for example, T cells, tumor infiltrating lymphocytes, natural killer cells, natural killer T cells, or progenitor cells, such as, for example, hematopoietic stem cells, mesenchymal stromal cells, stem cells, pluripotent stem cells, and embryonic stem cells may be used for cell therapy. The cells may be from a donor, or may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. Mesenchymal stromal cells have also, for example, been used to provide immunosuppressive activity, and may be used in the treatment of graft versus host disease and autoimmune disorders. The cells provided in the present application contain a safety switch that may be valuable in a situation where following cell therapy, the activity of the therapeutic cells needs to be increased, or decreased. For example, where T cells that express a T cell receptor, such as a Bob1 targeted TCR, are provided to the patient, in some situations there may be an adverse event, such as off-target toxicity. Ceasing the administration of the ligand would return the therapeutic T cells to a non-activated state, remaining at a low, non-toxic, level of expression. Or, for example, the therapeutic cell may work to decrease the tumor cell, or tumor size, and may no longer be needed. In this situation, administration of the ligand may cease, and the therapeutic cells would no longer be activated. If the tumor cells return, or the tumor size increases following the initial therapy, the ligand may be administered again, in order to further activate the TCR-expressing T cells, and re-treat the patient.

By “therapeutic cell” is meant a cell used for cell therapy, that is, a cell administered to a subject to treat or prevent a condition or disease.

The term “unit dose” as it pertains to the inoculum refers to physically discrete units suitable as unitary dosages for mammals, each unit containing a predetermined quantity of pharmaceutical composition calculated to produce the desired immune-stimulating effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition, such as the multimeric ligand presented herein, would be the amount that achieves this selected result of inducing apoptosis in the Caspase-9-expressing cells T cells, such that over 60%, 70%, 80%, 85%, 90%, 95%, or 97%, or that under 80%, 70%, 60%, 50%, 40%, 30%, 20%, or 10% of the therapeutic cells are killed. The term is also synonymous with “sufficient amount.” The effective amount where the pharmaceutical composition is the modified T cell may also be the amount that achieves the desired therapeutic response, such as, the reduction of tumor size, the decrease in the level of tumor cells, or the decrease in the level of leukemic cells, compared to the time before the ligand inducer is administered.

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms “contacted” and “exposed,” when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

Optimized and Personalized Therapeutic Treatment

The dosage and administration schedule of the modified cells may be optimized by determining the level of the disease or condition to be treated. For example, the size of any remaining solid tumor, or the level of targeted cells such as, for example, tumor cells or leukemic cells, which remain in the patient, may be determined.

For example, determining that a patient has clinically relevant levels of tumor cells, or a solid tumor, after initial therapy, provides an indication to a clinician that it may be necessary to administer the modified T cells. In another example, determining that a patient has a reduced level of tumor cells or reduced tumor size after treatment with the modified cells may indicate to the clinician that no additional dose of the modified cells is needed. Similarly, after treatment with the modified cells, determining that the patient continues to exhibit disease or condition symptoms, or suffers a relapse of symptoms may indicate to the clinician that it may be necessary to administer at least one additional dose of modified cells.

The term "dosage" is meant to include both the amount of the dose and the frequency of administration, such as, for example, the timing of the next dose. The term "dosage level" refers to the amount of the modified cells administered in relation to the body weight of the subject.

In certain embodiments the cells are in an animal, such as human, non-human primate, cow, horse, pig, sheep, goat, dog, cat, or rodent. The subject may be, for example, an animal, such as a mammal, for example, a human, non-human primate, cow, horse, pig, sheep, goat, dog, cat, or rodent. The subject may be, for example, human, for example, a patient suffering from an infectious disease, and/or a subject that is immunocompromised, or is suffering from a hyperproliferative disease.

Thus, for example, in certain embodiments, the methods comprise determining the presence or absence of a tumor size increase and/or increase in the number of tumor cells in a subject relative to the tumor size and/or the number of tumor cells following administration of the modified cells or nucleic acid, and administering an additional dose of the modified cells or nucleic acid to the subject in the event the presence of a tumor size increase and/or increase in the number of tumor cells is determined. The methods also comprise, for example, determining the presence or absence of an increase in leukemic cells in the subject relative to the level of leukemic cells following administration of the modified cells or nucleic acid, and administering an additional dose of the modified cells or nucleic acid to the subject in the event the presence of an increase in leukemic cells in the subject is determined. In these embodiments, for example, the patient is initially treated with the therapeutic cells or nucleic acid according to the methods provided herein. Following the initial treatment, the size of the tumor, the number of tumor cells, or the number of leukemic cells, for example, may decrease relative to the time prior to the initial treatment. At a certain time after this initial treatment, the patient is again tested, or the patient may be continually monitored for disease symptoms. If it is determined that the size of the tumor, the number of tumor cells, or the number of leukemic cells, for example, is increased relative to the time just after the initial treatment, then the modified cells or nucleic acid may be administered for an additional dose. This monitoring and treatment schedule may continue while noting that the therapeutic cells that express the Bob1 targeted T cell receptors remain in the patient.

In other embodiments, following administration of the modified cells or nucleic acid, wherein the modified cells or nucleic acid express the inducible Caspase-9 polypeptide, in the event of a need to reduce the number of modified cells or in vivo modified cells, the multimeric ligand may be administered to the patient. In these embodiments, the methods comprise determining the presence or absence of a negative symptom or condition, such as Graft vs Host Disease, or off target toxicity, and administering a dose of the multimeric ligand. The methods may further comprise monitoring the symptom or condition and administering an additional dose of the multimeric ligand in the event the symptom or condition persists. This monitoring and treatment schedule may continue while the therapeutic cells that express the Bob1 targeted TCRs remain in the patient.

An indication of adjusting or maintaining a subsequent drug dose, such as, for example, a subsequent dose of the modified cells or nucleic acid, and/or the subsequent drug dosage, can be provided in any convenient manner. An indication may be provided in tabular form (e.g., in a physical or electronic medium) in some embodiments. For example, the size of the tumor cell, or the number or level of tumor cells in a sample may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms are provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the activated cell, nucleic acid, or expression construct, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers, or other disease symptoms such as tumor size or tumor antigen expression, to evaluate the effectiveness of treatment and to control toxicity.

In further embodiments, the expression construct and/or expression vector can be utilized as a composition or substance that activates cells. Such a composition that "activates cells" or "enhances the activity of cells" refers to the ability to stimulate one or more activities associated with cells. For example, a composition, such as the expression construct or vector of the present methods, can stimulate upregulation of co-stimulating molecules on cells, induce nuclear translocation of NF-κB in cells, activate toll-like receptors in cells, or other activities involving cytokines or chemokines.

The expression construct, expression vector and/or transduced cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity by eliciting a particular cytokine profile.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In certain embodiments, the cell is transduced with the nucleic acid ex vivo and administered to the subject by intravenous administration. In other embodiments, the cell is administered using intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

In certain embodiments the cell is transduced with the nucleic acid ex vivo and administered to the subject by intradermal administration, and sometimes the cell is transduced with the nucleic acid ex vivo and administered to the subject by subcutaneous administration. The antigen may be a tumor antigen, and the CTL immune response can be induced by migration of the cell to a draining lymph node. A tumor antigen is any antigen such as, for example, a peptide or polypeptide, that triggers an immune response in a host. The tumor antigen may be a tumor-associated antigen, which is associated with a neoplastic tumor cell.

In some embodiments, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired T cells. It is contemplated that the present methods can be utilized to enhance the amount and/or activity of T cells in an immunocompromised subject.

Antigens

T cell receptors bind to target antigens. When assaying T cell activation in vitro or ex vivo, target antigens may be obtained or isolated from various sources. The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), Mycobacteria, *Legionella, Meningiococcus*, Group A *Streptococcus, Salmonella, Listeria, Hemophilus influenzae* (U.S. Pat. No. 5,955,596) and the like).

Target antigen may be derived or isolated from, for example, pathogenic yeast including *Aspergillus*, invasive *Candida* (U.S. Pat. No. 5,645,992), *Nocardia, Histoplasmosis, Cryptosporidia* and the like.

Target antigen may be derived or isolated from, for example, a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii.*

Target antigen includes an antigen associated with a preneoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat. No. 5,840,839), NY-ESO-1 (Chen et al PNAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each. An antigen may be expressed more frequently in cancer cells than in non-cancer cells. The antigen may result from contacting the modified cell with a prostate specific membrane antigen, for example, a prostate specific membrane antigen (PSMA) or fragment thereof.

Prostate antigen (PA001) is a recombinant protein consisting of the extracellular portion of PSMA antigen. PSMA is a ~100 kDa (84 kDa before glycosylation, ~180 kDa as dimer) type II membrane protein with neuropeptidase and folate hydrolase activities, but the true function of PSMA is currently unclear. Carter R E, et al., Proc Natl Acad Sci USA. 93: 749-53, 1996; Israeli R S, et al., Cancer Res. 53: 227-30, 1993; Pinto J T, et al., Clin Cancer Res. 2: 1445-51, 1996.

The cell may be contacted with tumor antigen, such as PSA, for example, PSMA polypeptide, by various methods, including, for example, pulsing immature DCs with unfractionated tumor lysates, MHC-eluted peptides, tumor-derived heat shock proteins (HSPs), tumor associated antigens (TAAs (peptides or proteins)), or transfecting DCs with bulk tumor mRNA, or mRNA coding for TAAs (reviewed in Gilboa, E. & Vieweg, J., Immunol Rev 199, 251-63 (2004); Gilboa, E, Nat Rev Cancer 4, 401-11 (2004)).

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by routine methods. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified, for example, by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of cells, such as, for example, dendritic cells, with antigens, such as, for example, a Bob1 epitope polypeptide, may be achieved, for example, by contacting cells, such as, for example, dendritic cells or progenitor cells with an antigen, for example, by incubating the cells with the antigen. Loading may also be achieved, for example, by incubating DNA (naked or within a plasmid vector) or RNA that code for the antigen; or with antigen-expressing recombinant bacterium or viruses (e.g., vaccinia, fowlpox, adenovirus or lentivirus vectors). Prior to loading, the antigen may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods (see Zitvogel L, et al., J Exp Med 1996. 183:87-97). The cells may be transduced or transfected with the chimeric protein-encoding nucleotide sequence according to the present methods before, after, or at the same time as the cells are loaded with antigen. In particular embodiments, antigen loading is subsequent to transduction or transfection.

In further embodiments, the transduced cell is transfected with tumor cell mRNA. The transduced transfected cell is administered to an animal to effect cytotoxic T lymphocytes and natural killer cell anti-tumor antigen immune response and regulated using dimeric FK506 and dimeric FK506 analogs. The tumor cell mRNA may be, for example, mRNA from a prostate tumor cell.

In some embodiments, the transduced cell may be loaded by pulsing with tumor cell lysates. The pulsed transduced cells are administered to an animal to effect cytotoxic T lymphocytes and natural killer cell anti-tumor antigen immune response and regulated using dimeric FK506 and dimeric FK506 analogs. The tumor cell lysate may be, for example, a prostate tumor cell lysate.

Immune Cells and Cytotoxic T Lymphocyte Response

T-lymphocytes may be activated by contact with the cell that comprises the expression vector discussed herein, where the cell has been challenged, transfected, pulsed, or electrofused with an antigen.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, which are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods discussed herein, for example. For example, CTLs may be assessed in freshly isolated peripheral blood mononuclear cells (PBMC), in a phytohaemaglutinin-stimulated IL-2 expanded cell line established from PBMC (Bernard et al., AIDS, 12(16):2125-2139, 1998) or by T cells isolated from a previously immunized subject and restimulated for 6 days with DC infected with an adenovirus vector containing antigen using standard 4 hour 51Cr release microtoxicity assays. One type of assay uses cloned T-cells. Cloned T-cells have been tested for their ability to mediate both perforin and Fas ligand-dependent killing in redirected cytotoxicity assays (Simpson et al., Gastroenterology, 115(4):849-855, 1998). The cloned cytotoxic T lymphocytes displayed both Fas- and perforin-dependent killing. Recently, an in vitro dehydrogenase release assay has been developed that takes advantage of a new fluorescent amplification system (Page, B., et al., Anticancer Res. 1998 July-August; 18(4A):2313-6). This approach is sensitive, rapid, and reproducible and may be used advantageously for mixed lymphocyte reaction (MLR). It may easily be further automated for large-scale cytotoxicity testing using cell membrane integrity, and is thus considered. In another fluorometric assay developed for detecting cell-mediated cytotoxicity, the fluorophore used is the non-toxic molecule AlamarBlue (Nociari et al., J. Immunol. Methods, 213(2): 157-167, 1998). The AlamarBlue is fluorescently quenched (i.e., low quantum yield) until mitochondrial reduction occurs, which then results in a dramatic increase in the AlamarBlue fluorescence intensity (i.e., increase in the quantum yield). This assay is reported to be extremely sensitive, specific and requires a significantly lower number of effector cells than the standard $^{51}Cr$ release assay.

Other immune cells that can be induced by the present methods include natural killer cells (NK). NKs are lymphoid cells that lack antigen-specific receptors and are part of the innate immune system. Typically, infected cells are usually destroyed by T cells alerted by foreign particles bound to the cell surface MHC. However, virus-infected cells signal infection by expressing viral proteins that are recognized by antibodies. These cells can be killed by NKs. In tumor cells, if the tumor cells lose expression of MHC I molecules, then it may be susceptible to NKs.

Formulations and Routes for Administration to Patients

Where clinical applications are contemplated, it will be necessary to prepare pharmaceutical compositions—expression constructs, expression vectors, fused proteins, transduced cells, activated T cells, transduced and loaded T cells—in a form appropriate for the intended application. Generally, this will entail preparing compositions that are essentially free of pyrogens, as well as other impurities that could be harmful to humans or animals.

The multimeric ligand, such as, for example, AP1903, may be delivered, for example at doses of about 0.01 to 1 mg/kg subject weight, of about 0.05 to 0.5 mg/kg subject weight, 0.1 to 2 mg/kg subject weight, of about 0.05 to 1.0 mg/kg subject weight, of about 0.1 to 5 mg/kg subject weight, of about 0.2 to 4 mg/kg subject weight, of about 0.3 to 3 mg/kg subject weight, of about 0.3 to 2 mg/kg subject weight, or about 0.3 to 1 mg/kg subject weight, for example, about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight. In some embodiments, the ligand is provided at 0.4 mg/kg per dose, for example at a concentration of 5 mg/mL. Vials or other containers may be provided containing the ligand at, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

One may generally desire to employ appropriate salts and buffers to render delivery vectors stable and allow for uptake by target cells. Buffers also may be employed when recombinant cells are introduced into a patient. Aqueous compositions comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route. This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form is sterile and is fluid to the extent that easy syringability exists. It is stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

The administration schedule may be determined as appropriate for the patient and may, for example, comprise a dosing schedule where the nucleic acid is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

The administration schedule may be determined as appropriate for the patient and may, for example, comprise a dosing schedule where the nucleic acid-transduced T cell or other cell is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

If needed, the method may further include additional leukaphereses to obtain more cells to be used in treatment.

Methods for Treating a Disease

The present methods also encompass methods of treatment or prevention of a disease caused by a hyperproliferative disease.

Preneoplastic or hyperplastic states which may be treated or prevented using the pharmaceutical composition (transduced T cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using the T cell and other therapeutic cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, and activated T cells, transduced and loaded T cells) may be for either "prophylactic" or "therapeutic" purpose. When provided prophylactically, the pharmaceutical composition is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the compositions presented herein may be provided either prior to the anticipated exposure to a disease-causing agent or disease state or after the initiation of the infection or disease. Thus provided herein are methods for prophylactic treatment of solid tumors such as those found in cancer, or for example, but not limited to, prostate cancer, using the nucleic acids and cells discussed herein. For example, methods are provided of prophylactically preventing or reducing the size of a tumor in a subject comprising administering a the nucleic acids or cells discussed herein, whereby the nucleic acids or cells are administered in an amount effect to prevent or reduce the size of a tumor in a subject.

Solid tumors from any tissue or organ may be treated using the present methods, including, for example, any tumor expressing PSA, for example, PSMA, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant myeloma.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation. Thus, for example, in one embodiment, the transduced T cells or other cells are administered to a subject in an amount effective to, for example, induce an immune response, or, for example, to reduce the size of a tumor or reduce the amount of tumor vasculature.

A. Genetic Based Therapies

In certain embodiments, a cell is provided with an expression construct capable of providing recombinant TCR polypeptide, such as the Bob1 TCR polypeptides, in a T cell. The lengthy discussion of expression vectors and the genetic elements employed therein is incorporated into this section by reference. In certain examples, the expression vectors may be viral vectors, such as adenovirus, adeno-associated virus, herpes virus, vaccinia virus, lentivirus, and retrovirus. In another example, the vector may be a lysosomal-encapsulated expression vector.

Gene delivery may be performed in both in vivo and ex vivo situations. For viral vectors, one generally will prepare a viral vector stock. Examples of viral vector-mediated gene delivery ex vivo and in vivo are presented in the present application. For in vivo delivery, depending on the kind of virus and the titer attainable, one will deliver, for example, about 1, 2, 3, 4, 5, 6, 7, 8, or $9\times10^4$, 1, 2, 3, 4, 5, 6, 7, 8, or $9\times10^5$, 1, 2, 3, 4, 5, 6, 7, 8, or $9\times10^8$, 1, 2, 3, 4, 5, 6, 7, 8, or $9\times10^7$, 1, 2, 3, 4, 5, 6, 7, 8, or $9\times10^8$, 1, 2, 3, 4, 5, 6, 7, 8, or $9\times10^9$, 1, 2, 3, 4, 5, 6, 7, 8, or $9\times10^{10}$, 1, 2, 3, 4, 5, 6, 7, 8, or $9\times10^{11}$ or 1, 2, 3, 4, 5, 6, 7, 8, or $9\times10^{12}$ infectious particles to the patient. Similar figures may be extrapolated for liposomal or other non-viral formulations by comparing relative uptake efficiencies. Formulation as a pharmaceutically acceptable composition is discussed below. The multimeric ligand, such as, for example, AP1903, may be delivered, for example at doses of about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight.

B. Cell Based Therapy

Another therapy that is contemplated is the administration of engineered T cells, such as, for example, the administration of transduced T cells. The T cells may be engineered in vitro. Formulation as a pharmaceutically acceptable composition is discussed herein.

In cell based therapies, the engineered cells may be, for example, transduced with retroviral or lentiviral vectors coding for target antigen nucleic acids or transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vectors presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing. The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

In some embodiments, the chemotherapeutic agent may be a lymphodepleting chemotherapeutic. In other examples, the chemotherapeutic agent may be Taxotere (docetaxel), or another taxane, such as, for example, cabazitaxel. The chemotherapeutic may be administered before, during, or after treatment with the cells and inducer. For example, the chemotherapeutic may be administered about 1 year, 11, 10, 9, 8, 7, 6, 5, or 4 months, or 18, 17, 16, 15, 14, 13, 12, 11, 10, 9, 8, 7, 6, 5, 4, 3, 2, weeks or 1 week prior to administering the first dose of activated nucleic acid. Or, for example, the chemotherapeutic may be administered about 1 week or 2, 3, 4, 5, 6, 7, 8, 9, 10, 11, 12, 13, 14, 15, 16, 17, or 18 weeks or 4, 5, 6, 7, 8, 9, 10, or 11 months or 1 year after administering the first dose of cells or inducer.

Administration of a chemotherapeutic agent may comprise the administration of more than one chemotherapeutic agent. For example, cisplatin may be administered in addition to Taxotere or other taxane, such as, for example, cabazitaxel.

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

An effective amount of the modified cell may be determined by a physician, considering the individual patient. Factors to be considered may include, for example, the extent of the disease or condition, tumor size, extent of infection, metastasis, age, and weight. The dosage and number of administrations may be determined by the physician, or other clinician, by monitoring the patient for disease or condition symptoms, and for responses to previous dosages, for example, by monitoring tumor size, or the level or concentration of tumor antigen. In certain examples, the modified cells may be administered at a dosage of $10^4$ to $10^9$ modified cells/kg body weight, $10^5$ to $10^6$, $10^9$-$10^{11}$, or $10^{10}$-$10^{11}$ modified cells/kg body weight.

EXAMPLES

The examples set forth below illustrate certain embodiments and do not limit the technology.

Example 1: Materials and Methods

Isolation of Bob 1-Specific T-Cell Clones Using pMHC-Tetramer

T-cells binding to pMHC-tetramer containing Bob1 peptides were isolated from cryopreserved PBMCs from healthy HLA-A*02:01 and HLA-B*07:02-negative individuals essentially following the protocol provided in (1). Peripheral blood mononuclear cells (PBMCs) were incubated with PE-labeled pMHC-tetramers for 1 hour at 4° C. Cells were washed twice and incubated with anti-PE magnetic microbeads (Miltenyi Biotec, Bergisch Gladbach, Germany). PE-labeled cells were isolated by MACS on a LS column (Miltenyi Biotec) according to the manufacturer's instruction. To obtain Bob1 specific T cell clones, the positive fractions were sorted by staining with PE-labeled pMHC-tetramers containing Bob1 peptides and an antibody against CD8 (Invitrogen/Caltag, Buckingham, UK) combined with antibodies against CD4, CD14, and CD19 (BD Pharmingen, San Jose, Calif., USA). Cells were first stained with PE-labeled pMHC-tetramers for 1 h at 4° C. before antibodies were added for an additional 15 min at 4° C. Single pMHC-tetramer+CD8+ T-cells were sorted into 96-well round-bottom culture plates containing $5\times10^4$ irradiated allogeneic PBMCs in 100 μl T-cell medium supplemented with 0.8 μg/ml PHA. Cell-sorting was performed on a FACSAria III (BD Biosciences, San Jose, Calif., USA). Two weeks after expansion the clones were screened for peptide specific reactivity by measuring the GM-CSF and IFN-γ production after stimulation.

Functional Analysis

Stimulator cells were peptide-pulsed at various peptide concentrations for 30 min at 37° C. Responder T-cells and peptide-pulsed or unloaded stimulator cells were co-incubated at various responder to stimulator ratios. After 18 h co-incubation, supernatants were harvested and IFN-γ production was measured by enzyme-linked immunosorbent assay (ELISA, Sanquin Reagents, Amsterdam, The Netherlands). In addition, responder T cells were stimulated with different primary B-cell malignancies and different hematopoietic and non-hematopoietic cell subsets. Primary HLA-A*0201 and HLA-B*0702 positive chronic lymphocytic leukemia (CLL), acute lymphoblastic leukemia (ALL), mantle cell lymphoma (MCL), and multiple myeloma (MM) were FACS sorted on the basis of their malignant phenotype from cryopreserved PBMCs of HLA-A*02:01 and B*07:02-positive patients at time of diagnosis and highly purified populations (>99%) were used in the stimulation assay. Primary hematopoietic cell subsets were purified from cryopreserved PBMCs of HLA-A*02:01 and B*07:02-positive healthy donors using anti-CD4, anti-CD14, anti-CD19 or anti-CD34 magnetic microbeads (Miltenyi Biotec, Bergisch Gladbach, Germany) according to the manufacturer's instructions. Purity of isolated cells was assessed using FACS analysis and cells were only used in experiments if the purity exceeded 95%. Immature and mature dendritic cells (DCs) were differentiated in vitro from isolated CD14+ cell populations as previously described (2). Activated CD4+ T-cells were generated by stimulating purified CD4+ T-cells with irradiated (35 Gy) PBMCs in a 1:5 ratio in T-cell medium supplemented with 0.8 μg/ml phytohemagglutinin (PHA, Remel, Lenexa, Kans., USA) for 10 days. Activated CD19+ B-cells were generated by co-culturing CD19+ cells on CD40L-transduced irradiated (70 Gy) mouse-fibroblasts for 7 days in IMDM supplemented with 2 ng/ml IL-4 (Schering-Plough, Kenilworth, N.J., USA) and 10% human serum. K562 cells expressing HLA-A2 (K562-A2) were previously described (3). K562 cells expressing HLA-B7 (K562-B7) were generated by retroviral transduction with HLA-B7. Fibroblasts were isolated and cultured as previously described (2). Fibroblasts were cultured in the presence or absence of 200 IU/ml IFN-γ for four days.

Construction of Retroviral Vectors Encoding Bob1 or Encoding Bob1-TCR and Generation of Retroviral Supernatant The POU2AF1 gene encoding for the Bob1 protein was codon-optimized (GeneArt, Life Technologies) and expressed on a MP71 retroviral backbone in combination with NGF-R (see Ruggieri L, et al., Hum Gene Ther. 1997; 8: 1611-1623).

From the Bob1 specific T cell clones mRNA was purified and cDNA was synthesized using TCRα and TCRβ constant region specific oligos. By template switching an oligo was anchored to each 5' cDNA end allowing subsequent TCR V-gene independent amplification of TCRα and TCRβ transcripts. PCR products of single T cell clones were barcoded, pooled and full length reads were generated in a single PacBio NGS run. Codon optimized, cysteine modified Bob1-TCRα and TCRβ chain sequences were cloned into a MP71 retroviral construct, linked by a 2A sequence and coupled to truncated nerve growth factor receptor (NGF-R) by the internal ribosomal entry sequence (IRES sequence), resulting in concordant stoichiometric expression of both TCRαβ-chains and NGF-R. Cysteine modification of Bob1-TCR was performed by introducing a cysteine residue in the constant domains of TCRα and β chains at positions 48 and 57, respectively. Codon optimization (CO) of the Bob1-TCR was performed by GENESCRIPT®. The same MP71 retroviral vector backbone encoding the HA1-TCR is used in our recent clinical study (4).

For retrovirus production, Phoenix-A cells were plated at $4\times10^4$ cells/$cm^2$ in T25 flasks. After 24 h, cells were transfected with 4 μg retroviral vector DNA and 2 μg M57 vector DNA using Fugene HD transfection reagent (Roche, Basel, Switzerland). Supernatant containing retroviral particles was harvested at 48 h and 72 h post transfection and stored at −80° C.

For transduction, retroviral supernatant was loaded on 24-well non-tissue-culture treated plates which had been coated with 30 μg/ml retronectine (Takara, Shiga, Japan) and blocked with 2% human serum albumin (Sanquin Reagents). Viral supernatant was spun down at 2,000 g for 20 min at 4° C. $1\times10^5$-$3\times10^5$ cells were added to retroviral supernatant and incubated for 18 h. High purity bulk Bob1-transduced K562-A2 and K562-B7 cell populations were obtained by sorting cells stained with an antibody against NGF-R. Bob1-TCR transduced CD8+ T cells were analyzed for tetramer staining and functional activity without additional sorting.

Cell Lines

Multiple myeloma cell-lines UM9 and U266, B-LCL-JY, and two ALL cell-lines ALL-BV and ALL-VG, as discussed herein, may be used to determine if the modified cells react against Bob1 in cytokine secretion assays and cytotoxicity assays.

Cells are maintained in complete IMDM (Sigma, St Louis, Mo.) containing 10% fetal bovine serum (Hyclone, Waltham, Mass.), and 2 mM L-glutamine in a humidified atmosphere containing 5% carbon dioxide (CO2) at 37° C. Bob1-TCR transduced T cells and PHA blasts are maintained in Cellgenix DC (Cellgenix) media supplemented with 100 U/ml IL-2 (Cellgenix)

Activation of T Cells

Activation of T cells for expansion and transduction is performed using soluble αCD3 and αCD28 (Miltenyi Biotec, Auburn, Calif.). PBMCs are resuspended in Cellgenix DC media supplemented with 100 U/ml IL-2 (Cellgenix) at $1\times10^6$ cells/ml and stimulated with 0.2 μg/ml αCD3 and 0.5 μg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

REFERENCE LIST

1. Hombrink, P., C. Hassan, M. G. Kester, A. H. de Ru, C. A. van Bergen, H. Nijveen, J. W. Drijfhout, J. H. Falkenburg, M. H. Heemskerk, and P. A. van Veelen. 2013. Discovery of T cell epitopes implementing HLA-peptidomics into a reverse immunology approach. J. Immunol. 190:3869-3877.
2. Amir, A. L., D. M. van der Steen, M. M. van Loenen, R. S. Hagedoorn, B. R. de, M. D. Kester, A. H. de Ru, G. J. Lugthart, K. C. van, P. S. Hiemstra, I. Jedema, M. Griffioen, P. A. van Veelen, J. H. Falkenburg, and M. H. Heemskerk. 2011. PRAME-specific Allo-HLA-restricted T cells with potent antitumor reactivity useful for therapeutic T-cell receptor gene transfer. Clin. Cancer Res. 17:5615-5625.
3. Heemskerk, M. H., R. A. de Paus, E. G. Lurvink, F. Koning, A. Mulder, R. Willemze, J. J. van Rood, and J. H. Falkenburg. 2001. Dual HLA class I and class II restricted recognition of alloreactive T lymphocytes mediated by a single T cell receptor complex. Proc. Natl. Acad. Sci. U.S.A 98:6806-6811.
4. van Loenen, M. M., B. R. de, L. E. van, P. Meij, I. Jedema, J. H. Falkenburg, and M. H. Heemskerk. 2014. A Good Manufacturing Practice procedure to engineer donor virus-specific T cells into potent anti-leukemic effector cells. Haematologica 99:759-768.

Example 2: Isolation of High Affinity Bob1 Specific TCRs from the Allo-HLA Repertoire The isolation of high avidity T-cells specific for non-polymorphic tumor-associated or tissue specific self-antigens is challenging because of self-tolerance. T-cells that exhibit high avidity for self-antigens presented by self-HLA are eliminated by negative selection during thymic development to prevent autoimmunity. As tolerance induction requires presentation of a given self-polypeptide by self-HLA, any polypeptide is a potential immunogen when presented in the context of a foreign HLA molecule. A complex of a common HLA molecule and a polypeptide derived from a protein with cell type-restricted or tumor specific expression could thus be a useful therapeutic target shared by many individuals. The present examples provide a strategy that allows isolation of antigen-specific T cells from the allo-HLA repertoire.

The Bob1 gene locus (POU2AF1) is a target of amplification in multiple myeloma, providing growth and survival benefit. Targeting a gene essential for the malignant proliferation could prevent the occurrence of escape variants. A protocol is developed in the following examples to identify high-affinity TCRs of therapeutic relevance targeting B-cell specific antigens. The use of a Bob1-TCR could broaden the application of immunotherapies targeting multiple myeloma as well as other malignant B-cell malignancies.

Figure 3:
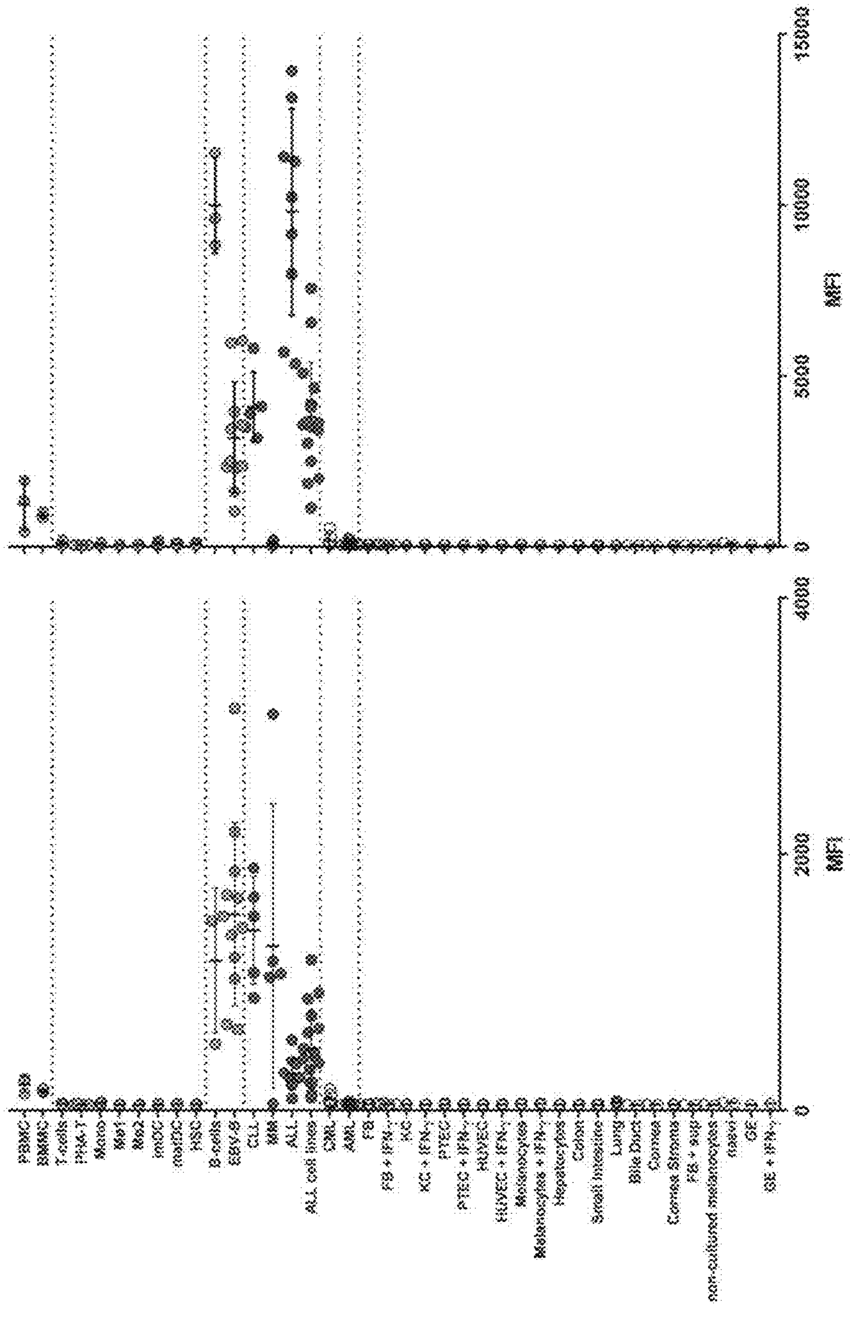
FIG. 3 is a micro-array analysis of hematopoietic malignant and non-malignant cell-subsets, and healthy non-hematopoietic cells.

A set of 15,000 eluted polypeptides present in an HLA polypeptide elution database, derived from 4 different HLA typed EBV-LCLs, was matched with a recently established microarray expression analysis system to generate a set of bona fide B-cell specific epitopes derived from both extracellular and intracellular proteins, and the top 18 high affinity HLA-A*02:01 and B*07:02 binding candidates were selected for further assessment. In FIG. 3 the microarray analysis of one representative extracellular (CD19) and one intracellular protein (Bob1) is shown. Micro-array analysis of highly purified hematopoietic malignant and non-malignant cell-subsets as well as healthy non-hematopoietic cells. FIG. 3 (left) Illumina HT-12 expression array of the POU2AF1 gene encoding for the transcription factor Bob1. FIG. 3 (right) Illumina HT-12 expression array of CD19.

The set of B-cell specific epitopes included 4 epitopes derived from Bob1, 3 binding to HLA-B*0702 and 1 binding to HLA-A*0201 (Table 1).

TABLE 1

Sequences and properties of BOB1 derived peptides.

| | Peptide sequence | HLA-restriction | netMHC affinity (nM)* |
|---|---|---|---|
| $BOB1_{245}$ | YALNHTLSV (SEQ ID NO: 119) | A*0201 | 15 |
| $BOB1_{197}$ | APALPGPQF (SEQ ID NO: 124) | B*0702 | 23 |
| $BOB1_{44}$ | APAPTAVVL (SEQ ID NO: 118) | B*0702 | 15 |

TABLE 1-continued

Sequences and properties of BOB1 derived peptides.

| | Peptide sequence | HLA-restriction | netMHC affinity (nM)* |
|---|---|---|---|
| $BOB1_{14}$ | APARPYQGV (SEQ ID NO: 125) | B*0702 | 49 |

*netMHC server 3.4

The set of polypeptides was first used for generation of HLA-tetramers by UV-mediated exchange technology. Peripheral blood mononuclear cells (PBMCs) ($0.5\text{-}1\times10^9$ cells) from six different HLA-A*02:01 and B*07:02 negative healthy donors were incubated with the mixture of HLA-tetramers, and by magnetic activated cell sorting (MACS) the HLA-tetramer positive T-cells were isolated. Subsequently, thousands of T-cell clones were generated by sorting the HLA-tetramer positive T-cells by fluorescence activated cell sorting (FACS) single cell per well.

Figure 4A:
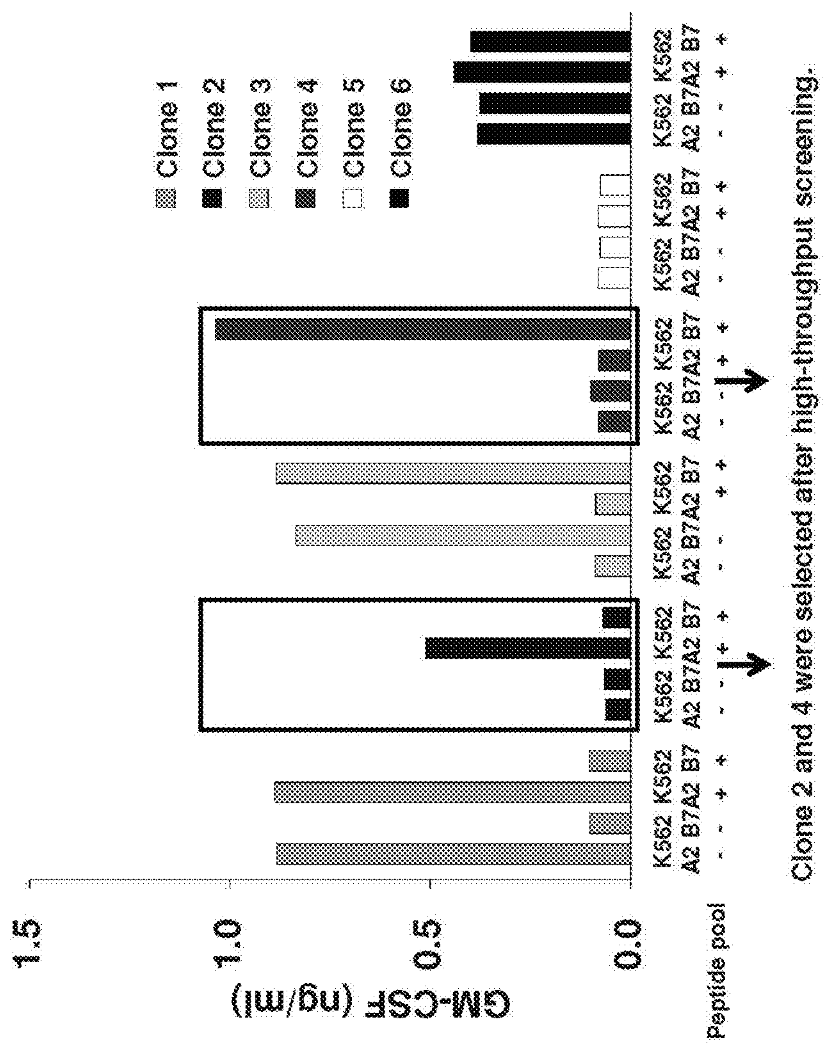
FIG. 4A is a bar graph.
Figure 4B:
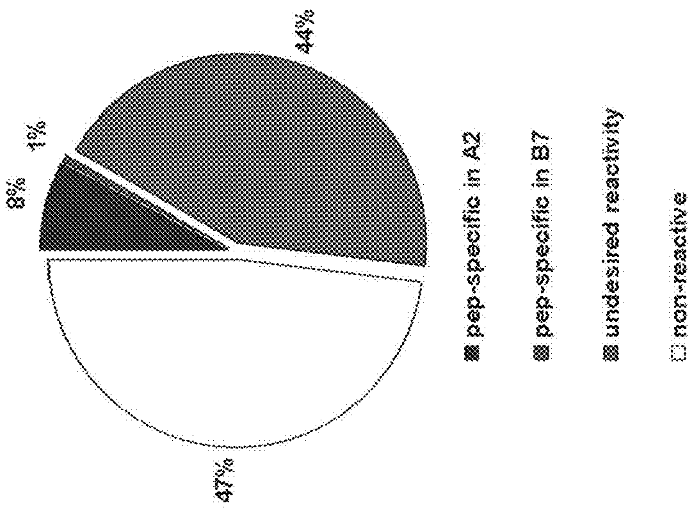
FIG. 4B is a pie chart graph of high-throughput screening of single cell sorted tetramer positive T cell clones.

By a high throughput method the approximately 5000 expanding T-cell clones were analyzed for B-cell specific polypeptide reactivity by stimulating all T-cell clones with K562-A2 unloaded or loaded with A2 binding polypeptide mixture and K562-B7 unloaded or loaded with B7 binding polypeptide mixture. All T-cell clones that exhibited a polypeptide specific reactivity pattern, either reactive against polypeptide loaded K562-A2 or polypeptide loaded K562-B7, and not reactive against unloaded K562-A2/B7 were selected and frozen (FIG. 4A). Of the 5000 expanding T-cell clones approximately 350 clones exhibited a polypeptide specific recognition pattern, and a high diversity was demonstrated in the TCR repertoire of these selected HLA-tetramer positive T-cell clones. The other 4650 T-cell clones were either non-reactive or demonstrated polypeptide independent recognition of either K562-A2 or K562-B7 (FIG. 4B). Within the pool of 350 allo-HLA restricted T-cell clones, polypeptide specific T-cell clones were identified for almost every B-lineage specific polypeptide. The number of different T-cell clones against one specific polypeptide ranged from two T-cell clones specific for one of the HLA-B*07:02 binding polypeptides to 217 T-cell clones specific for an HLA-A*02:01 binding polypeptide.

Figure 5B:
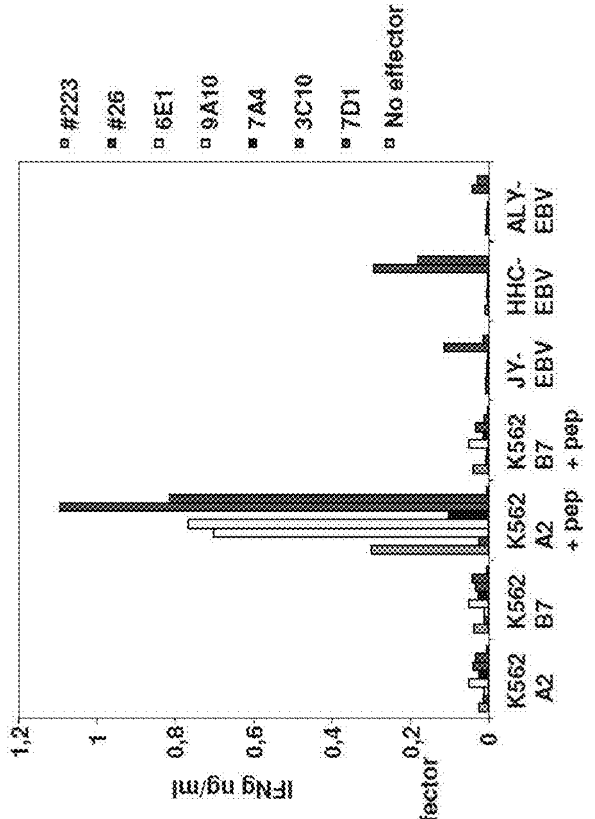
FIG. 5A is a line graph and FIG. 5B is a bar graph of variable avidity of Bob1 specific T cell clones.
Figure 5A:
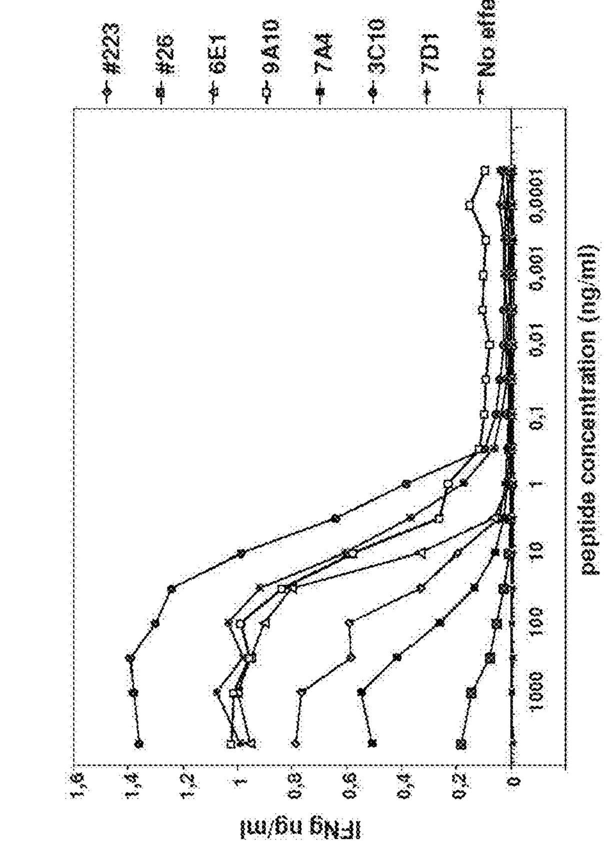
Figure 6:
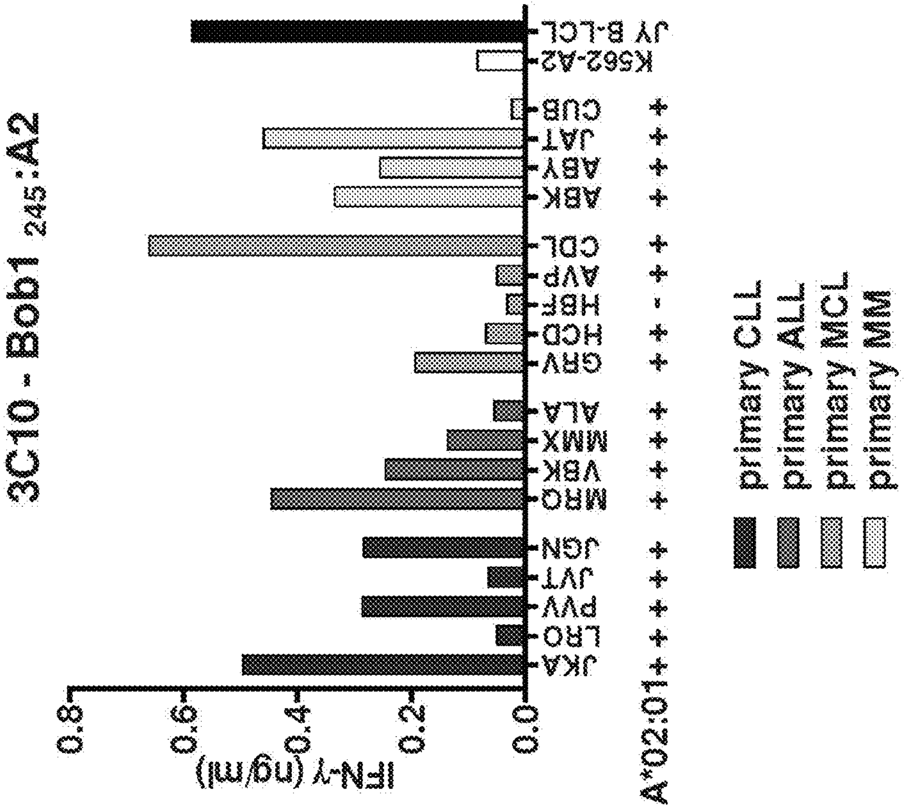
FIG. 6 is a bar graph of recognition of B cell malignancies by clone 3C10.

Within the pool of T-cell clones, high avidity T-cell clones were identified that were directed against two different epitopes derived from the intracellular expressed transcription factor Bob1, that is encoded by the gene POU2AF1. T-cell clones derived from 4 different healthy individuals and with a diverse TCRαβ repertoire were tested against K562-A2 loaded with titrated concentrations of Bob1 polypeptide. T cell clones with variable avidity were identified that were directed against the HLA-A*0201 epitope YALNHTLSV (SEQ ID NO: 119) of Bob1 (FIG. 5A). All seven Bob1 tetramer positive T cell clones were tested against K562-A2, K562-B7 unloaded or loaded with Bob1 polypeptide, and three HLA-A*0201 positive EBV-LCLs (JY-EBV, HHC-EBV, and ALY-EBV). The high avidity clones 3C10 and 7D1 exerted specific reactivity against the EBV-LCLs that endogenously present the Bob1 in the context of HLA-A*0201. Clone 3C10 exerted the highest reactivity against the three EBV-LCLs that endogenously processed and presented the Bob1 polypeptide in the context of HLA-A*0201 (FIG. 5B). This T-cell clone was tested against different primary HLA-A*0201 positive B-cell malignancies, including acute lymphoblastic leukemia (ALL), chronic lymphoblastic leukemia (CLL), mantle cell lymphoma (MCL) as well as multiple myeloma (MM). FIG. 6 shows the recognition of B-cell malignancies by clone 3C10. The HLA-A2 restricted Bob1 specific T cell clone 3C10 was tested against different primary HLA-A*0201 positive chronic lymphocytic leukemia (CLL), acute lymphoblastic leukemia (ALL), mantle cell lymphoma (MCL), and multiple myeloma (MM), and as positive control HLA-A*0201 positive EBV-LCLs, and as negative control the HLA-A*0201 positive K562 that is negative for Bob1. 18 h after stimulation the production of IFN-γ was measured. The B-cell malignancies were FACS sorted on the basis of their malignant phenotype and highly purified populations (>99%) were used in the stimulation assay. These results indicate that the avidity of these T-cell clones was high enough to exhibit reactivity towards these primary malignant cells.

Next, three different T cell clones were isolated based on difference in TCR VR that were specific for the Bob1 polypeptide APAPTAVVL (SEQ ID NO: 118) presented in HLA-B*07:02. FIG. 7 assesses whether the Bob1-reactive clone efficiently recognizes various primary B-cell malignancies, with a strict B-cell specific recognition pattern. A) The high avidity Bob1 specific T cell clone (4G11) was tested against primary HLA-B*0702 positive chronic lymphocytic leukemia (CLL), acute lymphoblastic leukemia (ALL), mantle cell lymphoma (MCL), and multiple myeloma, and as positive control EBV-LCLs, 18 h after stimulation the production of IFN-γ was measured.

Figures 7A, 7B, 7C:
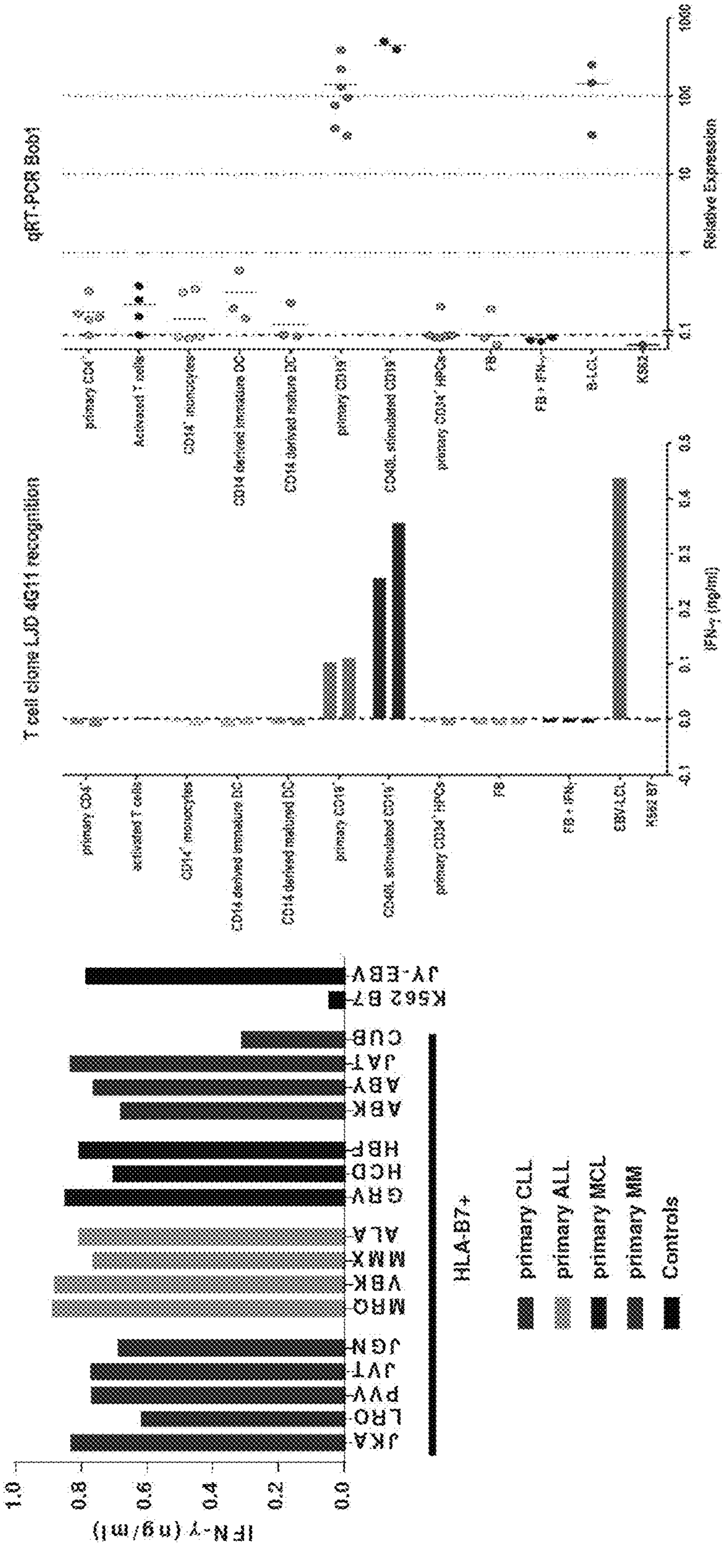
FIG. 7B is a bar graph.
FIG. 7C is a microarray analysis, which show the results of quantitative RT-PCR showing that the Bob1-reactive clone 4G11 efficiently recognizes primary B cell malignancies.

The B-cell malignancies were FACsorted on the basis of their malignant phenotype and highly purified populations (>99%) were used in the stimulation assay. B) The 4G11 clone was tested against purified CD3+, CD14+, CD19+, and CD34+ cell-subsets, as well as activated CD3+ cells and CD14+ cells differentiated into immature and mature DCs derived from 2 different HLA-A*02 positive healthy individuals. Fibroblasts were with or without IFN-γ treatment analyzed. C) Quantitative RT-PCR was performed on the same cell populations as indicated in B. All these cell subsets are derived from minimally 3 different healthy individuals. Of these 3 T-cell clones, clone 4G11 exhibited a high avidity Bob1 specific reactivity profile, demonstrated by polypeptide titration and recognition of HLA-B*0702 positive EBV-LCLs. In addition, clone 4G11 exerted high reactivity towards HLA-B*0702 positive primary CLL, ALL, MCL as well as MM (FIG. 7A). All the different malignant cell populations were sorted on the basis of their malignant phenotype, to exclude that the contaminating B-cells were responsible for triggering of the T-cells. To investigate the safety profile of the Bob1 specific T-cell clone, clone 4G11 was tested against HLA-B*0702 positive healthy hematopoietic and non-hematopoietic cell subsets. As demonstrated in FIG. 7B clone 4G11 is not reactive against the healthy non-B-cell lineages, including activated and non-activated T-cells, monocytes, DC and CD34+ hematopoietic stem cells. Reactivity towards fibroblasts even under inflamed conditions was in addition absent (FIG. 7B). Clone 4G11's recognition pattern strictly followed Bob1 gene expression measured by quantitative RT-PCR (FIG. 7C).

Bob1 epitopes binding to other HLA alleles are identified by performing additional elution experiments. The epitopes are confirmed by comparing the mass spectrometry patterns with the respective synthetic polypeptides (Table 2).

TABLE 2

Sequences and properties of Bob1 derived polypeptides.

| Location | polypeptide sequence | HLA restrict. | netMHC affinity (nM) |
|---|---|---|---|
| Bob1 44 | APAPTAVVL (SEQ ID NO: 118) | B*3501 | 196 |
| Bob1 52 | LPHQPLATY (SEQ ID NO: 126) | B*3501 | 6 |
| Bob1 133 | YVQPVcPSY (SEQ ID NO: 127) | A*2902 | 7 |
| Bob1 12 | APAPARPYQGV (SEQ ID NO: 128) | B*0702 | 27 |
| Bob1 168 | TPAVGPPL (SEQ ID NO: 129) | B*0702 | 410 |

Example 3: Cloning of Bob1 TCRs

The T cell receptors expressed by the 3C10 and 4G11 clones were sequenced. The sequence of the TCR derived from the highest avidity T-cell clone 3C10 specific for the Bob1 polypeptide presented in the context of HLA-A*0201 is presented in FIG. 8. AV13-1*01 represents the complete TCRα polypeptide. BV12-4*01 represents the complete TCRβ polypeptide. The sequence of the TCR derived from the high avidity Bob1 specific HLA-B*0702 restricted T cell clone is shown in FIG. 9. TRAV13-1*01 represents the complete TCRα polypeptide. TRBV4-1*-1 represents the complete TCRβ polypeptide.

Figure 10B:
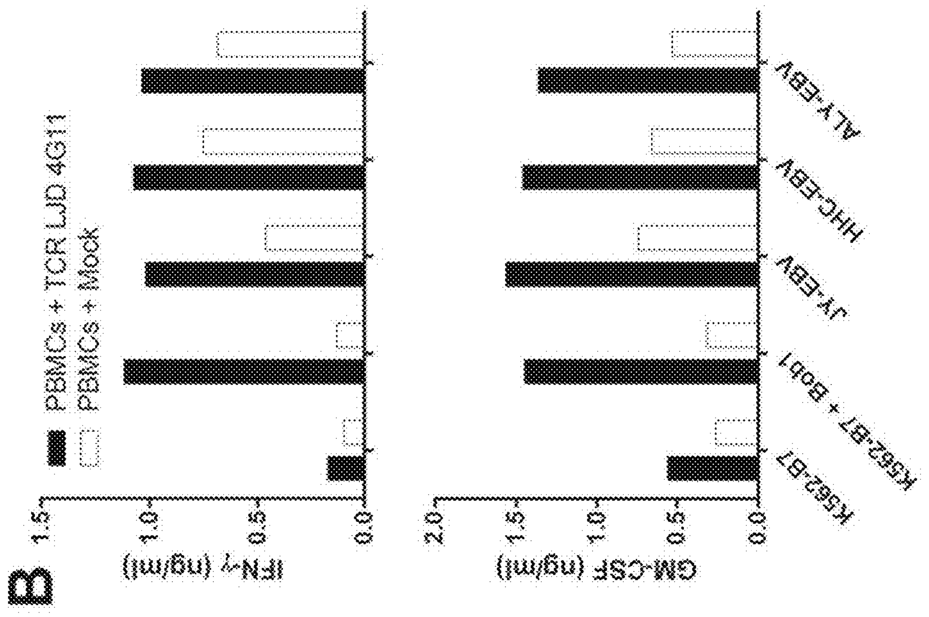
FIG. 10A provides four FACs plots and FIG. 10B provides two bar graphs, which show that the Bob1-TCR transduced $CD8^+$ T cells derived from peripheral blood have a Bob1 specific recognition pattern.
Figure 10A:
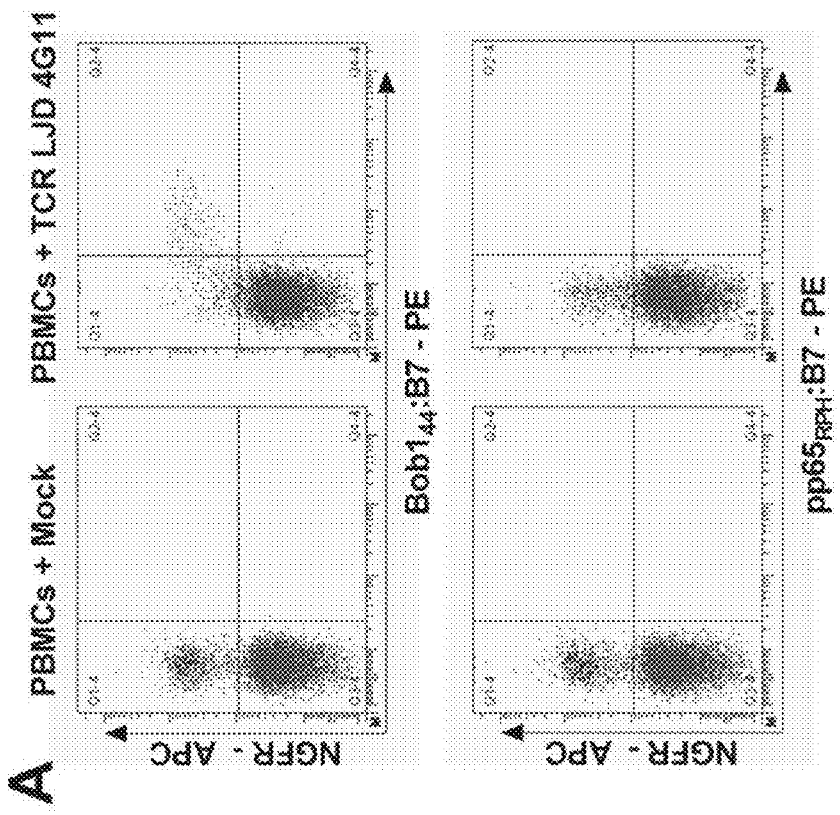

Because the T cell cloning experiments demonstrated that the HLA-B7 restricted T cell clone 4G11 exerts the most potent reactivity against the primary B cell malignancies, a retroviral vector was constructed that encoded the Bob1 specific HLA-B7 restricted TCR of 4G11, and used to transduce peripheral blood T cells. In FIG. 10, gene transfer of a codon optimized cysteine modified Bob1 specific TCR demonstrates specific Bob1 tetramer staining of the transduced CD8+ T cells (FIG. 10A), and in addition the transduced T cells exert a Bob1 polypeptide specific recognition pattern (FIG. 10B). FIG. 10. The Bob1-TCR transduced CD8+ T cells derived from peripheral blood have a Bob1 specific recognition pattern. A) Peripheral T cells were transduced with retroviral supernatant encoding for the Bob1-TCR in combination with truncated NGFR or with a retroviral supernatant encoding for only the truncated NGFR (mock) as a control. After 8 days the T cells were stained with anti-NGFR, anti-CD8 and either the Bob1-tetramer or a pp65 control tetramer. The CD8+ T cells are gated and shown in the dotplots. B). Transduced T cells were tested against K562 transduced with HLA-B7 (K562-B7) and Bob1 polypeptide loaded K562-B7. In addition, the transduced T cells were tested against the HLA-B*0702 positive EBV-LCLs (JY-EBV, HHC-EBV, and ALY-EBV) from which the different Bob1 polypeptides were eluted. FIGS. 11*a* and 11*b* provide the sequence of an example of a retroviral (MP71) multiple cloning site vector (SEQ ID NO: 49). The Bob1 TCR-encoding DNA may be inserted at approximately nucleotides 1106 till 1130.

Example 4: Examples of Bob1 Sequences

Provided herein are amino acid and nucleotide sequences of Bob1 TCR clones.

Bob1 4G11

α CDR3 AA

SEQ ID NO: 1

CAASKGSSNTGKLIFGQGTTLQVKP

α CDR3 NT

SEQ ID NO: 2

TGTGCAGCAAGTAAGGGCTCTAGCAACACAGGCAAACTAATCTTTGGGCA
AGGGACAACTTTACAAGTAAAACCA

α CDR3 NT codon-optimized*

SEQ ID NO: 3

TGCGCCGCTTCTAAGGGGTCCTCTAACACCGGAAAACTGATCTTCGGCCA
GGGGACCACACTGCAGGTGAAGCCT

β CDR3 AA

SEQ ID NO: 4

CASSHGPASYEQYFGPGTRLTVT

β CDR3 NT

SEQ ID NO: 5

TGCGCCAGCAGCCACGGCCCTGCTTCCTACGAGCAGTACTTCGGGCCGGG
CACCAGGCTCACGGTCACA

β CDR3 NT codon-optimized

SEQ ID NO: 6

TGCGCCTCTAGTCACGGGCCAGCCTCTTACGAGCAGTATTTTGGACCCGG
CACCAGACTGACTGTGACC

α VJ AA

SEQ ID NO: 7

MTSIRAVFIFLWLQLDLVNGENVEQHPSTLSVQEGDSAVIKCTYSDSASN
YFPWYKQELGKGPQLIIDIRSNVGEKKDQRIAVTLNKTAKHFSLHITETQ
PEDSAVYFCAASKGSSNTGKLIFGQGTTLQVKP

α VJ NT

SEQ ID NO: 8

ATGACATCCATTCGAGCTGTATTTATATTCCTGTGGCTGCAGCTGGACTT

GGTGAATGGAGAGAATGTGGAGCAGCATCCTTCAACCCTGAGTGTCCAGG

AGGGAGACAGCGCTGTTATCAAGTGTACTTATTCAGACAGTGCCTCAAAC

TACTTCCCTTGGTATAAGCAAGAACTTGGAAAAGGACCTCAGCTTATTAT

AGACATTCGTTCAAATGTGGGCGAAAAGAAAGACCAACGAATTGCTGTTA

CATTGAACAAGACAGCCAAACATTTCTCCCTGCACATCACAGAGACCCAA

CCTGAAGACTCGGCTGTCTACTTCTGTGCAGCAAGTAAGGGCTCTAGCAA

CACAGGCAAACTAATCTTTGGGCAAGGGACAACTTTACAAGTAAAACCA

α VJ NT codon-optimized

SEQ ID NO: 9

ATGACAAGCATCAGAGCCGTGTTCATTTTTCTGTGGCTGCAGCTGGATCT

GGTGAACGGAGAGAATGTCGAACAGCATCCTTCAACTCTGAGCGTGCAGG

AGGGCGATTCCGCAGTCATCAAGTGTACCTACTCAGACAGCGCCTCCAAT

TACTTTCCTTGGTATAAGCAGGAGCTGGGGAAAGGACCACAGCTGATCAT

TGATATCAGAAGCAACGTGGGCGAAAAGAAAGACCAGAGGATTGCTGTCA

CACTGAATAAGACTGCAAAACACTTCAGCCTGCATATTACAGAGACTCAG

CCCGAAGACTCCGCCGTGTATTTTTGCGCCGCTTCTAAGGGGTCCTCTAA

CACCGGAAAACTGATCTTCGGCCAGGGGACCACACTGCAGGTGAAGCCT

β VDJ AA

SEQ ID NO: 10

MGCRLLCCAVLCLLGAVPIDTEVTQTPKHLVMGMTNKKSLKCEQHMGHRA
MYWYKQKAKKPPELMFVYSYEKLSINESVPSRFSPECPNSSLLNLHLHAL
QPEDSALYLCASSHGPASYEQYFGPGTRLTVT

-continued

β VDJ NT

SEQ ID NO: 11

ATGGGCTGCAGGCTGCTCTGCTGTGCGGTTCTCTGTCTCCTGGGAGCAGT
TCCCATAGACACTGAAGTTACCCAGACACCAAAACACCTGGTCATGGGAA
TGACAAATAAGAAGTCTTTGAAATGTGAACAACATATGGGGCACAGGGCT
ATGTATTGGTACAAGCAGAAAGCTAAGAAGCCACCGGAGCTCATGTTTGT
CTACAGCTATGAGAAACTCTCTATAAATGAAAGTGTGCCAAGTCGCTTCT
CACCTGAATGCCCCAACAGCTCTCTCTTAAACCTTCACCTACACGCCCTG
CAGCCAGAAGACTCAGCCCTGTATCTCTGCGCCAGCAGCCACGGCCCTGC
TTCCTACGAGCAGTACTTCGGGCCGGGCACCAGGCTCACGGTCACA

β VDJ NT codon-optimized

SEQ ID NO: 12

ATGGGATGTAGACTGCTGTGCTGTGCTGTGCTGTGCCTGCTGGGGG
CTGTGCCTATTGATACCGAAGTGACTCAGACTCCAAAGCACCTGGT
CATGGGCATGACCAACAAGAAAAGCCTGAAATGCGAGCAGCACATG
GGGCATAGGGCCATGTACTGGTATAAGCAGAAAGCTAAGAAACCCC
CTGAACTGATGTTCGTGTACAGCTATGAGAAGCTGTCCATCAATGA
ATCCGTCCCCTCTCGCTTCAGTCCCGAGTGCCCTAACAGCTCCCTG
CTGAATCTGCACCTGCATGCTCTGCAGCCTGAAGACTCCGCACTGT
ACCTGTGCGCCTCTAGTCACGGGCCAGCCTCTTACGAGCAGTATTT
TGGACCCGGCACCAGACTGACTGTGACC

α VJ and constant AA

SEQ ID NO: 13

MTSIRAVFIFLWLQLDLVNGENVEQHPSTLSVQEGDSAVIKCTYSD
SASNYFPWYKQELGKGPQLIIDIRSNVGEKKDQRIAVTLNKTAKHF
SLHITETQPEDSAVYFCAASKGSSNTGKLIFGQGTTLQVKPDIQNP
DPAVYQLRDSKSSDKSVCLFTDFDSQTNVSQSKDSDVYITDKCVLD
MRSMDFKSNSAVAWSNKSDFACANAFNNSIIPEDTFFPSPESSCDV
KLVEKSFETDTNLNFQNLSVIGFRILLLKVAGFNLLMTLRLWSS

α VJ and constant (murine) AA

SEQ ID NO: 14

MTSIRAVFIFLWLQLDLVNGENVEQHPSTLSVQEGDSAVIKCTYS
DSASNYFPWYKQELGKGPQLIIDIRSNVGEKKDQRIAVTLNKTAK
HFSLHITETQPEDSAVYFCAASKGSSNTGKLIFGQGTTLQVKPDI
QNPEPAVYQLKDPRSQDSTLCLFTDFDSQINVPKTMESGTFITDK
CVLDMKAMDSKSNGAIAWSNQTSFTCQDIFKETNATYPSSDVPCD
ATLTEKSFETDMNLNFQNLSVMGLRILLLKVAGFNLLMTLRLWSS

α VJ and constant NT

SEQ ID NO: 15

ATGACATCCATTCGAGCTGTATTTATATTCCTGTGGCTGCAGCTG
GACTTGGTGAATGGAGAGAATGTGGAGCAGCATCCTTCAACCCTG
AGTGTCCAGGAGGGAGACAGCGCTGTTATCAAGTGTACTTATTCA
GACAGTGCCTCAAACTACTTCCCTTGGTATAAGCAAGAACTTGGA
AAAGGACCTCAGCTTATTATAGACATTCGTTCAAATGTGGGCGAA
AAGAAAGACCAACGAATTGCTGTTACATTGAACAAGACAGCCAAA
CATTTCTCCCTGCACATCACAGAGACCCAACCTGAAGACTCGGCT
GTCTACTTCTGTGCAGCAAGTAAGGGCTCTAGCAACACAGGCAAA
CTAATCTTTGGGCAAGGGACAACTTTACAAGTAAAACCAGATATC
CAGAACCCTGACCCTGCCGTGTACCAGCTGAGAGACTCTAAATCC
AGTGACAAGTCTGTCTGCCTATTCACCGATTTTGATTCTCAAACA
AATGTGTCACAAAGTAAGGATTCTGATGTGTATATCACAGACAAA
TGCGTGCTAGACATGAGGTCTATGGACTTCAAGAGCAACAGTGCT
GTGGCCTGGAGCAACAAATCTGACTTTGCATGTGCAAACGCCTTC
AACAACAGCATTATTCCAGAAGACACCTTCTTCCCCAGCCCAGAA
AGTTCCTGTGATGTCAAGCTGGTCGAGAAAAGCTTTGAAACAGAT
ACGAACCTAAACTTTCAAAACCTGTCAGTGATTGGGTTCCGAATC
CTCCTCCTGAAAGTGGCCGGGTTTAATCTGCTCATGACGCTGCGG
TTGTGGTCCAGC

α VJ and constant NT codon-optimized

SEQ ID NO: 16

ATGACAAGCATCAGAGCCGTGTTCATTTTTCTGTGGCTGCAGCTG
GATCTGGTGAACGGAGAGAATGTCGAACAGCATCCTTCAACTCTG
AGCGTGCAGGAGGGCGATTCCGCAGTCATCAAGTGTACCTACTCA
GACAGCGCCTCCAATTACTTTCCTTGGTATAAGCAGGAGCTGGGG
AAAGGACCACAGCTGATCATTGATATCAGAAGCAACGTGGGCGAA
AAGAAAGACCAGAGGATTGCTGTCACACTGAATAAGACTGCAAAA
CACTTCAGCCTGCATATTACAGAGACTCAGCCCGAAGACTCCGCC
GTGTATTTTTGCGCCGCTTCTAAGGGGTCCTCTAACACCGGAAAA
CTGATCTTCGGCCAGGGGACCACACTGCAGGTGAAGCCTGACATT
CAGAATCCAGATCCCGCCGTCTACCAGCTGCGAGACTCAAAGAGT
TCAGATAAAAGCGTGTGCCTGTTCACCGACTTTGATAGCCAGACA
AACGTGTCTCAGAGTAAGGACTCCGACGTGTACATCACCGACAAA
TGCGTGCTGGATATGCGCAGCATGGACTTCAAGAGCAACAGCGCC
GTGGCATGGTCCAACAAGTCTGATTTCGCCTGCGCTAACGCCTTC
AACAATTCTATCATTCCCGAGGATACATTCTTTCCTAGTCCAGAA
AGCTCCTGTGACGTGAAGCTGGTCGAGAAAAGTTTCGAAACCGAT
ACAAACCTGAATTTTCAGAATCTGTCCGTGATCGGCTTCCGGATT
CTGCTGCTGAAAGTGGCTGGGTTTAATCTGCTGATGACTCTGAGA
CTGTGGTCCTCC

SEQ ID NO: 17

Reserved

α VJ and constant (murine) NT codon-optimized

SEQ ID NO: 18

ATGACAAGCATCAGAGCCGTGTTCATTTTTCTGTGGCTGCAGCTG
GATCTGGTGAACGGAGAGAATGTCGAACAGCATCCTTCAACTCTG
AGCGTGCAGGAGGGCGATTCCGCAGTCATCAAGTGTACCTACTCA
GACAGCGCCTCCAATTACTTTCCTTGGTATAAGCAGGAGCTGGGG
AAAGGACCACAGCTGATCATTGATATCAGAAGCAACGTGGGCGAA

-continued

AAGAAAGACCAGAGGATTGCTGTCACACTGAATAAGACTGCAAAA
CACTTCAGCCTGCATATTACAGAGACTCAGCCCGAAGACTCCGCC
GTGTATTTTTGCGCCGCTTCTAAGGGGTCCTCTAACACCGGAAAA
CTGATCTTCGGCCAGGGGACCACACTGCAGGTGAAGCCTGACATT
CAGAACCCGGAACCGGCTGTATACCAGCTGAAGGACCCCCGATCT
CAGGATAGTACTCTGTGCCTGTTCACCGACTTTGATAGTCAGATC
AATGTGCCTAAAACCATGGAATCCGGAACTTTTATTACCGACAAG
TGCGTGCTGGATATGAAAGCCATGGACAGTAAGTCAAACGGCGCC
ATCGCTTGGAGCAATCAGACATCCTTCACTTGCCAGGATATCTTC
AAGGAGACCAACGCAACATACCCATCCTCTGACGTGCCCTGTGAT
GCCACCCTGACAGAGAAGTCTTTCGAAACAGACATGAACCTGAAT
TTTCAGAATCTGAGCGTGATGGGCCTGAGAATCCTGCTGCTGAAG
GTCGCTGGGTTTAATCTGCTGATGACACTGCGGCTGTGGTCCTCA

β VJ and constant AA

SEQ ID NO: 19

MGCRLLCCAVLCLLGAVPIDTEVTQTPKHLVMGMTNKKSLKCEQH
MGHRAMYWYKQKAKKPPELMFVYSYEKLSINESVPSRFSPECPNS
SLLNLHLHALQPEDSALYLCASSHGPASYEQYFGPGTRLTVTEDL
KNVFPPEVAVFEPSEAEISHTQKATLVCLATGFYPDHVELSWWVN
GKEVHSGVCTDPQPLKEQPALNDSRYCLSSRLRVSATFWQNPRNH
FRCQVQFYGLSENDEWTQDRAKPVTQIVSAEAWGRADCGFTSESY
QQGVLSATILYEILLGKATLYAVLVSALVLMAMVKRKDSRG

β VJ and constant (murine) AA

SEQ ID NO: 20

MGCRLLCCAVLCLLGAVPIDTEVTQTPKHLVMGMTNKKSLKCEQH
MGHRAMYWYKQKAKKPPELMFVYSYEKLSINESVPSRFSPECPNS
SLLNLHLHALQPEDSALYLCASSHGPASYEQYFGPGTRLTVTEDL
RNVTPPKVSLFEPSKAEIANKQKATLVCLARGFFPDHVELSWWVN
GKEVHSGVCTDPQAYKESNYSYCLSSRLRVSATFWHNPRNHFRCQ
VQFHGLSEEDKWPEGSPKPVTQNISAEAWGRADCGITSASYHQGV
LSATILYEILLGKATLYAVLVSGLVLMAMVKKKNS

β VJ and constant NT

SEQ ID NO: 21

ATGGGCTGCAGGCTGCTCTGCTGTGCGGTTCTCTGTCTCCTGGGA
GCAGTTCCCATAGACACTGAAGTTACCCAGACACCAAAACACCTG
GTCATGGGAATGACAAATAAGAAGTCTTTGAAATGTGAACAACAT
ATGGGGCACAGGGCTATGTATTGGTACAAGCAGAAAGCTAAGAAG
CCACCGGAGCTCATGTTTGTCTACAGCTATGAGAAACTCTCTATA
AATGAAAGTGTGCCAAGTCGCTTCTCACCTGAATGCCCCAACAGC
TCTCTCTTAAACCTTCACCTACACGCCCTGCAGCCAGAAGACTCA
GCCCTGTATCTCTGCGCCAGCAGCCACGGCCCTGCTTCCTACGAG
CAGTACTTCGGGCCGGGCACCAGGCTCACGGTCACAGAGGACCTG
AAAAACGTGTTCCCACCCGAGGTCGCTGTGTTTGAGCCATCAGAA
GCAGAGATCTCCCACACCCAAAAGGCCACACTGGTATGCCTGGCC
ACAGGCTTCTACCCCGACCACGTGGAGCTGAGCTGGTGGGTGAAT
GGGAAGGAGGTGCACAGTGGGGTCTGCACAGACCCGCAGCCCCTC
AAGGAGCAGCCCGCCCTCAATGACTCCAGATACTGCCTGAGCAGC
CGCCTGAGGGTCTCGGCCACCTTCTGGCAGAACCCCCGCAACCAC
TTCCGCTGTCAAGTCCAGTTCTACGGGCTCTCGGAGAATGACGAG
TGGACCCAGGATAGGGCCAAACCCGTCACCCAGATCGTCAGCGCC
GAGGCCTGGGGTAGAGCAGACTGTGGCTTCACCTCCGAGTCTTAC
CAGCAAGGGGTCCTGTCTGCCACCATCCTCTATGAGATCTTGCTA
GGGAAGGCCACCTTGTATGCCGTGCTGGTCAGTGCCCTCGTGCTG
ATGGCCATGGTCAAGAGAAAGGATTCCAGAGGC

β VJ and constant NT codon-optimized

SEQ ID NO: 22

ATGGGATGTAGACTGCTGTGCTGTGCTGTGCTGTGCCTGCTGGGG
GCTGTGCCTATTGATACCGAAGTGACTCAGACTCCAAAGCACCTG
GTCATGGGCATGACCAACAAGAAAAGCCTGAAATGCGAGCAGCAC
ATGGGGCATAGGGCCATGTACTGGTATAAGCAGAAAGCTAAGAAA
CCCCCTGAACTGATGTTCGTGTACAGCTATGAGAAGCTGTCCATC
AATGAATCCGTCCCCTCTCGCTTCAGTCCCGAGTGCCCTAACAGC
TCCCTGCTGAATCTGCACCTGCATGCTCTGCAGCCTGAAGACTCC
GCACTGTACCTGTGCGCCTCTAGTCACGGGCCAGCCTCTTACGAG
CAGTATTTTGGACCCGGCACCAGACTGACTGTGACCGAAGATCTG
AAGAACGTCTTCCCACCCGAGGTGGCAGTCTTTGAACCATCTGAG
GCCGAAATTAGTCATACTCAGAAAGCCACCCTGGTGTGCCTGGCT
ACAGGCTTCTATCCCGACCACGTGGAGCTGAGTTGGTGGGTCAAC
GGCAAGGAAGTGCATTCAGGGGTCTGCACTGACCCTCAGCCACTG
AAAGAGCAGCCTGCTCTGAATGATTCAAGGTACTGTCTGTCAAGC
CGGCTGAGAGTGAGCGCCACTTTTTGGCAGAACCCAAGGAATCAC
TTCCGCTGCCAGGTGCAGTTTTATGGCCTGAGCGAGAATGACGAA
TGGACTCAGGATCGCGCTAAGCCAGTGACCCAGATCGTCTCCGCA
GAGGCCTGGGGACGAGCAGACTGTGGCTTCACATCTGAAAGTTAC
CAGCAGGGGGTGCTGTCTGCCACAATCCTGTACGAGATTCTGCTG
GGAAAGGCCACTCTGTACGCCGTGCTGGTGAGCGCCTTAGTCTTA
ATGGCCATGGTGAAAAGAAAGGATTCCAGAGGA

SEQ ID NO: 23

Reserved

β VJ and constant (murine) NT codon-optimized

SEQ ID NO: 24

ATGGGATGCAGACTGCTGTGCTGTGCTGTGCTGTGCCTGCTGGGGGCTGT
GCCTATTGATACCGAAGTGACTCAGACTCCAAAGCACCTGGTCATGGGCA
TGACCAACAAGAAAAGCCTGAAATGCGAGCAGCACATGGGGCATAGGGCC
ATGTACTGGTATAAGCAGAAAGCTAAGAAACCCCCTGAACTGATGTTCGT
GTACAGCTATGAGAAGCTGTCCATCAATGAATCCGTCCCCTCTCGCTTCA
GTCCCGAGTGCCCTAACAGCTCCCTGCTGAATCTGCACCTGCATGCTCTG

-continued

CAGCCTGAAGACTCCGCACTGTACCTGTGCGCCTCTAGTCACGGGCCAGC

CTCTTACGAGCAGTATTTTGGACCCGGCACCAGACTGACTGTGACCGAAG

ATCTACGTAACGTGACACCACCCAAAGTCTCACTGTTTGAGCCTAGCAAG

GCAGAAATTGCCAACAAGCAGAAGGCCACCCTGGTGTGCCTGGCAAGAGG

GTTCTTTCCAGATCACGTGGAGCTGTCCTGGTGGGTCAACGGCAAAGAAG

TGCATTCTGGGGTCTGCACCGACCCCCAGGCTTACAAGGAGAGTAATTAC

TCATATTGTCTGTCAAGCCGGCTGAGAGTGTCCGCCACATTCTGGCACAA

CCCTAGGAATCATTTCCGCTGCCAGGTCCAGTTTCACGGCCTGAGTGAGG

AAGATAAATGGCCAGAGGGGTCACCTAAGCCAGTGACACAGAACATCAGC

GCAGAAGCCTGGGGACGAGCAGACTGTGGCATTACTAGCGCCTCCTATCA

TCAGGGCGTGCTGAGCGCCACTATCCTGTACGAGATTCTGCTGGGAAAGG

CCACCCTGTATGCTGTGCTGGTCTCCGGCCTGGTGCTGATGGCCATGGTC

AAGAAAAAGAACTCT

Bob1 3C10
α CDR3 AA

SEQ ID NO: 25
CAASTGGGYSTLTFGKGTMLLVSP

α CDR3 NT

SEQ ID NO: 26
TGTGCAGCAAGTACGGGGGGAGGATACAGCACCCTCACCTTTGGGAAGGG
GACTATGCTTCTAGTCTCTCCA

α CDR3 NT codon-optimized*

SEQ ID NO: 27
TGTGCCGCCTCTACCGGCGGAGGCTACTCCACCCTGACATTCGGCAAGGG
CACCATGCTGCTGGTGTCCCCC

β CDR3 AA

SEQ ID NO: 28
CASSGQGITLAGANVLTFGAGSRLTVL

β CDR3 NT

SEQ ID NO: 29
TGTGCCAGCAGTGGACAGGGAATTACCCTGGCTGGGGCCAACGTCCTGAC
TTTCGGGGCCGGCAGCAGGCTGACCGTGCTG

β CDR3 NT codon-optimized

SEQ ID NO: 30
TGTGCCAGCAGCGGCCAGGGCATCACACTGGCTGGCGCCAATGTGCTGAC
CTTCGGAGCCGGCAGCAGACTGACCGTGCTG

α VJ AA

SEQ ID NO: 31
MTSIRAVFIFLWLQLDLVNGENVEQHPSTLSVQEGDSAVIKCTYSDSASN
YFPWYKQELGKGPQLIIDIRSNVGEKKDQRIAVTLNKTAKHFSLHITETQ
PEDSAVYFCAASTGGGYSTLTFGKGTMLLVSP

α VJ NT

SEQ ID NO: 32
ATGACATCCATTCGAGCTGTATTTATATTCCTGTGGCTGCAGCTGGACTT

GGTGAATGGAGAGAATGTGGAGCAGCATCCTTCAACCCTGAGTGTCCAGG

AGGGAGACAGCGCTGTTATCAAGTGTACTTATTCAGACAGTGCCTCAAAC

TACTTCCCTTGGTATAAGCAAGAACTTGGAAAAGGACCTCAGCTTATTAT

AGACATTCGTTCAAATGTGGGCGAAAAGAAAGACCAACGAATTGCTGTTA

CATTGAACAAGACAGCCAAACATTTCTCCCTGCACATCACAGAGACCCAA

CCTGAAGACTCGGCTGTCTACTTCTGTGCAGCAAGTACGGGGGGAGGATA

CAGCACCCTCACCTTTGGGAAGGGGACTATGCTTCTAGTCTCTCCA

-continued

α VJ NT codon-optimized

SEQ ID NO: 33
ATGACCAGCATCCGGGCCGTGTTCATCTTCCTGTGGCTGCAGCTGGACCT

CGTGAACGGCGAGAACGTGGAACAGCACCCCAGCACCCTGAGCGTGCAGG

AAGGCGATAGCGCCGTGATCAAGTGCACCTACAGCGACAGCGCCAGCAAC

TACTTCCCCTGGTACAAGCAGGAACTGGGCAAGGGCCCCCAGCTGATCAT

CGACATCAGATCCAACGTGGGCGAGAAGAAGGACCAGCGGATCGCCGTGA

CCCTGAACAAGACCGCCAAGCACTTCAGCCTGCACATCACCGAGACACAG

CCCGAGGACAGCGCCGTGTACTTTTGTGCCGCCTCTACCGGCGGAGGCTA

CTCCACCCTGACATTCGGCAAGGGCACCATGCTGCTGGTGTCCCCC

β VDJ AA

SEQ ID NO: 34
MGSVVTLCCVSLCILVAKHTDAGVIQSPRHEVTEMGQEVTLRCKPISGHD
YLFWYRQTMMRGLELLIYFNNNVPIDDSGMPEDRFSAKMPNASFSTLKIQ
PSEPRDSAVYFCASSGQGITLAGANVLTFGAGSRLTVL

β VDJ NT

SEQ ID NO: 35
ATGGGCTCCTGGACCCTCTGCTGTGTGTCCCTTTGCATCCTGGTAGCAAA

GCACACAGATGCTGGAGTTATCCAGTCACCCCGGCACGAGGTGACAGAGA

TGGGACAAGAAGTGACTCTGAGATGTAAACCAATTTCAGGACACGACTAC

CTTTTCTGGTACAGACAGACCATGATGCGGGGACTGGAGTTGCTCATTTA

CTTTAACAACAACGTTCCGATAGATGATTCAGGGATGCCCGAGGATCGAT

TCTCAGCTAAGATGCCTAATGCATCATTCTCCACTCTGAAGATCCAGCCC

TCAGAACCCAGGGACTCAGCTGTGTACTTCTGTGCCAGCAGTGGACAGGG

AATTACCCTGGCTGGGGCCAACGTCCTGACTTTCGGGGCCGGCAGCAGGC

TGACCGTGCTG

β VDJ NT codon-optimized

SEQ ID NO: 36
ATGGGCAGCTGGACCCTGTGCTGCGTGTCCCTGTGTATCCTGGTGGCCAA

GCACACCGATGCCGGCGTGATCCAGAGCCCCAGACACGAAGTGACCGAGA

TGGGCCAGGAAGTGACCCTGCGCTGCAAGCCTATCAGCGGCCACGACTAC

CTGTTCTGGTACAGACAGACCATGATGCGGGGCCTGGAACTGCTGATCTA

CTTCAACAACAACGTGCCCATCGACGACAGCGGCATGCCCGAGGATAGAT

TCAGCGCCAAGATGCCCAACGCCAGCTTCAGCACCCTGAAGATCCAGCCC

AGCGAGCCCAGAGACAGCGCCGTGTACTTTTGTGCCAGCAGCGGCCAGGG

CATCACACTGGCTGGCGCCAATGTGCTGACCTTCGGAGCCGGCAGCAGAC

TGACCGTGCTG

α VJ and constant AA

SEQ ID NO: 37
MTSIRAVFIFLWLQLDLVNGENVEQHPSTLSVQEGDSAVIKCTYSDSASN

YFPWYKQELGKGPQLIIDIRSNVGEKKDQRIAVTLNKTAKHFSLHITETQ

PEDSAVYFCAASTGGGYSTLTFGKGTMLLVSPDIQNPDPAVYQLRDSKSS

DKSVCLFTDFDSQTNVSQSKDSDVYITDKTVLDMRSMDFKSNSAVAWSNK

SDFACANAFNNSIIPEDTFFPSPESSCDVKLVEKSFETDTNLNFQNLSVI

GFRILLLKVAGFNLLMTLRLWSS

-continued

α VJ and constant (murine) AA

SEQ ID NO: 38

MTSIRAVFIFLWLQLDLVNGENVEQHPSTLSVQEGDSAVIKCTYSDSASN

YFPWYKQELGKGPQLIIDIRSNVGEKKDQRIAVTLNKTAKHFSLHITETQ

PEDSAVYFCAASTGGGYSTLTFGKGTMLLVSPDIQNPEPAVYQLKDPRSQ

DSTLCLFTDFDSQINVPKTMESGTFITDKCVLDMKAMDSKSNGAIAWSNQ

TSFTCQDIFKETNATYPSSDVPCDATLTEKSFETDMNLNFQNLSVMGLRI

LLLKVAGFNLLMTLRLWSS

α VJ and constant NT

SEQ ID NO: 39

ATGACATCCATTCGAGCTGTATTTATATTCCTGTGGCTGCAGCTGGACTT

GGTGAATGGAGAGAATGTGGAGCAGCATCCTTCAACCCTGAGTGTCCAGG

AGGGAGACAGCGCTGTTATCAAGTGTACTTATTCAGACAGTGCCTCAAAC

TACTTCCCTTGGTATAAGCAAGAACTTGGAAAAGGACCTCAGCTTATTAT

AGACATTCGTTCAAATGTGGGCGAAAAGAAAGACCAACGAATTGCTGTTA

CATTGAACAAGACAGCCAAACATTTCTCCCTGCACATCACAGAGACCCAA

CCTGAAGACTCGGCTGTCTACTTCTGTGCAGCAAGTACGGGGGGAGGATA

CAGCACCCTCACCTTTGGGAAGGGGACTATGCTTCTAGTCTCTCCAGATA

TCCAGAACCCTGACCCTGCCGTGTACCAGCTGAGAGACTCTAAATCCAGT

GACAAGTCTGTCTGCCTATTCACCGATTTTGATTCTCAAACAAATGTGTC

ACAAAGTAAGGATTCTGATGTGTATATCACAGACAAAACTGTGCTAGACA

TGAGGTCTATGGACTTCAAGAGCAACAGTGCTGTGGCCTGGAGCAACAAA

TCTGACTTTGCATGTGCAAACGCCTTCAACAACAGCATTATTCCAGAAGA

CACCTTCTTCCCCAGCCCAGAAAGTTCCTGTGATGTCAAGCTGGTCGAGA

AAAGCTTTGAAACAGATACGAACCTAAACTTTCAAAACCTGTCAGTGATT

GGGTTCCGAATCCTCCTCCTGAAAGTGGCCGGGTTTAATCTGCTCATGAC

GCTGCGGTTGTGGTCCAGC

α VJ and constant NT codon-optimized

SEQ ID NO: 40

ATGACCAGCATCCGGGCCGTGTTCATCTTCCTGTGGCTGCAGCTGGACCT

CGTGAACGGCGAGAACGTGGAACAGCACCCCAGCACCCTGAGCGTGCAGG

AAGGCGATAGCGCCGTGATCAAGTGCACCTACAGCGACAGCGCCAGCAAC

TACTTCCCCTGGTACAAGCAGGAACTGGGCAAGGGCCCCCAGCTGATCAT

CGACATCAGATCCAACGTGGGCGAGAAGAAGGACCAGCGGATCGCCGTGA

CCCTGAACAAGACCGCCAAGCACTTCAGCCTGCACATCACCGAGACACAG

CCCGAGGACAGCGCCGTGTACTTTTGTGCCGCCTCTACCGGCGGAGGCTA

CTCCACCCTGACATTCGGCAAGGGCACCATGCTGCTGGTGTCCCCCGACA

TCCAGAACCCCGATCCTGCCGTGTACCAGCTGCGGGACAGCAAGAGCAGC

GACAAGAGCGTGTGCCTGTTCACCGACTTCGACAGCCAGACCAACGTGTC

CCAGAGCAAGGACTCCGACGTGTACATCACAGACAAGACCGTGCTGGACA

TGCGGAGCATGGACTTCAAGAGCAACTCCGCCGTGGCCTGGTCCAACAAG

AGCGATTTCGCCTGCGCCAACGCCTTCAACAACAGCATTATCCCTGAGGA

CACATTCTTCCCAAGCCCCGAGAGCAGCTGCGACGTGAAGCTGGTGGAAA

-continued

AGAGCTTCGAGACAGACACCAACCTGAACTTCCAGAACCTGTCCGTGATC

GGCTTCCGGATCCTGCTGCTGAAGGTGGCCGGCTTCAACCTGCTGATGAC

CCTGAGACTGTGGTCCTCC

α VJ and constant (murine) NT

SEQ ID NO: 41

ATGACATCCATTCGAGCTGTATTTATATTCCTGTGGCTGCAGCTGGACTT

GGTGAATGGAGAGAATGTGGAGCAGCATCCTTCAACCCTGAGTGTCCAGG

AGGGAGACAGCGCTGTTATCAAGTGTACTTATTCAGACAGTGCCTCAAAC

TACTTCCCTTGGTATAAGCAAGAACTTGGAAAAGGACCTCAGCTTATTAT

AGACATTCGTTCAAATGTGGGCGAAAAGAAAGACCAACGAATTGCTGTTA

CATTGAACAAGACAGCCAAACATTTCTCCCTGCACATCACAGAGACCCAA

CCTGAAGACTCGGCTGTCTACTTCTGTGCAGCAAGTACGGGGGGAGGATA

CAGCACCCTCACCTTTGGGAAGGGGACTATGCTTCTAGTCTCTCCAGACA

TTCAGAACCCGGAACCGGCTGTATACCAGCTGAAGGACCCCCGATCTCAG

GATAGTACTCTGTGCCTGTTCACCGACTTTGATAGTCAGATCAATGTGCC

TAAAACCATGGAATCCGGAACTTTTATTACCGACAAGTGCGTGCTGGATA

TGAAAGCCATGGACAGTAAGTCAAACGGCGCCATCGCTTGGAGCAATCAG

ACATCCTTCACTTGCCAGGATATCTTCAAGGAGACCAACGCAACATACCC

ATCCTCTGACGTGCCCTGTGATGCCACCCTGACAGAGAAGTCTTTCGAAA

CAGACATGAACCTGAATTTTCAGAATCTGAGCGTGATGGGCCTGAGAATC

CTGCTGCTGAAGGTCGCTGGGTTTAATCTGCTGATGACACTGCGGCTGTG

GTCCTCA

α VJ and constant (murine) NT codon-optimized

SEQ ID NO: 42

ATGACCAGCATCCGGGCCGTGTTCATCTTCCTGTGGCTGCAGCTGGACCT

CGTGAACGGCGAGAACGTGGAACAGCACCCCAGCACCCTGAGCGTGCAGG

AAGGCGATAGCGCCGTGATCAAGTGCACCTACAGCGACAGCGCCAGCAAC

TACTTCCCCTGGTACAAGCAGGAACTGGGCAAGGGCCCCCAGCTGATCAT

CGACATCAGATCCAACGTGGGCGAGAAGAAGGACCAGCGGATCGCCGTGA

CCCTGAACAAGACCGCCAAGCACTTCAGCCTGCACATCACCGAGACACAG

CCCGAGGACAGCGCCGTGTACTTTTGTGCCGCCTCTACCGGCGGAGGCTA

CTCCACCCTGACATTCGGCAAGGGCACCATGCTGCTGGTGTCCCCCGACA

TCCAGAATCCCGAGCCTGCCGTGTACCAGCTGAAGGACCCCAGAAGCCAG

GATAGCACCCTGTGCCTGTTCACCGACTTCGACAGCCAGATCAACGTGCC

CAAGACCATGGAAAGCGGCACCTTCATCACCGATAAGTGCGTGCTGGACA

TGAAGGCCATGGACAGCAAGAGCAACGGCGCCATTGCCTGGTCCAACCAG

ACCAGCTTCACATGCCAGGACATCTTCAAAGAGACAAACGCCACCTACCC

CAGCAGCGACGTGCCCTGTGATGCCACACTGACCGAGAAGTCCTTCGAGA

CAGACATGAACCTGAACTTCCAGAACCTGTCCGTGATGGGCCTGCGGATC

CTGCTGCTGAAGGTGGCCGGCTTCAACCTGCTGATGACCCTGAGACTGTG

GTCCTCC

-continued

β VJ and constant AA

SEQ ID NO: 43

MGSWTLCCVSLCILVAKHTDAGVIQSPRHEVTEMGQEVTLRCKPISGHDY
LFWYRQTMMRGLELLIYFNNNVPIDDSGMPEDRFSAKMPNASFSTLKIQP
SEPRDSAVYFCASSGQGITLAGANVLTFGAGSRLTVLEDLKNVFPPEVAV
FEPSEAEISHTQKATLVCLATGFYPDHVELSWWVNGKEVHSGVSTDPQPL
KEQPALNDSRYCLSSRLRVSATFWQNPRNHFRCQVQFYGLSENDEWTQDR
AKPVTQIVSAEAWGRADCGFTSESYQQGVLSATILYEILLGKATLYAVLV
SALVLMAMVKRKDSRG

β VJ and constant (murine) AA

SEQ ID NO: 44

MGSWTLCCVSLCILVAKHTDAGVIQSPRHEVTEMGQEVTLRCKPISGHDY
LFWYRQTMMRGLELLIYFNNNVPIDDSGMPEDRFSAKMPNASFSTLKIQP
SEPRDSAVYFCASSGQGITLAGANVLTFGAGSRLTVLEDLRNVTPPKVSL
FEPSKAEIANKQKATLVCLARGFFPDHVELSWWVNGKEVHSGVCTDPQAY
KESNYSYCLSSRLRVSATFWHNPRNHFRCQVQFHGLSEEDKWPEGSPKPV
TQNISAEAWGRADCGITSASYHQGVLSATILYEILLGKATLYAVLVSGLV
LMAMVKKKNS

β VJ and constant NT

SEQ ID NO: 45

ATGGGCTCCTGGACCCTCTGCTGTGTGTCCCTTTGCATCCTGGTAGCAAA
GCACACAGATGCTGGAGTTATCCAGTCACCCCGGCACGAGGTGACAGAGA
TGGGACAAGAAGTGACTCTGAGATGTAAACCAATTTCAGGACACGACTAC
CTTTTCTGGTACAGACAGACCATGATGCGGGGACTGGAGTTGCTCATTTA
CTTTAACAACAACGTTCCGATAGATGATTCAGGGATGCCCGAGGATCGAT
TCTCAGCTAAGATGCCTAATGCATCATTCTCCACTCTGAAGATCCAGCCC
TCAGAACCCAGGGACTCAGCTGTGTACTTCTGTGCCAGCAGTGGACAGGG
AATTACCCTGGCTGGGGCCAACGTCCTGACTTTCGGGGCCGGCAGCAGGC
TGACCGTGCTGGAGGACCTGAAAAACGTGTTCCCACCCGAGGTCGCTGTG
TTTGAGCCATCAGAAGCAGAGATCTCCCACACCCAAAAGGCCACACTGGT
ATGCCTGGCCACAGGCTTCTACCCCGACCACGTGGAGCTGAGCTGGTGGG
TGAATGGGAAGGAGGTGCACAGTGGGGTCAGCACAGACCCGCAGCCCCTC
AAGGAGCAGCCCGCCCTCAATGACTCCAGATACTGCCTGAGCAGCCGCCT
GAGGGTCTCGGCCACCTTCTGGCAGAACCCCCGCAACCACTTCCGCTGTC
AAGTCCAGTTCTACGGGCTCTCGGAGAATGACGAGTGGACCCAGGATAGG
GCCAAACCCGTCACCCAGATCGTCAGCGCCGAGGCCTGGGGTAGAGCAGA
CTGTGGCTTCACCTCCGAGTCTTACCAGCAAGGGGTCCTGTCTGCCACCA
TCCTCTATGAGATCTTGCTAGGGAAGGCCACCTTGTATGCCGTGCTGGTC
AGTGCCCTCGTGCTGATGGCCATGGTCAAGAGAAAGGATTCCAGAGGC

β VJ and constant NT codon-optimized

SEQ ID NO: 46

ATGGGCAGCTGGACCCTGTGCTGCGTGTCCCTGTGTATCCTGGTGGCC
AAGCACACCGATGCCGGCGTGATCCAGAGCCCCAGACACGAAGTGACC
GAGATGGGCCAGGAAGTGACCCTGCGCTGCAAGCCTATCAGCGGCCAC
GACTACCTGTTCTGGTACAGACAGACCATGATGCGGGGCCTGGAACTG
CTGATCTACTTCAACAACAACGTGCCCATCGACGACAGCGGCATGCCC
GAGGATAGATTCAGCGCCAAGATGCCCAACGCCAGCTTCAGCACCCTG
AAGATCCAGCCCAGCGAGCCCAGAGACAGCGCCGTGTACTTTTGTGCC
AGCAGCGGCCAGGGCATCACACTGGCTGGCGCCAATGTGCTGACCTTC
GGAGCCGGCAGCAGACTGACCGTGCTGGAAGATCTGAAGAACGTGTTC
CCCCCAGAGGTGGCCGTGTTCGAGCCTTCTGAGGCCGAGATCAGCCAC
ACCCAGAAAGCCACCCTCGTGTGTCTGGCCACCGGCTTCTACCCCGAC
CACGTGGAACTGTCTTGGTGGGTCAACGGCAAAGAGGTGCACAGCGGC
GTGTCCACCGATCCCCAGCCTCTGAAAGAACAGCCCGCCCTGAACGAC
AGCCGGTACTGCCTGTCCAGCAGGCTGAGAGTGTCCGCCACCTTCTGG
CAGAACCCCCGGAACCACTTCAGATGCCAGGTGCAGTTCTACGGCCTG
AGCGAGAACGACGAGTGGACCCAGGACAGAGCCAAGCCCGTGACCCAG
ATCGTGTCTGCCGAAGCCTGGGGCAGAGCCGATTGCGGCTTTACCAGC
GAGAGCTACCAGCAGGGCGTGCTGAGCGCCACCATCCTGTACGAGATC
CTGCTGGGCAAGGCCACCCTGTACGCCGTGCTGGTGTCTGCCCTGGTG
CTGATGGCCATGGTCAAGCGGAAGGACAGCCGGGGC

β VJ and constant (murine) NT

SEQ ID NO: 47

ATGGGCTCCTGGACCCTCTGCTGTGTGTCCCTTTGCATCCTGGTAGCA
AAGCACACAGATGCTGGAGTTATCCAGTCACCCCGGCACGAGGTGACA
GAGATGGGACAAGAAGTGACTCTGAGATGTAAACCAATTTCAGGACAC
GACTACCTTTTCTGGTACAGACAGACCATGATGCGGGGACTGGAGTTG
CTCATTTACTTTAACAACAACGTTCCGATAGATGATTCAGGGATGCCC
GAGGATCGATTCTCAGCTAAGATGCCTAATGCATCATTCTCCACTCTG
AAGATCCAGCCCTCAGAACCCAGGGACTCAGCTGTGTACTTCTGTGCC
AGCAGTGGACAGGGAATTACCCTGGCTGGGGCCAACGTCCTGACTTTC
GGGGCCGGCAGCAGGCTGACCGTGCTGGAAGATCTACGTAACGTGACA
CCACCCAAAGTCTCACTGTTTGAGCCTAGCAAGGCAGAAATTGCCAAC
AAGCAGAAGGCCACCCTGGTGTGCCTGGCAAGAGGGTTCTTTCCAGAT
CACGTGGAGCTGTCCTGGTGGGTCAACGGCAAAGAAGTGCATTCTGGG
GTCTGCACCGACCCCCAGGCTTACAAGGAGAGTAATTACTCATATTGT
CTGTCAAGCCGGCTGAGAGTGTCCGCCACATTCTGGCACAACCCTAGG
AATCATTTCCGCTGCCAGGTCCAGTTTCACGGCCTGAGTGAGGAAGAT
AAATGGCCAGAGGGGTCACCTAAGCCAGTGACACAGAACATCAGCGCA
GAAGCCTGGGGACGAGCAGACTGTGGCATTACTAGCGCCTCCTATCAT
CAGGGCGTGCTGAGCGCCACTATCCTGTACGAGATTCTGCTGGGAAAG
GCCACCCTGTATGCTGTGCTGGTCTCCGGCCTGGTGCTGATGGCCATG
GTCAAGAAAAAGAACTCT

β VJ and constant (murine) NT codon-optimized

SEQ ID NO: 48

ATGGGCAGCTGGACCCTGTGCTGCGTGTCCCTGTGTATCCTGGTGGCCA
AGCACACCGATGCCGGCGTGATCCAGAGCCCCAGACACGAAGTGACCGA

-continued

GATGGGCCAGGAAGTGACCCTGCGCTGCAAGCCTATCAGCGGCCACGAC

TACCTGTTCTGGTACAGACAGACCATGATGCGGGGCCTGGAACTGCTGA

TCTACTTCAACAACAACGTGCCCATCGACGACAGCGGCATGCCCGAGGA

TAGATTCAGCGCCAAGATGCCCAACGCCAGCTTCAGCACCCTGAAGATC

CAGCCCAGCGAGCCCAGAGACAGCGCCGTGTACTTTTGTGCCAGCAGCG

GGCCAGGGCATCACACTGGCTGGCGCCAATGTGCTGACCTTCGGAGCCG

GCAGCAGACTGACCGTGCTGGAAGATCTGCGGAACTGACCCCCCCCAAA

GTGTCTCTGTTCGAGCCCAGCAAGGCCGAGATCGCCAACAAGCAGAAAG

CCACCCTCGTGTGCCTGGCCAGAGGCTTCTTCCCCGACCACGTGGAACT

GTCTTGGTGGGTCAACGGCAAAGAGGTGCACTCCGGCGTGTGCACCGAT

CCCCAGGCCTACAAAGAGAGCAACTACAGCTACTGCCTGAGCAGCAGGC

TGCGGGTGTCCGCCACCTTCTGGCACAACCCCCGGAACCACTTCAGATG

CCAGGTGCAGTTTCACGGCCTGAGCGAAGAGGACAAGTGGCCCGAGGGC

AGCCCTAAGCCCGTGACCCAGAATATCTCTGCCGAAGCCTGGGGCAGAG

CCGACTGTGGCATTACCAGCGCCAGCTACCATCAGGGCGTGCTGAGCGC

CACCATCCTGTACGAGATCCTGCTGGGCAAGGCCACCCTGTACGCCGTG

CTGGTGTCTGGCCTGGTGCTGATGGCCATGGTCAAGAAGAAGAACAGC

Figure 12A:
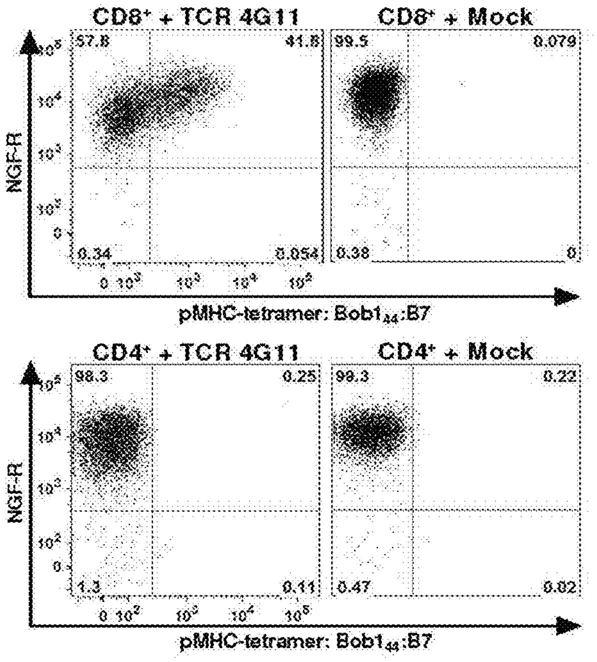
FIG. 12A provides four FACS plots of transduced T cells after enrichment via expression of marker gene NGF-R and MACS isolation. Numbers in quadrant indicate percentage cells. FACS plots are shown with biexponential axes.
Figure 12B:
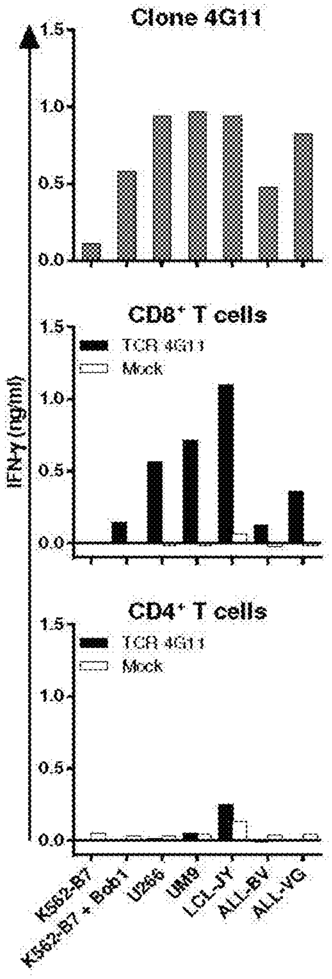
FIG. 12B provides three bar graphs of IFN-γ concentration assessed after 18 h of co-culture of T-cell clone 4G11 or purified transduced $CD8^+$ or $CD4^+$ T cells with various HLA-$B7^{pos}$ cell-lines.

Example 5: TCR Gene Transfer Installs Bob1-Reactivity onto Recipient T Cells and Induces Efficient Lysis of Primary Malignancies The TCR of clone 4G11 (TCR-4G11) was tested for its ability to install Bob1 reactivity onto recipient cells by gene transfer. TCR-4G11 was sequenced, codon-optimized, modified with a disulfide bond to increase preferential pairing of the TCRα and TCRβ chain, and cloned into the MP71 vector expressing NGF-R as a marker gene. Expression of NGF-R was used to enrich TCR-transduced T cells to high purity by MACS-guided isolation of NGF-R expressing cells. Retrovirally-transduced $CD8^+$ T cells from a HLA-$B7^{pos}$ healthy individual expressed TCR-4G11 on the cell surface indicated by their capacity to bind pMHC-tetramer $Bob1_{44}$:B7 (FIG. 12*a*). More intensive staining with pMHC-tetramer correlated with higher NGF-R expression suggesting that cells expressing higher quantities of introduced TCR bound pMHC-tetramer more efficiently. Tetramer binding was not observed for mock-transduced T cells. $CD4^+$ T cells could be transduced as indicated by the expression of NGF-R, however, no binding to $Bob1_{44}$:B7 tetramer was observed (FIG. 12*a*). TCR-transduced $CD8^+$ T cells readily recognized Bob1-expressing HLA-$B7^{pos}$ stimulator cells such as multiple myeloma cell-lines UM9 and U266, B-LCL-JY, and two ALL cell-lines ALL-BV and ALL-VG mirroring the reactivity profile of T-cell clone 4G11 (FIG. 12*b*). In contrast, TCR-transduced $CD4^+$ T cells failed to recognize any of these cell-lines. No recognition for mock-transduced $CD8^+$ T cells was observed indicating that recognition was due to introduction of TCR-4G11.

FIG. 12. Transfer of TCR-4G11 installs Bob1-reactivity on recipient $CD8^+$ T cells. $CD4^+$ and $CD8^+$ T cells were isolated from a healthy HLA-$B7^{pos}$ individual and transduced with retroviral supernatant to express TCR-4G11 together with NGF-R. Transduction with an empty vector (Mock) containing only the NGF-R marker gene served as control. For FIG. 12A, FACS plots of transduced T cells after enrichment via expression of marker gene NGF-R and MACS isolation. Isolated $CD8^+$ (top row) or $CD4^+$ (bottom row) T cells were stained with pMHC-tetramer $Bob1_{44}$:B7 and an antibody against NGF-R. Numbers in quadrant indicate percentage cells. FACS plots are shown with biexponential axes. For FIG. 12B, T-cell clone 4G11 or purified transduced $CD8^+$ or $CD4^+$ T cells were co-incubated with various HLA-$B7^{pos}$ cell-lines. Cell-lines included K562-B7 transduced to express Bob1 (K562-B7+Bob1), two multiple myeloma cell-lines UM9 and U266, B-LCL-JY, and two ALL cell-lines ALL-By and ALL-VG. IFN-γ concentration was assessed after 18 h of co-culture.

Figure 13A:
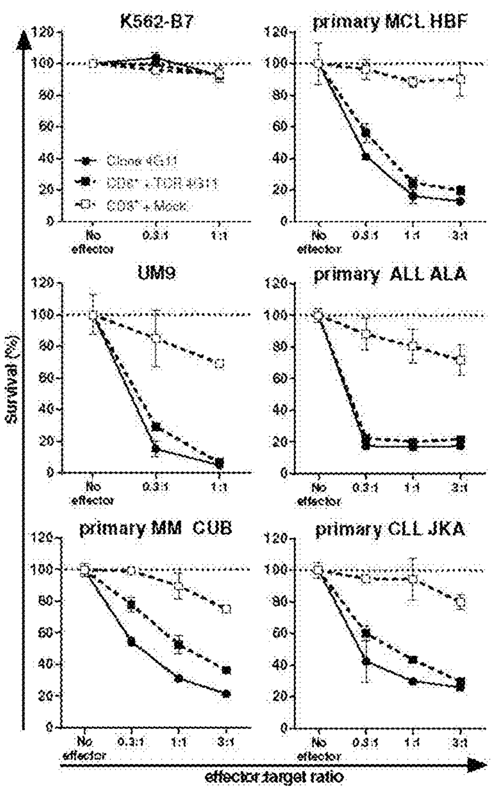
FIGS. 13A and 13B provide bar graphs of the survival percentage of live target cells, assessed by flow cytometry, following incubation with T-cell clone 4G11, or purified TCR- or mock-transduced $CD8^+$ T cells.

Furthermore, TCR-transduced $CD8^+$ T cells efficiently lysed primary HLA-$B7^{pos}$ malignant cell samples (FIG. 13*a*). Complete or nearly complete lysis was observed for primary ALL and MCL samples and multiple myeloma cell-lines at equal effector-to-target ratio even when target cells exceeded effector cells threefold. Efficient lysis by TCR-transduced T cells could also be observed for both tested primary CLL samples as well as 2 out of 2 ALL cell-lines. In addition, both purified HLA-B7-positive primary multiple myeloma samples were readily lysed by TCR-transduced T cells at low effector-to-target ratios. In all cases, no lysis was observed for mock-transduced T cells indicating that lysis was due to the introduction of TCR-4G11. Bob1 expression in healthy B cells also led to their lysis by autologous TCR-transduced $CD8^+$ T cells. (FIG. 13*b*) Lysis was specific as the Bob1-negative K562-B7 cell-line was not lysed (FIG. 13*a*). In addition, TCR-transduced $CD8^+$ T cells did not lyse autologous activated T cells or $CD14^+$ monocytes indicating a safe reactivity profile (FIG. 13*b*).

Figure 13B:
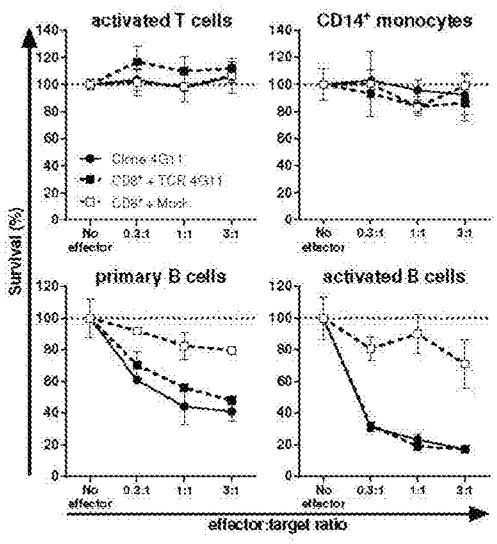

FIG. 13. TCR-transduced $CD8^+$ T cells efficiently lyse primary B-cell malignancies and multiple myeloma. For FIGS. 13A and 13B, T-cell clone 4G11 or purified TCR- or mock-transduced $CD8^+$ T cells were tested for their lytic capacity of HLA-$B7^{pos}$ target cells. PKH-labelled target cells were co-cultured at various effector:target ratios with effector T cells. After 18 h of co-culture, the number of live targets cells was assessed by flow cytometry and percent survival calculated. FIG. 13A: Malignant cell samples included multiple myeloma cell-line UM9, primary multiple myeloma (MM), mantle cell lymphoma (MCL), acute lymphoblastic (ALL) and chronic lymphocytic leukemia (CLL). Controls included Bob1-negative cell-line K562-B7. FIG. 13B: Healthy hematopoietic cells were of same origin as transduced T cells (autologous setting) and included PHA-activated T cells, $CD14^+$ monocytes, $CD19^+$ primary B cells and CD40L-activated B cells.

Figure 14A:
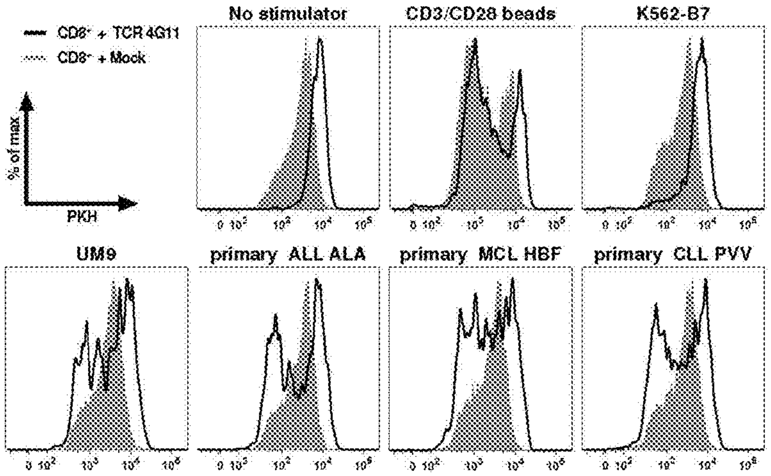
FIGS. 14A and 14B provide histograms of TCR-transduced (black line) or mock-transduced (grey area) $CD8^+$ T cells after 5 days of co-culture with stimulator or negative control cells.

TCR-transduced $CD8^+$ T cells proliferated upon stimulation with various HLA-$B7^{pos}$ Bob1-expressing primary samples including ALL, CLL, MCL, multiple myeloma cell-lines and autologous activated B cells (FIG. 14*a,b*). In contrast, stimulation with antigen-negative cell-line K562-B7 or autologous activated T cells did not lead to proliferation of TCR-transduced T cells.

Figure 14B:
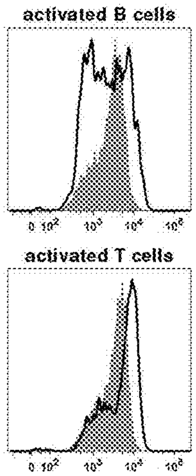

FIG. 14. TCR-transduced $CD8^+$ T cells proliferate upon antigen encounter. For FIGS. 14A and 14B, PKH-labelled transduced $CD8^+$ T cells were co-cultured with irradiated HLA-$B7^{pos}$ stimulator cells. Histograms show TCR-transduced (black line) or mock-transduced (grey area) $CD8^+$ T cells after 5 days of co-culture. FIG. 14A: Stimulator cells included cell-line UM9 and primary ALL, CLL and MCL. Negative controls included culture in absence of stimulator cells (No stimulators) or co-culture with Bob1-negative K562-B7 cells. Positive control included stimulation in the presence of CD3/CD28 T-cell activator beads (CD3/CD28 beads). FIG. 14B: Autologous CD40L-stimulated B cells or PHA-activated T cells were used as stimulator cells.

Mouse models may be used to further assay the Bob1-TCR-expressing modified T cells in vivo. In humanized multiple myeloma (MM) mouse models in which luciferase positive MM cell line UM9 cells can be injected into the joints of mice, the potency of the Bob1-TCR modified T cells can be monitored. Also, $RAG2^{-/-}\gamma_c^{-/-}$ mice implanted with hybrid scaffolds consisting of three 2- to 3-mm biphasic calcium phosphate particles coated with human mesenchymal stromal cells (MSC) and loaded with $Luc^+$ MM cell line UM9 or U266 can be used to monitor the potency of the T cells (Groen R W, et al., Blood 2012; 120:e9-e16).

In summary, TCR gene transfer of TCR-4G11 installed Bob1 reactivity onto recipient $CD8^+$ T cells. TCR-transduced T cells efficiently lysed primary ALL, CLL, MCL and multiple myeloma at low effector-to-target ratios while sparing non-B cells. Furthermore, TCR-transduced T cells readily proliferated upon antigen encounter.

Example 6: Addition of a Suicide Gene—Selective Apoptosis of the Modified Cells The modified cells that express the Bob1-targeted TCR may be provided with a mechanism to remove some, or all of the cells if the patient experiences negative effects, or if there is a need to reduce, or stop treatment. In some examples, the suicide gene mechanism is provided to reduce the level of on-target, off-organ toxicity, where there is a need for an option to rapidly terminate therapy.

An example of a chimeric polypeptide that may be expressed in the modified cells is provided in the present examples. In some examples, the modified cells comprise a nucleic acid that comprises a polynucleotide that encodes a chimeric Caspase-9 polypeptide, and a polynucleotide that encodes the Bob1 TCR. In other examples, the nucleic acid comprises a polynucleotide that encodes both the chimeric Caspase-9 polypeptide and the Bob1 TCR; the inducible Caspase-9 polypeptide is separated from the Bob1 TCR polypeptide during translation, due to skipping of a peptide bond. (see, for example, Donnelly, M L 2001, J. Gen. Virol. 82:1013-25). Methods for inducing selective apoptosis of cells comprising a nucleic acid comprising a polynucleotide encoding a chimeric Caspase-9 polypeptide are discussed in U.S. Pat. No. 9,089,520, entitled "Methods for Inducing Selective Apoptosis," issued Jul. 28, 2015; methods for the coexpression of a chimeric Caspase-9 polypeptide and another polypeptide in T cells are discussed in Internatioal Patent Application Serial Number PCT/US2015/015829, published as WO2015/123527 on Aug. 20, 2015, entitled "Methods for Activating T cells Using an Inducible Chimeric Polypeptide," which are incorporated by reference in their entireties herein. Additional chimeric Caspase-9 polypeptides that may be used in the Bob1 TCR constructs also include, for example, those discussed in International Patent Application Serial Number PCT/US2014/022004, published as WO2014/164348 on Mar. 5, 2015, entitled "Modified Caspase Polypeptides and Uses Thereof," and in International Patent Application Serial Number PCT/US2015/019186, published as WO2015/134877 on Sep. 11, 2015, and entitled "Caspase Polypeptides having Modified Activity and Uses Thereof," which are incorporated by reference in their entireties herein. The example provided herein discusses the administration of modified T cells that express a chimeric Caspase-9 polypeptide to a subject, and the allodepletion of modified T cells following the development of graft vs host disease in the subject by administration of the CID AP1903 (rimiducid) or AP20187). This method may be adapted for use in the Bob1TCR-modified cells discussed herein.

Vector Construction and Confirmation of Expression

A safety switch that can be stably and efficiently expressed in human T cells is presented herein. Expression vectors suitable for use as a therapeutic agent were constructed that included a modified human Caspase-9 activity fused to a human FK506 binding protein (FKBP), such as, for example, FKBP12v36. The Caspase-9/FK506 hybrid activity can be dimerized using a small molecule pharmaceutical. Full length, truncated, and modified versions of the Caspase-9 activity were fused to the ligand binding domain, or multimerization region, and inserted into the retroviral vector MSCV.IRES.GRP, which also allows expression of the fluorescent marker, GFP. The full-length inducible Caspase-9 molecule (F'-F-C-Casp9) includes 2, 3, or more FK506 binding proteins (FKBPs—for example, FKBP12v36 variants) linked with a Gly-Ser-Gly-Gly-Gly-Ser linker (SEQ ID NO: 130) to the small and large subunit of the caspase molecule. Full-length inducible Caspase-9 (F'-F-C-Casp9.I.GFP) has a full-length Caspase-9, also includes a caspase recruitment domain (CARD; GenBank NM001 229) linked to 2 12-kDa human FK506 binding proteins (FKBP12; GenBank AH002 818) that contain an F36V mutation. The amino acid sequence of one or more of the FKBPs (F') was codon-wobbled (e.g., the 3rd nucleotide of each amino acid codon was altered by a silent mutation that maintained the originally encoded amino acid) to prevent homologous recombination when expressed in a retrovirus. F'F-C-Casp9C3S includes a cysteine to serine mutation at position 287 that disrupts its activation site. In constructs F'F-Casp9, F-C-Casp9, and F'-Casp9, either the caspase activation domain (CARD), one FKBP, or both, were deleted, respectively. All constructs were cloned into MSCV.IRES.GFP as EcoRI-XhoI fragments. Coexpression of the inducible Caspase-9 constructs of the expected size with the marker gene GFP in transfected 293T cells was demonstrated by Western blot using a Caspase-9 antibody specific for amino acid residues 299-318, present both in the full-length and truncated caspase molecules as well as a GFP-specific antibody.

An initial screen indicated that the full length iCasp9 could not be maintained stably at high levels in T cells, possibly due to transduced cells being eliminated by the basal activity of the transgene. The CARD domain is involved in physiologic dimerization of Caspase-9 molecules, by a cyto¬chrome C and adenosine triphosphate (ATP)-driven interaction with apoptotic protease-activating factor 1 (Apaf-1). Because of the use of a CID to induce dimerization and activation of the suicide switch, the function of the CARD domain is superfluous in this context and removal of the CARD domain was investigated as a method of reducing basal activity.

Using the iCasp9 Suicide Gene to Improve the Safety of Allodepleted T Cells after Haploidentical Stem Cell Transplantation Presented in this example are expression constructs and methods of using the expression constructs to improve the safety of allodepleted T cells after haploidentical stem cell transplantation. Similar methods may be used to express the Caspase-9 expression constructs in non allodepleted cells. These methods may also be used to express the chimeric Caspase-9 polypeptide in Bob1 TCR-expressing cells. A retroviral vector encoding iCasp9 and a selectable marker (truncated CD19) was generated as a safety switch for donor T cells. Even after allodepletion (using anti-CD25 immunotoxin), donor T cells could be efficiently transduced, expanded, and subsequently enriched by CD19 immunomagnetic selection to >90% purity. The engineered cells retained anti-viral specificity and functionality, and contained a subset with regulatory phenotype and function. Activating iCasp9 with a small-molecule dimerizer rapidly produced >90% apoptosis. Although transgene expression was downregulated in quiescent T cells, iCasp9 remained an efficient suicide gene, as expression was rapidly upregulated in activated (alloreactive) T cells.

Materials and Methods

Generation of Allodepleted T Cells

Allodepleted cells were generated from healthy volunteers as previously presented. Briefly, peripheral blood mononuclear cells (PBMCs) from healthy donors were co-cultured with irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that expressed CD25 were depleted from the co-culture by overnight incubation in RFT5-SMPT-dgA immunotoxin. Allodepletion was considered adequate if the residual CD3+CD25+ population was <1% and residual proliferation by 3H-thymidine incorporation was <10%.

Plasmid and Retrovirus

SFG.iCasp9.2A.CD19 consists of inducible Caspase-9 (iCasp9) linked, via a cleavable 2A-like sequence, to truncated human CD19. iCasp9 consists of a human FK506-binding protein (FKBP12; GenBank AH002 818) with an F36V mutation, connected via a Ser-Gly-Gly-Gly-Ser-Gly linker (SEQ ID NO: 54) to human Caspase-9 (CASP9; GenBank NM 001229). The F36V mutation increases the binding affinity of FKBP12 to the synthetic homodimerizer, AP20187 or AP1903. The caspase recruitment domain (CARD) has been deleted from the human Caspase-9 sequence because its physiological function has been replaced by FKBP12, and its removal increases transgene expression and function. The 2A-like sequence encodes an 20 amino acid peptide from Thosea asigna insect virus, which mediates >99% cleavage between a glycine and terminal proline residue, resulting in 19 extra amino acids in the C terminus of iCasp9, and one extra proline residue in the N terminus of CD19. CD19 consists of full-length CD19 (GenBank NM 001770) truncated at amino acid 333 (TDPTRRF (SEQ ID NO: 123)), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus was made by transiently transfecting Phoenix Eco cell line (ATCC product #5D3444; ATCC, Manassas, Va.) with SFG.iCasp9.2A.CD19. This produced Eco-pseudotyped retrovirus. The PG13 packaging cell line (ATCC) was transduced three times with Eco-pseudotyped or retrovirus to generate a producer line that contained multiple SFG.iCasp9.2A.CD19 proviral integrants per cell. Single cell cloning was performed, and the PG13 clone that produced the highest titer was expanded and used for vector production.

Retroviral Transduction

Culture medium for T cell activation and expansion consisted of 45% RPMI 1640 (Hyclone, Logan, Utah), 45% Clicks (Irvine Scientific, Santa Ana, Calif.) and 10% fetal bovine serum (FBS; Hyclone). Allodepleted cells were activated by immobilized anti-CD3 (OKT3; Ortho Biotech, Bridgewater, N.J.) for 48 hours before transduction with retroviral vector. Selective allodepletion was performed by co-culturing donor PBMC with recipient EBV-LCL to activate alloreactive cells: activated cells expressed CD25 and were subsequently eliminated by anti-CD25 immunotoxin. The allodepleted cells were activated by OKT3 and transduced with the retroviral vector 48 hours later. Immunomagnetic selection was performed on day 4 of transduction; the positive fraction was expanded for a further 4 days and cryopreserved.

In small-scale experiments, non-tissue culture-treated 24-well plates (Becton Dickinson, San Jose, Calif.) were coated with OKT3 1 microgram/ml for 2 to 4 hours at 37° C. Allodepleted cells were added at $1\times10^6$ cells per well. At 24 hours, 100 U/ml of recombinant human interleukin-2 (IL-2) (Proleukin; Chiron, Emeryville, Calif.) was added. Retroviral transduction was performed 48 hours after activation. Non-tissue culture-treated 24-well plates were coated with 3.5 micrograms/cm$^2$ recombinant fibronectin fragment (CH-296; Retronectin; Takara Mirus Bio, Madison, Wis.) and the wells loaded twice with retroviral vector-containing supernatant at 0.5 ml per well for 30 minutes at 37° C., following which OKT3-activated cells were plated at $5\times10^5$ cells per well in fresh retroviral vector-containing supernatant and T cell culture medium at a ratio of 3:1, supplemented with 100 U/ml IL-2. Cells were harvested after 2 to 3 days and expanded in the presence of 50 U/ml IL-2. Similar methods, as discussed herein, may be used for lentiviral expression of the Bob1TCR and chimeric Caspase-9 polypeptides.

Scaling-Up Production of Gene-Modified Allodepleted Cells

Scale-up of the transduction process for clinical application used non-tissue culture-treated T75 flasks (Nunc, Rochester, N.Y.), which were coated with 10 ml of OKT3 1 μg/ml or 10 ml of fibronectin 7 μg/ml at 4° C. overnight. Fluorinated ethylene propylene bags corona-treated for increased cell adherence (2PF-0072AC, American Fluoroseal Corporation, Gaithersburg, Md.) were also used. Allodepleted cells were seeded in OKT3-coated flasks at $1\times10^6$ cells/ml. 100 U/ml IL-2 was added the next day. For retroviral transduction, retronectin-coated flasks or bags were loaded once with 10 ml of retrovirus-containing supernatant for 2 to 3 hours. OKT3-activated T cells were seeded at 1×106 cells/ml in fresh retroviral vector-containing medium and T cell culture medium at a ratio of 3:1, supplemented with 100 U/ml IL-2. Cells were harvested the following morning and expanded in tissue-culture treated T75 or T175 flasks in culture medium supplemented with between about 50 to 100 U/ml IL-2 at a seeding density of between about $5\times10^6$ cells/ml to $8\times10^6$ cells/ml.

CD19 Immunomagnetic Selection

CD19 was used as a marker; other suitable markers may be used for immunomagnetic selection. Immunomagnetic selection for CD19 was performed 4 days after transduction. Cells were labeled with paramagnetic microbeads conjugated to monoclonal mouse anti-human CD19 antibodies (Miltenyi Biotech, Auburn, Calif.) and selected on MS or LS columns in small scale experiments and on a CliniMacs Plus automated selection device in large scale experiments. CD19-selected cells were expanded for a further 4 days and cryopreserved on day 8 post transduction. These cells were referred to as "gene-modified allodepleted cells".

Immunophenotyping and Pentamer Analysis

Flow cytometric analysis (FACSCalibur and CellQuest software; Becton Dickinson) was performed using the following antibodies: CD3, CD4, CD8, CD19, CD25, CD27, CD28, CD45RA, CD45RO, CD56 and CD62L. CD19-PE (Clone 4G7; Becton Dickinson) was found to give optimum staining and was used in all subsequent analysis. A Non-transduced control was used to set the negative gate for CD19. An HLA-pentamer, HLA-B8-RAKFKQLL ("RAKFKQLL" disclosed as SEQ ID NO: 131) (Proimmune, Springfield, Va.) was used to detect T cells recognizing an epitope from EBV lytic antigen (BZLF1). HLA-A2-NLVPMVATV pentamer ("NLVPMVATV" disclosed as SEQ ID NO: 132) was used to detect T cells recognizing an epitope from CMV-pp65 antigen.

Induction of Apoptosis with Chemical Inducer of Dimerization, AP20187

Suicide gene functionality was assessed by adding a small molecule synthetic homodimerizer, AP20187 (Ariad Pharmaceuticals; Cambridge, Mass.), at 10 nM final concentration the day following CD19 immunomagnetic selection. AP1903 may also be used. Cells were stained with annexin V and 7-amino¬ actinomycin (7-AAD)(BD Pharmingen) at 24 hours and analyzed by flow cytometry. Cells negative for both annexin V and 7-AAD were considered viable, cells that were annexin V positive were apoptotic, and cells that were both annexin V and 7-AAD positive were necrotic. The percentage killing induced by dimerization was corrected for baseline viability as follows: Percentage killing=100%−(% Viability in AP20187-treated cells÷% Viability in non-treated cells).

Assessment of Transgene Expression Following Extended Culture and Reactivation

Cells were maintained in T cell medium containing 50 U/ml IL-2 until 22 days after transduction. A portion of cells was reactivated on 24-well plates coated with 1 microgram/ml OKT3 and 1 microgram/ml anti-CD28 (Clone CD28.2, BD Pharmingen, San Jose, Calif.) for 48 to 72 hours. CD19 expression and suicide gene function in both reactivated and non-reactivated cells were measured on day 24 or 25 post transduction.

In some experiments, cells also were cultured for 3 weeks post transduction and stimulated with 30 Girradiated allogeneic PBMC at a responder: stimulator ratio of 1:1. After 4 days of co-culture, a portion of cells was treated with 10 nM AP20187. Killing was measured by annexin V/7-AAD staining at 24 hours, and the effect of dimerizer on bystander virus-specific T cells was assessed by pentamer analysis on AP20187-treated and untreated cells.

Optimal culture conditions for maintaining the immunological competence of suicide gene-modified T cells must be determined and defined for each combination of safety switch, selectable marker and cell type, since phenotype, repertoire and functionality can all be affected by the stimulation used for polyclonal T cell activation, the method for selection of transduced cells, and duration of culture.

Phase I Clinical Trial of Allodepleted T Cells Transduced with Inducible Caspase-9 Suicide Gene after Haploidentical Stem Cell Transplantation This example presents results of a phase 1 clinical trial using an alternative suicide gene strategy. Briefly, donor peripheral blood mononuclear cells were co-cultured with recipient irradiated EBV-transformed lymphoblastoid cells (40:1) for 72 hrs, allodepleted with a CD25 immunotoxin and then transduced with a retroviral supernatant carrying the iCasp9 suicide gene and a selection marker (ΔCD19); ΔCD19 allowed enrichment to >90% purity via immunomagnetic selection.

An example of a protocol for generation of a T cell therapy product that comprises a chimeric Casase-9-encoding nucleic acid is provided herein. This example may be modified for the use of a Bob1 vector, as discussed herein. In certain embodimens, Autologous T cells can be used for this approach, or T cells after allogeneic SCT (donor origin but tolerized) or donor T cells This example discusses the use of allodepleted cells, however, either allodepleted donor T cells, or nonallodepleted donor T cells may be used, as discussed herein. The modified cells comprising the Bob1 vector may further comprise a chimeric Caspase-9 encoding nucleic acid, or other polypeptide-encoding nucleic acid, such as the chimeric stimulating polypeptides discussed herein.

In some compositions and methods, the Bob1 specific TCR may be expressed in T cells along with a chimeric Caspase-9 polypeptide, thus providing modified T cells comprising a nucleic acid that comprises a polynucleotide encoding a Bob1 TCR, and a nucleic acid that comprises a polynucleotide encoding a chimeric Caspase-9 polypeptide. Polynucleotides encoding the chimeric Caspase-9 polypeptide and polynucleotides encoding the Bob1 TCR may be transfected or transduced into the cells either on the same vector, in cis, or on separate vectors, in trans. Thus, the two polypeptides may be expressed using two nucleic acids, such as, for example, two plasmids or two viruses, and the T cells may be, for example, transfected twice, or in particular embodiments, the two nucleic acids may be co-transfected. In other embodiments, the two polypeptides may be expressed in one nucleic acid, such as, for example, in the same plasmid or virus. The nucleic acid may express the two polypeptides using two separate promoters, one for the TCR and one for the chimeric Caspase-9 polypeptide. Or, in other embodiments, the two polypeptides may be expressed using the same promoter. In this embodiment, the two polypeptides may be separated by a cleavable polypeptide, such as, for example, a 2A sequence.

Source Material

Up to 240 ml (in 2 collections) of peripheral blood was obtained from the transplant donor according to established protocols. In some cases, dependent on the size of donor and recipient, a leukopheresis was performed to isolate sufficient T cells. 10-30 cc of blood also was drawn from the recipient and was used to generate the Epstein Barr virus (EBV)-transformed lymphoblastoid cell line used as stimulator cells. In some cases, dependent on the medical history and/or indication of a low B cell count, the LCLs were generated using appropriate 1st degree relative (e.g., parent, sibling, or offspring) peripheral blood mononuclear cells.

Generation of Allodepleted Cells

Allodepleted cells were generated from the transplant donors as presented herein. Peripheral blood mononuclear cells (PBMCs) from healthy donors were co-cultured with irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that express CD25 were depleted from the co-culture by overnight incubation in RFT5-SMPT-dgA immunotoxin. Allodepletion is considered adequate if the residual CD3+ CD25+ population was <1% and residual proliferation by 3H-thymidine incorporation was <10%.

For the methods discussed in these examples, autologous T cells, obtained from the patient, may also be used.

Retroviral Production

A retroviral producer line clone was generated for the iCasp9-ΔCD19 construct. A master cell-bank of the producer also was generated. Testing of the master-cell bank was performed to exclude generation of replication competent retrovirus and infection by *Mycoplasma*, HIV, HBV, HCV and the like. The producer line was grown to confluency, supernatant harvested, filtered, aliquoted and rapidly frozen and stored at −80° C. Additional testing was performed on all batches of retroviral supernatant to exclude Replication Competent Retrovirus (RCR) and issued with a certificate of analysis, as per protocol.

Transduction of Allodepleted Cells

Allodepleted T-lymphocytes were transduced using Fibronectin. Plates or bags were coated with recombinant Fibronectin fragment CH-296 (Retronectin™, Takara Shuzo, Otsu, Japan). Virus was attached to retronectin by incubating producer supernatant in coated plates or bags. Cells were then transferred to virus coated plates or bags. After transduction allodepleted T cells were expanded, feeding them with IL-2 twice a week to reach the sufficient number of cells as per protocol.

CD19 Immunomagnetic Selection

Immunomagnetic selection for CD19 was performed 4 days after transduction. Cells are labeled with paramagnetic microbeads conjugated to monoclonal mouse anti-human CD19 antibodies (Miltenyi Biotech, Auburn, Calif.) and selected on a CliniMacs Plus automated selection device. Depending upon the number of cells required for clinical infusion cells were either cryopreserved after the CliniMacs selection or further expanded with IL-2 and cryopreserved on day 6 or day 8 post transduction.

Freezing

Aliquots of cells were removed for testing of transduction efficiency, identity, phenotype and microbiological culture as required for final release testing by the FDA. The cells were cryopreserved prior to administration according to protocol.

Study Drugs

RFT5-SMPT-dgA

RFT5-SMPT-dgA is a murine IgG1 anti-CD25 (IL-2 receptor a chain) conjugated via a hetero-bifunctional crosslinker [N-succinimidyloxycarbonyl-α-methyl-d-(2-pyridylthio)toluene] (SMPT) to chemically deglycosylated ricin A chain (dgA). RFT5-SMPT-dgA is formulated as a sterile solution at 0.5 mg/ml.

Synthetic Homodimerizer, AP1903

Mechanism of Action: AP1903-inducible cell death is achieved by expressing a chimeric protein comprising the intracellular portion of the human (Caspase-9 protein) receptor, which signals apoptotic cell death, fused to a drug-binding domain derived from human FK506-binding protein (FKBP). This chimeric protein remains quiescent inside cells until administration of AP1903, which cross-links the FKBP domains, initiating caspase signaling and apoptosis.

Toxicology: AP1903 has been evaluated as an Investigational New Drug (IND) by the FDA and has successfully completed a phase I clinical safety study. No significant adverse effects were noted when AP1903 was administered over a 0.01 mg/kg to 1.0 mg/kg dose range.

Pharmacology/Pharmacokinetics: Patients received 0.4 mg/kg of AP1903 as a 2 h infusion—based on published Pk data which show plasma concentrations of 10 ng/mL-over the 0.01 mg/kg to 1.0 mg/kg dose range with plasma levels falling to 18% and 7% of maximum at 0.5 and 2 hrs post dose (see, for example, Iuliucci, J. D., et al., J. Clin. Pharmacol. 2001, 41: 870-9).

Side Effect Profile in Humans: No serious adverse events occurred during the Phase 1 study in volunteers. The incidence of adverse events was very low following each treatment, with all adverse events being mild in severity. Only one adverse event was considered possibly related to AP1903. This was an episode of vasodilatation, presented as "facial flushing" for 1 volunteer at the 1.0 mg/kg AP1903 dosage. This event occurred at 3 minutes after the start of infusion and resolved after 32 minutes duration. All other adverse events reported during the study were considered by the investigator to be unrelated or to have improbable relationship to the study drug. These events included chest pain, flu syndrome, halitosis, headache, injection site pain, vasodilatation, increased cough, rhinitis, rash, gum hemorrhage, and ecchymosis.

Patients developing Grade I GvHD were treated with 0.4 mg/kg AP1903 as a 2-hour infusion. Protocols for administration of AP1903 to patients developing Grade I GvHD were established as follows. Patients developing GvHD after infusion of allodepleted T cells are biopsied to confirm the diagnosis and receive 0.4 mg/kg of AP1903 as a 2 h infusion. Patients with Grade I GvHD received no other therapy initially, however if they showed progression of GvHD conventional GvHD therapy was administered as per institutional guidelines. Patients developing grades 2-4 GvHD were administered standard systemic immunosuppressive therapy per institutional guidelines, in addition to the AP1903 dimerizer drug.

Instructions for preparation and infusion: AP1903 for injection is obtained as a concentrated solution of 2.33 ml in a 3 ml vial, at a concentration of 5 mg/ml, (i.e., 10.66 mg per vial). Prior to administration, the calculated dose was diluted to 100 mL in 0.9% normal saline for infusion. AP1903 for injection (0.4 mg/kg) in a volume of 100 ml was administered via IV infusion over 2 hours, using a non-DEHP, non-ethylene oxide sterilized infusion set and infusion pump.

The iCasp9 suicide gene expression construct (e.g., SFG.iCasp9.2A.ΔCD19) consists of inducible Caspase-9 (iCasp9) linked, via a cleavable 2A-like sequence, to truncated human CD19 (ΔCD19). iCasp9 includes a human FK506-binding protein (FKBP12; GenBank AH002 818) with an F36V mutation, connected via a Ser-Gly-Gly-Gly-Ser-Gly linker (SEQ ID NO: 54) to human Caspase-9 (CASP9; GenBank NM 001229). The F36V mutation may increase the binding affinity of FKBP12 to the synthetic homodimerizer, AP20187 or AP1903. The caspase recruitment domain (CARD) has been deleted from the human Caspase-9 sequence and its physiological function has been replaced by FKBP12. The replacement of CARD with FKBP12 increases transgene expression and function. The 2A-like sequence encodes an 18 amino acid peptide from Thosea Asigna insect virus, which mediates >99% cleavage between a glycine and terminal proline residue, resulting in 17 extra amino acids in the C terminus of iCasp9, and one extra proline residue in the N terminus of CD19. ΔCD19 consists of full length CD19 (GenBank NM 001770) truncated at amino acid 333 (TDPTRRF (SEQ ID NO: 123)), which shortens the intracytoplasmic domain from 242 to 19 amino acids, and removes all conserved tyrosine residues that are potential sites for phosphorylation.

In Vivo Studies

Three patients received iCasp9+ T cells after haplo-CD34+ stem cell transplantation (SCT), at dose levels between about $1\times10^6$ to about $3\times10^6$ cells/kg.

Infused T cells were detected in vivo by flow cytometry (CD3+ΔCD19+) or qPCR as early as day 7 after infusion, with a maximum fold expansion of 170±5 (day 29±9 after infusion. Two patients developed grade I/II aGvHD and AP1903 administration caused >90% ablation of CD3+ΔCD19+ cells, within 30 minutes of infusion, with a further log reduction within 24 hours, and resolution of skin and liver aGvHD within 24 hrs, showing that iCasp9 transgene was functional in vivo.

Ex vivo experiments confirmed this data. Furthermore, the residual allodepleted T cells were able to expand and were reactive to viruses (CMV) and fungi (*Aspergillus fumigatus*) (IFN-γ production). These in vivo studies found that a single dose of dimerizer drug can reduce or eliminate the subpopulation of T cells causing GvHD, but can spare virus specific CTLs, which can then re-expand.

Immune Reconstitution

Depending on availability of patient cells and reagents, immune reconstitution studies (Immunophenotyping, T and B cell function) may be obtained at serial intervals after transplant. Several parameters measuring immune reconstitution resulting from icaspase transduced allodepleted T cells will be analyzed. The analysis includes repeated measurements of total lymphocyte counts, T and CD19 B cell numbers, and FACS analysis of T cell subsets (CD3, CD4, CD8, CD16, CD19, CD27, CD28, CD44, CD62L, CCR7, CD56, CD45RA, CD45RO, alpha/beta and gamma/delta T cell receptors). Depending on the availability of a patients T cells T regulatory cell markers such as CD41CD251FoxP3 also are analyzed. Approximately 10-60 ml of patient blood is taken, when possible, 4 hours after infusion, weekly for 1 month, monthly×9 months, and then at 1 and 2 years. The amount of blood taken is dependent on the size of the recipient and does not exceed 1-2 cc/kg in total (allowing for blood taken for clinical care and study evaluation) at any one blood draw.

Modified Caspase-9 Polypeptides with Lower Basal Activity and Minimal Loss of Ligand IC50 Basal signaling, signaling in the absence of agonist or activating agent, is prevalent in a multitude of biomolecules. For example, it has been observed in more than 60 wild-type G protein coupled receptors (GPCRs) from multiple subfamilies [1], kinases, such as ERK and abl [2], surface immunoglobulins [3], and proteases. Basal signaling has been hypothesized to contribute to a vast variety of biological events, from maintenance of embryonic stem cell pluripotency, B cell development and differentiation [4-6], T cell differentiation [2, 7], thymocyte development [8], endocytosis and drug tolerance [9], autoimmunity [10], to plant growth and development [11]. While its biological significance is not always fully understood or apparent, defective basal signaling can lead to serious consequences. Defective basal G protein signaling has led to diseases, such as retinitis pigmentosa, color blindness, nephrogenic diabetes insipidus, familial ACTH resistance, and familial hypocalciuric hypercalcemia [12, 13].

Even though homo-dimerization of wild-type initiator Caspase-9 is energetically unfavorable, making them mostly monomers in solution [14-16], the low-level inherent basal activity of unprocessed Caspase-9 [15, 17] is enhanced in the presence of the Apaf-1-based "apoptosome", its natural allosteric regulator [6]. Moreover, supra-physiological expression levels and/or co-localization could lead to proximity-driven dimerization, further enhancing basal activation. The modified cells of the present application may comprise nucleic acids coding for a chimeric Caspase-9 polypeptide having lower basal signaling activity. Examples of Caspase-9 mutants with lower basal signaling are provided in the table below. Polynucleotides comprising Caspase-9 mutants with lower basal signaling may be expressed in the modified cells used for cell therapy herein. In these examples, the modified cells may include a safety switch, comprising a polynucleotide encoding a lower basal signaling chimeric Caspase-9 polypeptide. In the event of an adverse event following administration of the modified cells comprising the Bob1 TCRs herein, Caspase-9 activity may be induced by administering the dimerizer to the patient, thus inducing apoptosis and clearance of some, or all of the modified cells. In some examples, the amount of dimerizer administered may be determined as an amount designed to remove the highest amount, at least 80% or 90% of the modified cells. In other examples, the amount of dimerizer administered may be determined as an amount designed to remove only a portion of the modified cells, in order to alleviate negative symptoms or conditions, while leaving a sufficient amount of therapeutic modified cells in the patient, in order to continue therapy. Methods for using chimeric Caspase-9 polypeptides to induce apoptosis are discussed in PCT Application Number PCT/US2011/037381 by Malcolm K. Brenner et al., titled Methods for Inducing Selective Apoptosis, filed May 20, 2011, and in U.S. patent application Ser. No. 13/112,739 by Malcolm K. Brenner et al., titled Methods for Inducing Selective Apoptosis, filed May 20, 2011, now U.S. Pat. No. 9,089,520. Chimeric caspase polypeptides having modified basal activity are discussed in International Patent Application Serial Number PCT/US2014/022004, published as WO2014/164348 on Mar. 5, 2015, entitled "Modified Caspase Polypeptides and Uses Thereof," and in International Patent Application Serial Number PCT/US2015/019186, published as WO2015/134877 on Sep. 11, 2015, and entitled "Caspase Polypeptides having Modified Activity and Uses Thereof." Methods for inducing partial apoptosis of the therapeutic modified cells are discussed in PCT Application Number PCT/US14/40964, published as WO2014/197638 on Dec. 11, 2014, by Kevin Slawin et al., titled Methods for Inducing Partial Apoptosis Using Caspase Polypeptides. These patent applications and publications are all incorporated by reference herein in their entireties.

TABLE 3

Caspase Mutant Classes and Basal Activity

| Basal Activity | Homodimerization domain | Cleavage sites & XIAP Interaction | Phosphorylation | Double mutants, Misc. | Total mutants |
|---|---|---|---|---|---|
| Decreased basal and | | | S144A | | 80 |
| | | | S144D | | *, predicted |
| similar $IC_{50}$ | | T317S | S196D | | |
| Decreased basal but | **N405Q** | **D330A** | S183A | D330A-N405Q | Bold, Tested in T cells |
| higher $IC_{50}$ | $^{402}$GCFNF$^{406}$ISAQT (Casp-10) (SEQ ID NOS 133 and 134) | **D330E** | S195A | D330A-S144A | |
| | **F404Y** | **D330G** | S196A | D330A-S144D | |
| | F406A | **D330N** | | D330A-S183A | |
| | **F406W** | **D330S** | | D330A-S196A | |

TABLE 3-continued

| Caspase Mutant Classes and Basal Activity | | | | | |
|---|---|---|---|---|---|
| Basal Activity | Homodimerization domain | Cleavage sites & XIAP Interaction | Phosphorylation | Double mutants, Misc. | Total mutants |
| | **F406Y** | **D330V** | | N405Q-S144A | |
| | **N405Qco** | L329E | | N405Q-S144D | |
| | | T317A | | N405Q-S196D | |
| | | | | N405Q-T317S | |
| | | | | *N405Q-S144Aco | |
| | | | | *N405Q-T317Sco | |
| Decreased basal but much higher $IC_{50}$ | F404T | D315A | Y153A | | |
| | F404W | A316G | Y153F | | |
| | N405F | F319W | S307A | | |
| | **F406T** | | | | |
| Similar basal and $IC_{50}$ | C403A | $^{316}$ATPF$^{319}$AVPI (SEQ ID NOS 135 and 136) (SMAC/Diablo) | | | |
| | C403S | T317C | | | |
| | C403T | P318A | | | |
| | N405A | F319A | | | |
| Increased basal | N405T | T317E | | D330A-N405T | |
| | | F326K | | | |
| | | D327G | | | |
| | | D327K | | | |
| | | D327R | | | |
| | | Q328K | | | |
| | | Q328R | | | |
| | | L329G | | | |
| | | L329K | | | |
| | | A331K | | | |
| Catalytically dead | $^{402}$GCFNF$^{406}$AAAAA (SEQ ID NOS 133 and 137) | | | C285A | |
| | $^{402}$GCFNF$^{406}$YCSTL (Casp-2) (SEQ ID NOS 133 and 138) | | | D315A-D330A | |
| | $^{402}$GCFNF$^{406}$CIVSM (Casp-3) (SEQ ID NOS 133 and 139) | | | D330A-Y153A | |
| | $^{402}$GCFNF$^{406}$QPTFT (Casp-8) (SEQ ID NOS 133 and 140) | | | D330A-Y153F | |
| | G402A | | | D330A-T317E | |
| | G402I | | | | |
| | G402Q | | | | |
| | G402Y | | | | |
| | C403P | | | | |
| | F404A | | | | |
| | F404S | | | | |
| | F406L | | | | |

Figure 15:
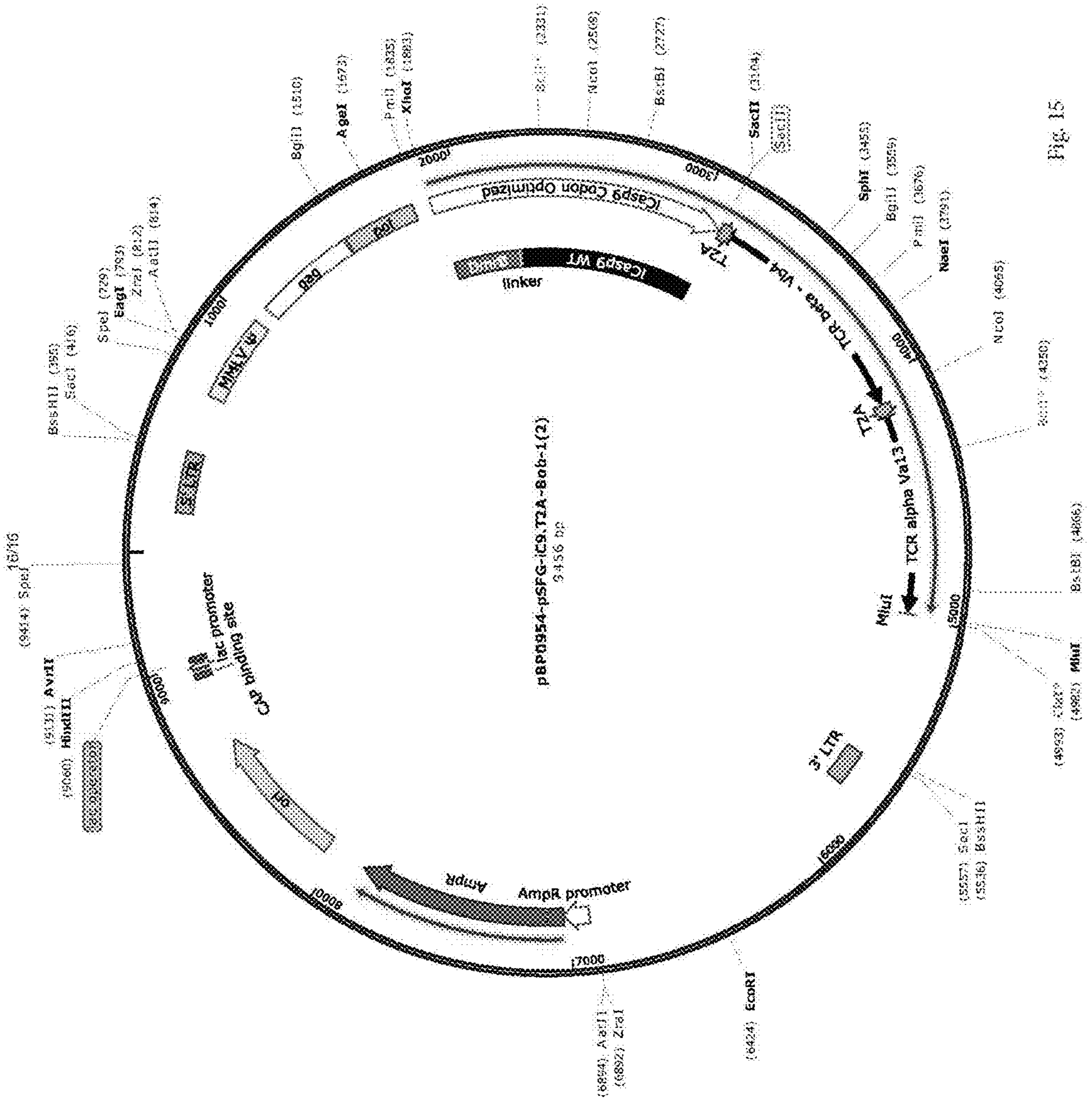
FIG. 15 is a plasmid map of a pBP0954-pSFG-iC9.T2A-Bob-1 plasmid that encodes a Bob1 TCR and an inducible Caspase-9 polypeptide, linked by a cleavabe 2A linker. The plasmid comprises a modified truncated Caspase-9 polypeptide (N405Q).

Provided in FIG. 15 is an example of a plasmid, pBP0954-pSFG-iC9.T2A-Bob-1, that may be used to express a nucleic acid of the present application, comprising polynucleotides coding for a Bob1 TCR and an inducible chimeric Caspase-9 polypeptide. In this example, the truncated Caspase-9 polypeptide includes the N405Q mutation; other truncated Caspase-9 polypeptides, for example, the truncated Caspase-9 polypeptides provided herein, for example those having amino acid sequences SEQ ID NOs: 58, 108, 110, 112, or 116, for example, those encoded by nucleotide sequences SEQ ID NOs: 57, 107, 109, 111, or 115, may be substituted for the N405Q Caspase-9 polypeptide-encoding polynucleotide used in the plasmid. Also, it is understood that the order of the polypeptides, as separated by 2A polypeptide cleavable linker-encoding polynucleotides, may vary. In this example, the polynucleotide coding for the inducible chimeric Caspase-9 polypeptide is located adjacent to, and separated by a 2A polypeptide-encoding polynucleotide from, the Bob1TCRβ polypeptide. In other embodiments, the polynucleotide coding for the inducible chimeric Caspase-9 polypeptide may be located adjacent to, and separated by a 2A polypeptide-encoding polynucleotide from, the Bob1TCRα polypeptide. In yet other embodiments, the polynucleotide coding for the inducible chimeric Caspase09 polypeptide may be located between the Bob1 TCRα and Bob1 TCRβ polypeptides, separated on either side of the inducible Caspase-9-encoding polynucleotide by two polynucleotides, each encoding 2A polypeptides. Appropriate polynucleotide linker sequences, for example, those provided herein, may also be located directly adjacent to any of the polynucleotides discussed herein.

LITERATURE REFERENCES CITED OR PROVIDING ADDITIONAL SUPPORT TO THE PRESENT EXAMPLE

1. Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
2. Roose, J. P., et al., T cell receptor-independent basal signaling via Erk and Abl kinases suppresses RAG gene expression. PLoS Biol, 2003. 1(2): p. E53.
3. Tze, L. E., et al., Basal immunoglobulin signaling actively maintains developmental stage in immature B cells. PLoS Biol, 2005. 3(3): p. e82.
4. Schram, B. R., et al., B cell receptor basal signaling regulates antigen-induced Ig light chain rearrangements. J Immunol, 2008. 180(7): p. 4728-41.

5. Randall, K. L., et al., Dock8 mutations cripple B cell immunological synapses, germinal centers and long-lived antibody production. Nat Immunol, 2009. 10(12): p. 1283-91.

6. Kouskoff, V., et al., B cell receptor expression level determines the fate of developing B lymphocytes: receptor editing versus selection. Proc Natl Acad Sci USA, 2000. 97(13): p. 7435-9.

7. Hong, T., et al., A simple theoretical framework for understanding heterogeneous differentiation of CD4+ T cells. BMC Syst Biol, 2012. 6: p. 66.

8. Rudd, M. L., A. Tua-Smith, and D. B. Straus, Lck SH3 domain function is required for T-cell receptor signals regulating thymocyte development. Mol Cell Biol, 2006. 26(21): p. 7892-900.

9. Sorkin, A. and M. von Zastrow, Endocytosis and signalling: intertwining molecular networks. Nat Rev Mol Cell Biol, 2009. 10(9): p. 609-22.

10. Luning Prak, E. T., M. Monestier, and R. A. Eisenberg, B cell receptor editing in tolerance and autoimmunity. Ann N Y Acad Sci, 2011. 1217: p. 96-121.

11. Boss, W. F., et al., Basal signaling regulates plant growth and development. Plant Physiol, 2010. 154(2): p. 439-43.

12. Tao, Y. X., Constitutive activation of G protein-coupled receptors and diseases: insights into mechanisms of activation and therapeutics. Pharmacol Ther, 2008. 120(2): p. 129-48.

13. Spiegel, A. M., Defects in G protein-coupled signal transduction in human disease. Annu Rev Physiol, 1996. 58: p. 143-70.

14. Shiozaki, E. N., et al., Mechanism of XIAP-mediated inhibition of caspase-9. Mol Cell, 2003. 11(2): p. 519-27.

15. Renatus, M., et al., Dimer formation drives the activation of the cell death protease caspase-9. Proc Natl Acad Sci USA, 2001. 98(25): p. 14250-5.

16. Shi, Y., Mechanisms of Caspase activation and inhibition during apoptosis. Mol Cell, 2002. 9(3): p. 459-70.

17. Shiozaki, E. N., J. Chai, and Y. Shi, Oligomerization and activation of caspase-9, induced by Apaf-1 CARD. Proc Natl Acad Sci USA, 2002. 99(7): p. 4197-202.

18. Straathof, K. C., et al., An inducible caspase-9 safety switch for T-cell therapy. Blood, 2005. 105(11): p. 4247-54.

19. MacCorkle, R. A., K. W. Freeman, and D. M. Spencer, Synthetic activation of Caspases: artificial death switches. Proc Natl Acad Sci USA, 1998. 95(7): p. 3655-60.

20. Di Stasi, A., et al., Inducible apoptosis as a safety switch for adoptive cell therapy. N Engl J Med, 2011. 365(18): p. 1673-83.

21. Chang, W. C., et al., Modifying ligand-induced and constitutive signaling of the human 5-HT4 receptor. PLoS One, 2007. 2(12): p. e1317.

22. Bloom, J. D. and F. H. Arnold, In the light of directed evolution: pathways of adaptive protein evolution. Proc Natl Acad Sci USA, 2009. 106 Suppl 1: p. 9995-10000.

23. Boatright, K. M. and G. S. Salvesen, Mechanisms of Caspase activation. Curr Opin Cell Biol, 2003. 15(6): p. 725-31.

24. Boatright, K. M., et al., A unified model for apical Caspase activation. Mol Cell, 2003. 11(2): p. 529-41.

25. Chao, Y., et al., Engineering a dimeric caspase-9: a re-evaluation of the induced proximity model for Caspase activation. PLoS Biol, 2005. 3(6): p. e183.

26. Stennicke, H. R., et al., caspase-9 can be activated without proteolytic processing. J Biol Chem, 1999. 274 (13): p. 8359-62.

27. Brady, S. C., L. A. Allan, and P. R. Clarke, Regulation of caspase-9 through phosphorylation by protein kinase C zeta in response to hyperosmotic stress. Mol Cell Biol, 2005. 25(23): p. 10543-55.

28. Martin, M. C., et al., Protein kinase A regulates caspase-9 activation by Apaf-1 downstream of cytochrome c. J Biol Chem, 2005. 280(15): p. 15449-55.

29. Cardone, M. H., et al., Regulation of cell death protease caspase-9 by phosphorylation. Science, 1998. 282(5392): p. 1318-21.

30. Raina, D., et al., c-Abl tyrosine kinase regulates caspase-9 autocleavage in the apoptotic response to DNA damage. J Biol Chem, 2005. 280(12): p. 11147-51.

31. Papworth, C., Bauer, J. C., Braman, J. and Wright, D. A., Site-directed mutagenesis in one day with >80% efficiency. Strategies, 1996. 9(3): p. 3-4.

32. Spencer, D. M., et al., Functional analysis of Fas signaling in vivo using synthetic inducers of dimerization. Curr Biol, 1996. 6(7): p. 839-47.

33. Hsiao, E. C., et al., Constitutive Gs activation using a single-construct tetracycline-inducible expression system in embryonic stem cells and mice. Stem Cell Res Ther, 2011. 2(2): p. 11.

34. Waldner, C., et al., Double conditional human embryonic kidney cell line based on FLP and PhiC31 mediated transgene integration. BMC Res Notes, 2011. 4: p. 420.

Examples of sequences that may be used to express chimeric Caspase-9 polypeptides include the following sequences. Sequences herein may be selected for inclusion in to the appropriate expression vector as discussed herein.

```
nucleotide sequence of 5'LTR sequence
                                             SEQ ID NO: 50
TGAAAGACCCCACCTGTAGGTTTGGCAAGCTAGCTTAAGTAACGCCATT

TTGCAAGGCATGGAAAAATACATAACTGAGAATAGAAAAGTTCAGATCA

AGGTCAGGAACAGATGGAACAGCTGAATATGGGCCAAACAGGATATCTG

TGGTAAGCAGTTCCTGCCCCGGCTCAGGGCCAAGAACAGATGGAACAGC

TGAATATGGGCCAAACAGGATATCTGTGGTAAGCAGTTCCTGCCCCGGC

TCAGGGCCAAGAACAGATGGTCCCCAGATGCGGTCCAGCCCTCAGCAGT

TTCTAGAGAACCATCAGATGTTTCCAGGGTGCCCCAAGGACCTGAAATG

ACCCTGTGCCTTATTTGAACTAACCAATCAGTTCGCTTCTCGCTTCTGT

TCGCGCGCTTATGCTCCCCGAGCTCAATAAAAGAGCCCACAACCCCTCA

CTCGGGGCGCCAGTCCTCCGATTGACTGAGTCGCCCGGGTACCCGTGTA

TCCAATAAACCCTCTTGCAGTTGCATCCGACTTGTGGTCTCGCTGTTCC

TTGGGAGGGTCTCCTCTGAGTGATTGACTACCCGTCAGCGGGGGTCTTT

CA

nucleotide sequence of Fv (human FKBP12v36)
                                             SEQ ID NO: 51
GGAGTGCAGGTGGAAACCATCTCCCCAGGAGACGGGCGCACCTTCCCCA

AGCGCGGCCAGACCTGCGTGGTGCACTACACCGGGATGCTTGAAGATGG

AAAGAAAGTTGATTCCTCCCGGGACAGAAACAAGCCCTTTAAGTTTATG

CTAGGCAAGCAGGAGGTGATCCGAGGCTGGGAAGAAGGGGTTGCCCAGA

TGAGTGTGGGTCAGAGAGCCAAACTGACTATATCTCCAGATTATGCCTA

TGGTGCCACTGGGCACCCAGGCATCATCCCACCACATGCCACTCTCGTC

TTCGATGTGGAGCTTCTAAAACTGGAA
```

-continued amino acid sequence of Fv (human FKBP12v36)

SEQ ID NO: 52

GVQVETISPGDGRTFPKRGQTCVVHYTGMLEDGKK

VDSSRDRNKPFKFMLGKQEVIRGWEEGVAQMSVGQ

RAKLTISPDYAYGATGHPGIIPPHATLVFDVELLKLE

GS linker nucleotide sequence

SEQ ID NO: 53

TCTGGCGGTGGATCCGGA

GS linker amino acid sequence

SEQ ID NO: 54

SGGGSG linker nucleotide sequence (between GS linker and Casp 9)

SEQ ID NO: 55

GTCGAC linker amino acid sequence (between GS linker and Casp 9)

SEQ ID NO: 56

VD

Casp 9 (truncated) nucleotide sequence

SEQ ID NO: 57

GGATTTGGTGATGTCGGTGCTCTTGAGAGTTTGAGGGGAAATGCAGATTT

GGCTTACATCCTGAGCATGGAGCCCTGTGGCCACTGCCTCATTATCAACA

ATGTGAACTTCTGCCGTGAGTCCGGGCTCCGCACCCGCACTGGCTCCAAC

ATCGACTGTGAGAAGTTGCGGCGTCGCTTCTCCTCGCTGCATTTCATGGT

GGAGGTGAAGGGCGACCTGACTGCCAAGAAAATGGTGCTGGCTTTGCTGG

AGCTGGCGCAGCAGGACCACGGTGCTCTGGACTGCTGCGTGGTGGTCATT

CTCTCTCACGGCTGTCAGGCCAGCCACCTGCAGTTCCCAGGGGCTGTCTA

CGGCACAGATGGATGCCCTGTGTCGGTCGAGAAGATTGTGAACATCTTCA

ATGGGACCAGCTGCCCCAGCCTGGGAGGGAAGCCCAAGCTCTTTTTCATC

CAGGCCTGTGGTGGGGAGCAGAAAGACCATGGGTTTGAGGTGGCCTCCAC

TTCCCCTGAAGACGAGTCCCCTGGCAGTAACCCCGAGCCAGATGCCACCC

CGTTCCAGGAAGGTTTGAGGACCTTCGACCAGCTGGACGCCATATCTAGT

TTGCCCACACCCAGTGACATCTTTGTGTCCTACTCTACTTTCCCAGGTTT

TGTTTCCTGGAGGGACCCCAAGAGTGGCTCCTGGTACGTTGAGACCCTGG

ACGACATCTTTGAGCAGTGGGCTCACTCTGAAGACCTGCAGTCCCTCCTG

CTTAGGGTCGCTAATGCTGTTTCGGTGAAAGGGATTTATAAACAGATGCC

TGGTTGCTTTAATTTCCTCCGGAAAAAACTTTTCTTTAAAACATCA

Caspase 9 (truncated) amino acid sequence-CARD domain deleted

SEQ ID NO: 58

GFGDVGALESLRGNADLAYILSMEPCGHCLIINNVN

FCRESGLRTRTGSNIDCEKLRRRFSSLHFMVEVKGD

LTAKKMVLALLELAQQDHGALDCCVVVILSHGCQAS

HLQFPGAVYGTDGCPVSVEKIVNIFNGTSCPSLGGK

PKLFFIQACGGEQKDHGFEVASTSPEDESPGSNPEP

DATPFQEGLRTFDQLDAISSLPTPSDIFVSYSTFPGF

VSWRDPKSGSWYVETLDDIFEQWAHSEDLQSLLLR

VANAVSVKGIYKQMPGCFNFLRKKLFFKTS linker nucleotide sequence (between caspase 9 and 2A)

SEQ ID NO: 59

GCTAGCAGA linker amino acid sequence (between caspase 9 and 2A)

SEQ ID NO: 60

ASR

Thosea asigna virus-2A from capsid protein precursor nucleotide sequence

SEQ ID NO: 61

GCCGAGGGCAGGGGAAGTCTTCTAACATGCGGGGACGTGGAGGAAAATCC
CGGGCCC

Thosea asigna virus-2A from capsid protein precursor amino acid sequence

SEQ ID NO: 62

AEGRGSLLTCGDVEENPGP human CD19 (Δ cytoplasmic domain) nucleotide sequence (transmembrane domain in bold)

SEQ ID NO: 63

ATGCCACCTCCTCGCCTCCTCTTCTTCCTCCTCTTCCTCACCCCCATGGA

AGTCAGGCCCGAGGAACCTCTAGTGGTGAAGGTGGAAGAGGGAGATAACG

CTGTGCTGCAGTGCCTCAAGGGGACCTCAGATGGCCCCACTCAGCAGCTG

ACCTGGTCTCGGGAGTCCCCGCTTAAACCCTTCTTAAAACTCAGCCTGGG

GCTGCCAGGCCTGGGAATCCACATGAGGCCCCTGGCCATCTGGCTTTTCA

TCTTCAACGTCTCTCAACAGATGGGGGGCTTCTACCTGTGCCAGCCGGGG

CCCCCCTCTGAGAAGGCCTGGCAGCCTGGCTGGACAGTCAATGTGGAGGG

CAGCGGGGAGCTGTTCCGGTGGAATGTTTCGGACCTAGGTGGCCTGGGCT

GTGGCCTGAAGAACAGGTCCTCAGAGGGCCCCAGCTCCCCTTCCGGGAAG

CTCATGAGCCCCAAGCTGTATGTGTGGGCCAAAGACCGCCCTGAGATCTG

GGAGGGAGAGCCTCCGTGTCTCCCACCGAGGGACAGCCTGAACCAGAGCC

TCAGCCAGGACCTCACCATGGCCCCTGGCTCCACACTCTGGCTGTCCTGT

GGGGTACCCCCTGACTCTGTGTCCAGGGGCCCCCTCTCCTGGACCCATGT

GCACCCCAAGGGGCCTAAGTCATTGCTGAGCCTAGAGCTGAAGGACGATC

GCCCGGCCAGAGATATGTGGGTAATGGAGACGGGTCTGTTGTTGCCCCGG

GCCACAGCTCAAGACGCTGGAAAGTATTATTGTCACCGTGGCAACCTGAC

CATGTCATTCCACCTGGAGATCACTGCTCGGCCAGTACTATGGCACTGGC

TGCTGAGGACTGGTGGCTGGAAGGTCTCAGCTGTGACTTTGGCTTATCTG

ATCTTCTGCCTGTGTTCCCTTGTGGGCATTCTTCATCTTCAAAGAGCCCT

GGTCCTGAGGAGGAAAAGAAAGCGAATGACTGACCCCACCAGGAGATTC human CD19 (Δ cytoplasmic domain) amino acid sequence

SEQ ID NO: 64

MPPPRLLFFLLFLTPMEVRPEEPLVVKVEEGDNAVL

QCLKGTSDGPTQQLTWSRESPLKPFLKLSLGLPGLG

IHMRPLAIWLFIFNVSQQMGGFYLCQPGPPSEKAWQ

PGWTVNVEGSGELFRWNVSDLGGLGCGLKNRSSEG

PSSPSGKLMSPKLYVWAKDRPEIWEGEPPCLPPRD

SLNQSLSQDLTMAPGSTLWLSCGVPPDSVSRGPLS

WTHVHPKGPKSLLSLELKDDRPARDMWVMETGLLL

-continued

PRATAQDAGKYYCHRGNLTMSFHLEITARPVLWHW

LLRTGGWKVSAVTLAYLIFCLCSLVGILHLQRALVLR

RKRKRMTDPTRRF

3'LTR nucleotide sequence

SEQ ID NO: 65

TGAAAGACCCCACCTGTAGGTTTGGCAAGCTAGCTTAAGTAACGCCATT

TGCAAGGCATGGAAAAATACATAACTGAGAATAGAGAAGTTCAGATCAAG

GTCAGGAACAGATGGAACAGCTGAATATGGGCCAAACAGGATATCTGTGG

TAAGCAGTTCCTGCCCCGGCTCAGGGCCAAGAACAGATGGAACAGCTGAA

TATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAG

AGAACCATCAGATGTTTCCAGGGTGCCCCAAGGACCTGAAATGACCCTGT

GCCTTATTTGAACTAACCAATCAGTTCGCTTCTCGCTTCTGTTCGCGCGC

TTCTGCTCCCCGAGCTCAATAAAAGAGCCCACAACCCCTCACTCGGGGCG

CCAGTCCTCCGATTGACTGAGTCGCCCGGGTACCCGTGTATCCAATAAAC

CCTCTTGCAGTTGCATCCGACTTGTGGTCTCGCTGTTCCTTGGGAGGGTC

TCCTCTGAGTGATTGACTACCCGTCAGCGGGGGTCTTTCA

Example 7: Addition of an Inducible Chimeric Costimulating Polypolypeptide

T cell receptor signaling can be induced using a chemical inducer of dimerization (CID) in combination with a chimeric costimulating polypeptide that includes a multimerization region that binds to the CID, T cells were engineered to express the inducible chimeric costimulating polypeptide, which was linked with 1, 2, or 3 FKBP fragments. The cells expressed the chimeric receptor, and demonstrated CID-dependent T cell activation (Spencer, D. M., et al., Science, 1993. 262: p. 1019-1024). Methods and compositions for the coexpression of a polypeptide having an antigen-recognition region, such as, for example, chimeric antigen receptors or TCRs in T cells, are discussed, for example, in International Patent Application Serial Number PCT/US2014/026734, published as WO2014/151960 on Sep. 25, 2014, entitled "Methods for Controlling T Cell Proliferation" and in Internatioal Patent Application Serial Number PCT/US2015/015829, published as WO2015/123527 on Aug. 20, 2015, entitled "Methods for Activating T cells Using an Inducible Chimeric Polypeptide," which are incorporated by referenced in their entirety herein.).

Example 8: Examples of Particular Nucleic Acid and Amino Acid Sequences

The following additional sequences may be used in the design of expression vectors that encode the Bob1 TCRs and chimeric Caspase-9 polypeptides provided herein.

SEQ ID NO: 66, nucleotide sequence of 5'LTR sequence

TGAAAGACCCCACCTGTAGGTTTGGCAAGCTAGCTTAAGTAACGCCATT

TTGCAAGGCATGGAAAAATACATAACTGAGAATAGAAAAGTTCAGATCA

AGGTCAGGAACAGATGGAACAGCTGAATATGGGCCAAACAGGATATCTG

-continued

TGGTAAGCAGTTCCTGCCCCGGCTCAGGGCCAAGAACAGATGGAACAGC

TGAATATGGGCCAAACAGGATATCTGTGGTAAGCAGTTCCTGCCCCGGC

TCAGGGCCAAGAACAGATGGTCCCCAGATGCGGTCCAGCCCTCAGCAGT

TTCTAGAGAACCATCAGATGTTTCCAGGGTGCCCCAAGGACCTGAAATG

ACCCTGTGCCTTATTTGAACTAACCAATCAGTTCGCTTCTCGCTTCTGT

TCGCGCGCTTATGCTCCCCGAGCTCAATAAAAGAGCCCACAACCCCTCA

CTCGGGGCGCCAGTCCTCCGATTGACTGAGTCGCCCGGGTACCCGTGTA

TCCAATAAACCCTCTTGCAGTTGCATCCGACTTGTGGTCTCGCTGTTCC

TTGGGAGGGTCTCCTCTGAGTGATTGACTACCCGTCAGCGGGGGTCTTT

CA

SEQ ID NO, 67 Thosea asigna virus-2A from capsid protein precursor nucleotide sequence

GCCGAGGGCAGGGGAAGTCTTCTAACATGCGGGGACGTGGAGGAAAATC

CCGGGCCC

SEQ ID NO: 68, Thosea asigna virus-2A from capsid protein precursor amino acid sequence

AEGRGSLLTCGDVEENPGP

SEQ ID NO: 69, 3'LTR nucleotide sequence

TGAAAGACCCCACCTGTAGGTTTGGCAAGCTAGCTTAAGTAACGCCATT

TTGCAAGGCATGGAAAAATACATAACTGAGAATAGAGAAGTTCAGATCA

AGGTCAGGAACAGATGGAACAGCTGAATATGGGCCAAACAGGATATCTG

TGGTAAGCAGTTCCTGCCCCGGCTCAGGGCCAAGAACAGATGGAACAGC

TGAATATGGGCCAAACAGGATATCTGTGGTAAGCAGTTCCTGCCCCGGC

TCAGGGCCAAGAACAGATGGTCCCCAGATGCGGTCCAGCCCTCAGCAGT

TTCTAGAGAACCATCAGATGTTTCCAGGGTGCCCCAAGGACCTGAAATG

ACCCTGTGCCTTATTTGAACTAACCAATCAGTTCGCTTCTCGCTTCTGT

TCGCGCGCTTCTGCTCCCCGAGCTCAATAAAAGAGCCCACAACCCCTCA

CTCGGGGCGCCAGTCCTCCGATTGACTGAGTCGCCCGGGTACCCGTGTA

TCCAATAAACCCTCTTGCAGTTGCATCCGACTTGTGGTCTCGCTGTTCC

TTGGGAGGGTCTCCTCTGAGTGAT

TGACTACCCGTCAGCGGGGGTCTTTCA

SEQ ID NO: 70, (nucleotide sequence of linker-Fv1-Fv2-linker with XhoI/SalI sites, (wobbled codons lowercase in Fv2'))

CTCGAGTCTGGCGGTGGATCCGGAGGCGTTCAAGTAGAAACAATCAGCC

CAGGAGACGGAAGGACTTTCCCCAAACGAGGCCAAACATGCGTAGTTCA

TTATACTGGGATGCTCGAAGATGGAAAAAAAGTAGATAGTAGTAGAGAC

CGAAACAAACCATTTAAATTTATGTTGGGAAAACAAGAAGTAATAAGGG

GCTGGGAAGAAGGTGTAGCACAAATGTCTGTTGGCCAGCGCGCAAAACT

CACAATTTCTCCTGATTATGCTTACGGAGCTACCGGCCACCCCGGCATC

ATACCCCCTCATGCCACACTGGTGTTTGACGTCGAATTGCTCAAACTGG

AAGTCGAGGGaGTgCAgGTgGAgACgATtAGtCCtGGgGAtGGgAGaAC cTTtCCaAAgCGcGGtCAgACcTGtGTtGTcCAcTAcACcGGtATGCTg

GAgGAcGGgAAgAAgGTgGActcTtcacGcGAtCGcAAtAAgCCtTTcA

AgTTcATGcTcGGcAAgCAgGAgGTgAtccGGGGgTGGGAgGAgGGcGT

-continued gGCtCAgATGTCgGTcGGgCAaCGaGCgAAgCTtACcATcTCaCCcGAc

TAcGCgTAtGGgGCaACgGGgCAtCCgGGaATtATcCCtCCcCAcGCtA

CgCTcGTaTTcGAtGTgGAgcTcttgAAgCTtGagTCTGGCGGTGGATC

CGGAGTCGAC

SEQ ID NO: 71, (FV'FVLS amino acid sequence)
LESGGGSGGVQVETISPGDGRTFPKRGQTCVVHYTGMLEDGKKVDSSRD

RNKPFKFMLGKQEVIRGWEEGVAQMSVGQRAKLTISPDYAYGATGHPGI

IPPHATLVFDVELLKLEVEGVQVETISPGDGRTFPKRGQTCVVHYTGML

EDGKKVDSSRDRNKPFKFMLGKQEVIRGWEEGVAQMSVGQRAKLTISPD

YAYGATGHPGIIPPHATLVFDVELLKLESGGGSGVD

SEQ ID NO: 72, FKBPv36 (Fv1) nucleotide sequence
GGCGTTCAAGTAGAAACAATCAGCCCAGGAGACGGAAGGACTTTCCCCA

AACGAGGCCAAACATGCGTAGTTCATTATACTGGGATGCTCGAAGATGG

AAAAAAAGTAGATAGTAGTAGAGACCGAAACAAACCATTTAAATTTATG

TTGGGAAAACAAGAAGTAATAAGGGGCTGGGAAGAAGGTGTAGCACAAA

TGTCTGTTGGCCAGCGCGCAAAACTCACAATTTCTCCTGATTATGCTTA

CGGAGCTACCGGCCACCCCGGCATCATACCCCCTCATGCCACACTGGTG

TTTGACGTCGAATTGCTCAAACTGGAA

SEQ ID NO: 73, FKBPv36 (Fv1) amino acid sequence
GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE

SEQ ID NO: 74, FKBPv36 (Fv2) nucleotide sequence
GGaGTgCAgGTgGAgACgATtAGtCCtGGgGAtGGgAGaACcTTtCCaA AgCGcGGtCAgACcTGtGTtGTcCAcTAcACcGGtATGCTgGAgGAcGG gAAgAAgGTgGActcTtcacGcGAtCGcAAtAAgCCtTTcAAgTTcATG cTcGGcAAgCAgGAgGTgATccGGGGgTGGGAgGAgGGcGTgGCtCAgA TGTCgGTcGGgCAaCGaGCgAAgCTtACcATcTCaCCcGAcTAcGCgTA tGGgGCaACgGGgCAtCCgGGaATtATcCCtCCcCAcGCtACgCTcGTa TTcGAtGTgGAgcTcttgAAgCTtGag SEQ ID NO: 75, FKBPv36 (Fv2) amino acid sequence
GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE

SEQ ID NO: 76, Linker nucleotide sequence
(linker 1)
CTCGAG

SEQ ID NO: 77, Linker amino acid sequence
(linker 1)
LE

SEQ ID NO: 78, Linker nucleotide sequence
(linker 2)
GTCGAGTCTGGCGGTGGATCCGGA

SEQ ID NO: 79, Linker amino acid sequence
(linker 2)
VESGGGSG

-continued

SEQ ID NO: 80, FKBPv36 (Fv1) nucleotide sequence
GGCGTTCAAGTAGAAACAATCAGCCCAGGAGACGGAAGGACTTTCCCCA

AACGAGGCCAAACATGCGTAGTTCATTATACTGGGATGCTCGAAGATGG

AAAAAAAGTAGATAGTAGTAGAGACCGAAACAAACCATTTAAATTTATG

TTGGGAAAACAAGAAGTAATAAGGGGCTGGGAAGAAGGTGTAGCACAAA

TGTCTGTTGGCCAGCGCGCAAAACTCACAATTTCTCCTGATTATGCTTA

CGGAGCTACCGGCCACCCCGGCATCATACCCCCTCATGCCACACTGGTG

TTTGACGTCGAATTGCTCAAACTGGAA

SEQ ID NO: 81, FKBPv36 (Fv1) amino acid sequence
GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE

SEQ ID NO: 82, Linker nucleotide sequence
(linker 3)
GTCGAG

SEQ ID NO: 83, Linker amino acid sequence
(linker 3)
VE

SEQ ID NO: 84, FKBPv36 (Fv2) nucleotide sequence
GGaGTgCAgGTgGAgACgATtAGtCCtGGgGAtGGgAGaACcTTtCCaA AgCGcGGtCAgACcTGtGTtGTcCAcTAcACcGGtATGCTgGAgGAcGG gAAgAAgGTgGActcTtcacGcGAtCGcAAtAAgCCtTTcAAgTTcATG cTcGGcAAgCAgGAgGTgATccGGGGgTGGGAgGAgGGcGTgGCtCAgA TGTCgGTcGGgCAaCGaGCgAAgCTtACcATcTCaCCcGAcTAcGCgTA tGGgGCaACgGGgCAtCCgGGaATtATcCCtCCcCAcGCtACgCTcGTa TTcGAtGTgGAgcTcttgAAgCTtGag SEQ ID NO: 85, FKBPv36 (Fv2) amino acid sequence
GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE

SEQ ID NO: 86, Linker nucleotide sequence
(linker 4)
TCTGGCGGTGGATCCGGAGTCGAC

SEQ ID NO: 87, Linker amino acid sequence
(linker 4)
SGGGSGVD

SEQ ID NO: 88, Furin protease consensus cleavage
site nucleotide sequence
CGCGCAAAGCGT SEQ ID NO: 89, Furin protease consensus cleavage
site amino acid sequence
RAKR SEQ ID NO: 90, V5 epitope nucleotide sequence
GGAAAACCTATACCTAATCCATTGCTGGGCTTAGACTCAACA SEQ ID NO: 91, V5 epitope nucleotide sequence
GKPIPNPLLGLDST SEQ ID NO: 92, Linker nucleotide sequence
(linker 5)
GGCAGCGGAAGC -continued SEQ ID NO: 93, Linker amino acid sequence
(linker 5)
GSGS SEQ ID NO: 94, P2A nucleotide sequence
GCAACGAATTTTTCCCTGCTGAAACAGGCAGGGGACGTAGAGGAAAATC
CTGGTCCT SEQ ID NO: 95, P2A amino acid sequence
ATNFSLLKQAGDVEENPGP SEQ ID NO 96 Linker nucleotide sequence
(linker 6)
ACGCGT SEQ ID NO: 97, Linker amino acid sequence
(linker 6)
TR SEQ ID NO: 98, ΔCD19 nucleotide sequence
ATGCCCCCTCCTAGACTGCTGTTTTTCCTGCTCTTTCTCACCCCAATGG
AAGTTAGACCTGAGGAACCACTGGTCGTTAAAGTGGAAGAAGGTGATAA
TGCTGTCCTCCAATGCCTTAAAGGGACCAGCGACGGACCAACGCAGCAA
CTGACTTGGAGCCGGGAGTCCCCTCTCAAGCCGTTTCTCAAGCTGTCAC
TTGGCCTGCCAGGTCTTGGTATTCACATGCGCCCCCTTGCCATTTGGCT
CTTCATATTCAATGTGTCTCAACAAATGGGTGGATTCTACCTTTGCCAG
CCCGGCCCCCCTTCTGAGAAAGCTTGGCAGCCTGGATGGACCGTCAATG
TTGAAGGCTCCGGTGAGCTGTTTAGATGGAATGTGAGCGACCTTGGCGG
ACTCGGTTGCGGACTGAAAAATAGGAGCTCTGAAGGACCCTCTTCTCCC
TCCGGTAAGTTGATGTCACCTAAGCTGTACGTGTGGGCCAAGGACCGCC
CCGAAATCTGGGAGGGCGAGCCTCCATGCCTGCCGCCTCGCGATTCACT
GAACCAGTCTCTGTCCCAGGATCTCACTATGGCGCCCGGATCTACTCTT
TGGCTGTCTTGCGGCGTTCCCCCAGATAGCGTGTCAAGAGGACCTCTGA
GCTGGACCCACGTACACCCTAAGGGCCCTAAGAGCTTGTTGAGCCTGGA
ACTGAAGGACGACAGACCCGCACGCGATATGTGGGTAATGGAGACCGGC
CTTCTGCTCCCTCGCGCTACCGCACAGGATGCAGGGAAATACTACTGTC
ATAGAGGGAATCTGACTATGAGCTTTCATCTCGAAATTACAGCACGGCC
CGTTCTTTGGCATTGGCTCCTCCGGACTGGAGGCTGGAAGGTGTCTGCC
GTAACACTCGCTTACTTGATTTTTTGCCTGTGTAGCCTGGTTGGGATCC
TGCATCTTCAGCGAGCCCTTGTATTGCGCCGAAAAAGAAAACGAATGAC
TGACCCTACACGACGATTCTGA SEQ ID NO: 99, ΔCD19 amino acid sequence
MPPPRLLFFLLFLTPMEVRPEEPLVVKVEEGDNAVLQCLKGTSDGPTQQ
LTWSRESPLKPFLKLSLGLPGLGIHMRPLAIWLFIFNVSQQMGGFYLCQ
PGPPSEKAWQPGVVTVNVEGSGELFRWNVSDLGGLGCGLKNRSSEGPSS
PSGKLMSPKLYVWAKDRPEIWEGEPPCLPPRDSLNQSLSQDLTMAPGST
LWLSCGVPPDSVSRGPLSVVTHVHPKGPKSLLSLELKDDRPARDMVVVM
ETGLLLPRATAQDAGKYYCHRGNLTMSFHLEITARPVLWHWLLRTGGWK
VSAVTLAYLIFCLCSLVGILHLQRALVLRRKRKRMTDPTRRF*

Fv'
SEQ ID NO: 100
GGcGTcCAaGTcGAaACcATtagtCCcGGcGAtGGcaGaACaTTtCCtA
AaaGgGGaCAaACaTGtGTcGTcCAtTAtACaGGcATGtTgGAgGAcGG
cAAaAAgGTgGAcagtagtaGaGAtcGcAAtAAaCCtTTcAAaTTcATG
tTgGGaAAaCAaGAaGTcATtaGgGGaTGGGAgGAgGGcGTgGCtCAaA
TGtccGTcGGcCAacGcGCtAAgCTcACcATcagcCCcGAcTAcGCaTA
cGGcGCtACcGGaCAtCCcGGaATtATtCCcCCtCAcGCtACctTgGTg
TTtGAcGTcGAaCTgtTgAAgCTc SEQ ID NO: 101: Fv'
GVQVETISPGDGRTFPKRGQTCVVHYTGMLEDGKKVDSSRDRNKPFKFM
LGKQEVIRGWEEGVAQMSVGQRAKLTISPDYAYGATGHPGIIPPHATLV
FDVELLKL Fv
SEQ ID NO: 102
ggagtgcaggtggagactatctccccaggagacgggcgcaccttcccca
agcgcggccagacctgcgtggtgcactacaccgggatgcttgaagatgg
aaagaaagttgattcctcccgggacagaaacaagccctttaagtttatg
ctaggcaagcaggaggtgatccgaggctgggaagaaggggttgcccaga
tgagtgtgggtcagagagccaaactgactatatctccagattatgccta
tggtgccactgggcacccaggcatcatcccaccacatgccactctcgtc
ttcgatgtggagcttctaaaactggaa Fv
SEQ ID NO: 103
GVQVETISPGDGRTFPKRGQTCVVHYTGMLEDGKKVDSSRDRNKPFKFM
LGKQEVIRGWEEGVAQMSVGQRAKLTISPDYAYGATGHPGIIPPHATLV
FDVELLKLE

P2A
SEQ ID NO: 104
GCTACTAACTTCAGCCTGCTGAAGCAGGCTGGAGACGTGGAGGAGAACC
CTGGACCT

P2A
SEQ ID NO: 105
ATNFSLLKQAGDVEENPGP

SEQ ID NO: 106, ΔCasp9 (res. 135-416)
GFGDVGALESLRGNADLAYILSMEPCGHCLIINNVN
FCRESGLRTRTGSNIDCEKLRRRFSSLHFMVEVKGD
LTAKKMVLALLELARQDHGALDCCVVVILSHGCQAS
HLQFPGAVYGTDGCPVSVEKIVNIFNGTSCPSLGGK
PKLFFIQACGGEQKDHGFEVASTSPEDESPGSNPEP
DATPFQEGLRTFDQLDAISSLPTPSDIFVSYSTFPGF
VSWRDPKSGSWYVETLDDIFEQWAHSEDLQSLLLR
VANAVSVKGIYKQMPGCFNFLRKKLFFKTS SEQ ID NO: 107, ΔCasp9 (res. 135-416) D330A,
nucleotide sequence
GGATTTGGTGATGTCGGTGCTCTTGAGAGTTTGAGGGGAAATGCAGATT
TGGCTTACATCCTGAGCATGGAGCCCTGTGGCCACTGCCTCATTATCAA
CAATGTGAACTTCTGCCGTGAGTCCGGGCTCCGCACCCGCACTGGCTCC -continued

AACATCGACTGTGAGAAGTTGCGGCGTCGCTTCTCCTCGCTGCATTTCA

TGGTGGAGGTGAAGGGCGACCTGACTGCCAAGAAAATGGTGCTGGCTTT

GCTGGAGCTGGCGCgGCAGGACCACGGTGCTCTGGACTGCTGCGTGGTG

GTCATTCTCTCTCACGGCTGTCAGGCCAGCCACCTGCAGTTCCCAGGGG

CTGTCTACGGCACAGATGGATGCCCTGTGTCGGTCGAGAAGATTGTGAA

CATCTTCAATGGGACCAGCTGCCCCAGCCTGGGAGGGAAGCCCAAGCTC

TTTTTCATCCAGGCCTGTGGTGGGGAGCAGAAAGACCATGGGTTTGAGG

TGGCCTCCACTTCCCCTGAAGACGAGTCCCCTGGCAGTAACCCCGAGCC

AGATGCCACCCCGTTCCAGGAAGGTTTGAGGACCTTCGACCAGCTGGCC

GCCATATCTAGTTTGCCCACACCCAGTGACATCTTTGTGTCCTACTCTA

CTTTCCCAGGTTTTGTTTCCTGGAGGGACCCCAAGAGTGGCTCCTGGTA

CGTTGAGACCCTGGACGACATCTTTGAGCAGTGGGCTCACTCTGAAGAC

CTGCAGTCCCTCCTGCTTAGGGTCGCTAATGCTGTTTCGGTGAAAGGGA

TTTATAAACAGATGCCTGGTTGCTTTAATTTCCTCCGGAAAAAACTTTT

CTTTAAAACATCA

SEQ ID NO: 108, ΔCasp9 (res. 135-416) D330A, amino acid sequence

GFGDVGALESLRGNADLAYILSMEPCGHCLIINNVN

FCRESGLRTRTGSNIDCEKLRRRFSSLHFMVEVKGD

LTAKKMVLALLELARQDHGALDCCVVVILSHGCQAS

HLQFPGAVYGTDGCPVSVEKIVNIFNGTSCPSLGGK

PKLFFIQACGGEQKDHGFEVASTSPEDESPGSNPEP

DATPFQEGLRTFDQLAAISSLPTPSDIFVSYSTFPGF

VSWRDPKSGSWYVETLDDIFEQWAHSEDLQSLLLR

VANAVSVKGIYKQMPGCFNFLRKKLFFKTS

SEQ ID NO: 109, ΔCasp9 (res. 135-416) N405Q nucleotide sequence

GGATTTGGTGATGTCGGTGCTCTTGAGAGTTTGAGGGGAAATGCAGA

TTTGGCTTACATCCTGAGCATGGAGCCCTGTGGCCACTGCCTCATTA

TCAACAATGTGAACTTCTGCCGTGAGTCCGGGCTCCGCACCCGCACT

GGCTCCAACATCGACTGTGAGAAGTTGCGGCGTCGCTTCTCCTCGCT

GCATTTCATGGTGGAGGTGAAGGGCGACCTGACTGCCAAGAAAATGG

TGCTGGCTTTGCTGGAGCTGGCGCgGCAGGACCACGGTGCTCTGGAC

TGCTGCGTGGTGGTCATTCTCTCTCACGGCTGTCAGGCCAGCCACCT

GCAGTTCCCAGGGGCTGTCTACGGCACAGATGGATGCCCTGTGTCGG

TCGAGAAGATTGTGAACATCTTCAATGGGACCAGCTGCCCCAGCCTG

GGAGGGAAGCCCAAGCTCTTTTTCATCCAGGCCTGTGGTGGGGAGCA

GAAAGACCATGGGTTTGAGGTGGCCTCCACTTCCCCTGAAGACGAGT

CCCCTGGCAGTAACCCCGAGCCAGATGCCACCCCGTTCCAGGAAGGT

TTGAGGACCTTCGACCAGCTGGACGCCATATCTAGTTTGCCCACACC

CAGTGACATCTTTGTGTCCTACTCTACTTTCCCAGGTTTTGTTTCCT

GGAGGGACCCCAAGAGTGGCTCCTGGTACGTTGAGACCCTGGACGAC

-continued

ATCTTTGAGCAGTGGGCTCACTCTGAAGACCTGCAGTCCCTCCTGCT

TAGGGTCGCTAATGCTGTTTCGGTGAAAGGGATTTATAAACAGATGC

CTGGTTGCTTTCAGTTCCTCCGGAAAAAACTTTTCTTTAAAACATCA

SEQ ID NO: 110, ΔCasp9 (res. 135-416) N405Q amino acid sequence

GFGDVGALESLRGNADLAYILSMEPCGHCLIINNVN

FCRESGLRTRTGSNIDCEKLRRRFSSLHFMVEVKGD

LTAKKMVLALLELARQDHGALDCCVVVILSHGCQAS

HLQFPGAVYGTDGCPVSVEKIVNIFNGTSCPSLGGK

PKLFFIQACGGEQKDHGFEVASTSPEDESPGSNPEP

DATPFQEGLRTFDQLDAISSLPTPSDIFVSYSTFPGF

VSWRDPKSGSWYVETLDDIFEQWAHSEDLQSLLLR

VANAVSVKGIYKQMPGCFQFLRKKLFFKTS

SEQ ID NO: 111, ΔCasp9 (res. 135-416) D330A N405Q nucleotide sequence

GGATTTGGTGATGTCGGTGCTCTTGAGAGTTTGAGGGGAAATGCAGA

TTTGGCTTACATCCTGAGCATGGAGCCCTGTGGCCACTGCCTCATTA

TCAACAATGTGAACTTCTGCCGTGAGTCCGGGCTCCGCACCCGCACT

GGCTCCAACATCGACTGTGAGAAGTTGCGGCGTCGCTTCTCCTCGCT

GCATTTCATGGTGGAGGTGAAGGGCGACCTGACTGCCAAGAAAATGG

TGCTGGCTTTGCTGGAGCTGGCGCgGCAGGACCACGGTGCTCTGGAC

TGCTGCGTGGTGGTCATTCTCTCTCACGGCTGTCAGGCCAGCCACCT

GCAGTTCCCAGGGGCTGTCTACGGCACAGATGGATGCCCTGTGTCGG

TCGAGAAGATTGTGAACATCTTCAATGGGACCAGCTGCCCCAGCCTG

GGAGGGAAGCCCAAGCTCTTTTTCATCCAGGCCTGTGGTGGGGAGCA

GAAAGACCATGGGTTTGAGGTGGCCTCCACTTCCCCTGAAGACGAGT

CCCCTGGCAGTAACCCCGAGCCAGATGCCACCCCGTTCCAGGAAGGT

TTGAGGACCTTCGACCAGCTGGCCGCCATATCTAGTTTGCCCACACC

CAGTGACATCTTTGTGTCCTACTCTACTTTCCCAGGTTTTGTTTCCT

GGAGGGACCCCAAGAGTGGCTCCTGGTACGTTGAGACCCTGGACGAC

ATCTTTGAGCAGTGGGCTCACTCTGAAGACCTGCAGTCCCTCCTGCT

TAGGGTCGCTAATGCTGTTTCGGTGAAAGGGATTTATAAACAGATGC

CTGGTTGCTTTCAGTTCCTCCGGAAAAAACTTTTCTTTAAAACATCA

SEQ ID NO: 112, ΔCasp9 (res. 135-416) D330A N405Q amino acid sequence

GFGDVGALESLRGNADLAYILSMEPCGHCLIINNVN

FCRESGLRTRTGSNIDCEKLRRRFSSLHFMVEVKGD

LTAKKMVLALLELARQDHGALDCCVVVILSHGCQAS

HLQFPGAVYGTDGCPVSVEKIVNIFNGTSCPSLGGK

PKLFFIQACGGEQKDHGFEVASTSPEDESPGSNPEP

DATPFQEGLRTFDQLAAISSLPTPSDIFVSYSTFPGF

VSWRDPKSGSWYVETLDDIFEQWAHSEDLQSLLLR

VANAVSVKGIYKQMPGCFQFLRKKLFFKTS

SEQ ID NO: 113, Caspase-9.co nucleotide sequence
GTGGACGGGTTTGGAGATGTGGGAGCCCTGGAATCCCTGCGGGGCAATG

CCGATCTGGCTTACATCCTGTCTATGGAGCCTTGCGGCCACTGTCTGAT

CATTAACAATGTGAACTTCTGCAGAGAGAGCGGGCTGCGGACCAGAACA

GGATCCAATATTGACTGTGAAAAGCTGCGGAGAAGGTTCTCTAGTCTGC

ACTTTATGGTCGAGGTGAAAGGCGATCTGACCGCTAAGAAAATGGTGCT

GGCCCTGCTGGAACTGGCTCGGCAGGACCATGGGGCACTGGATTGCTGC

GTGGTCGTGATCCTGAGTCACGGCTGCCAGGCTTCACATCTGCAGTTCC

CTGGGGCAGTCTATGGAACTGACGGCTGTCCAGTCAGCGTGGAGAAGAT

CGTGAACATCTTCAACGGCACCTCTTGCCCAAGTCTGGGCGGGAAGCCC

AAACTGTTCTTTATTCAGGCCTGTGGAGGCGAGCAGAAAGATCACGGCT

TCGAAGTGGCTAGCACCTCCCCCGAGGACGAATCACCTGGAAGCAACCC

TGAGCCAGATGCAACCCCCTTCCAGGAAGGCCTGAGGACATTTGACCAG

CTGGATGCCATCTCAAGCCTGCCCACACCTTCTGACATTTTCGTCTCTT

ACAGTACTTTCCCTGGATTTGTGAGCTGGCGCGATCCAAAGTCAGGCAG

CTGGTACGTGGAGACACTGGACGATATCTTTGAGCAGTGGGCCCATTCT

GAAGACCTGCAGAGTCTGCTGCTGCGAGTGGCCAATGCTGTCTCTGTGA

AGGGGATCTACAAACAGATGCCAGGATGCTTCCAGTTTCTGAGAAAGAA

ACTGTTCTTTAAGACCTCCGCATCTAGGGCC

SEQ ID NO: 114, Caspase-9.co amino acid sequence
VDGFGDVGALESLRGNADLAYILSMEPCGHCLIINNVNFCRESGLRTRT

GSNIDCEKLRRRFSSLHFMVEVKGDLTAKKMVLALLELARQDHGALDCC

VVVILSHGCQASHLQFPGAVYGTDGCPVSVEKIVNIFNGTSCPSLGGKP

KLFFIQACGGEQKDHGFEVASTSPEDESPGSNPEPDATPFQEGLRTFDQ

LDAISSLPTPSDIFVSYSTFPGFVSWRDPKSGSVVYVETLDDIFEQWAH

SEDLQSLLLRVANAVSVKGIYKQMPGCFQFLRKKLFFKTSASRA

SEQ ID NO: 115: Caspase9 D330E nucleotide sequence
GTCGACGGATTTGGTGATGTCGGTGCTCTTGAGAGTTTGAGGGGAAATG

CAGATTTGGCTTACATCCTGAGCATGGAGCCCTGTGGCCACTGCCTCAT

TATCAACAATGTGAACTTCTGCCGTGAGTCCGGGCTCCGCACCCGCACT

GGCTCCAACATCGACTGTGAGAAGTTGCGGCGTCGCTTCTCCTCGCTGC

ATTTCATGGTGGAGGTGAAGGGCGACCTGACTGCCAAGAAAATGGTGCT

GGCTTTGCTGGAGCTGGCGCGGCAGGACCACGGTGCTCTGGACTGCTGC

GTGGTGGTCATTCTCTCTCACGGCTGTCAGGCCAGCCACCTGCAGTTCC

CAGGGGCTGTCTACGGCACAGATGGATGCCCTGTGTCGGTCGAGAAGAT

TGTGAACATCTTCAATGGGACCAGCTGCCCCAGCCTGGGAGGGAAGCCC

AAGCTCTTTTTCATCCAGGCCTGTGGTGGGGAGCAGAAAGACCATGGGT

TTGAGGTGGCCTCCACTTCCCCTGAAGACGAGTCCCCTGGCAGTAACCC

CGAGCCAGATGCCACCCCGTTCCAGGAAGGTTTGAGGACCTTCGACCAG

CTGGcCGCCATATCTAGTTTGCCCACACCCAGTGACATCTTTGTGTCCT

ACTCTACTTTCCCAGGTTTTGTTTCCTGGAGGGACCCCAAGAGTGGCTC

CTGGTACGTTGAGACCCTGGACGACATCTTTGAGCAGTGGGCTCACTCT

GAAGACCTGCAGTCCCTCCTGCTTAGGGTCGCTAATGCTGTTTCGGTGA

AAGGGATTTATAAACAGATGCCTGGTTGCTTTAATTTCCTCCGGAAAAA

ACTTTTCTTTAAAACATCAGCTAGCAGAGCC

SEQ ID NO: 116: Caspase9 D330E amino acid sequence
VDGFGDVGALESLRGNADLAYILSMEPCGHCLIINNVNFCRESGLRTRT

GSNIDCEKLRRRFSSLHFMVEVKGDLTAKKMVLALLELARQDHGALDCC

VVVILSHGCQASHLQFPGAVYGTDGCPVSVEKIVNIFNGTSCPSLGGKP

KLFFIQACGGEQKDHGFEVASTSPEDESPGSNPEPDATPFQEGLRTFDQ

LeAISSLPTPSDIFVSYSTFPGFVSWRDPKSGSVVYVETLDDIFEQWAH

SEDLQSLLLRVANAVSVKGIYKQMPGCFNFLRKKLFFKTSASRA

SEQ ID NO: 117: pBP0954-pSFG-iC9.T2A-Bob-1
plasmid nucleotide sequence
TGAAAGACCCCACCTGTAGGTTTGGCAAGCTAGCTTAAGTAACGCCATT

TTGCAAGGCATGGAAAAATACATAACTGAGAATAGAAAAGTTCAGATCA

AGGTCAGGAACAGATGGAACAGCTGAATATGGGCCAAACAGGATATCTG

TGGTAAGCAGTTCCTGCCCCGGCTCAGGGCCAAGAACAGATGGAACAGC

TGAATATGGGCCAAACAGGATATCTGTGGTAAGCAGTTCCTGCCCCGGC

TCAGGGCCAAGAACAGATGGTCCCCAGATGCGGTCCAGCCCTCAGCAGT

TTCTAGAGAACCATCAGATGTTTCCAGGGTGCCCCAAGGACCTGAAATG

ACCCTGTGCCTTATTTGAACTAACCAATCAGTTCGCTTCTCGCTTCTGT

TCGCGCGCTTATGCTCCCCGAGCTCAATAAAAGAGCCCACAACCCCTCA

CTCGGGGCGCCAGTCCTCCGATTGACTGAGTCGCCCGGGTACCCGTGTA

TCCAATAAACCCTCTTGCAGTTGCATCCGACTTGTGGTCTCGCTGTTCC

TTGGGAGGGTCTCCTCTGAGTGATTGACTACCCGTCAGCGGGGGTCTTT

CATTTGGGGGCTCGTCCGGGATCGGGAGACCCCTGCCCAGGGACCACCG

ACCCACCACCGGGAGGTAAGCTGGCCAGCAACTTATCTGTGTCTGTCCG

ATTGTCTAGTGTCTATGACTGATTTTATGCGCCTGCGTCGGTACTAGTT

AGCTAACTAGCTCTGTATCTGGCGGACCCGTGGTGGAACTGACGAGTTC

GGAACACCCGGCCGCAACCCTGGGAGACGTCCCAGGGACTTCGGGGGCC

GTTTTTGTGGCCCGACCTGAGTCCTAAAATCCCGATCGTTTAGGACTCT

TTGGTGCACCCCCCTTAGAGGAGGGATATGTGGTTCTGGTAGGAGACGA

GAACCTAAAACAGTTCCCGCCTCCGTCTGAATTTTTGCTTTCGGTTTGG

GACCGAAGCCGCGCCGCGCGTCTTGTCTGCTGCAGCATCGTTCTGTGTT

GTCTCTGTCTGACTGTGTTTCTGTATTTGTCTGAAAATATGGGCCCGGG

CTAGCCTGTTACCACTCCCTTAAGTTTGACCTTAGGTCACTGGAAAGAT

GTCGAGCGGATCGCTCACAACCAGTCGGTAGATGTCAAGAAGAGACGTT

GGGTTACCTTCTGCTCTGCAGAATGGCCAACCTTTAACGTCGGATGGCC

GCGAGACGGCACCTTTAACCGAGACCTCATCACCCAGGTTAAGATCAAG

GTCTTTTCACCTGGCCCGCATGGACACCCAGACCAGGTGGGGTACATCG

TGACCTGGGAAGCCTTGGCTTTTGACCCCCCTCCCTGGGTCAAGCCCTT

TGTACACCCTAAGCCTCCGCCTCCTCTTCCTCCATCCGCCCCGTCTCTC

-continued

CCCCTTGAACCTCCTCGTTCGACCCCGCCTCGATCCTCCCTTTATCCAG

CCCTCACTCCTTCTCTAGGCGCCCCCATATGGCCATATGAGATCTTATA

TGGGGCACCCCCGCCCCTTGTAAACTTCCCTGACCCTGACATGACAAGA

GTTACTAACAGCCCCTCTCTCCAAGCTCACTTACAGGCTCTCTACTTAG

TCCAGCACGAAGTCTGGAGACCTCTGGCGGCAGCCTACCAAGAACAACT

GGACCGACCGGTGGTACCTCACCCTTACCGAGTCGGCGACACAGTGTGG

GTCCGCCGACACCAGACTAAGAACCTAGAACCTCGCTGGAAAGGACCTT

ACACAGTCCTGCTGACCACCCCCACCGCCCTCAAAGTAGACGGCATCGC

AGCTTGGATACACGCCGCCCACGTGAAGGCTGCCGACCCCGGGGGTGGA

CCATCCTCTAGACTGCCATGCTCGAGATGCTGGAGGGAGTGCAGGTGGA

GACTATTAGCCCCGGAGATGGCAGAACATTCCCCAAAAGAGGACAGACT

TGCGTCGTGCATTATACTGGAATGCTGGAAGACGGCAAGAAGGTGGACA

GCAGCCGGGACCGAAACAAGCCCTTCAAGTTCATGCTGGGGAAGCAGGA

AGTGATCCGGGGCTGGGAGGAAGGAGTCGCACAGATGTCAGTGGGACAG

AGGGCCAAACTGACTATTAGCCCAGACTACGCTTATGGAGCAACCGGCC

ACCCCGGGATCATTCCCCCTCATGCTACACTGGTCTTCGATGTGGAGCT

GCTGAAGCTGGAAAGCGGAGGAGGATCCGGAGTGGACGGGTTTGGAGAT

GTGGGAGCCCTGGAATCCCTGCGGGGCAATGCCGATCTGGCTTACATCC

TGTCTATGGAGCCTTGCGGCCACTGTCTGATCATTAACAATGTGAACTT

CTGCAGAGAGAGCGGGCTGCGGACCAGAACAGGATCCAATATTGACTGT

GAAAAGCTGCGGAGAAGGTTCTCTAGTCTGCACTTTATGGTCGAGGTGA

AAGGCGATCTGACCGCTAAGAAAATGGTGCTGGCCCTGCTGGAACTGGC

TCGGCAGGACCATGGGGCACTGGATTGCTGCGTGGTCGTGATCCTGAGT

CACGGCTGCCAGGCTTCACATCTGCAGTTCCCTGGGGCAGTCTATGGAA

CTGACGGCTGTCCAGTCAGCGTGGAGAAGATCGTGAACATCTTCAACGG

CACCTCTTGCCCAAGTCTGGGCGGGAAGCCCAAACTGTTCTTTATTCAG

GCCTGTGGAGGCGAGCAGAAAGATCACGGCTTCGAAGTGGCTAGCACCT

CCCCCGAGGACGAATCACCTGGAAGCAACCCTGAGCCAGATGCAACCCC

CTTCCAGGAAGGCCTGAGGACATTTGACCAGCTGGATGCCATCTCAAGC

CTGCCCACACCTTCTGACATTTTCGTCTCTTACAGTACTTTCCCTGGAT

TTGTGAGCTGGCGCGATCCAAAGTCAGGCAGCTGGTACGTGGAGACACT

GGACGATATCTTTGAGCAGTGGGCCCATTCTGAAGACCTGCAGAGTCTG

CTGCTGCGAGTGGCCAATGCTGTCTCTGTGAAGGGGATCTACAAACAGA

TGCCAGGATGCTTCAACTTTCTGAGAAAGAAACTGTTCTTTAAGACCTC

CGCATCTAGGGCCCCGCGGGAAGGTAGAGGGAGCCTGCTGACATGTGGC

GATGTCGAGGAGAATCCGGGACCTATGGGATGTAGACTGCTGTGCTGTG

CTGTGCTGTGCCTGCTGGGGGCTGTGCCTATTGATACCGAAGTGACTCA

GACTCCAAAGCACCTGGTCATGGGCATGACCAACAAGAAAAGCCTGAAA

TGCGAGCAGCACATGGGGCATAGGGCCATGTACTGGTATAAGCAGAAAG

CTAAGAAACCCCCTGAACTGATGTTCGTGTACAGCTATGAGAAGCTGTC

CATCAATGAATCCGTCCCCTCTCGCTTCAGTCCCGAGTGCCCTAACAGC

-continued

TCCCTGCTGAATCTGCACCTGCATGCTCTGCAGCCTGAAGACTCCGCAC

TGTACCTGTGCGCCTCTAGTCACGGGCCAGCCTCTTACGAGCAGTATTT

TGGACCCGGCACCAGACTGACTGTGACCGAAGATCTGAAGAACGTCTTC

CCACCCGAGGTGGCAGTCTTTGAACCATCTGAGGCCGAAATTAGTCATA

CTCAGAAAGCCACCCTGGTGTGCCTGGCTACAGGCTTCTATCCCGACCA

CGTGGAGCTGAGTTGGTGGGTCAACGGCAAGGAAGTGCATTCAGGGGTC

TGCACTGACCCTCAGCCACTGAAAGAGCAGCCTGCTCTGAATGATTCAA

GGTACTGTCTGTCAAGCCGGCTGAGAGTGAGCGCCACTTTTTGGCAGAA

CCCAAGGAATCACTTCCGCTGCCAGGTGCAGTTTTATGGCCTGAGCGAG

AATGACGAATGGACTCAGGATCGCGCTAAGCCAGTGACCCAGATCGTCT

CCGCAGAGGCCTGGGGACGAGCAGACTGTGGCTTCACATCTGAAAGTTA

CCAGCAGGGGGTGCTGTCTGCCACAATCCTGTACGAGATTCTGCTGGGA

AAGGCCACTCTGTACGCCGTGCTGGTGAGCGCCTTAGTCTTAATGGCCA

TGGTGAAAAGAAAGGATTCCAGAGGAGGATCCGGCGAGGGCAGAGGAAG

TCTTCTAACATGCGGTGACGTGGAGGAGAATCCCGGCCCTATGACAAGC

ATCAGAGCCGTGTTCATTTTTCTGTGGCTGCAGCTGGATCTGGTGAACG

GAGAGAATGTCGAACAGCATCCTTCAACTCTGAGCGTGCAGGAGGGCGA

TTCCGCAGTCATCAAGTGTACCTACTCAGACAGCGCCTCCAATTACTTT

CCTTGGTATAAGCAGGAGCTGGGGAAAGGACCACAGCTGATCATTGATA

TCAGAAGCAACGTGGGCGAAAAGAAAGACCAGAGGATTGCTGTCACACT

GAATAAGACTGCAAAACACTTCAGCCTGCATATTACAGAGACTCAGCCC

GAAGACTCCGCCGTGTATTTTTGCGCCGCTTCTAAGGGGTCCTCTAACA

CCGGAAAACTGATCTTCGGCCAGGGGACCACACTGCAGGTGAAGCCTGA

CATTCAGAATCCAGATCCCGCCGTCTACCAGCTGCGAGACTCAAAGAGT

TCAGATAAAAGCGTGTGCCTGTTCACCGACTTTGATAGCCAGACAAACG

TGTCTCAGAGTAAGGACTCCGACGTGTACATCACCGACAAATGCGTGCT

GGATATGCGCAGCATGGACTTCAAGAGCAACAGCGCCGTGGCATGGTCC

AACAAGTCTGATTTCGCCTGCGCTAACGCCTTCAACAATTCTATCATTC

CCGAGGATACATTCTTTCCTAGTCCAGAAAGCTCCTGTGACGTGAAGCT

GGTCGAGAAAAGTTTCGAAACCGATACAAACCTGAATTTTCAGAATCTG

TCCGTGATCGGCTTCCGGATTCTGCTGCTGAAAGTGGCTGGGTTTAATC

TGCTGATGACTCTGAGACTGTGGTCCTCCTGAACGCGTCATCATCGATC

CGGATTAGTCCAATTTGTTAAAGACAGGATATCAGTGGTCCAGGCTCTA

GTTTTGACTCAACAATATCACCAGCTGAAGCCTATAGAGTACGAGCCAT

AGATAAAATAAAAGATTTTATTTAGTCTCCAGAAAAAGGGGGGAATGAA

AGACCCCACCTGTAGGTTTGGCAAGCTAGCTTAAGTAACGCCATTTTGC

AAGGCATGGAAAAATACATAACTGAGAATAGAGAAGTTCAGATCAAGGT

CAGGAACAGATGGAACAGCTGAATATGGGCCAAACAGGATATCTGTGGT

AAGCAGTTCCTGCCCCGGCTCAGGGCCAAGAACAGATGGAACAGCTGAA

TATGGGCCAAACAGGATATCTGTGGTAAGCAGTTCCTGCCCCGGCTCAG

-continued

GGCCAAGAACAGATGGTCCCCAGATGCGGTCCAGCCCTCAGCAGTTTCT

AGAGAACCATCAGATGTTTCCAGGGTGCCCCAAGGACCTGAAATGACCC

TGTGCCTTATTTGAACTAACCAATCAGTTCGCTTCTCGCTTCTGTTCGC

GCGCTTCTGCTCCCCGAGCTCAATAAAAGAGCCCACAACCCCTCACTCG

GGGCGCCAGTCCTCCGATTGACTGAGTCGCCCGGGTACCCGTGTATCCA

ATAAACCCTCTTGCAGTTGCATCCGACTTGTGGTCTCGCTGTTCCTTGG

GAGGGTCTCCTCTGAGTGATTGACTACCCGTCAGCGGGGGTCTTTCACA

CATGCAGCATGTATCAAAATTAATTTGGTTTTTTTTCTTAAGTATTTAC

ATTAAATGGCCATAGTACTTAAAGTTACATTGGCTTCCTTGAAATAAAC

ATGGAGTATTCAGAATGTGTCATAAATATTTCTAATTTTAAGATAGTAT

CTCCATTGGCTTTCTACTTTTTCTTTTATTTTTTTTTGTCCTCTGTCTT

CCATTTGTTGTTGTTGTTGTTTGTTTGTTTGTTTGTTGGTTGGTTGGTT

AATTTTTTTTTAAAGATCCTACACTATAGTTCAAGCTAGACTATTAGCT

ACTCTGTAACCCAGGGTGACCTTGAAGTCATGGGTAGCCTGCTGTTTTA

GCCTTCCCACATCTAAGATTACAGGTATGAGCTATCATTTTTGGTATAT

TGATTGATTGATTGATTGATGTGTGTGTGTGTGATTGTGTTTGTGTGTG

TGACTGTGAAAATGTGTGTATGGGTGTGTGTGAATGTGTGTATGTATGT

GTGTGTGTGAGTGTGTGTGTGTGTGTGTGCATGTGTGTGTGTGTGACTG

TGTCTATGTGTATGACTGTGTGTGTGTGTGTGTGTGTGTGTGTGTGTGT

GTGTGTGTGTGTGTTGTGAAAAAAATATTCTATGGTAGTGAGAGCCAACG

CTCCGGCTCAGGTGTCAGGTTGGTTTTTGAGACAGAGTCTTTCACTTAG

CTTGGAATTCACTGGCCGTCGTTTTACAACGTCGTGACTGGGAAAACCC

TGGCGTTACCCAACTTAATCGCCTTGCAGCACATCCCCCTTTCGCCAGC

TGGCGTAATAGCGAAGAGGCCCGCACCGATCGCCCTTCCCAACAGTTGC

GCAGCCTGAATGGCGAATGGCGCCTGATGCGGTATTTTCTCCTTACGCA

TCTGTGCGGTATTTCACACCGCATATGGTGCACTCTCAGTACAATCTGC

TCTGATGCCGCATAGTTAAGCCAGCCCCGACACCCGCCAACACCCGCTG

ACGCGCCCTGACGGGCTTGTCTGCTCCCGGCATCCGCTTACAGACAAGC

TGTGACCGTCTCCGGGAGCTGCATGTGTCAGAGGTTTTCACCGTCATCA

CCGAAACGCGCGATGACGAAAGGGCCTCGTGATACGCCTATTTTTATAG

GTTAATGTCATGATAATAATGGTTTCTTAGACGTCAGGTGGCACTTTTC

GGGGAAATGTGCGCGGAACCCCTATTTGTTTATTTTTCTAAATACATTC

AAATATGTATCCGCTCATGAGACAATAACCCTGATAAATGCTTCAATAA

TATTGAAAAAGGAAGAGTATGAGTATTCAACATTTCCGTGTCGCCCTTA

TTCCCTTTTTTGCGGCATTTTGCCTTCCTGTTTTTGCTCACCCAGAAAG

CTGGTGAAAGTAAAAGATGCTGAAGATCAGTTGGGTGCACGAGTGGGTT

ACATCGAACTGGATCTCAACAGCGGTAAGATCCTTGAGAGTTTTCGCCC

CGAAGAACGTTTTCCAATGATGAGCACTTTTAAAGTTCTGCTATGTGGC

GCGGTATTATCCCGTATTGACGCCGGGCAAGAGCAACTCGGTCGCCGCA

TACACTATTCTCAGAATGACTTGGTTGAGTACTCACCAGTCACAGAAAA

GCATCTTACGGATGGCATGACAGTAAGAGAATTATGCAGTGCTGCCATA

-continued

ACCATGAGTGATAACACTGCGGCCAACTTACTTCTGACAACGATCGGAG

GACCGAAGGAGCTAACCGCTTTTTTGCACAACATGGGGGATCATGTAA

CTCGCCTTGATCGTTGGGAACCGGAGCTGAATGAAGCCATACCAAACGA

CGAGCGTGACACCACGATGCCTGTAGCAATGGCAACAACGTTGCGCAAA

CTATTAACTGGCGAACTACTTACTCTAGCTTCCCGGCAACAATTAATAG

ACTGGATGGAGGCGGATAAAGTTGCAGGACCACTTCTGCGCTCGGCCCT

TCCGGCTGGCTGGTTTATTGCTGATAAATCTGGAGCCGGTGAGCGTGGG

TCTCGCGGTATCATTGCAGCACTGGGGCCAGATGGTAAGCCCTCCCGTA

TCGTAGTTATCTACACGACGGGGAGTCAGGCAACTATGGATGAACGAAA

TAGACAGATCGCTGAGATAGGTGCCTCACTGATTAAGCATTGGTAACTG

TCAGACCAAGTTTACTCATATATACTTTAGATTGATTTAAAACTTCATT

TTTAATTTAAAAGGATCTAGGTGAAGATCCTTTTTGATAATCTCATGAC

CAAAATCCCTTAACGTGAGTTTTCGTTCCACTGAGCGTCAGACCCCGTA

GAAAAGATCAAAGGATCTTCTTGAGATCCTTTTTTTCTGCGCGTAATCT

GCTGCTTGCAAACAAAAAAACCACCGCTACCAGCGGTGGTTTGTTTGCC

GGATCAAGAGCTACCAACTCTTTTTCCGAAGGTAACTGGCTTCAGCAGA

GCGCAGATACCAAATACTGTCCTTCTAGTGTAGCCGTAGTTAGGCCACC

ACTTCAAGAACTCTGTAGCACCGCCTACATACCTCGCTCTGCTAATCCT

GTTACCAGTGGCTGCTGCCAGTGGCGATAAGTCGTGTCTTACCGGGTTG

GACTCAAGACGATAGTTACCGGATAAGGCGCAGCGGTCGGGCTGAACGG

GGGGTTCGTGCACACAGCCCAGCTTGGAGCGAACGACCTACACCGAACT

GAGATACCTACAGCGTGAGCATTGAGAAAGCGCCACGCTTCCCGAAGGG

AGAAAGGCGGACAGGTATCCGGTAAGCGGCAGGGTCGGAACAGGAGAGC

GCACGAGGGAGCTTCCAGGGGGAAACGCCTGGTATCTTTATAGTCCTGT

CGGGTTTCGCCACCTCTGACTTGAGCGTCGATTTTTGTGATGCTCGTCA

GGGGGGCGGAGCCTATGGAAAAACGCCAGCAACGCGGCCTTTTTACGGT

TCCTGGCCTTTTGCTGGCCTTTTGCTCACATGTTCTTTCCTGCGTTATC

CCCTGATTCTGTGGATAACCGTATTACCGCCTTTGAGTGAGCTGATACC

GCTCGCCGCAGCCGAACGACCGAGCGCAGCGAGTCAGTGAGCGAGGAAG

CGGAAGAGCGCCCAATACGCAAACCGCCTCTCCCCGCGCGTTGGCCGAT

TCATTAATGCAGCTGGCACGACAGGTTTCCCGACTGGAAAGCGGGCAGT

GAGCGCAACGCAATTAATGTGAGTTAGCTCACTCATTAGGCACCCCAGG

CTTTACACTTTATGCTTCCGGCTCGTATGTTGTGTGGAATTGTGAGCGG

ATAACAATTTCACACAGGAAACAGCTATGACCATGATTACGCCAAGCTT

TGCTCTTAGGAGTTTCCTAATACATCCCAAACTCAAATATATAAAGCAT

TTGACTTGTTCTATGCCCTAGGGGGCGGGGGGAAGCTAAGCCAGCTTTT

TTTAACATTTAAAATGTTAATTCCATTTTAAATGCACAGATGTTTTTAT

TTCATAAGGGTTTCAATGTGCATGAATGCTGCAATATTCCTGTTACCAA

AGCTAGTATAAATAAAAATAGATAAACGTGGAAATTACTTAGAGTTTCT

GTCATTAACGTTTCCTTCCTCAGTTGACAACATAAATGCGCTGCTGAGC

-continued

AAGCCAGTTTGCATCTGTCAGGATCAATTTCCCATTATGCCAGTCATAT

TAATTACTAGTCAATTAGTTGATTTTTATTTTTGACATATACATGTGA

Example 9: Additional References

The following references are cited in the present examples, or provide additional general information.

1. Till B G, Jensen M C, Wang J, et al: CD20-specific adoptive immunotherapy for lymphoma using a chimeric antigen receptor with both CD28 and 4-1 BB domains: pilot clinical trial results. Blood 119:3940-50, 2012.
2. Pule M A, Savoldo B, Myers G D, et al: Virus-specific T cells engineered to coexpress tumor-specific receptors: persistence and antitumor activity in individuals with neuroblastoma. Nat Med 14:1264-70, 2008.
3. Kershaw M H, Westwood J A, Parker L L, et al: A phase I study on adoptive immunotherapy using gene-modified T cells for ovarian cancer. Clin Cancer Res 12:6106-15, 2006.
4. Carpenito C, Milone M C, Hassan R, et al: Control of large, established tumor xenografts with genetically retargeted human T cells containing CD28 and CD137 domains. Proc Natl Acad Sci USA 106:3360-5, 2009.
5. Song D G, Ye Q, Poussin M, et al: CD27 costimulation augments the survival and antitumor activity of redirected human T cells in vivo. Blood 119:696-706, 2012.
6. Kalos M, Levine B L, Porter D L, et al: T cells with chimeric antigen receptors have potent antitumor effects and can establish memory in patients with advanced leukemia. Sci Transl Med 3:95ra73, 2011.
7. Porter D L, Levine B L, Kalos M, et al: Chimeric antigen receptor-modified T cells in chronic lymphoid leukemia. N Engl J Med 365:725-33, 2011.
8. Brentjens R J, Davila M L, Riviere I, et al: CD19-targeted T cells rapidly induce molecular remissions in adults with chemotherapy-refractory acute lymphoblastic leukemia. Sci Transl Med 5:177ra38, 2013.
9. Pule M A, Straathof K C, Dotti G, et al: A chimeric T cell antigen receptor that augments cytokine release and supports clonal expansion of primary human T cells. Mol Ther 12:933-41, 2005.
10. Finney H M, Akbar A N, Lawson A D: Activation of resting human primary T cells with chimeric receptors: costimulation from CD28, inducible costimulator, CD134, and CD137 in series with signals from the TCR zeta chain. J Immunol 172:104-13, 2004.
11. Guedan S, Chen X, Madar A, et al: ICOS-based chimeric antigen receptors program bipolar TH17/TH1 cells. Blood, 2014.
12. Narayanan P, Lapteva N, Seethammagari M, et al: A composite MyD88/CD40 switch synergistically activates mouse and human dendritic cells for enhanced antitumor efficacy. J Clin Invest 121:1524-34, 2011.
13. Anurathapan U, Chan R C, Hindi H F, et al: Kinetics of tumor destruction by chimeric antigen receptor-modified T cells. Mol Ther 22:623-33, 2014.
14. Craddock J A, Lu A, Bear A, et al: Enhanced tumor trafficking of GD2 chimeric antigen receptor T cells by expression of the chemokine receptor CCR2b. J Immunother 33:780-8, 2010.
15. Lee D W, Gardner R, Porter D L, et al: Current concepts in the diagnosis and management of cytokine release syndrome. Blood 124:188-95, 2014.
16. Becker M L, Near R, Mudgett-Hunter M, et al: Expression of a hybrid immunoglobulin-T cell receptor protein in transgenic mice. Cell 58:911-21, 1989.
17. Goverman J, Gomez S M, Segesman K D, et al: Chimeric immunoglobulin-T cell receptor proteins form functional receptors: implications for T cell receptor complex formation and activation. Cell 60:929-39, 1990.
18. Gross G, Waks T, Eshhar Z: Expression of immunoglobulin-T-cell receptor chimeric molecules as functional receptors with antibody-type specificity. Proc Natl Acad Sci USA 86:10024-8, 1989.
19. Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
20. Jensen M C, Popplewell L, Cooper L J, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
21. Park J R, Digiusto D L, Slovak M, et al: Adoptive transfer of chimeric antigen receptor re-directed cytolytic T lymphocyte clones in patients with neuroblastoma. Mol Ther 15:825-33, 2007.
22. Ramos C A, Dotti G: Chimeric antigen receptor (CAR)-engineered lymphocytes for cancer therapy. Expert Opin Biol Ther 11:855-73, 2011.
23. Finney H M, Lawson A D, Bebbington C R, et al: Chimeric receptors providing both primary and costimulatory signaling in T cells from a single gene product. J Immunol 161:2791-7, 1998.
24. Hombach A, Weczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
25. Maher J, Brentjens R J, Gunset G, et al: Human T-lymphocyte cytotoxicity and proliferation directed by a single chimeric TCRzeta/CD28 receptor. Nat Biotechnol 20:70-5, 2002.
26. Imai C, Mihara K, Andreansky M, et al: Chimeric receptors with 4-1 BB signaling capacity provoke potent cytotoxicity against acute lymphoblastic leukemia. Leukemia 18:676-84, 2004.
27. Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
28. Zhao Y, Wang Q J, Yang S, et al: A herceptin-based chimeric antigen receptor with modified signaling domains leads to enhanced survival of transduced T lymphocytes and antitumor activity. J Immunol 183:5563-74, 2009.
29. Milone M C, Fish J D, Carpenito C, et al: Chimeric receptors containing CD137 signal transduction domains mediate enhanced survival of T cells and increased antileukemic efficacy in vivo. Mol Ther 17:1453-64, 2009.
30. Yvon E, Del Vecchio M, Savoldo B, et al: Immunotherapy of metastatic melanoma using genetically engineered GD2-specific T cells. Clin Cancer Res 15:5852-60, 2009.
31. Savoldo B, Ramos C A, Liu E, et al: CD28 costimulation improves expansion and persistence of chimeric antigen receptor-modified T cells in lymphoma patients. J Clin Invest 121:1822-6, 2011.

32. Kalinski P, Hilkens C M, Werenga E A, et al: T-cell priming by type-1 and type-2 polarized dendritic cells: the concept of a third signal. Immunol Today 20:561-7, 1999.
33. Kemnade J O, Seethammagari M, Narayanan P, et al: Off-the-shelf Adenoviral-mediated Immunotherapy via Bicistronic Expression of Tumor Antigen and iMyD88/CD40 Adjuvant. Mol Ther, 2012.
34. Schenten D, Nish S A, Yu S, et al: Signaling through the adaptor molecule MyD88 in CD4+ T cells is required to overcome suppression by regulatory T cells. Immunity 40:78-90, 2014.
35. Martin S, Pahari S, Sudan R, et al: CD40 signaling in CD8+CD40+ T cells turns on contra-T regulatory cell functions. J Immunol 184:5510-8, 2010.

Example 10: Representative Embodiments

Provided hereafter are examples of certain embodiments of the technology.

A1. A nucleic acid molecule that encodes the CDR3 region of a T cell receptor that recognizes Bob1, comprising a. a first polynucleotide that encodes a first polypeptide comprising the CDR3 region of a TCRα polypeptide; and b. a second polynucleotide that encodes a second polypeptide comprising the CDR3 region of a TCRβ polypeptide.

A2. The nucleic acid molecule of embodiment A1, wherein a. the first polynucleotide encodes a first polypeptide comprising the VJ regions of a TCRα polypeptide; and b. the second polynucleotide encodes a second polypeptide comprising the VDJ regions of a TCRβ polypeptide.

A3. The nucleic acid molecule of embodiment A1, wherein the first polypeptide further comprises the constant region of the TCRα polypeptide and the second polypeptide further comprises the constant region of the TCRβ polypeptide.

A4. The nucleic acid molecule of any one of embodiments A1-A3, wherein the nucleic acid molecule encodes a T cell receptor.

A5. The nucleic acid molecule of any one of embodiments A1-A4, wherein the CDR3 region of the T cell receptor recognizes a Bob1 polypeptide comprising the amino acid sequence APAPTAVVL (SEQ ID NO: 118).

A6. The nucleic acid molecule of any one of embodiments A1-A4, wherein the CDR3 region of the T cell receptor recognizes a Bob1 polypeptide comprising the amino acid sequence YALNHTLSV (SEQ ID NO: 119).

A7. The nucleic acid molecule of any one of embodiments A3-A6, wherein the constant region of the first or second polypeptide, is a heterologous constant region.

A8. The nucleic acid molecule of any one of embodiments A3-A7, wherein the constant regions of the first and second polypeptides are derived from murine TCR constant regions.

A9. The nucleic acid molecule of any one of embodiments A1-A8, wherein the first polypeptide comprises the amino acid sequence of SEQ ID NO: 1.

A10. The nucleic acid molecule of embodiment A9, wherein the first polynucleotide comprises the nucleotide sequence of SEQ ID NO: 2 or SEQ ID NO: 3, or a derivative thereof.

A1. The nucleic acid molecule of any one of embodiments A1-A10, wherein the second polypeptide comprises the amino acid sequence of SEQ ID NO: 4.

A12. The nucleic acid molecule of embodiment A11, wherein the second polynucleotide comprises the nucleotide sequence of SEQ ID NO: 5 or SEQ ID NO: 6, or a derivative thereof.

A13. The nucleic acid molecule of any one of embodiments A1-A8, wherein the first polypeptide comprises the amino acid sequence of SEQ ID NO: 7.

A14. The nucleic acid molecule of embodiment A13, wherein the first polynucleotide comprises the nucleotide sequence of SEQ ID NO: 8 or SEQ ID NO: 9, or a derivative thereof.

A15. The nucleic acid molecule of any one of embodiments A1-A8, or A13-A14, wherein the second polypeptide comprises the amino acid sequence of SEQ ID NO: 10.

A16. The nucleic acid molecule of embodiment A15, wherein the second polynucleotide comprises the nucleotide sequence of SEQ ID NO: 11 or SEQ ID NO: 12, or a derivative thereof.

A17. The nucleic acid molecule of any one of embodiments A1-A8, wherein the first polypeptide comprises the amino acid sequence of SEQ ID NOs: 13 or 14.

A18. The nucleic acid molecule of embodiment A17, wherein the first polynucleotide comprises the nucleotide sequence of SEQ ID NOs: 15, 16, or 18.

A19. The nucleic acid molecule of any one of embodiments A1-A8, or A17-A18, wherein the second polypeptide comprises the amino acid sequence of SEQ ID NOs: 19 or 20.

A20. The nucleic acid molecule of embodiment A19, wherein the second polynucleotide comprises the nucleotide sequence of SEQ ID NOs: 21, 22, or 24.

A21. The nucleic acid molecule of any one of embodiments A1-A8, wherein the first polypeptide comprises the amino acid sequence of SEQ ID NO: 25.

A22. The nucleic acid molecule of embodiment A21, wherein the first polynucleotide comprises the nucleotide sequence of SEQ ID NO: 26 or SEQ ID NO: 27, or a derivative thereof.

A23. The nucleic acid molecule of any one of embodiments A1-A8, or A21-A22, wherein the second polypeptide comprises the amino acid sequence of SEQ ID NO: 28.

A24. The nucleic acid molecule of embodiment 23, wherein the second polynucleotide comprises the nucleotide sequence of SEQ ID NO: 29 or SEQ ID NO: 30, or a derivative thereof.

A25. The nucleic acid molecule of any one of embodiments A1-A8, wherein the first polypeptide comprises the amino acid sequence of SEQ ID NO: 31.

A26. The nucleic acid molecule of embodiment A25, wherein the first polynucleotide comprises the nucleotide sequence of SEQ ID NO: 32 or SEQ ID NO: 33, or a derivative thereof.

A27. The nucleic acid molecule of any one of embodiments A1-A8, or A25-A26, wherein the second polypeptide comprises the amino acid sequence of SEQ ID NO: 34.

A28. The nucleic acid molecule of embodiment A27, wherein the second polynucleotide comprises the nucleotide sequence of SEQ ID NO: 35 or SEQ ID NO: 36, or a derivative thereof.

A29. The nucleic acid molecule of any one of embodiments A1-A8, wherein the first polypeptide comprises the amino acid sequence of SEQ ID NOs: 37 or 38.

A30. The nucleic acid molecule of embodiment A29, wherein the first polynucleotide comprises the nucleotide sequence of SEQ ID NOs: 39, 40, 41, or 42.

A31. The nucleic acid molecule of any one of embodiments A1-A8, or A29-A30, wherein the second polypeptide comprises the amino acid sequence of SEQ ID NOs: 43 or 44.

A32. The nucleic acid molecule of embodiment A31, wherein the second polynucleotide comprises the nucleotide sequence of SEQ ID NOs: 45, 46, 47, or 48.

B1. The nucleic acid molecule of any one of embodiments A1-A32, further comprising a polynucleotide encoding a chimeric Caspase-9 polypeptide comprising a multimeric ligand binding region and a Caspase-9 polypeptide.

B2. The nucleic acid molecule of embodiment B1, further comprising a polynucleotide encoding a linker polypeptide between the polynucleotide coding for TCRα or TCRβ, and the polynucleotide coding for the chimeric Caspase-9 polypeptide, wherein the linker polypeptide separates the translation products of the polynucleotides during or after translation.

B3. The nucleic acid molecule of any one of embodiments B1 or B2, wherein the multimeric ligand binding region is an FKBP region.

B4. The nucleic acid molecule of any one of embodiments B1 or B2, wherein the multimeric ligand binding region is an FKB12v36 region.

B5. The nucleic acid molecule of any one of embodiments B1-B4, wherein the multimeric ligand is AP1903 or AP20187.

B6. The nucleic acid molecule of any one of embodiments B1-B5, wherein the Caspase-9 polypeptide is a modified Caspase-9 polypeptide comprising an amino acid substitution selected from the group consisting of the caspase variants in Table 3.

C1. A method for stimulating a cell mediated immune response to a target cell population or tissue in a subject, comprising administering a modified cell comprising a nucleic acid of any one of embodiments A1-B6 to the subject.

C2. The method of embodiment C1, wherein the target cell is a tumor cell.

C3. The method of any one of embodiments C1 or C2, wherein the target cell is a B cell malignancy, a primary B cell malignancy, or a multiple myeloma cell.

C4. The method of any one of embodiments C1-C3, wherein the number or concentration of target cells in the subject is reduced following administration of the modified cell.

C5. The method of any one of embodiments C1-C4, comprising measuring the number or concentration of target cells in a first sample obtained from the subject before administering the modified cell, measuring the number or concentration of target cells in a second sample obtained from the subject after administration of the modified cell, and determining an increase or decrease of the number or concentration of target cells in the second sample compared to the number or concentration of target cells in the first sample.

C6. The method of embodiment C5, wherein the concentration of target cells in the second sample is decreased compared to the concentration of target cells in the first sample.

C7. The method of embodiment C5 wherein the concentration of target cells in the second sample is increased compared to the concentration target cells in the first sample.

C8. The method of any one of embodiments C1-C7, wherein an additional dose of the modified cell is administered to the subject.

C9. The method of any one of embodiments C1-C8, wherein the target cells express Bob1.

C10. The method of any one of embodiments C1-C8, wherein the subject has at least one tumor.

C11. The method of embodiment C10, wherein the size of at least one tumor is reduced following administration of the pharmaceutical composition.

C12. The method of any one of embodiments C1-C11, wherein the subject has been diagnosed with a B cell malignancy or multiple myeloma.

C13 The method of embodiment C12, wherein the B cell malignancy is a B cell lymphoma.

C14. The method of embodiment C13, wherein the B cell lymphoma is selected from the group consisting of mantle cell lymphoma, acute lymphoblastic leukemia, chronic lymphocytic leukemia, follicular lymphoma, and large B cell lymphoma.

D1. A nucleic acid molecule comprising a promoter operatively linked to a polynucleotide that encodes the CDR3 region of a T cell receptor that specifically binds to Bob1, comprising a. a first polynucleotide that encodes a first polypeptide comprising the CDR3 region of a TCRα polypeptide; and b. a second polynucleotide that encodes a second polypeptide comprising the CDR3 region of a TCRβ polypeptide, wherein the CDR3 region of the TCRα polypeptide and TCR β polypeptide together specifically bind to Bob1.

D2. The nucleic acid molecule of embodiment D1, wherein the CDR3 region of the T cell receptor specifically binds to a Bob1 polypeptide comprising the amino acid sequence APAPTAVVL (SEQ ID NO: 118) or the amino acid sequence YALNHTLSV (SEQ ID NO: 119).

D3. The nucleic acid molecule of embodiment D1, wherein the first polypeptide comprises the amino acid sequence of SEQ ID NO: 1, or SEQ ID NO: 25 and the second polypeptide comprises the amino acid sequence of SEQ ID NO: 4 or SEQ ID NO: 28.

D4. The nucleic acid molecule of embodiment D1, wherein a) the first polynucleotide comprises the nucleotide sequence of SEQ ID NO: 2 or SEQ ID NO: 3, or a derivative thereof and the second polynucleotide comprises the nucleotide sequence of SEQ ID NO: 5 or SEQ ID NO: 6, or a derivative thereof; or b) the first polynucleotide comprises the nucleotide sequence of SEQ ID NO: 26 or SEQ ID NO: 27, or a derivative thereof and the second polynucleotide comprises the nucleotide sequence of SEQ ID NO: 29 or SEQ ID NO: 30, or a derivative thereof.

D5. The nucleic acid molecule of embodiment D1, further comprising a polynucleotide encoding a chimeric Caspase-9 polypeptide comprising a multimeric ligand binding region and a Caspase-9 polypeptide.

D6. A plasmid or viral vector comprising a nucleic acid molecule of embodiment D1.

D7. A modified cell transfected or transduced with a nucleic acid molecule of embodiment D1.

D8. The modified cell of embodiment D7, wherein the cell further comprises a nucleic acid molecule comprising a polynucleotide encoding a chimeric Caspase-9 polypeptide comprising a multimeric ligand binding region and a Caspase-9 polypeptide.

D9. A modified cell transfected or transduced with a nucleic acid molecule of embodiment D5.

D10. A pharmaceutical composition comprising a modified cell of embodiment D7 and a pharmaceutically acceptable carrier.

D11. A pharmaceutical composition comprising a nucleic acid of embodiment D1 and a pharmaceutically acceptable carrier.

D12. A method of enhancing an immune response in a subject diagnosed with a hyperproliferative disease or condition, comprising administering a therapeutically effective amount of a modified cell of embodiment D7 to the subject.

D13. A method for stimulating a cell mediated immune response to a target cell population or tissue in a subject, comprising administering a modified cell of embodiment D7 to the subject.

D14. The method of embodiment D13, wherein the number or concentration of target cells in the subject is reduced following administration of the modified cell.

D15. The method of embodiment D13, wherein the modified cell comprises a nucleic acid comprising a polynucleotide encoding a chimeric Caspase-9 polypeptide comprising a multimeric ligand binding region and a Caspase-9 polypeptide.

D16. The method of embodiment D15, further comprising administering a multimeric ligand that binds to the multimeric ligand binding region to the subject following administration of the modified cells to the subject.

D17. The method of embodiment D16, wherein after administration of the multimeric ligand, the number or concentration of modified cells comprising the chimeric Caspase-9 polypeptide is reduced in a sample obtained from the subject after administering the multimeric ligand compared to the number or concentration of modified cells comprising the chimeric Caspase-9 polypeptide in a sample obtained from the subject before administering the multimeric ligand.

D18. A method for expressing a T cell receptor that specifically binds to Bob1 in a cell, comprising contacting a nucleic acid of embodiment 1 with a cell under conditions in which the nucleic acid is incorporated into the cell, whereby the cell expresses the T cell receptor from the incorporated nucleic acid.

D19. An immunogenic peptide epitope of Bob1.

D20. The immunogenic peptide epitope of embodiment D19, wherein the immunogenic peptide epitope comprises a polypeptide selected from the group consisting of the Bob1 polypeptides of Table 1.

D21. The immunogenic peptide epitope of embodiment D19, wherein the immunogenic peptide epitope comprises a polypeptide having the amino acid sequence APAPTAVVL (SEQ ID NO: 118) or having the amino acid sequence YALNHTLS (SEQ ID NO: 120).

D22. A modified cell transduced or transfected with a nucleic acid comprising a polynucleotide coding for the immunogenic peptide epitope of embodiment D19.

D23. A method of enhancing an immune response in a subject diagnosed with a hyperproliferative disease or condition, comprising administering a therapeutically effective amount of an immunogenic peptide epitope of embodiment D19 to the subject.

D24. A method for stimulating a cell mediated immune response to a target cell population or tissue in a subject, comprising administering a therapeutically effective amount of an immunogenic peptide epitope of embodiment D19 to the subject.

D25. A method for providing anti-tumor immunity to a subject, comprising administering to the subject an effective amount of an immunogenic peptide epitope of embodiment D19 to the subject.

E1. A vector comprising the nucleic acid molecule of any one of embodiments A1-B65.

E2. A cell transfected or transduced with a nucleic acid molecule of any one of embodiments A1-A32, or a vector of embodiment E1.

E2.1. The cell of embodiment E2, wherein the cell further comprises a nucleic acid molecule comprising a polynucleotide encoding a chimeric Caspase-9 polypeptide comprising a multimeric ligand binding region and a Caspase-9 polypeptide.

E2.2. The cell of embodiment E2.1, wherein the multimeric ligand binding region is an FKBP region.

E2.3. The cell of any one of embodiments E2.1 or E2.2, wherein the multimeric ligand binding region is an FKB12v36 region.

E2.4. The cell of any one of embodiments E2.1-E2.3, wherein the multimeric ligand is AP1903 or AP20187.

E2.5. The cell of any one of embodiments E2.1-E2.4, wherein the Caspase-9 polypeptide is a modified Caspase-9 polypeptide comprising an amino acid substitution selected from the group consisting of the caspase variants in Table 3.

E3. A cell transfected or transduced with a nucleic acid molecule of any one of embodiments B1-B6.

E4. A cell transfected or transduced with a nucleic acid molecule of any one of embodiments C1-C5.

E5. A cell transfected or transduced with a nucleic acid molecule of any one of embodiments D1-D5.

E6. The cell of any one of embodiments E4, or E5, wherein the cell further comprises a nucleic acid molecule comprising a polynucleotide encoding a chimeric Caspase-9 polypeptide comprising a multimeric ligand binding region and a Caspase-9 polypeptide.

F1. An immunogenic peptide epitope of Bob1.

F2. The immunogenic epitope of embodiment F1, wherein the immunogenic peptide epitope comprises a polypeptide selected from the group consisting of the Bob1 polypeptides of Table 1.

F3. The immunogenic epitope of embodiment F1, wherein the immunogenic peptide epitope comprises a polypeptide having the amino acid sequence APAPTAVVL (SEQ ID NO: 118).

F4. The immunogenic epitope of embodiment F1, wherein the immunogenic peptide epitope comprises a polypeptide having the amino acid sequence YALNHTLSV (SEQ ID NO: 119).

F5. Reserved.

F6. The immunogenic epitope of any one of embodiments F1-F5, wherein the immunogenic epitope has no more than 20 amino acids.

F7. The immunogenic epitope of any one of embodiments F1-F5, wherein the immunogenic epitope has no more than 10 amino acids.

F7.1. The immunogenic epitope of any one of embodiments F1-F5, wherein the immunogenic epitope has no more than 12 amino acids.

F7.2. The immunogenic epitope of any one of embodiments F1-F5, wherein the immunogenic epitope has no more than 14 amino acids.

F7.3. The immunogenic epitope of any one of embodiments F1-F5, wherein the immunogenic epitope has no more than 16 amino acids.

F7.4. The immunogenic epitope of any one of embodiments F1-F5, wherein the immunogenic epitope has no more than 18 amino acids.

F7.5. The immunogenic epitope of any one of embodiments F1-F5, wherein the immunogenic epitope has no more than 20 amino acids.

F8. A nucleic acid comprising a polynucleotide encoding an immunogenic epitope of any one of embodiments F1-F7.

F9. The nucleic acid of embodiment F8, wherein the polynucleotide is operatively linked to a promoter sequence capable of directing expression of the immunogenic epitope.

F10. A vector comprising the nucleic acid of embodiment F9.

F11. The vector of embodiment F10, selected from the group consisting of a plasmid, yeast, poxvirus, retrovirus, adenovirus, herpes virus, polio virus, alphavirus, baculorvirus, and Sindbis virus.

F12. The vector of embodiment F10, wherein the vector is a MP71 retroviral vector.

F13. An isolated cell comprising the immunogenic epitope of any one of embodiments F1-F7.

F13.1. The isolated cell of embodiment F13, comprising a nucleic acid or vector of any one of embodiments F8-F12.

F14. The isolated cell of any one of embodiments F13 or F13.1, wherein the cell is a human cell.

F15. The isolated cell of any one of embodiments F13, F13.1, or F14, wherein the cell is an antigen presenting cell or a tumor cell.

F16. A composition comprising an isolated cell of any one of embodiments F13-F15, and a pharmaceutically acceptable carrier.

F17. A composition comprising a nucleic acid of any one of embodiments F8-F9, or a vector of any one of embodiments F10-F12, and a pharmaceutically acceptable carrier.

F18. A composition comprising an immunogenic epitope of any one of embodiments F1-F7, and a pharmaceutically acceptable carrier.

F19. The composition of embodiment F18, further comprising an adjuvant.

F20. A method of enhancing an immune response in a subject diagnosed with a hyperproliferative disease or condition, comprising administering a therapeutically effective amount of a composition of any one of embodiments F16-F19 to the subject.

F21. The method of embodiment F20, wherein the subject has at least one tumor.

F22. The method of embodiment F21, wherein the size of at least one tumor is reduced following administration of the pharmaceutical composition.

F23. The method of any one of embodiments F20-F22, wherein the subject has been diagnosed with a B cell malignancy or multiple myeloma.

F23.5 The method of embodiment F23, wherein the B cell malignancy is a B cell lymphoma.

F23.6. The method of embodiment F23.5, wherein the B cell lymphoma is selected from the group consisting of mantle cell lymphoma, acute lymphoblastic leukemia, chronic lymphocytic leukemia, follicular lymphoma, and large B cell lymphoma.

F24. The method of any one of embodiments F20-F23, comprising administering to the subject a composition comprising dendritric cells, wherein the dendritic cells present on their surface at least one immunogenic HLA epitope of a Bob1 polypeptide antigen.

F25. A method for stimulating a cell mediated immune response to a target cell population or tissue in a subject, comprising administering a pharmaceutical composition of any one of embodiments F16-F19 to the subject.

F26. The method of embodiment F25, wherein the target cell is a tumor cell.

F27. The method of any one of embodiments F25 or F26, wherein the target cell is a B cell malignancy, a primary B cell malignancy, or a multiple myeloma cell.

F28. The method of any one of embodiments F25-F27, wherein the number or concentration of target cells in the subject is reduced following administration of the pharmaceutical composition.

F29. The method of any one of embodiments F25-F28, comprising measuring the number or concentration of target cells in a first sample obtained from the subject before administering the pharmaceutical composition, measuring the number concentration of target cells in a second sample obtained from the subject after administration of the pharmaceutical composition, and determining an increase or decrease of the number or concentration of target cells in the second sample compared to the number or concentration of target cells in the first sample.

F30. The method of embodiment F29, wherein the concentration of target cells in the second sample is decreased compared to the concentration of target cells in the first sample.

F31. The method of embodiment F29, wherein the concentration of target cells in the second sample is increased compared to the concentration target cells in the first sample.

F32. The method of any one of embodiments F25-F31, wherein an additional dose of the pharmaceutical composition is administered to the subject.

F33. A method for providing anti-tumor immunity to a subject, comprising administering to the subject an effective amount of a pharmaceutical composition of any one of embodiments F16-F19.

F34. A method for treating a subject having a disease or condition associated with an elevated expression of a target antigen, comprising administering to the subject an effective amount of a pharmaceutical composition of any one of embodiments F16-F19.

F35. The method of embodiment F34, wherein the target antigen is a tumor antigen.

G1. A nucleic acid molecule comprising a promoter operatively linked to a polynucleotide that encodes the CDR3 region of a T cell receptor that specifically binds to Bob1, comprising a. a first polynucleotide that encodes a first polypeptide comprising the CDR3 region of a TCRα polypeptide; and b. a second polynucleotide that encodes a second polypeptide comprising the CDR3 region of a TCRβ polypeptide, wherein the CDR3 region of the TCRα polypeptide and TCR β polypeptide together specifically bind to Bob1.

G2. The nucleic acid molecule of embodiment G1, wherein a. the first polynucleotide encodes a first polypeptide comprising the VJ regions of a TCRα polypeptide; and b. the second polynucleotide encodes a second polypeptide comprising the VDJ regions of a TCRβ polypeptide.

G3. The nucleic acid molecule of embodiment G1, wherein the first polypeptide further comprises the constant region of the TCRα polypeptide and the second polypeptide further comprises the constant region of the TCRβ polypeptide.

G4. The nucleic acid molecule of any one of embodiments G1-G3, wherein the nucleic acid molecule encodes a T cell receptor.

G5. The nucleic acid molecule of any one of embodiments G1-G4, wherein the CDR3 region of the T cell receptor specifically binds to a Bob1 polypeptide comprising the amino acid sequence APAPTAVVL (SEQ ID NO: 118).

G6. The nucleic acid molecule of any one of embodiments G1-G4, wherein the CDR3 region of the T cell receptor specifically binds to a Bob1 polypeptide comprising the amino acid sequence YALNHTLSV (SEQ ID NO: 119).

G7. The nucleic acid molecule of any one of embodiments G3-G6, wherein the constant region of the first or second polypeptide is a heterologous constant region.

G8. The nucleic acid molecule of any one of embodiments G3-G7, wherein the constant regions of the first and second polypeptides are derived from murine TCR constant regions.

G9. The nucleic acid molecule of any one of embodiments G1-G8, wherein the first polypeptide comprises the amino acid sequence of SEQ ID NO: 1.

G10. The nucleic acid molecule of embodiment G9, wherein the first polynucleotide comprises the nucleotide sequence of SEQ ID NO: 2 or SEQ ID NO: 3, or a derivative thereof.

G11. The nucleic acid molecule of any one of embodiments G1-G10, wherein the second polypeptide comprises the amino acid sequence of SEQ ID NO: 4.

G12. The nucleic acid molecule of embodiment G11, wherein the second polynucleotide comprises the nucleotide sequence of SEQ ID NO: 5 or SEQ ID NO: 6, or a derivative thereof.

G13. The nucleic acid molecule of any one of embodiments G1-G8, wherein the first polypeptide comprises the amino acid sequence of SEQ ID NO: 7.

G14. The nucleic acid molecule of embodiment G13, wherein the first polynucleotide comprises the nucleotide sequence of SEQ ID NO: 8 or SEQ ID NO: 9, or a derivative thereof.

G15. The nucleic acid molecule of any one of embodiments G1-G8, or G13-G14, wherein the second polypeptide comprises the amino acid sequence of SEQ ID NO: 10.

G16. The nucleic acid molecule of embodiment G15, wherein the second polynucleotide comprises the nucleotide sequence of SEQ ID NO: 11 or SEQ ID NO: 12, or a derivative thereof.

G17. The nucleic acid molecule of any one of embodiments G1-G8, wherein the first polypeptide comprises the amino acid sequence of SEQ ID NOs: 13 or 14.

G18. The nucleic acid molecule of embodiment G17, wherein the first polynucleotide comprises the nucleotide sequence of SEQ ID NOs: 15, 16, or 18.

G19. The nucleic acid molecule of any one of embodiments G1-G8, or G17-G18, wherein the second polypeptide comprises the amino acid sequence of SEQ ID NOs: 19 or 20.

G20. The nucleic acid molecule of embodiment G19, wherein the second polynucleotide comprises the nucleotide sequence of SEQ ID NOs: 21, 22, or 24.

G21. The nucleic acid molecule of any one of embodiments G1-G8, wherein the first polypeptide comprises the amino acid sequence of SEQ ID NO: 25.

G22. The nucleic acid molecule of embodiment G21, wherein the first polynucleotide comprises the nucleotide sequence of SEQ ID NO: 26 or SEQ ID NO: 27, or a derivative thereof.

G23. The nucleic acid molecule of any one of embodiments G1-G8, or G21-G22, wherein the second polypeptide comprises the amino acid sequence of SEQ ID NO: 28.

G24. The nucleic acid molecule of embodiment G23, wherein the second polynucleotide comprises the nucleotide sequence of SEQ ID NO: 29 or SEQ ID NO: 30, or a derivative thereof.

G25. The nucleic acid molecule of any one of embodiments G1-G8, wherein the first polypeptide comprises the amino acid sequence of SEQ ID NO: 31.

G26. The nucleic acid molecule of embodiment G25, wherein the first polynucleotide comprises the nucleotide sequence of SEQ ID NO: 32 or SEQ ID NO: 33, or a derivative thereof.

G27. The nucleic acid molecule of any one of embodiments G1-G8, or G25-G26, wherein the second polypeptide comprises the amino acid sequence of SEQ ID NO: 34.

G28. The nucleic acid molecule of embodiment G27, wherein the second polynucleotide comprises the nucleotide sequence of SEQ ID NO: 35 or SEQ ID NO: 36, or a derivative thereof.

G29. The nucleic acid molecule of any one of embodiments G1-G8, wherein the first polypeptide comprises the amino acid sequence of SEQ ID NOs: 37 or 38.

G30. The nucleic acid molecule of embodiment G29, wherein the first polynucleotide comprises the nucleotide sequence of SEQ ID NOs: 39, 40, 41, or 42.

G31. The nucleic acid molecule of any one of embodiments G1-G8, or G29-G30, wherein the second polypeptide comprises the amino acid sequence of SEQ ID NOs: 43 or 44.

G32. The nucleic acid molecule of embodiment G31, wherein the second polynucleotide comprises the nucleotide sequence of SEQ ID NOs: 45, 46, 47, or 48.

G33. The nucleic acid molecule of any one of embodiments G1-G32, further comprising a polynucleotide encoding a chimeric Caspase-9 polypeptide comprising a multimeric ligand binding region and a Caspase-9 polypeptide.

G34. The nucleic acid molecule of embodiment G33, further comprising a polynucleotide encoding a linker polypeptide between the polynucleotide coding for TCRα or TCRβ, and the polynucleotide coding for the chimeric Caspase-9 polypeptide, wherein the linker polypeptide separates the translation products of the polynucleotides during or after translation.

G35. The nucleic acid molecule of any one of embodiments G33 or G34, wherein the multimeric ligand binding region is an FKBP ligand binding region.

G36. The nucleic acid molecule of any one of embodiments G33-G35, wherein the multimeric ligand binding region comprises an FKBP12 region.

G37. The nucleic acid molecule of embodiment G36, wherein the FKBP12 region has an amino acid substitution at position 36 selected from the group consisting of valine, leucine, isoleuceine and alanine.

G38. The nucleic acid molecule of embodiment G36 wherein the FKBP12 region is an FKBP12v36 region.

G39. The nucleic acid molecule of any one of embodiments G33-G38, wherein the multimeric ligand binding region comprises Fv'Fvls.

G40. The nucleic acid molecule of any one of embodiments G33-G39 wherein the multimeric ligand binding region comprises a polypeptide having an amino acid sequence of SEQ ID NO: 52, or a functional fragment thereof, or a polypeptide having an amino acid sequence of SEQ ID NO: 71, or a functional fragment thereof.

G41. The nucleic acid molecule of any one of embodiments G35-G37, wherein the multimeric ligand binding region further comprises an Fv polypeptide variant wherein residue 36 is valine.

G42. The nucleic acid molecule of any one of embodiments G34-G41, wherein the linker polypeptide is a 2A polypeptide.

G43. The nucleic acid molecule of any one of embodiments G33 to G42, wherein the multimeric ligand is AP1903 or AP20187.

G44. The nucleic acid molecule of any one of embodiments G33-G43 wherein the Caspase-9 polypeptide has the amino acid sequence of SEQ ID NO:58, or is encoded by the nucleotide sequence of SEQ ID NO: 57.

G45. The nucleic acid molecule of any one of embodiments G33-G43, wherein the Caspase-9 polypeptide is a modified Caspase-9 polypeptide comprising an amino acid substitution selected from the group consisting of the caspase variants in Table 3.

G46. A composition comprising a) a nucleic acid molecule of any one of embodiments G1-G32; and b) a nucleic acid molecule comprising a polynucleotide encoding a chimeric Caspase-9 polypeptide comprising a multimeric ligand binding region and a Caspase-9 polypeptide.

G47. The composition of embodiment G46, wherein the multimeric ligand binding region is an FKBP ligand binding region.

G48. The composition of any one of embodiments G46-G47, wherein the multimeric ligand binding region comprises an FKBP12 region.

G49. The composition of embodiment G48, wherein the FKBP12 region has an amino acid substitution at position 36 selected from the group consisting of valine, leucine, isoleuceine and alanine.

G50. The composition of embodiment G48 wherein the FKBP12 region is an FKBP12v36 region.

G51. The composition of any one of embodiments G46-G50, wherein the multimeric ligand binding region comprises Fv'Fvls.

G52. The composition of any one of embodiments G46-G51 wherein the multimeric ligand binding region comprises a polypeptide having an amino acid sequence of SEQ ID NO: 52, or a functional fragment thereof, or a polypeptide having an amino acid sequence of SEQ ID NO: 71, or a functional fragment thereof.

G53. The composition of any one of embodiments G46-G51, wherein the multimeric ligand binding region comprises an Fv polypeptide variant wherein residue 36 is valine.

G54 The composition of any one of embodiments G46-G53 wherein the Caspase-9 polypeptide has the amino acid sequence of SEQ ID NO: 58, or is encoded by the nucleotide sequence of SEQ ID NO: 57.

G55. The composition of any one of embodiments G46-G53, wherein the Caspase-9 polypeptide is a modified Caspase-9 polypeptide comprising an amino acid substitution selected from the group consisting of the caspase variants in Table 3.

G56. A vector comprising a nucleic acid molecule of any one of embodiments G1-G32.

G57. The vector of embodiment G56, wherein the vector is a plasmid vector.

G58. The vector of embodiment G56, wherein the vector is a viral vector.

G59. The vector of embodiment G56, wherein the vector is a retroviral vector.

G60. The vector of embodiment G56, wherein the vector is a lentiviral vector.

G61. A modified cell transfected or transduced with a nucleic acid molecule of any one of embodiments G1-G32, or a vector of any one of embodiments G56-G60.

G62. The modified cell of embodiment G61, wherein the cell further comprises a nucleic acid molecule comprising a polynucleotide encoding a chimeric Caspase-9 polypeptide comprising a multimeric ligand binding region and a Caspase-9 polypeptide.

G63. A vector comprising a nucleic acid molecule of any one of embodiments G33-G45.

G64. The vector of embodiment G63, wherein the vector is a plasmid vector.

G65. The vector of embodiment G63, wherein the vector is a viral vector.

G66. The vector of embodiment G63, wherein the vector is a retroviral vector.

G67. The vector of embodiment G63, wherein the vector is a lentiviral vector.

G68. A modified cell transfected or transduced with a nucleic acid molecule of any one of embodiments G33-G45, or a vector of any one of embodiments G63-G67.

G69. The modified cell of any one of embodiments G62 or G68, wherein the multimeric ligand binding region is an FKBP ligand binding region.

G70. The modified cell of any one of embodiments G62 or G68, wherein the multimeric ligand binding region comprises an FKBP12 region.

G71. The modified cell of embodiment G70, wherein the FKBP12 region has an amino acid substitution at position 36 selected from the group consisting of valine, leucine, isoleuceine and alanine.

G72. The modified cell of embodiment G70 wherein the FKBP12 region is an FKBP12v36 region.

G73. The modified cell of any one of embodiments G62 or G68-G72, wherein the multimeric ligand binding region comprises Fv'Fvls.

G74. The modified cell of any one of embodiments G62 or G68-G72 wherein the multimeric ligand binding region comprises a polypeptide having an amino acid sequence of SEQ ID NO: 52, or a functional fragment thereof, or a polypeptide having an amino acid sequence of SEQ ID NO: 71, or a functional fragment thereof.

G75. The modified cell of any one of embodiments G62 or G68-G72, wherein the multimeric ligand binding region comprises an Fv polypeptide variant wherein residue 36 is valine.

G76 The modified cell of any one of embodiments G62 or G68-G75 wherein the Caspase-9 polypeptide has the amino acid sequence of SEQ ID NO: 58, or is encoded by the nucleotide sequence of SEQ ID NO: 57.

G77. The modified cell of any one of embodiments G62 or G68-G75, wherein the Caspase-9 polypeptide is a modified Caspase-9 polypeptide comprising an amino acid substitution selected from the group consisting of the caspase variants in Table 3.

G78. A modified cell transfected or transduced with a nucleic acid molecule of any one of embodiments G1-G45, a vector of any one of embodiments G56-G60 or G63-G67, or a composition of any one of embodiments G47-G55.

G79. A pharmaceutical composition comprising a modified cell of any one of embodiments G61-G62 or G68-G78 and a pharmaceutically acceptable carrier.

G80. A pharmaceutical composition comprising a nucleic acid of any one of embodiments G1-G45 or a vector of any one of embodiments G56-G60 or G63-G67 and a pharmaceutically acceptable carrier.

G81. A method of enhancing an immune response in a subject diagnosed with a hyperproliferative disease or condition, comprising administering a therapeutically effective amount of a modified cell of any one of embodiments G61-G62 or G68-G78 to the subject.

G82. The method of embodiment G81, wherein the subject has at least one tumor.

G83. The method of embodiment G82, wherein the size of at least one tumor is reduced following administration of the pharmaceutical composition.

G84. The method of any one of embodiments G81-G83, wherein the subject has been diagnosed with a B cell malignancy or multiple myeloma.

G85. A method for stimulating a cell mediated immune response to a target cell population or tissue in a subject, comprising administering a modified cell of any one of embodiments G61-G62 or G68-G78 to the subject.

G86. The method of embodiment G85, wherein the target cell is a tumor cell.

G87. The method of any one of embodiments G85 or G86, wherein the target cell is a B cell malignancy, a primary B cell malignancy, or a multiple myeloma cell.

G88. The method of any one of embodiments G85-G87, wherein the number or concentration of target cells in the subject is reduced following administration of the modified cell.

G89. The method of any one of embodiments G85-G88, comprising measuring the number or concentration of target cells in a first sample obtained from the subject before administering the modified cell, measuring the number or concentration of target cells in a second sample obtained from the subject after administration of the modified cell, and determining an increase or decrease of the number or concentration of target cells in the second sample compared to the number or concentration of target cells in the first sample.

G90. The method of embodiment G89, wherein the concentration of target cells in the second sample is decreased compared to the concentration of target cells in the first sample.

G91. The method of embodiment G89, wherein the concentration of target cells in the second sample is increased compared to the concentration target cells in the first sample.

G92. The method of any one of embodiments G85-G91, wherein an additional dose of the modified cell is administered to the subject.

G93. The method of any one of embodiments G85-G92, wherein the target cells express Bob1.

G94. A method for providing anti-tumor immunity to a subject, comprising administering to the subject an effective amount of a modified cell of any one of embodiments G61-G62 or G68-G78.

G95. A method for treating a subject having a disease or condition associated with an elevated expression of a target antigen, comprising administering to the subject an effective amount of a modified cell of any one of embodiments G61-G62 or G68-G78.

G96. The method of embodiment G95, wherein the target antigen is a tumor antigen.

G97. The method of embodiment G95, wherein the target antigen is Bob1.

G98. The method of any one of embodiments G81-G97, further comprising administering an additional dose of the modified cell to the subject, wherein the disease or condition symptoms remain or are detected following a reduction in symptoms.

G99. The method of any one of embodiments G81-G97 further comprising identifying the presence, absence or stage of a condition or disease in a subject; and transmitting an indication to administer modified cell of any one of embodiments G61-G62 or G68-G78, maintain a subsequent dosage of the modified cell, or adjust a subsequent dosage of the modified cell administered to the patient based on the presence, absence or stage of the condition or disease identified in the subject.

G100. The method of any one of embodiments G81-G99, wherein the condition is leukemia.

G101. The method of any one of embodiments G81-G99, wherein the subject has been diagnosed with multiple myeloma or a B cell malignancy.

G102. The method of embodiment G101, wherein the B cell malignancy is a lymphoma.

G103. The method of any one of embodiments G81-G102, wherein the modified cell comprises a chimeric Caspase-9 polypeptide comprising a multimeric ligand binding region and a Caspase-9 polypeptide.

G104. The method of embodiment G103, further comprising administering a multimeric ligand that binds to the multimeric ligand binding region to the subject following administration of the modified cells to the subject.

G105. The method of embodiment G104, wherein after administration of the multimeric ligand, the number or concentration of modified cells comprising the chimeric Caspase-9 polypeptide is reduced in a sample obtained from the subject after administering the multimeric ligand compared to the number or concentration of modified cells comprising the chimeric Caspase-9 polypeptide in a sample obtained from the subject before administering the multimeric ligand.

G106. The method of embodiment G105, wherein the number of modified cells comprising the chimeric Caspase-9 polypeptide is reduced by 50%.

G107. The method of embodiment G105, wherein the number of modified cells comprising the chimeric Caspase-9 polypeptide is reduced by 75%.

G108. The method of embodiment G105, wherein the number of modified cells comprising the chimeric Caspase-9 polypeptide is reduced by 90%.

G109. The method of any one of embodiments G104-G108, comprising determining that the subject is experiencing a negative symptom following administration of the modified cells to the subject, and administering the ligand to reduce or alleviate the negative symptom.

G110. The method of any one of embodiments G104-G109, wherein the ligand is AP1903 or AP20187.

G111. The method of any one of embodiments G81-G110, wherein the modified cells are autologous T cells.

G112. The method of any one of embodiments G81-G110, wherein the modified cells are allogeneic T cells.

G113. The method of any one of embodiments G81-G110, wherein the modified cells are transfected or transduced in vivo.

G114. The modified cell of any one of embodiments G81-G110, wherein the modified cells are transfected or transduced ex vivo.

G115. A method for expressing a T cell receptor that specifically binds to Bob1 in a cell, comprising contacting a nucleic acid of any one of embodiments G1-G45 with a cell under conditions in which the nucleic acid is incorporated into the cell, whereby the cell expresses the T cell receptor from the incorporated nucleic acid.

G116. The method of embodiment G115, wherein the nucleic acid is contacted with the cell ex vivo.

G117. The method of embodiment G115, wherein the nucleic acid is contacted with the cell in vivo.

G118. An immunogenic peptide epitope of Bob1.

G119. The immunogenic peptide epitope of embodiment G118, wherein the immunogenic peptide epitope comprises a polypeptide selected from the group consisting of the Bob1 polypeptides of Table 1.

G120. The immunogenic peptide epitope of embodiment G118, wherein the immunogenic peptide epitope comprises a polypeptide having the amino acid sequence APAPTAVVL (SEQ ID NO: 118).

G121. The immunogenic peptide epitope of embodiment G118, wherein the immunogenic peptide epitope comprises a polypeptide having the amino acid sequence YALNHTLS (SEQ ID NO: 120).

G122. The immunogenic peptide epitope of any one of embodiments G118-G121, wherein the immunogenic epitope has no more than 20 amino acids.

G123. The immunogenic peptide epitope of any one of embodiments G118-G121, wherein the immunogenic epitope has no more than 10 amino acids.
G124. The immunogenic peptide epitope of any one of embodiments G118-G121, wherein the immunogenic epitope has no more than 12 amino acids.
G125. The immunogenic peptide epitope of any one of embodiments G118-G121, wherein the immunogenic epitope has no more than 14 amino acids.
G126. The immunogenic peptide epitope of any one of embodiments G118-G121, wherein the immunogenic epitope has no more than 16 amino acids.
G127. The immunogenic peptide epitope of any one of embodiments G118-G121, wherein the immunogenic epitope has no more than 18 amino acids.
G128. The immunogenic peptide epitope of any one of embodiments G118-G121, wherein the immunogenic epitope has no more than 20 amino acids.
G129. A nucleic acid comprising a polynucleotide encoding an immunogenic peptide epitope of any one of embodiments G118-G128.
G130. The nucleic acid of embodiment G128, wherein the polynucleotide is operatively linked to a promoter sequence capable of directing expression of the immunogenic epitope.
G131. A vector comprising the nucleic acid of any one of embodiments G129 or G130.
G132. The vector of embodiment G131, selected from the group consisting of a plasmid, yeast, poxvirus, retrovirus, lentivirus, adenovirus, herpes virus, polio virus, alphavirus, baculorvirus, and Sindbis virus.
G133. The vector of embodiment G131, wherein the vector is a MP71 retroviral vector.
G134. A modified cell transduced or transfected with a nucleic acid comprising a polynucleotide coding for the immunogenic peptide epitope of any one of embodiments G118-G128.
G135. The modified cell of embodiment G134, comprising a nucleic acid or vector of any one of embodiments G128-G132.
G136. The modified cell of any one of embodiments G134 or G135, wherein the cell is a human cell.
G137. The modified cell of any one of embodiments G134-G136, wherein the cell is an antigen presenting cell or a tumor cell.
G138. A pharmaceutical composition comprising a modified cell of any one of embodiments G134-G137, and a pharmaceutically acceptable carrier.
G139. A pharmaceutical composition comprising a nucleic acid of any one of embodiments G129-G130, or a vector of any one of embodiments G131-G133, and a pharmaceutically acceptable carrier.
G140. A pharmaceutical composition comprising an immunogenic epitope of any one of embodiments G118-G128, and a pharmaceutically acceptable carrier.
G141. The pharmaceutical composition of embodiment 140, further comprising an adjuvant.
G142. A method of enhancing an immune response in a subject diagnosed with a hyperproliferative disease or condition, comprising administering a therapeutically effective amount of a pharmaceutical composition of any one of embodiments G138-G141 to the subject.
G143. The method of embodiment G142, wherein the subject has at least one tumor.
G144. The method of embodiment G143, wherein the size of at least one tumor is reduced following administration of the pharmaceutical composition.
G145. The method of any one of embodiments G142-G144, wherein the subject has been diagnosed with a B cell malignancy or multiple myeloma.
G146. The method of embodiment G145, wherein the B cell malignancy is a lymphoma.
G147. The method of any one of embodiments G142-G146, comprising administering to the subject a composition comprising dendritric cells, wherein the dendritic cells present on their surface at least one immunogenic HLA epitope of a Bob1 polypeptide antigen.
G148. A method for stimulating a cell mediated immune response to a target cell population or tissue in a subject, comprising administering a pharmaceutical composition of any one of embodiments G138-G140 to the subject.
G149. The method of embodiment G148, wherein the target cell is a tumor cell.
G150. The method of any one of embodiments G148-G149, wherein the target cell is a B cell malignancy, a primary B cell malignancy, or a multiple myeloma cell.
G151. The method of any one of embodiments G148-G150, wherein the number or concentration of target cells in the subject is reduced following administration of the pharmaceutical composition.
G152. The method of any one of embodiments G148-G151, comprising measuring the number or concentration of target cells in a first sample obtained from the subject before administering the pharmaceutical composition, measuring the number concentration of target cells in a second sample obtained from the subject after administration of the pharmaceutical composition, and determining an increase or decrease of the number or concentration of target cells in the second sample compared to the number or concentration of target cells in the first sample.
G153. The method of embodiment G152, wherein the concentration of target cells in the second sample is decreased compared to the concentration of target cells in the first sample.
G154. The method of embodiment G152, wherein the concentration of target cells in the second sample is increased compared to the concentration target cells in the first sample.
G155. The method of any one of embodiments G148-G154, wherein an additional dose of the pharmaceutical composition is administered to the subject.
G156. A method for providing anti-tumor immunity to a subject, comprising administering to the subject an effective amount of a pharmaceutical composition of any one of embodiments G138-G140.
G157. A method for treating a subject having a disease or condition associated with an elevated expression of a target antigen, comprising administering to the subject an effective amount of a pharmaceutical composition of any one of embodiments G138-G140.
G158. The method of embodiment G157, wherein the target antigen is a tumor antigen.
G159. The method of embodiment G157, wherein the target antigen is Bob1.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

---

What is claimed is:

1. An isolated nucleic acid molecule comprising a promoter operatively linked to a polynucleotide that encodes a T cell receptor comprising a CDR3 region that specifically binds to Bob1, comprising a. a first polynucleotide that encodes a TCRα polypeptide comprising a CDR3 region comprising the amino acid sequence of SEQ ID NO: 1, or SEQ ID NO: 25; and b. a second polynucleotide that encodes a TCRβ polypeptide comprising a CDR3 region comprising the amino acid sequence of SEQ ID NO: 4 or SEQ ID NO: 28, wherein the CDR3 region of the TCRα polypeptide and TCR β polypeptide together specifically bind to Bob1.

2. The isolated nucleic acid molecule of claim 1, wherein the CDR3 region of the T cell receptor specifically binds to a Bob1 polypeptide comprising the amino acid sequence APAPTAVVL (SEQ ID NO: 118) or the amino acid sequence YALNHTLSV (SEQ ID NO: 119).

3. The isolated nucleic acid molecule of claim 1, wherein a) the first polynucleotide comprises the nucleotide sequence of SEQ ID NO: 2 or SEQ ID NO: 3, and the second polynucleotide comprises the nucleotide sequence of SEQ ID NO: 5 or SEQ ID NO: 6; or b) the first polynucleotide comprises the nucleotide sequence of SEQ ID NO: 26 or SEQ ID NO: 27, and the second polynucleotide comprises the nucleotide sequence of SEQ ID NO: 29 or SEQ ID NO: 30.

4. The isolated nucleic acid molecule of claim 1, further comprising a polynucleotide encoding a chimeric Caspase-9 polypeptide comprising a multimeric ligand binding region and a Caspase-9 polypeptide.

5. A plasmid or viral vector comprising the isolated nucleic acid molecule of claim 1.

6. An isolated and modified cell transfected or transduced with the isolated nucleic acid molecule of claim 1.

7. The isolated and modified cell of claim 6, wherein the cell further comprises a nucleic acid molecule comprising a polynucleotide encoding a chimeric Caspase-9 polypeptide comprising a multimeric ligand binding region and a Caspase-9 polypeptide.

8. An isolated and modified cell transfected or transduced with the isolated nucleic acid molecule of claim 4.

9. A pharmaceutical composition comprising the isolated and modified cell of claim 6 and a pharmaceutically acceptable carrier.

10. A pharmaceutical composition comprising the isolated nucleic acid of claim 1 and a pharmaceutically acceptable carrier.

11. A method for expressing a T cell receptor that specifically binds to Bob1 in a cell, comprising contacting the isolated nucleic acid of claim 1 with a cell under conditions in which the nucleic acid is incorporated into the cell, whereby the cell expresses the T cell receptor from the incorporated nucleic acid.

12. The isolated nucleic acid molecule of claim 1, wherein i) the TCRα polypeptide comprises a VJ region comprising the amino acid sequence of SEQ ID NO: 7 or SEQ ID NO: 31; and ii) the TCRβ polypeptide comprises a VDJ region comprising the amino acid sequence of SEQ ID NO: 10 or SEQ ID NO: 34.

13. The isolated nucleic acid molecule of claim 12, wherein a) the first polynucleotide comprises the nucleotide sequence of SEQ ID NO: 8 or SEQ ID NO: 9, and the second polynucleotide comprises the nucleotide sequence of SEQ ID NO: 11 or SEQ ID NO: 12; or b) the first polynucleotide comprises the nucleotide sequence of SEQ ID NO: 32 or SEQ ID NO: 33, and the second polynucleotide comprises the nucleotide sequence of SEQ ID NO: 35 or SEQ ID NO: 36.

14. The isolated nucleic acid molecule of claim 4, wherein the multimeric ligand binding region is an FKBP ligand binding region.

* * * * *

SEQUENCE LISTING

```
<160> NUMBER OF SEQ ID NOS: 142

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ala Ala Ser Lys Gly Ser Ser Asn Thr Gly Lys Leu Ile Phe Gly
1               5                   10                  15

Gln Gly Thr Thr Leu Gln Val Lys Pro
            20                  25


<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tgtgcagcaa gtaagggctc tagcaacaca ggcaaactaa tctttgggca agggacaact      60

ttacaagtaa aacca                                                       75


<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

tgcgccgctt ctaaggggtc ctctaacacc ggaaaactga tcttcggcca ggggaccaca      60

ctgcaggtga agcct                                                       75


<210> SEQ ID NO 4
<211> LENGTH: 23
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

```
Cys Ala Ser Ser His Gly Pro Ala Ser Tyr Glu Gln Tyr Phe Gly Pro
1               5                   10                  15

Gly Thr Arg Leu Thr Val Thr
            20
```

<210> SEQ ID NO 5
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5

```
tgcgccagca gccacggccc tgcttcctac gagcagtact tcgggccggg caccaggctc     60

acggtcaca                                                             69
```

<210> SEQ ID NO 6
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6

```
tgcgcctcta gtcacgggcc agcctcttac gagcagtatt ttggacccgg caccagactg     60

actgtgacc                                                             69
```

<210> SEQ ID NO 7
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Lys Gly Ser Ser Asn Thr Gly Lys Leu Ile Phe Gly Gln Gly Thr Thr
        115                 120                 125
```

Leu Gln Val Lys Pro
    130

<210> SEQ ID NO 8
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgacatcca ttcgagctgt atttatattc ctgtggctgc agctggactt ggtgaatgga 60
gagaatgtgg agcagcatcc ttcaaccctg agtgtccagg agggagacag cgctgttatc 120
aagtgtactt attcagacag tgcctcaaac tacttccctt ggtataagca agaacttgga 180
aaaggacctc agcttattat agacattcgt tcaaatgtgg gcgaaaagaa agaccaacga 240
attgctgtta cattgaacaa gacagccaaa catttctccc tgcacatcac agagacccaa 300
cctgaagact cggctgtcta cttctgtgca gcaagtaagg gctctagcaa cacaggcaaa 360
ctaatctttg ggcaagggac aactttacaa gtaaaacca 399

<210> SEQ ID NO 9
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgacaagca tcagagccgt gttcattttt ctgtggctgc agctggatct ggtgaacgga 60
gagaatgtcg aacagcatcc ttcaactctg agcgtgcagg agggcgattc cgcagtcatc 120
aagtgtacct actcagacag cgcctccaat tactttcctt ggtataagca ggagctgggg 180
aaaggaccac agctgatcat tgatatcaga agcaacgtgg gcgaaaagaa agaccagagg 240
attgctgtca cactgaataa gactgcaaaa cacttcagcc tgcatattac agagactcag 300
cccgaagact ccgccgtgta tttttgcgcc gcttctaagg ggtcctctaa caccggaaaa 360
ctgatcttcg gccaggggac cacactgcag gtgaagcct 399

<210> SEQ ID NO 10
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

-continued

```
Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser His Gly Pro Ala Ser Tyr Glu Gln Tyr Phe Gly Pro Gly Thr Arg
        115                 120                 125

Leu Thr Val Thr
    130
```

<210> SEQ ID NO 11
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atgggctgca ggctgctctg ctgtgcggtt ctctgtctcc tgggagcagt tcccatagac     60

actgaagtta cccagacacc aaaacacctg gtcatgggaa tgacaaataa gaagtctttg    120

aaatgtgaac aacatatggg gcacagggct atgtattggt acaagcagaa agctaagaag    180

ccaccggagc tcatgtttgt ctacagctat gagaaactct ctataaatga aagtgtgcca    240

agtcgcttct cacctgaatg ccccaacagc tctctcttaa accttcacct acacgccctg    300

cagccagaag actcagccct gtatctctgc gccagcagcc acggccctgc ttcctacgag    360

cagtacttcg ggccgggcac caggctcacg gtcaca                              396
```

<210> SEQ ID NO 12
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atgggatgta gactgctgtg ctgtgctgtg ctgtgcctgc tgggggctgt gcctattgat     60

accgaagtga ctcagactcc aaagcacctg gtcatgggca tgaccaacaa gaaaagcctg    120

aaatgcgagc agcacatggg gcatagggcc atgtactggt ataagcagaa agctaagaaa    180

ccccctgaac tgatgttcgt gtacagctat gagaagctgt ccatcaatga atccgtcccc    240

tctcgcttca gtcccgagtg ccctaacagc tccctgctga atctgcacct gcatgctctg    300

cagcctgaag actccgcact gtacctgtgc gcctctagtc acgggccagc ctcttacgag    360

cagtattttg gacccggcac cagactgact gtgacc                              396
```

<210> SEQ ID NO 13
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30
```

```
Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Lys Gly Ser Ser Asn Thr Gly Lys Leu Ile Phe Gly Gln Gly Thr Thr
        115                 120                 125

Leu Gln Val Lys Pro Asp Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser


<210> SEQ ID NO 14
<211> LENGTH: 270
<212> TYPE: PRT
<213> ORGANISM: Mus musculus

<400> SEQUENCE: 14

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Lys Gly Ser Ser Asn Thr Gly Lys Leu Ile Phe Gly Gln Gly Thr Thr
        115                 120                 125
```

-continued

```
Leu Gln Val Lys Pro Asp Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 15
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

atgacatcca ttcgagctgt atttatattc ctgtggctgc agctggactt ggtgaatgga     60

gagaatgtgg agcagcatcc ttcaaccctg agtgtccagg agggagacag cgctgttatc    120

aagtgtactt attcagacag tgcctcaaac tacttccctt ggtataagca agaacttgga    180

aaaggacctc agcttattat agacattcgt tcaaatgtgg gcgaaaagaa agaccaacga    240

attgctgtta cattgaacaa gacagccaaa catttctccc tgcacatcac agagacccaa    300

cctgaagact cggctgtcta cttctgtgca gcaagtaagg gctctagcaa cacaggcaaa    360

ctaatctttg ggcaagggac aactttacaa gtaaaaccag atatccagaa ccctgaccct    420

gccgtgtacc agctgagaga ctctaaatcc agtgacaagt ctgtctgcct attcaccgat    480

tttgattctc aaacaaatgt gtcacaaagt aaggattctg atgtgtatat cacagacaaa    540

tgcgtgctag acatgaggtc tatggacttc aagagcaaca gtgctgtggc ctggagcaac    600

aaatctgact ttgcatgtgc aaacgccttc aacaacagca ttattccaga agacaccttc    660

ttccccagcc cagaaagttc ctgtgatgtc aagctggtcg agaaaagctt tgaaacagat    720

acgaacctaa actttcaaaa cctgtcagtg attgggttcc gaatcctcct cctgaaagtg    780

gccgggttta atctgctcat gacgctgcgg ttgtggtcca gc                       822


<210> SEQ ID NO 16
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

atgacaagca tcagagccgt gttcattttt ctgtggctgc agctggatct ggtgaacgga     60
```

-continued

```
gagaatgtcg aacagcatcc ttcaactctg agcgtgcagg agggcgattc cgcagtcatc    120

aagtgtacct actcagacag cgcctccaat tactttcctt ggtataagca ggagctgggg    180

aaaggaccac agctgatcat tgatatcaga agcaacgtgg gcgaaaagaa agaccagagg    240

attgctgtca cactgaataa gactgcaaaa cacttcagcc tgcatattac agagactcag    300

cccgaagact ccgccgtgta tttttgcgcc gcttctaagg ggtcctctaa caccggaaaa    360

ctgatcttcg gccaggggac cacactgcag gtgaagcctg acattcagaa tccagatccc    420

gccgtctacc agctgcgaga ctcaaagagt tcagataaaa gcgtgtgcct gttcaccgac    480

tttgatagcc agacaaacgt gtctcagagt aaggactccg acgtgtacat caccgacaaa    540

tgcgtgctgg atatgcgcag catggacttc aagagcaaca gcgccgtggc atggtccaac    600

aagtctgatt tcgcctgcgc taacgccttc aacaattcta tcattcccga ggatacattc    660

tttcctagtc cagaaagctc ctgtgacgtg aagctggtcg agaaaagttt cgaaaccgat    720

acaaacctga attttcagaa tctgtccgtg atcggcttcc ggattctgct gctgaaagtg    780

gctgggttta atctgctgat gactctgaga ctgtggtcct cc                        822
```

<210> SEQ ID NO 17

<400> SEQUENCE: 17

000

<210> SEQ ID NO 18
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgacaagca tcagagccgt gttcattttt ctgtggctgc agctggatct ggtgaacgga     60

gagaatgtcg aacagcatcc ttcaactctg agcgtgcagg agggcgattc cgcagtcatc    120

aagtgtacct actcagacag cgcctccaat tactttcctt ggtataagca ggagctgggg    180

aaaggaccac agctgatcat tgatatcaga agcaacgtgg gcgaaaagaa agaccagagg    240

attgctgtca cactgaataa gactgcaaaa cacttcagcc tgcatattac agagactcag    300

cccgaagact ccgccgtgta tttttgcgcc gcttctaagg ggtcctctaa caccggaaaa    360

ctgatcttcg gccaggggac cacactgcag gtgaagcctg acattcagaa cccggaaccg    420

gctgtatacc agctgaagga cccccgatct caggatagta ctctgtgcct gttcaccgac    480

tttgatagtc agatcaatgt gcctaaaacc atggaatccg gaacttttat taccgacaag    540

tgcgtgctgg atatgaaagc catggacagt aagtcaaacg gcgccatcgc ttggagcaat    600

cagacatcct tcacttgcca ggatatcttc aaggagacca acgcaacata cccatcctct    660

gacgtgccct gtgatgccac cctgacagag aagtctttcg aaacagacat gaacctgaat    720

tttcagaatc tgagcgtgat gggcctgaga atcctgctgc tgaaggtcgc tgggtttaat    780

ctgctgatga cactgcggct gtggtcctca                                      810
```

<210> SEQ ID NO 19
<211> LENGTH: 311
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser His Gly Pro Ala Ser Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

<210> SEQ ID NO 20
<211> LENGTH: 305
<212> TYPE: PRT
<213> ORGANISM: Mus musculus

<400> SEQUENCE: 20

```
Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
```

```
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser His Gly Pro Ala Ser Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305


<210> SEQ ID NO 21
<211> LENGTH: 933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

atgggctgca ggctgctctg ctgtgcggtt ctctgtctcc tgggagcagt tcccatagac      60

actgaagtta cccagacacc aaaacacctg gtcatgggaa tgacaaataa gaagtctttg     120

aaatgtgaac aacatatggg gcacagggct atgtattggt acaagcagaa agctaagaag     180

ccaccggagc tcatgtttgt ctacagctat gagaaactct ctataaatga aagtgtgcca     240

agtcgcttct cacctgaatg ccccaacagc tctctcttaa accttcacct acacgccctg     300

cagccagaag actcagccct gtatctctgc gccagcagcc acggccctgc ttcctacgag     360

cagtacttcg ggccgggcac caggctcacg gtcacagagg acctgaaaaa cgtgttccca     420

cccgaggtcg ctgtgtttga gccatcagaa gcagagatct cccacaccca aaaggccaca     480
```

ctggtatgcc tggccacagg cttctacccc gaccacgtgg agctgagctg gtgggtgaat 540
gggaaggagg tgcacagtgg ggtctgcaca gacccgcagc ccctcaagga gcagcccgcc 600
ctcaatgact ccagatactg cctgagcagc cgcctgaggg tctcggccac cttctggcag 660
aacccccgca accacttccg ctgtcaagtc cagttctacg ggctctcgga gaatgacgag 720
tggacccagg atagggccaa acccgtcacc cagatcgtca gcgccgaggc ctggggtaga 780
gcagactgtg gcttcacctc cgagtcttac cagcaagggg tcctgtctgc caccatcctc 840
tatgagatct tgctagggaa ggccaccttg tatgccgtgc tggtcagtgc cctcgtgctg 900
atggccatgg tcaagagaaa ggattccaga ggc 933

<210> SEQ ID NO 22
<211> LENGTH: 933
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
atgggatgta gactgctgtg ctgtgctgtg ctgtgcctgc tgggggctgt gcctattgat 60
accgaagtga ctcagactcc aaagcacctg gtcatgggca tgaccaacaa gaaaagcctg 120
aaatgcgagc agcacatggg gcatagggcc atgtactggt ataagcagaa agctaagaaa 180
ccccctgaac tgatgttcgt gtacagctat gagaagctgt ccatcaatga atccgtcccc 240
tctcgcttca gtcccgagtg ccctaacagc tccctgctga atctgcacct gcatgctctg 300
cagcctgaag actccgcact gtacctgtgc gcctctagtc acgggccagc ctcttacgag 360
cagtattttg gacccggcac cagactgact gtgaccgaag atctgaagaa cgtcttccca 420
cccgaggtgg cagtctttga accatctgag gccgaaatta gtcatactca gaaagccacc 480
ctggtgtgcc tggctacagg cttctatccc gaccacgtgg agctgagttg gtgggtcaac 540
ggcaaggaag tgcattcagg ggtctgcact gaccctcagc cactgaaaga gcagcctgct 600
ctgaatgatt caaggtactg tctgtcaagc cggctgagag tgagcgccac tttttggcag 660
aacccaagga atcacttccg ctgccaggtg cagttttatg gcctgagcga gaatgacgaa 720
tggactcagg atcgcgctaa gccagtgacc cagatcgtct ccgcagaggc ctggggacga 780
gcagactgtg gcttcacatc tgaaagttac cagcaggggg tgctgtctgc cacaatcctg 840
tacgagattc tgctgggaaa ggccactctg tacgccgtgc tggtgagcgc cttagtctta 900
atggccatgg tgaaaagaaa ggattccaga gga 933

<210> SEQ ID NO 23

<400> SEQUENCE: 23

000

<210> SEQ ID NO 24
<211> LENGTH: 915
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
atgggatgca gactgctgtg ctgtgctgtg ctgtgcctgc tgggggctgt gcctattgat 60
accgaagtga ctcagactcc aaagcacctg gtcatgggca tgaccaacaa gaaaagcctg 120
aaatgcgagc agcacatggg gcatagggcc atgtactggt ataagcagaa agctaagaaa 180
ccccctgaac tgatgttcgt gtacagctat gagaagctgt ccatcaatga atccgtcccc 240
tctcgcttca gtcccgagtg ccctaacagc tccctgctga atctgcacct gcatgctctg 300
cagcctgaag actccgcact gtacctgtgc gcctctagtc acgggccagc ctcttacgag 360
cagtattttg gacccggcac cagactgact gtgaccgaag atctacgtaa cgtgacacca 420
cccaaagtct cactgtttga gcctagcaag gcagaaattg ccaacaagca gaaggccacc 480
ctggtgtgcc tggcaagagg gttctttcca gatcacgtgg agctgtcctg gtgggtcaac 540
ggcaaagaag tgcattctgg ggtctgcacc gacccccagg cttacaagga gagtaattac 600
tcatattgtc tgtcaagccg gctgagagtg tccgccacat tctggcacaa ccctaggaat 660
catttccgct gccaggtcca gtttcacggc ctgagtgagg aagataaatg gccagagggg 720
tcacctaagc cagtgacaca gaacatcagc gcagaagcct ggggacgagc agactgtggc 780
attactagcg cctcctatca tcagggcgtg ctgagcgcca ctatcctgta cgagattctg 840
ctgggaaagg ccaccctgta tgctgtgctg gtctccggcc tggtgctgat ggccatggtc 900
aagaaaaaga actct 915

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Cys Ala Ala Ser Thr Gly Gly Gly Tyr Ser Thr Leu Thr Phe Gly Lys
1 5 10 15

Gly Thr Met Leu Leu Val Ser Pro
20

<210> SEQ ID NO 26
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
tgtgcagcaa gtacgggggg aggatacagc accctcacct ttgggaaggg gactatgctt 60
ctagtctctc ca 72

<210> SEQ ID NO 27
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tgtgccgcct ctaccggcgg aggctactcc accctgacat tcggcaaggg caccatgctg 60
ctggtgtccc cc 72

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

```
Cys Ala Ser Ser Gly Gln Gly Ile Thr Leu Ala Gly Ala Asn Val Leu
1               5                   10                  15

Thr Phe Gly Ala Gly Ser Arg Leu Thr Val Leu
            20                  25
```

<210> SEQ ID NO 29
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29

```
tgtgccagca gtggacaggg aattaccctg gctggggcca acgtcctgac tttcggggcc     60

ggcagcaggc tgaccgtgct g                                               81
```

<210> SEQ ID NO 30
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30

```
tgtgccagca gcggccaggg catcacactg gctggcgcca atgtgctgac cttcggagcc     60

ggcagcagac tgaccgtgct g                                               81
```

<210> SEQ ID NO 31
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Thr Gly Gly Gly Tyr Ser Thr Leu Thr Phe Gly Lys Gly Thr Met Leu
```

115 120 125

Leu Val Ser Pro
130

<210> SEQ ID NO 32
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
atgacatcca ttcgagctgt atttatattc ctgtggctgc agctggactt ggtgaatgga 60
gagaatgtgg agcagcatcc ttcaaccctg agtgtccagg agggagacag cgctgttatc 120
aagtgtactt attcagacag tgcctcaaac tacttccctt ggtataagca agaacttgga 180
aaaggacctc agcttattat agacattcgt tcaaatgtgg gcgaaaagaa agaccaacga 240
attgctgtta cattgaacaa gacagccaaa catttctccc tgcacatcac agagacccaa 300
cctgaagact cggctgtcta cttctgtgca gcaagtacgg ggggaggata cagcaccctc 360
acctttggga aggggactat gcttctagtc tctcca 396

<210> SEQ ID NO 33
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
atgaccagca tccgggccgt gttcatcttc ctgtggctgc agctggacct cgtgaacggc 60
gagaacgtgg aacagcaccc cagcaccctg agcgtgcagg aaggcgatag cgccgtgatc 120
aagtgcacct acagcgacag cgccagcaac tacttcccct ggtacaagca ggaactgggc 180
aagggccccc agctgatcat cgacatcaga tccaacgtgg gcgagaagaa ggaccagcgg 240
atcgccgtga ccctgaacaa gaccgccaag cacttcagcc tgcacatcac cgagacacag 300
cccgaggaca gcgccgtgta cttttgtgcc gcctctaccg gcggaggcta ctccaccctg 360
acattcggca agggcaccat gctgctggtg tccccc 396

<210> SEQ ID NO 34
<211> LENGTH: 137
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Met Gly Ser Trp Thr Leu Cys Cys Val Ser Leu Cys Ile Leu Val Ala
1 5 10 15

Lys His Thr Asp Ala Gly Val Ile Gln Ser Pro Arg His Glu Val Thr
20 25 30

Glu Met Gly Gln Glu Val Thr Leu Arg Cys Lys Pro Ile Ser Gly His
35 40 45

Asp Tyr Leu Phe Trp Tyr Arg Gln Thr Met Met Arg Gly Leu Glu Leu
50 55 60

Leu Ile Tyr Phe Asn Asn Asn Val Pro Ile Asp Asp Ser Gly Met Pro

```
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Gly Gln Gly Ile Thr Leu Ala Gly Ala Asn Val Leu Thr Phe
        115                 120                 125

Gly Ala Gly Ser Arg Leu Thr Val Leu
    130                 135


<210> SEQ ID NO 35
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

atgggctcct ggaccctctg ctgtgtgtcc ctttgcatcc tggtagcaaa gcacacagat     60

gctggagtta tccagtcacc ccggcacgag gtgacagaga tgggacaaga agtgactctg    120

agatgtaaac caatttcagg acacgactac cttttctggt acagacagac catgatgcgg    180

ggactggagt tgctcattta ctttaacaac aacgttccga tagatgattc agggatgccc    240

gaggatcgat tctcagctaa gatgcctaat gcatcattct ccactctgaa gatccagccc    300

tcagaaccca gggactcagc tgtgtacttc tgtgccagca gtggacaggg aattaccctg    360

gctggggcca acgtcctgac tttcggggcc ggcagcaggc tgaccgtgct g             411


<210> SEQ ID NO 36
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

atgggcagct ggaccctgtg ctgcgtgtcc ctgtgtatcc tggtggccaa gcacaccgat     60

gccggcgtga tccagagccc cagacacgaa gtgaccgaga tgggccagga agtgaccctg    120

cgctgcaagc ctatcagcgg ccacgactac ctgttctggt acagacagac catgatgcgg    180

ggcctggaac tgctgatcta cttcaacaac aacgtgccca tcgacgacag cggcatgccc    240

gaggatagat tcagcgccaa gatgcccaac gccagcttca gcaccctgaa gatccagccc    300

agcgagccca gagacagcgc cgtgtacttt tgtgccagca gcggccaggg catcacactg    360

gctggcgcca atgtgctgac cttcggagcc ggcagcagac tgaccgtgct g             411


<210> SEQ ID NO 37
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
```

```
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Thr Gly Gly Gly Tyr Ser Thr Leu Thr Phe Gly Lys Gly Thr Met Leu
        115                 120                 125

Leu Val Ser Pro Asp Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 38
<211> LENGTH: 269
<212> TYPE: PRT
<213> ORGANISM: Mus musculus

<400> SEQUENCE: 38

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Thr Gly Gly Gly Tyr Ser Thr Leu Thr Phe Gly Lys Gly Thr Met Leu
```

```
        115                 120                 125

Leu Val Ser Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 39
<211> LENGTH: 819
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
atgacatcca ttcgagctgt atttatattc ctgtggctgc agctggactt ggtgaatgga     60

gagaatgtgg agcagcatcc ttcaaccctg agtgtccagg agggagacag cgctgttatc    120

aagtgtactt attcagacag tgcctcaaac tacttccctt ggtataagca agaacttgga    180

aaaggacctc agcttattat agacattcgt tcaaatgtgg gcgaaaagaa agaccaacga    240

attgctgtta cattgaacaa gacagccaaa catttctccc tgcacatcac agagacccaa    300

cctgaagact cggctgtcta cttctgtgca gcaagtacgg ggggaggata cagcaccctc    360

acctttggga aggggactat gcttctagtc tctccagata tccagaaccc tgaccctgcc    420

gtgtaccagc tgagagactc taaatccagt gacaagtctg tctgcctatt caccgatttt    480

gattctcaaa caaatgtgtc acaaagtaag gattctgatg tgtatatcac agacaaaact    540

gtgctagaca tgaggtctat ggacttcaag agcaacagtg ctgtggcctg gagcaacaaa    600

tctgactttg catgtgcaaa cgccttcaac aacagcatta ttccagaaga caccttcttc    660

cccagcccag aaagttcctg tgatgtcaag ctggtcgaga aaagctttga aacagatacg    720

aacctaaact ttcaaaacct gtcagtgatt gggttccgaa tcctcctcct gaaagtggcc    780

gggtttaatc tgctcatgac gctgcggttg tggtccagc                           819
```

<210> SEQ ID NO 40
<211> LENGTH: 819
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

-continued atgaccagca tccgggccgt gttcatcttc ctgtggctgc agctggacct cgtgaacggc 60
gagaacgtgg aacagcaccc cagcaccctg agcgtgcagg aaggcgatag cgccgtgatc 120
aagtgcacct acagcgacag cgccagcaac tacttcccct ggtacaagca ggaactgggc 180
aagggccccc agctgatcat cgacatcaga tccaacgtgg gcgagaagaa ggaccagcgg 240
atcgccgtga ccctgaacaa gaccgccaag cacttcagcc tgcacatcac cgagacacag 300
cccgaggaca gcgccgtgta cttttgtgcc gcctctaccg gcggaggcta ctccaccctg 360
acattcggca agggcaccat gctgctggtg tcccccgaca tccagaaccc cgatcctgcc 420
gtgtaccagc tgcgggacag caagagcagc gacaagagcg tgtgcctgtt caccgacttc 480
gacagccaga ccaacgtgtc ccagagcaag gactccgacg tgtacatcac agacaagacc 540
gtgctggaca tgcggagcat ggacttcaag agcaactccg ccgtggcctg gtccaacaag 600
agcgatttcg cctgcgccaa cgccttcaac aacagcatta tccctgagga cacattcttc 660
ccaagccccg agagcagctg cgacgtgaag ctggtggaaa agagcttcga gacagacacc 720
aacctgaact tccagaacct gtccgtgatc ggcttccgga tcctgctgct gaaggtggcc 780
ggcttcaacc tgctgatgac cctgagactg tggtcctcc 819

<210> SEQ ID NO 41
<211> LENGTH: 807
<212> TYPE: DNA
<213> ORGANISM: Mus musculus

<400> SEQUENCE: 41
atgacatcca ttcgagctgt atttatattc ctgtggctgc agctggactt ggtgaatgga 60
gagaatgtgg agcagcatcc ttcaaccctg agtgtccagg agggagacag cgctgttatc 120
aagtgtactt attcagacag tgcctcaaac tacttccctt ggtataagca agaacttgga 180
aaaggacctc agcttattat agacattcgt tcaaatgtgg gcgaaaagaa agaccaacga 240
attgctgtta cattgaacaa gacagccaaa catttctccc tgcacatcac agagacccaa 300
cctgaagact cggctgtcta cttctgtgca gcaagtacgg ggggaggata cagcaccctc 360
acctttggga aggggactat gcttctagtc tctccagaca ttcagaaccc ggaaccggct 420
gtataccagc tgaaggaccc ccgatctcag gatagtactc tgtgcctgtt caccgacttt 480
gatagtcaga tcaatgtgcc taaaaccatg gaatccggaa cttttattac cgacaagtgc 540
gtgctggata tgaaagccat ggacagtaag tcaaacggcg ccatcgcttg gagcaatcag 600
acatccttca cttgccagga tatcttcaag gagaccaacg caacataccc atcctctgac 660
gtgccctgtg atgccaccct gacagagaag tctttcgaaa cagacatgaa cctgaatttt 720
cagaatctga gcgtgatggg cctgagaatc ctgctgctga aggtcgctgg gtttaatctg 780
ctgatgacac tgcggctgtg gtcctca 807

<210> SEQ ID NO 42
<211> LENGTH: 807
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
atgaccagca tccgggccgt gttcatcttc ctgtggctgc agctggacct cgtgaacggc 60
gagaacgtgg aacagcaccc cagcaccctg agcgtgcagg aaggcgatag cgccgtgatc 120

-continued

```
aagtgcacct acagcgacag cgccagcaac tacttcccct ggtacaagca ggaactgggc    180

aagggccccc agctgatcat cgacatcaga tccaacgtgg gcgagaagaa ggaccagcgg    240

atcgccgtga ccctgaacaa gaccgccaag cacttcagcc tgcacatcac cgagacacag    300

cccgaggaca gcgccgtgta cttttgtgcc gcctctaccg gcggaggcta ctccaccctg    360

acattcggca agggcaccat gctgctggtg tcccccgaca tccagaatcc cgagcctgcc    420

gtgtaccagc tgaaggaccc cagaagccag gatagcaccc tgtgcctgtt caccgacttc    480

gacagccaga tcaacgtgcc caagaccatg gaaagcggca ccttcatcac cgataagtgc    540

gtgctggaca tgaaggccat ggacagcaag agcaacggcg ccattgcctg gtccaaccag    600

accagcttca catgccagga catcttcaaa gagacaaacg ccacctaccc cagcagcgac    660

gtgccctgtg atgccacact gaccgagaag tccttcgaga cagacatgaa cctgaacttc    720

cagaacctgt ccgtgatggg cctgcggatc ctgctgctga aggtggccgg cttcaacctg    780

ctgatgaccc tgagactgtg gtcctcc                                        807
```

```
<210> SEQ ID NO 43
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Gly Gln Gly Ile Thr Leu Ala Gly Ala Asn Val Leu Thr Phe
        115                 120                 125

Gly Ala Gly Ser Arg Leu Thr Val Leu Glu Asp Leu Lys Asn Val Phe
    130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Tyr Pro Asp
                165                 170                 175

His Val Glu Leu Ser Trp Trp Val Asn Gly Lys Glu Val His Ser Gly
            180                 185                 190

Val Ser Thr Asp Pro Gln Pro Leu Lys Glu Gln Pro Ala Leu Asn Asp
        195                 200                 205

Ser Arg Tyr Cys Leu Ser Ser Arg Leu Arg Val Ser Ala Thr Phe Trp
    210                 215                 220

Gln Asn Pro Arg Asn His Phe Arg Cys Gln Val Gln Phe Tyr Gly Leu
225                 230                 235                 240
```

-continued

```
Ser Glu Asn Asp Glu Trp Thr Gln Asp Arg Ala Lys Pro Val Thr Gln
                245                 250                 255

Ile Val Ser Ala Glu Ala Trp Gly Arg Ala Asp Cys Gly Phe Thr Ser
            260                 265                 270

Glu Ser Tyr Gln Gln Gly Val Leu Ser Ala Thr Ile Leu Tyr Glu Ile
        275                 280                 285

Leu Leu Gly Lys Ala Thr Leu Tyr Ala Val Leu Val Ser Ala Leu Val
    290                 295                 300

Leu Met Ala Met Val Lys Arg Lys Asp Ser Arg Gly
305                 310                 315


<210> SEQ ID NO 44
<211> LENGTH: 310
<212> TYPE: PRT
<213> ORGANISM: Mus musculus

<400> SEQUENCE: 44

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Gly Gln Gly Ile Thr Leu Ala Gly Ala Asn Val Leu Thr Phe
        115                 120                 125

Gly Ala Gly Ser Arg Leu Thr Val Leu Glu Asp Leu Arg Asn Val Thr
    130                 135                 140

Pro Pro Lys Val Ser Leu Phe Glu Pro Ser Lys Ala Glu Ile Ala Asn
145                 150                 155                 160

Lys Gln Lys Ala Thr Leu Val Cys Leu Ala Arg Gly Phe Phe Pro Asp
                165                 170                 175

His Val Glu Leu Ser Trp Trp Val Asn Gly Lys Glu Val His Ser Gly
            180                 185                 190

Val Cys Thr Asp Pro Gln Ala Tyr Lys Glu Ser Asn Tyr Ser Tyr Cys
        195                 200                 205

Leu Ser Ser Arg Leu Arg Val Ser Ala Thr Phe Trp His Asn Pro Arg
    210                 215                 220

Asn His Phe Arg Cys Gln Val Gln Phe His Gly Leu Ser Glu Glu Asp
225                 230                 235                 240

Lys Trp Pro Glu Gly Ser Pro Lys Pro Val Thr Gln Asn Ile Ser Ala
                245                 250                 255

Glu Ala Trp Gly Arg Ala Asp Cys Gly Ile Thr Ser Ala Ser Tyr His
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Gly Leu Val Leu Met Ala Met
```

```
    290                 295                 300

Val Lys Lys Lys Asn Ser
305                 310


<210> SEQ ID NO 45
<211> LENGTH: 948
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

atgggctcct ggaccctctg ctgtgtgtcc ctttgcatcc tggtagcaaa gcacacagat     60

gctggagtta tccagtcacc ccggcacgag gtgacagaga tgggacaaga agtgactctg    120

agatgtaaac caatttcagg acacgactac cttttctggt acagacagac catgatgcgg    180

ggactggagt tgctcattta ctttaacaac aacgttccga tagatgattc agggatgccc    240

gaggatcgat tctcagctaa gatgcctaat gcatcattct ccactctgaa gatccagccc    300

tcagaaccca gggactcagc tgtgtacttc tgtgccagca gtggacaggg aattaccctg    360

gctggggcca acgtcctgac tttcggggcc ggcagcaggc tgaccgtgct ggaggacctg    420

aaaaacgtgt tcccacccga ggtcgctgtg tttgagccat cagaagcaga gatctcccac    480

acccaaaagg ccacactggt atgcctggcc acaggcttct accccgacca cgtggagctg    540

agctggtggg tgaatgggaa ggaggtgcac agtggggtca gcacagaccc gcagcccctc    600

aaggagcagc ccgccctcaa tgactccaga tactgcctga gcagccgcct gagggtctcg    660

gccaccttct ggcagaaccc ccgcaaccac ttccgctgtc aagtccagtt ctacgggctc    720

tcggagaatg acgagtggac ccaggatagg gccaaacccg tcacccagat cgtcagcgcc    780

gaggcctggg gtagagcaga ctgtggcttc acctccgagt cttaccagca aggggtcctg    840

tctgccacca tcctctatga gatcttgcta gggaaggcca ccttgtatgc cgtgctggtc    900

agtgccctcg tgctgatggc catggtcaag agaaaggatt ccagaggc                 948


<210> SEQ ID NO 46
<211> LENGTH: 948
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

atgggcagct ggaccctgtg ctgcgtgtcc ctgtgtatcc tggtggccaa gcacaccgat     60

gccggcgtga tccagagccc cagacacgaa gtgaccgaga tgggccagga agtgaccctg    120

cgctgcaagc ctatcagcgg ccacgactac ctgttctggt acagacagac catgatgcgg    180

ggcctggaac tgctgatcta cttcaacaac aacgtgccca tcgacgacag cggcatgccc    240

gaggatagat tcagcgccaa gatgcccaac gccagcttca gcaccctgaa gatccagccc    300

agcgagccca gagacagcgc cgtgtacttt tgtgccagca gcggccaggg catcacactg    360

gctggcgcca atgtgctgac cttcggagcc ggcagcagac tgaccgtgct ggaagatctg    420

aagaacgtgt tcccccccaga ggtggccgtg ttcgagcctt ctgaggccga gatcagccac    480

acccagaaag ccaccctcgt gtgtctggcc accggcttct accccgacca cgtggaactg    540

tcttggtggg tcaacggcaa agaggtgcac agcggcgtgt ccaccgatcc ccagcctctg    600
```

aaagaacagc ccgccctgaa cgacagccgg tactgcctgt ccagcaggct gagagtgtcc 660
gccaccttct ggcagaaccc ccggaaccac ttcagatgcc aggtgcagtt ctacggcctg 720
agcgagaacg acgagtggac ccaggacaga gccaagcccg tgacccagat cgtgtctgcc 780
gaagcctggg gcagagccga ttgcggcttt accagcgaga gctaccagca gggcgtgctg 840
agcgccacca tcctgtacga gatcctgctg ggcaaggcca ccctgtacgc cgtgctggtg 900
tctgccctgg tgctgatggc catggtcaag cggaaggaca gccggggc 948

<210> SEQ ID NO 47
<211> LENGTH: 930
<212> TYPE: DNA
<213> ORGANISM: Mus musculus

<400> SEQUENCE: 47
atgggctcct ggaccctctg ctgtgtgtcc ctttgcatcc tggtagcaaa gcacacagat 60
gctggagtta tccagtcacc ccggcacgag gtgacagaga tgggacaaga agtgactctg 120
agatgtaaac caatttcagg acacgactac cttttctggt acagacagac catgatgcgg 180
ggactggagt tgctcattta ctttaacaac aacgttccga tagatgattc agggatgccc 240
gaggatcgat tctcagctaa gatgcctaat gcatcattct ccactctgaa gatccagccc 300
tcagaaccca gggactcagc tgtgtacttc tgtgccagca gtggacaggg aattaccctg 360
gctggggcca acgtcctgac tttcggggcc ggcagcaggc tgaccgtgct ggaagatcta 420
cgtaacgtga caccacccaa agtctcactg tttgagccta gcaaggcaga aattgccaac 480
aagcagaagg ccaccctggt gtgcctggca agagggttct ttccagatca cgtggagctg 540
tcctggtggg tcaacggcaa agaagtgcat tctggggtct gcaccgaccc ccaggcttac 600
aaggagagta attactcata ttgtctgtca agccggctga gagtgtccgc cacattctgg 660
cacaacccta ggaatcattt ccgctgccag gtccagtttc acggcctgag tgaggaagat 720
aaatggccag aggggtcacc taagccagtg acacagaaca tcagcgcaga agcctgggga 780
cgagcagact gtggcattac tagcgcctcc tatcatcagg gcgtgctgag cgccactatc 840
ctgtacgaga ttctgctggg aaaggccacc ctgtatgctg tgctggtctc cggcctggtg 900
ctgatggcca tggtcaagaa aaagaactct 930

<210> SEQ ID NO 48
<211> LENGTH: 930
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
atgggcagct ggaccctgtg ctgcgtgtcc ctgtgtatcc tggtggccaa gcacaccgat 60
gccggcgtga tccagagccc cagacacgaa gtgaccgaga tgggccagga agtgaccctg 120
cgctgcaagc ctatcagcgg ccacgactac ctgttctggt acagacagac catgatgcgg 180
ggcctggaac tgctgatcta cttcaacaac aacgtgccca tcgacgacag cggcatgccc 240
gaggatagat tcagcgccaa gatgcccaac gccagcttca gcaccctgaa gatccagccc 300
agcgagccca gagacagcgc cgtgtacttt tgtgccagca gcggccaggg catcacactg 360
gctggcgcca atgtgctgac cttcggagcc ggcagcagac tgaccgtgct ggaagatctg 420
cggaacgtga ccccccccaa agtgtctctg ttcgagccca gcaaggccga gatcgccaac 480

-continued

```
aagcagaaag ccaccctcgt gtgcctggcc agaggcttct tccccgacca cgtggaactg    540

tcttggtggg tcaacggcaa agaggtgcac tccggcgtgt gcaccgatcc ccaggcctac    600

aaagagagca actacagcta ctgcctgagc agcaggctgc gggtgtccgc caccttctgg    660

cacaaccccc ggaaccactt cagatgccag gtgcagtttc acggcctgag cgaagaggac    720

aagtggcccg agggcagccc taagcccgtg acccagaata tctctgccga agcctggggc    780

agagccgact gtggcattac cagcgccagc taccatcagg gcgtgctgag cgccaccatc    840

ctgtacgaga tcctgctggg caaggccacc ctgtacgccg tgctggtgtc tggcctggtg    900

ctgatggcca tggtcaagaa gaagaacagc                                      930
```

```
<210> SEQ ID NO 49
<211> LENGTH: 4435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
```

```
tagcttaagt aacccatttt gcaaggcatg gaaaatacat aactgagaat agagaagttc     60

agatcaaggt taggaacaga gagacagcag aatatgggcc aaacaggata tctgtggtaa    120

gcagttcctg ccccggctca gggccaagaa cagttggaac agcagaatat gggccaaaca    180

ggatatctgt ggtaagcagt tcctgccccg gctcagggcc aagaacagat ggtccccaga    240

tgcggtcccg ccctcagcag tttctagaga accatcagat gtttccaggg tgccccaagg    300

acctgaaatg accctgtgcc ttatttgaac taaccaatca gttcgcttct cgcttctgtt    360

cgcgcgcttc tgctccccga gctcaataaa agagcccaca acccctcact cggcgcgcca    420

gtcctccgat agactgcgtc gcccgggtac ccgtattccc aataaagcct cttgctgttt    480

gcatccgaat cgtggactcg ctgatccttg ggagggtctc ctcagattga ttgactgccc    540

acctcggggg tctttcattt ggaggttcca ccgagatttg gagacccctg cccagggacc    600

accgaccccc ccgccgggag gtaagctggc cagcggtcgt ttcgtgtctg tctctgtctt    660

tgtgcgtgtt tgtgccggca tctaatgttt gcgcctgcgt ctgtactagt tggctaacta    720

gatctgtatc tggcggtccc gcggaagaac tgacgagttc gtattcccgg ccgcagcccc    780

tgggagacgt cccagcggcc tcgggggccc gttttgtggc ccattctgta tcagttaacc    840

tacccgagtc ggactttttg gagctccgcc actgtccgag ggtacgtgg ctttgttggg    900

ggacgagaga cagagacact tcccgccccc gtctgaattt ttgctttcgg ttttacgccg    960

aaaccgcgcc gcgcgtcttg tctgctgcag catcgttctg tgttgtctct gtctgactgt   1020

gtttctgtat ttgtctgaaa attagctcga caaagttaag taatagtccc tctctccaag   1080

ctcacttaca ggcggccacg cgtggatccg aattcctcga gatcgataag cttaacacga   1140

gccatagata gaataaaaga ttttatttag tctccagaaa aaggggggaa tgaaagaccc   1200

cacctgtagg tttggcaagc tagcttaagt aacgccattt tgcaaggcat ggaaaataca   1260

taactgagaa tagagaagtt cagatcaagg ttaggaacag agagacagca gaatatgggc   1320

caaacaggat atctgtggta agcagttcct gccccggctc agggccaaga acagttggaa   1380

cagcagaata tgggccaaac aggatatctg tggtaagcag ttcctgcccc ggctcagggc   1440

caagaacaga tggtccccag atgcggtccc gccctcagca gtttctagag aaccatcaga   1500

tgtttccagg gtgccccaag gacctgaaat gaccctgtgc cttatttgaa ctaaccaatc   1560
```

-continued

```
agttcgcttc tcgcttctgt tcgcgcgctt ctgctccccg agctcaataa aagagcccac   1620

aacccctcac tcggcgcgcc agtcctccga tagactgcgt cgcccgggta cccgtgttct   1680

caataaaccc tcttgcagtt gcatccgact cgtggtctcg ctgttccttg ggagggtctc   1740

ctctgagtga ttgactgccc acctcggggg tctttcattc tcgatcgagc agcttggcgt   1800

aatcatggtc atagctgttt cctgtgtgaa attgttatcc gctcacaatt ccacacaaca   1860

tacgagccgg aagcataaag tgtaaagcct ggggtgccta atgagtgagc taactcacat   1920

taattgcgtt gcgctcactg cccgctttcc agtcgggaaa cctgtcgtgc cagctgcatt   1980

aatgaatcgg ccaacgcgcg gggagaggcg gtttgcgtat tgggcgctct tccgcttcct   2040

cgctcactga ctcgctgcgc tcggtcgttc ggctgcggcg agcggtatca gctcactcaa   2100

aggcggtaat acggttatcc acagaatcag gggataacgc aggaaagaac atgtgagcaa   2160

aaggccagca aaaggccagg aaccgtaaaa aggccgcgtt gctggcgttt ttccataggc   2220

tccgcccccc tgacgagcat cacaaaaatc gacgctcaag tcagaggtgg cgaaacccga   2280

caggactata aagataccag gcgtttcccc ctggaagctc cctcgtgcgc tctcctgttc   2340

cgaccctgcc gcttaccgga tacctgtccg cctttctccc ttcgggaagc gtggcgcttt   2400

ctcatagctc acgctgtagg tatctcagtt cggtgtaggt cgttcgctcc aagctgggct   2460

gtgtgcacga accccccgtt cagcccgacc gctgcgcctt atccggtaac tatcgtcttg   2520

agtccaaccc ggtaagacac gacttatcgc cactggcagc agccactggt aacaggatta   2580

gcagagcgag gtatgtaggc ggtgctacag agttcttgaa gtggtggcct aactacggct   2640

acactagaag aacagtattt ggtatctgcg ctctgctgaa gccagttacc ttcggaaaaa   2700

gagttggtag ctcttgatcc ggcaaacaaa ccaccgctgg tagcggtggt ttttttgttt   2760

gcaagcagca gattacgcgc agaaaaaaag gatctcaaga agatcctttg atcttttcta   2820

cggggtctga cgctcagtgg aacgaaaact cacgttaagg gattttggtc atgagattat   2880

caaaaaggat cttcacctag atccttttaa attaaaaatg aagttttaaa tcaatctaaa   2940

gtatatatga gtaaacttgg tctgacagtt accaatgctt aatcagtgag gcacctatct   3000

cagcgatctg tctatttcgt tcatccatag ttgcctgact ccccgtcgtg tagataacta   3060

cgatacggga gggcttacca tctggcccca gtgctgcaat gataccgcga gacccacgct   3120

caccggctcc agatttatca gcaataaacc agccagccgg aagggccgag cgcagaagtg   3180

gtcctgcaac tttatccgcc tccatccagt ctattaattg ttgccgggaa gctagagtaa   3240

gtagttcgcc agttaatagt ttgcgcaacg ttgttgccat tgctacaggc atcgtggtgt   3300

cacgctcgtc gtttggtatg gcttcattca gctccggttc ccaacgatca aggcgagtta   3360

catgatcccc catgttgtgc aaaaaagcgg ttagctcctt cggtcctccg atcgttgtca   3420

gaagtaagtt ggccgcagtg ttatcactca tggttatggc agcactgcat aattctctta   3480

ctgtcatgcc atccgtaaga tgcttttctg tgactggtga gtactcaacc aagtcattct   3540

gagaatagtg tatgcggcga ccgagttgct cttgcccggc gtcaatacgg gataataccg   3600

cgccacatag cagaacttta aaagtgctca tcattggaaa acgttcttcg gggcgaaaac   3660

tctcaaggat cttaccgctg ttgagatcca gttcgatgta acccactcgt gcacccaact   3720

gatcttcagc atcttttact ttcaccagcg tttctgggtg agcaaaaaca ggaaggcaaa   3780

atgccgcaaa aaagggaata agggcgacac ggaaatgttg aatactcata ctcttccttt   3840

ttcaatatta ttgaagcatt tatcagggtt attgtctcat gagcggatac atatttgaat   3900

gtatttagaa aaataaacaa ataggggttc cgcgcacatt tccccgaaaa gtgccacctg   3960
```

acgtctaaga aaccattatt atcatgacat taacctataa aaataggcgt atcacgaggc 4020
cctttcgtct cgcgcgtttc ggtgatgacg gtgaaaacct ctgacacatg cagctcccgg 4080
agacggtcac agcttgtctg taagcggatg ccgggagcag acaagcccgt cagggcgcgt 4140
cagcgggtgt tggcgggtgt cggggctggc ttaatatgcg gcatcagagc agattgtact 4200
gagagtgcac catatgcggt gtgaaatacc gcacagatgc gtaaggagaa aataccgcat 4260
caggcgccat tcgccattca ggctgcgcaa ctgttgggaa gggcgatcgg tgcgggcctc 4320
ttcgctatta cgccagctgg cgaaaggggg atgtgctgca aggcgattaa gttgggtaac 4380
gccagggttt tcccagtcac gacgttgtaa aacgacggcc agtgaattag tactc 4435

<210> SEQ ID NO 50
<211> LENGTH: 590
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
tgaaagaccc cacctgtagg tttggcaagc tagcttaagt aacgccattt tgcaaggcat 60
ggaaaaatac ataactgaga atagaaaagt tcagatcaag gtcaggaaca gatggaacag 120
ctgaatatgg gccaaacagg atatctgtgg taagcagttc ctgccccggc tcagggccaa 180
gaacagatgg aacagctgaa tatgggccaa acaggatatc tgtggtaagc agttcctgcc 240
ccggctcagg gccaagaaca gatggtcccc agatgcggtc cagccctcag cagtttctag 300
agaaccatca gatgtttcca gggtgcccca aggacctgaa atgaccctgt gccttatttg 360
aactaaccaa tcagttcgct tctcgcttct gttcgcgcgc ttatgctccc cgagctcaat 420
aaaagagccc acaacccctc actcggggcg ccagtcctcc gattgactga gtcgcccggg 480
tacccgtgta tccaataaac cctcttgcag ttgcatccga cttgtggtct cgctgttcct 540
tgggagggtc tcctctgagt gattgactac ccgtcagcgg gggtctttca 590

<210> SEQ ID NO 51
<211> LENGTH: 321
<212> TYPE: DNA
<213> ORGANISM: Homo sapiens

<400> SEQUENCE: 51
ggagtgcagg tggaaaccat ctccccagga gacgggcgca ccttccccaa gcgcggccag 60
acctgcgtgg tgcactacac cgggatgctt gaagatggaa agaaagttga ttcctcccgg 120
gacagaaaca agccctttaa gtttatgcta ggcaagcagg aggtgatccg aggctgggaa 180
gaaggggttg cccagatgag tgtgggtcag agagccaaac tgactatatc tccagattat 240
gcctatggtg ccactgggca cccaggcatc atcccaccac atgccactct cgtcttcgat 300
gtggagcttc taaaactgga a 321

<210> SEQ ID NO 52
<211> LENGTH: 107
<212> TYPE: PRT
<213> ORGANISM: Homo sapiens

<400> SEQUENCE: 52

Gly Val Gln Val Glu Thr Ile Ser Pro Gly Asp Gly Arg Thr Phe Pro
1 5 10 15

-continued

```
Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
tctggcggtg gatccgga 18

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

```
Ser Gly Gly Gly Ser Gly
1               5
```

<210> SEQ ID NO 55
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55 gtcgac 6

<210> SEQ ID NO 56
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

```
Val Asp
1
```

<210> SEQ ID NO 57
<211> LENGTH: 846
<212> TYPE: DNA
<213> ORGANISM: Homo sapiens

<400> SEQUENCE: 57

```
ggatttggtg atgtcggtgc tcttgagagt ttgaggggaa atgcagattt ggcttacatc     60

ctgagcatgg agccctgtgg ccactgcctc attatcaaca atgtgaactt ctgccgtgag    120

tccgggctcc gcacccgcac tggctccaac atcgactgtg agaagttgcg gcgtcgcttc    180

tcctcgctgc atttcatggt ggaggtgaag ggcgacctga ctgccaagaa aatggtgctg    240

gctttgctgg agctggcgca gcaggaccac ggtgctctgg actgctgcgt ggtggtcatt    300

ctctctcacg gctgtcaggc cagccacctg cagttcccag ggctgtcta cggcacagat    360

ggatgccctg tgtcggtcga gaagattgtg aacatcttca atgggaccag ctgccccagc    420

ctgggaggga agcccaagct ctttttcatc caggcctgtg gtggggagca gaaagaccat    480

gggtttgagg tggcctccac ttcccctgaa gacgagtccc ctggcagtaa ccccgagcca    540

gatgccaccc cgttccagga aggtttgagg accttcgacc agctggacgc catatctagt    600

ttgcccacac ccagtgacat ctttgtgtcc tactctactt tcccaggttt tgtttcctgg    660

agggacccca agagtggctc ctggtacgtt gagaccctgg acgacatctt tgagcagtgg    720

gctcactctg aagacctgca gtccctcctg cttagggtcg ctaatgctgt ttcggtgaaa    780

gggatttata aacagatgcc tggttgcttt aatttcctcc ggaaaaaact tttctttaaa    840

acatca                                                               846
```

<210> SEQ ID NO 58
<211> LENGTH: 282
<212> TYPE: PRT
<213> ORGANISM: Homo sapiens

<400> SEQUENCE: 58

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
```

210 215 220

Ser Gly Ser Trp Tyr Val Glu Thr Leu Asp Asp Ile Phe Glu Gln Trp
225 230 235 240

Ala His Ser Glu Asp Leu Gln Ser Leu Leu Leu Arg Val Ala Asn Ala
245 250 255

Val Ser Val Lys Gly Ile Tyr Lys Gln Met Pro Gly Cys Phe Asn Phe
260 265 270

Leu Arg Lys Lys Leu Phe Phe Lys Thr Ser
275 280

<210> SEQ ID NO 59
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59 gctagcaga 9

<210> SEQ ID NO 60
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ala Ser Arg
1

<210> SEQ ID NO 61
<211> LENGTH: 57
<212> TYPE: DNA
<213> ORGANISM: Thosea asigna virus

<400> SEQUENCE: 61
gccgagggca ggggaagtct tctaacatgc ggggacgtgg aggaaaatcc cgggccc 57

<210> SEQ ID NO 62
<211> LENGTH: 19
<212> TYPE: PRT
<213> ORGANISM: Thosea asigna virus

<400> SEQUENCE: 62

Ala Glu Gly Arg Gly Ser Leu Leu Thr Cys Gly Asp Val Glu Glu Asn
1 5 10 15

Pro Gly Pro

<210> SEQ ID NO 63
<211> LENGTH: 999
<212> TYPE: DNA
<213> ORGANISM: Homo sapiens

<400> SEQUENCE: 63
atgccacctc ctcgcctcct cttcttcctc ctcttcctca cccccatgga agtcaggccc 60
gaggaacctc tagtggtgaa ggtggaagag ggagataacg ctgtgctgca gtgcctcaag 120
gggacctcag atggccccac tcagcagctg acctggtctc gggagtcccc gcttaaaccc 180
ttcttaaaac tcagcctggg gctgccaggc ctgggaatcc acatgaggcc cctggccatc 240

-continued tggcttttca tcttcaacgt ctctcaacag atggggggct tctacctgtg ccagccgggg 300 ccccccctctg agaaggcctg gcagcctggc tggacagtca atgtggaggg cagcggggag 360
ctgttccggt ggaatgtttc ggacctaggt ggcctgggct gtggcctgaa gaacaggtcc 420
tcagagggcc ccagctcccc ttccgggaag ctcatgagcc ccaagctgta tgtgtgggcc 480
aaagaccgcc ctgagatctg ggagggagag cctccgtgtc tcccaccgag ggacagcctg 540
aaccagagcc tcagccagga cctcaccatg gcccctggct ccacactctg gctgtcctgt 600
ggggtacccc ctgactctgt gtccaggggc cccctctcct ggacccatgt gcaccccaag 660
gggcctaagt cattgctgag cctagagctg aaggacgatc gcccggccag agatatgtgg 720
gtaatggaga cgggtctgtt gttgccccgg gccacagctc aagacgctgg aaagtattat 780
tgtcaccgtg gcaacctgac catgtcattc cacctggaga tcactgctcg gccagtacta 840
tggcactggc tgctgaggac tggtggctgg aaggtctcag ctgtgacttt ggcttatctg 900
atcttctgcc tgtgttccct tgtgggcatt cttcatcttc aaagagccct ggtcctgagg 960
aggaaaagaa agcgaatgac tgaccccacc aggagattc 999

<210> SEQ ID NO 64
<211> LENGTH: 333
<212> TYPE: PRT
<213> ORGANISM: Homo sapiens

<400> SEQUENCE: 64

Met Pro Pro Pro Arg Leu Leu Phe Phe Leu Leu Phe Leu Thr Pro Met
1 5 10 15

Glu Val Arg Pro Glu Glu Pro Leu Val Val Lys Val Glu Glu Gly Asp
20 25 30

Asn Ala Val Leu Gln Cys Leu Lys Gly Thr Ser Asp Gly Pro Thr Gln
35 40 45

Gln Leu Thr Trp Ser Arg Glu Ser Pro Leu Lys Pro Phe Leu Lys Leu
50 55 60

Ser Leu Gly Leu Pro Gly Leu Gly Ile His Met Arg Pro Leu Ala Ile
65 70 75 80

Trp Leu Phe Ile Phe Asn Val Ser Gln Gln Met Gly Gly Phe Tyr Leu
85 90 95

Cys Gln Pro Gly Pro Pro Ser Glu Lys Ala Trp Gln Pro Gly Trp Thr
100 105 110

Val Asn Val Glu Gly Ser Gly Glu Leu Phe Arg Trp Asn Val Ser Asp
115 120 125

Leu Gly Gly Leu Gly Cys Gly Leu Lys Asn Arg Ser Ser Glu Gly Pro
130 135 140

Ser Ser Pro Ser Gly Lys Leu Met Ser Pro Lys Leu Tyr Val Trp Ala
145 150 155 160

Lys Asp Arg Pro Glu Ile Trp Glu Gly Glu Pro Pro Cys Leu Pro Pro
165 170 175

Arg Asp Ser Leu Asn Gln Ser Leu Ser Gln Asp Leu Thr Met Ala Pro
180 185 190

Gly Ser Thr Leu Trp Leu Ser Cys Gly Val Pro Pro Asp Ser Val Ser
195 200 205

Arg Gly Pro Leu Ser Trp Thr His Val His Pro Lys Gly Pro Lys Ser
210 215 220

Leu Leu Ser Leu Glu Leu Lys Asp Asp Arg Pro Ala Arg Asp Met Trp
225 230 235 240

```
Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330
```

<210> SEQ ID NO 65
<211> LENGTH: 590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
tgaaagaccc cacctgtagg tttggcaagc tagcttaagt aacgccattt tgcaaggcat     60

ggaaaaatac ataactgaga atagagaagt tcagatcaag gtcaggaaca gatggaacag    120

ctgaatatgg gccaaacagg atatctgtgg taagcagttc ctgccccggc tcagggccaa    180

gaacagatgg aacagctgaa tatgggccaa acaggatatc tgtggtaagc agttcctgcc    240

ccggctcagg gccaagaaca gatggtcccc agatgcggtc cagccctcag cagtttctag    300

agaaccatca gatgtttcca gggtgcccca aggacctgaa atgaccctgt gccttatttg    360

aactaaccaa tcagttcgct tctcgcttct gttcgcgcgc ttctgctccc cgagctcaat    420

aaaagagccc acaacccctc actcggggcg ccagtcctcc gattgactga gtcgcccggg    480

tacccgtgta tccaataaac cctcttgcag ttgcatccga cttgtggtct cgctgttcct    540

tgggagggtc tcctctgagt gattgactac ccgtcagcgg gggtctttca               590
```

<210> SEQ ID NO 66
<211> LENGTH: 590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
tgaaagaccc cacctgtagg tttggcaagc tagcttaagt aacgccattt tgcaaggcat     60

ggaaaaatac ataactgaga atagaaaagt tcagatcaag gtcaggaaca gatggaacag    120

ctgaatatgg gccaaacagg atatctgtgg taagcagttc ctgccccggc tcagggccaa    180

gaacagatgg aacagctgaa tatgggccaa acaggatatc tgtggtaagc agttcctgcc    240

ccggctcagg gccaagaaca gatggtcccc agatgcggtc cagccctcag cagtttctag    300

agaaccatca gatgtttcca gggtgcccca aggacctgaa atgaccctgt gccttatttg    360

aactaaccaa tcagttcgct tctcgcttct gttcgcgcgc ttatgctccc cgagctcaat    420

aaaagagccc acaacccctc actcggggcg ccagtcctcc gattgactga gtcgcccggg    480

tacccgtgta tccaataaac cctcttgcag ttgcatccga cttgtggtct cgctgttcct    540
```

tgggagggtc tcctctgagt gattgactac ccgtcagcgg gggtctttca 590

<210> SEQ ID NO 67
<211> LENGTH: 57
<212> TYPE: DNA
<213> ORGANISM: Thosea asigna virus

<400> SEQUENCE: 67
gccgagggca ggggaagtct tctaacatgc ggggacgtgg aggaaaatcc cgggccc 57

<210> SEQ ID NO 68
<211> LENGTH: 19
<212> TYPE: PRT
<213> ORGANISM: Thosea asigna virus

<400> SEQUENCE: 68

Ala Glu Gly Arg Gly Ser Leu Leu Thr Cys Gly Asp Val Glu Glu Asn
1 5 10 15

Pro Gly Pro

<210> SEQ ID NO 69
<211> LENGTH: 590
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
tgaaagaccc cacctgtagg tttggcaagc tagcttaagt aacgccattt tgcaaggcat 60
ggaaaaatac ataactgaga atagagaagt tcagatcaag gtcaggaaca gatggaacag 120
ctgaatatgg gccaaacagg atatctgtgg taagcagttc ctgccccggc tcagggccaa 180
gaacagatgg aacagctgaa tatgggccaa acaggatatc tgtggtaagc agttcctgcc 240
ccggctcagg gccaagaaca gatggtcccc agatgcggtc cagccctcag cagtttctag 300
agaaccatca gatgtttcca gggtgcccca aggacctgaa atgaccctgt gccttatttg 360
aactaaccaa tcagttcgct tctcgcttct gttcgcgcgc ttctgctccc cgagctcaat 420
aaaagagccc acaacccctc actcggggcg ccagtcctcc gattgactga gtcgcccggg 480
tacccgtgta tccaataaac cctcttgcag ttgcatccga cttgtggtct cgctgttcct 540
tgggagggtc tcctctgagt gattgactac ccgtcagcgg gggtctttca 590

<210> SEQ ID NO 70
<211> LENGTH: 696
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
ctcgagtctg gcggtggatc cggaggcgtt caagtagaaa caatcagccc aggagacgga 60
aggactttcc ccaaacgagg ccaaacatgc gtagttcatt atactgggat gctcgaagat 120
ggaaaaaaag tagatagtag tagagaccga aacaaaccat ttaaatttat gttgggaaaa 180
caagaagtaa taaggggctg ggaagaaggt gtagcacaaa tgtctgttgg ccagcgcgca 240
aaactcacaa tttctcctga ttatgcttac ggagctaccg gccaccccgg catcataccc 300
cctcatgcca cactggtgtt tgacgtcgaa ttgctcaaac tggaagtcga gggagtgcag 360

-continued

```
gtggagacga ttagtcctgg ggatgggaga acctttccaa agcgcggtca gacctgtgtt    420

gtccactaca ccggtatgct ggaggacggg aagaaggtgg actcttcacg cgatcgcaat    480

aagcctttca agttcatgct cggcaagcag gaggtgatcc gggggtggga ggagggcgtg    540

gctcagatgt cggtcgggca acgagcgaag cttaccatct cacccgacta cgcgtatggg    600

gcaacggggc atccgggaat tatccctccc cacgctacgc tcgtattcga tgtggagctc    660

ttgaagcttg agtctggcgg tggatccgga gtcgac                              696
```

<210> SEQ ID NO 71
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Leu Glu Ser Gly Gly Gly Ser Gly Gly Val Gln Val Glu Thr Ile Ser
1               5                   10                  15

Pro Gly Asp Gly Arg Thr Phe Pro Lys Arg Gly Gln Thr Cys Val Val
            20                  25                  30

His Tyr Thr Gly Met Leu Glu Asp Gly Lys Lys Val Asp Ser Ser Arg
        35                  40                  45

Asp Arg Asn Lys Pro Phe Lys Phe Met Leu Gly Lys Gln Glu Val Ile
    50                  55                  60

Arg Gly Trp Glu Glu Gly Val Ala Gln Met Ser Val Gly Gln Arg Ala
65                  70                  75                  80

Lys Leu Thr Ile Ser Pro Asp Tyr Ala Tyr Gly Ala Thr Gly His Pro
                85                  90                  95

Gly Ile Ile Pro Pro His Ala Thr Leu Val Phe Asp Val Glu Leu Leu
            100                 105                 110

Lys Leu Glu Val Glu Gly Val Gln Val Glu Thr Ile Ser Pro Gly Asp
        115                 120                 125

Gly Arg Thr Phe Pro Lys Arg Gly Gln Thr Cys Val Val His Tyr Thr
    130                 135                 140

Gly Met Leu Glu Asp Gly Lys Lys Val Asp Ser Ser Arg Asp Arg Asn
145                 150                 155                 160

Lys Pro Phe Lys Phe Met Leu Gly Lys Gln Glu Val Ile Arg Gly Trp
                165                 170                 175

Glu Glu Gly Val Ala Gln Met Ser Val Gly Gln Arg Ala Lys Leu Thr
            180                 185                 190

Ile Ser Pro Asp Tyr Ala Tyr Gly Ala Thr Gly His Pro Gly Ile Ile
        195                 200                 205

Pro Pro His Ala Thr Leu Val Phe Asp Val Glu Leu Leu Lys Leu Glu
    210                 215                 220

Ser Gly Gly Gly Ser Gly Val Asp
225                 230
```

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
ggcgttcaag tagaaacaat cagcccagga gacggaagga ctttccccaa acgaggccaa     60

acatgcgtag ttcattatac tgggatgctc gaagatggaa aaaaagtaga tagtagtaga    120

gaccgaaaca aaccatttaa atttatgttg ggaaaacaag aagtaataag gggctgggaa    180

gaaggtgtag cacaaatgtc tgttggccag cgcgcaaaac tcacaatttc tcctgattat    240

gcttacggag ctaccggcca ccccggcatc atacccccctc atgccacact ggtgtttgac    300

gtcgaattgc tcaaactgga a                                              321
```

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 74
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
ggagtgcagg tggagacgat tagtcctggg gatgggagaa cctttccaaa gcgcggtcag     60

acctgtgttg tccactacac cggtatgctg gaggacggga agaaggtgga ctcttcacgc    120

gatcgcaata agcctttcaa gttcatgctc ggcaagcagg aggtgatccg ggggtgggag    180

gagggcgtgg ctcagatgtc ggtcgggcaa cgagcgaagc ttaccatctc acccgactac    240

gcgtatgggg caacggggca tccgggaatt atccctcccc acgctacgct cgtattcgat    300

gtggagctct tgaagcttga g                                              321
```

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Gly Val Gln Val Glu Thr Ile Ser Pro Gly Asp Gly Arg Thr Phe Pro
```

```
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105


<210> SEQ ID NO 76
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76

ctcgag                                                                6


<210> SEQ ID NO 77
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Glu
1


<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78

gtcgagtctg gcggtggatc cgga                                            24


<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Glu Ser Gly Gly Gly Ser Gly
1               5


<210> SEQ ID NO 80
<211> LENGTH: 321
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 80
ggcgttcaag tagaaacaat cagcccagga gacggaagga ctttccccaa acgaggccaa 60
acatgcgtag ttcattatac tgggatgctc gaagatggaa aaaaagtaga tagtagtaga 120
gaccgaaaca aaccatttaa atttatgttg ggaaaacaag aagtaataag gggctgggaa 180
gaaggtgtag cacaaatgtc tgttggccag cgcgcaaaac tcacaatttc tcctgattat 240
gcttacggag ctaccggcca ccccggcatc atacccccctc atgccacact ggtgtttgac 300
gtcgaattgc tcaaactgga a 321

<210> SEQ ID NO 81
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 82
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 gtcgag 6

<210> SEQ ID NO 83
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Glu
1

<210> SEQ ID NO 84

<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
ggagtgcagg tggagacgat tagtcctggg gatgggagaa cctttccaaa gcgcggtcag 60
acctgtgttg tccactacac cggtatgctg gaggacggga agaaggtgga ctcttcacgc 120
gatcgcaata agcctttcaa gttcatgctc ggcaagcagg aggtgatccg ggggtgggag 180
gagggcgtgg ctcagatgtc ggtcgggcaa cgagcgaagc ttaccatctc acccgactac 240
gcgtatgggg caacggggca tccgggaatt atccctcccc acgctacgct cgtattcgat 300
gtggagctct tgaagcttga g 321

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Gly Val Gln Val Glu Thr Ile Ser Pro Gly Asp Gly Arg Thr Phe Pro
1 5 10 15

Lys Arg Gly Gln Thr Cys Val Val His Tyr Thr Gly Met Leu Glu Asp
20 25 30

Gly Lys Lys Val Asp Ser Ser Arg Asp Arg Asn Lys Pro Phe Lys Phe
35 40 45

Met Leu Gly Lys Gln Glu Val Ile Arg Gly Trp Glu Glu Gly Val Ala
50 55 60

Gln Met Ser Val Gly Gln Arg Ala Lys Leu Thr Ile Ser Pro Asp Tyr
65 70 75 80

Ala Tyr Gly Ala Thr Gly His Pro Gly Ile Ile Pro Pro His Ala Thr
85 90 95

Leu Val Phe Asp Val Glu Leu Leu Lys Leu Glu
100 105

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
tctggcggtg gatccggagt cgac 24

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ser Gly Gly Gly Ser Gly Val Asp
1 5

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
cgcgcaaagc gt 12

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Arg Ala Lys Arg
1

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
ggaaaaccta tacctaatcc attgctgggc ttagactcaa ca 42

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Gly Lys Pro Ile Pro Asn Pro Leu Leu Gly Leu Asp Ser Thr
1 5 10

<210> SEQ ID NO 92
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
ggcagcggaa gc 12

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Gly Ser Gly Ser
1

<210> SEQ ID NO 94
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
gcaacgaatt tttccctgct gaaacaggca ggggacgtag aggaaaatcc tggtcct 57

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Ala Thr Asn Phe Ser Leu Leu Lys Gln Ala Gly Asp Val Glu Glu Asn
1 5 10 15

Pro Gly Pro

<210> SEQ ID NO 96
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96 acgcgt 6

<210> SEQ ID NO 97
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Thr Arg
1

<210> SEQ ID NO 98
<211> LENGTH: 1002
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
atgccccctc ctagactgct gtttttcctg ctctttctca ccccaatgga agttagacct 60
gaggaaccac tggtcgttaa agtggaagaa ggtgataatg ctgtcctcca atgccttaaa 120
gggaccagcg acggaccaac gcagcaactg acttggagcc gggagtcccc tctcaagccg 180
tttctcaagc tgtcacttgg cctgccaggt cttggtattc acatgcgccc ccttgccatt 240
tggctcttca tattcaatgt gtctcaacaa atgggtggat tctacctttg ccagcccggc 300

```
ccccccttctg agaaagcttg gcagcctgga tggaccgtca atgttgaagg ctccggtgag    360

ctgtttagat ggaatgtgag cgaccttggc ggactcggtt gcggactgaa aaataggagc    420

tctgaaggac cctcttctcc ctccggtaag ttgatgtcac ctaagctgta cgtgtgggcc    480

aaggaccgcc ccgaaatctg ggagggcgag cctccatgcc tgccgcctcg cgattcactg    540

aaccagtctc tgtcccagga tctcactatg gcgcccggat ctactctttg gctgtcttgc    600

ggcgttcccc cagatagcgt gtcaagagga cctctgagct ggacccacgt acaccctaag    660

ggccctaaga gcttgttgag cctggaactg aaggacgaca gacccgcacg cgatatgtgg    720

gtaatggaga ccggccttct gctccctcgc gctaccgcac aggatgcagg gaaatactac    780

tgtcatagag ggaatctgac tatgagcttt catctcgaaa ttacagcacg gcccgttctt    840

tggcattggc tcctccggac tggaggctgg aaggtgtctg ccgtaacact cgcttacttg    900

atttttgcc tgtgtagcct ggttgggatc ctgcatcttc agcgagccct tgtattgcgc    960

cgaaaaagaa aacgaatgac tgaccctaca cgacgattct ga                       1002
```

<210> SEQ ID NO 99
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
```

```
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330


<210> SEQ ID NO 100
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

ggcgtccaag tcgaaaccat tagtcccggc gatggcagaa catttcctaa aaggggacaa      60

acatgtgtcg tccattatac aggcatgttg gaggacggca aaaaggtgga cagtagtaga     120

gatcgcaata aacctttcaa attcatgttg ggaaaacaag aagtcattag gggatgggag     180

gagggcgtgg ctcaaatgtc cgtcggccaa cgcgctaagc tcaccatcag ccccgactac     240

gcatacggcg ctaccggaca tcccggaatt attccccctc acgctacctt ggtgtttgac     300

gtcgaactgt tgaagctc                                                   318


<210> SEQ ID NO 101
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu
            100                 105


<210> SEQ ID NO 102
<211> LENGTH: 321
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 102
ggagtgcagg tggagactat ctccccagga gacgggcgca ccttccccaa gcgcggccag     60
acctgcgtgg tgcactacac cgggatgctt gaagatggaa agaaagttga ttcctcccgg    120
gacagaaaca agccctttaa gtttatgcta ggcaagcagg aggtgatccg aggctgggaa    180
gaaggggttg cccagatgag tgtgggtcag agagccaaac tgactatatc tccagattat    240
gcctatggtg ccactgggca cccaggcatc atcccaccac atgccactct cgtcttcgat    300
gtggagcttc taaaactgga a                                              321

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 104
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gctactaact tcagcctgct gaagcaggct ggagacgtgg aggagaaccc tggacct        57

<210> SEQ ID NO 105
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Thr Asn Phe Ser Leu Leu Lys Gln Ala Gly Asp Val Glu Glu Asn
1               5                   10                  15

Pro Gly Pro

<210> SEQ ID NO 106
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 107
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
ggatttggtg atgtcggtgc tcttgagagt ttgaggggaa atgcagattt ggcttacatc     60
```

```
ctgagcatgg agccctgtgg ccactgcctc attatcaaca atgtgaactt ctgccgtgag    120

tccgggctcc gcacccgcac tggctccaac atcgactgtg agaagttgcg gcgtcgcttc    180

tcctcgctgc atttcatggt ggaggtgaag ggcgacctga ctgccaagaa aatggtgctg    240

gctttgctgg agctggcgcg gcaggaccac ggtgctctgg actgctgcgt ggtggtcatt    300

ctctctcacg gctgtcaggc cagccacctg cagttcccag ggctgtcta cggcacagat     360

ggatgccctg tgtcggtcga gaagattgtg aacatcttca atgggaccag ctgccccagc    420

ctgggaggga agcccaagct ctttttcatc caggcctgtg gtggggagca gaaagaccat    480

gggtttgagg tggcctccac ttcccctgaa gacgagtccc ctggcagtaa ccccgagcca    540

gatgccaccc cgttccagga aggtttgagg accttcgacc agctggccgc catatctagt    600

ttgcccacac ccagtgacat ctttgtgtcc tactctactt tcccaggttt tgtttcctgg    660

agggacccca agagtggctc ctggtacgtt gagaccctgg acgacatctt tgagcagtgg    720

gctcactctg aagacctgca gtccctcctg cttagggtcg ctaatgctgt ttcggtgaaa    780

gggatttata aacagatgcc tggttgcttt aatttcctcc ggaaaaaact tttctttaaa    840

acatca                                                                846
```

<210> SEQ ID NO 108
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Ala Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
```

```
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 109
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
ggatttggtg atgtcggtgc tcttgagagt ttgaggggaa atgcagattt ggcttacatc     60

ctgagcatgg agccctgtgg ccactgcctc attatcaaca atgtgaactt ctgccgtgag    120

tccgggctcc gcacccgcac tggctccaac atcgactgtg agaagttgcg gcgtcgcttc    180

tcctcgctgc atttcatggt ggaggtgaag ggcgacctga ctgccaagaa aatggtgctg    240

gctttgctgg agctggcgcg gcaggaccac ggtgctctgg actgctgcgt ggtggtcatt    300

ctctctcacg gctgtcaggc cagccacctg cagttcccag ggctgtcta cggcacagat    360

ggatgccctg tgtcggtcga gaagattgtg aacatcttca atgggaccag ctgccccagc    420

ctgggaggga agcccaagct ctttttcatc caggcctgtg gtggggagca gaaagaccat    480

gggtttgagg tggcctccac ttcccctgaa gacgagtccc ctggcagtaa ccccgagcca    540

gatgccaccc cgttccagga aggtttgagg accttcgacc agctggacgc catatctagt    600

ttgcccacac ccagtgacat ctttgtgtcc tactctactt tcccaggttt tgtttcctgg    660

agggacccca agagtggctc ctggtacgtt gagaccctgg acgacatctt tgagcagtgg    720

gctcactctg aagacctgca gtccctcctg cttagggtcg ctaatgctgt ttcggtgaaa    780

gggatttata aacagatgcc tggttgcttt cagttcctcc ggaaaaaact tttctttaaa    840

acatca                                                               846
```

<210> SEQ ID NO 110
<211> LENGTH: 282
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
```

-continued

```
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Gln Phe
            260                 265                 270

Leu Arg Lys Lys Leu Phe Phe Lys Thr Ser
        275                 280
```

<210> SEQ ID NO 111
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
ggatttggtg atgtcggtgc tcttgagagt ttgaggggaa atgcagattt ggcttacatc     60

ctgagcatgg agccctgtgg ccactgcctc attatcaaca atgtgaactt ctgccgtgag    120

tccgggctcc gcacccgcac tggctccaac atcgactgtg agaagttgcg gcgtcgcttc    180

tcctcgctgc atttcatggt ggaggtgaag ggcgacctga ctgccaagaa aatggtgctg    240

gctttgctgg agctggcgcg gcaggaccac ggtgctctgg actgctgcgt ggtggtcatt    300

ctctctcacg gctgtcaggc cagccacctg cagttcccag ggctgtcta cggcacagat    360

ggatgccctg tgtcggtcga gaagattgtg aacatcttca atgggaccag ctgccccagc    420

ctgggaggga agcccaagct ctttttcatc caggcctgtg gtggggagca gaaagaccat    480

gggtttgagg tggcctccac ttcccctgaa gacgagtccc ctggcagtaa ccccgagcca    540

gatgccaccc cgttccagga aggtttgagg accttcgacc agctggccgc catatctagt    600

ttgcccacac ccagtgacat ctttgtgtcc tactctactt tcccaggttt tgtttcctgg    660

agggacccca agagtggctc ctggtacgtt gagaccctgg acgacatctt tgagcagtgg    720

gctcactctg aagacctgca gtccctcctg cttagggtcg ctaatgctgt ttcggtgaaa    780

gggatttata aacagatgcc tggttgcttt cagttcctcc ggaaaaaact tttctttaaa    840
```

acatca 846

<210> SEQ ID NO 112
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 112

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Ala Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Gln Phe
            260                 265                 270

Leu Arg Lys Lys Leu Phe Phe Lys Thr Ser
        275                 280

<210> SEQ ID NO 113
<211> LENGTH: 864
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 113

-continued

```
gtggacgggt ttggagatgt gggagccctg gaatccctgc ggggcaatgc cgatctggct     60

tacatcctgt ctatggagcc ttgcggccac tgtctgatca ttaacaatgt gaacttctgc    120

agagagagcg ggctgcggac cagaacagga tccaatattg actgtgaaaa gctgcggaga    180

aggttctcta gtctgcactt tatggtcgag gtgaaaggcg atctgaccgc taagaaaatg    240

gtgctggccc tgctggaact ggctcggcag gaccatgggg cactggattg ctgcgtggtc    300

gtgatcctga gtcacggctg ccaggcttca catctgcagt tccctggggc agtctatgga    360

actgacggct gtccagtcag cgtggagaag atcgtgaaca tcttcaacgg cacctcttgc    420

ccaagtctgg gcgggaagcc caaactgttc tttattcagg cctgtggagg cgagcagaaa    480

gatcacggct tcgaagtggc tagcacctcc cccgaggacg aatcacctgg aagcaaccct    540

gagccagatg caaccccctt ccaggaaggc ctgaggacat ttgaccagct ggatgccatc    600

tcaagcctgc ccacaccttc tgacattttc gtctcttaca gtactttccc tggatttgtg    660

agctggcgcg atccaaagtc aggcagctgg tacgtggaga cactggacga tatctttgag    720

cagtgggccc attctgaaga cctgcagagt ctgctgctgc gagtggccaa tgctgtctct    780

gtgaagggga tctacaaaca gatgccagga tgcttccagt ttctgagaaa gaaactgttc    840

tttaagacct ccgcatctag ggcc                                           864


<210> SEQ ID NO 114
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Val Asp Gly Phe Gly Asp Val Gly Ala Leu Glu Ser Leu Arg Gly Asn
1               5                   10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
        35                  40                  45

Thr Gly Ser Asn Ile Asp Cys Glu Lys Leu Arg Arg Arg Phe Ser Ser
    50                  55                  60

Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
        115                 120                 125

Glu Lys Ile Val Asn Ile Phe Asn Gly Thr Ser Cys Pro Ser Leu Gly
    130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175

Gly Ser Asn Pro Glu Pro Asp Ala Thr Pro Phe Gln Glu Gly Leu Arg
            180                 185                 190

Thr Phe Asp Gln Leu Asp Ala Ile Ser Ser Leu Pro Thr Pro Ser Asp
        195                 200                 205
```

```
Ile Phe Val Ser Tyr Ser Thr Phe Pro Gly Phe Val Ser Trp Arg Asp
    210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Leu Arg Val Ala
                245                 250                 255

Asn Ala Val Ser Val Lys Gly Ile Tyr Lys Gln Met Pro Gly Cys Phe
            260                 265                 270

Gln Phe Leu Arg Lys Lys Leu Phe Phe Lys Thr Ser Ala Ser Arg Ala
        275                 280                 285
```

<210> SEQ ID NO 115
<211> LENGTH: 864
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
gtcgacggat ttggtgatgt cggtgctctt gagagtttga ggggaaatgc agatttggct      60

tacatcctga gcatggagcc ctgtggccac tgcctcatta tcaacaatgt gaacttctgc     120

cgtgagtccg ggctccgcac ccgcactggc tccaacatcg actgtgagaa gttgcggcgt     180

cgcttctcct cgctgcattt catggtggag gtgaagggcg acctgactgc caagaaaatg     240

gtgctggctt tgctggagct ggcgcggcag gaccacggtg ctctggactg ctgcgtggtg     300

gtcattctct ctcacggctg tcaggccagc cacctgcagt tcccaggggc tgtctacggc     360

acagatggat gccctgtgtc ggtcgagaag attgtgaaca tcttcaatgg gaccagctgc     420

cccagcctgg gagggaagcc caagctcttt ttcatccagg cctgtggtgg ggagcagaaa     480

gaccatgggt ttgaggtggc ctccacttcc cctgaagacg agtcccctgg cagtaacccc     540

gagccagatg ccaccccgtt ccaggaaggt ttgaggacct tcgaccagct ggccgccata     600

tctagtttgc ccacacccag tgacatcttt gtgtcctact ctactttccc aggttttgtt     660

tcctggaggg accccaagag tggctcctgg tacgttgaga ccctggacga catctttgag     720

cagtgggctc actctgaaga cctgcagtcc ctcctgctta gggtcgctaa tgctgtttcg     780

gtgaaaggga tttataaaca gatgcctggt tgctttaatt tcctccggaa aaaacttttc     840

tttaaaacat cagctagcag agcc                                            864
```

<210> SEQ ID NO 116
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Val Asp Gly Phe Gly Asp Val Gly Ala Leu Glu Ser Leu Arg Gly Asn
1               5                   10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
        35                  40                  45

Thr Gly Ser Asn Ile Asp Cys Glu Lys Leu Arg Arg Arg Phe Ser Ser
    50                  55                  60
```

```
Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
        115                 120                 125

Glu Lys Ile Val Asn Ile Phe Asn Gly Thr Ser Cys Pro Ser Leu Gly
    130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175

Gly Ser Asn Pro Glu Pro Asp Ala Thr Pro Phe Gln Glu Gly Leu Arg
            180                 185                 190

Thr Phe Asp Gln Leu Glu Ala Ile Ser Ser Leu Pro Thr Pro Ser Asp
        195                 200                 205

Ile Phe Val Ser Tyr Ser Thr Phe Pro Gly Phe Val Ser Trp Arg Asp
    210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Leu Arg Val Ala
                245                 250                 255

Asn Ala Val Ser Val Lys Gly Ile Tyr Lys Gln Met Pro Gly Cys Phe
            260                 265                 270

Asn Phe Leu Arg Lys Lys Leu Phe Phe Lys Thr Ser Ala Ser Arg Ala
        275                 280                 285
```

<210> SEQ ID NO 117
<211> LENGTH: 9456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
tgaaagaccc cacctgtagg tttggcaagc tagcttaagt aacgccattt tgcaaggcat      60

ggaaaaatac ataactgaga atagaaaagt tcagatcaag gtcaggaaca gatggaacag     120

ctgaatatgg gccaaacagg atatctgtgg taagcagttc ctgccccggc tcagggccaa     180

gaacagatgg aacagctgaa tatgggccaa acaggatatc tgtggtaagc agttcctgcc     240

ccggctcagg gccaagaaca gatggtcccc agatgcggtc cagccctcag cagtttctag     300

agaaccatca gatgtttcca gggtgcccca aggacctgaa atgaccctgt gccttatttg     360

aactaaccaa tcagttcgct tctcgcttct gttcgcgcgc ttatgctccc cgagctcaat     420

aaaagagccc acaacccctc actcggggcg ccagtcctcc gattgactga gtcgcccggg     480

tacccgtgta tccaataaac cctcttgcag ttgcatccga cttgtggtct cgctgttcct     540

tgggagggtc tcctctgagt gattgactac ccgtcagcgg gggtctttca tttgggggct     600

cgtccgggat cgggagaccc ctgcccaggg accaccgacc caccaccggg aggtaagctg     660

gccagcaact tatctgtgtc tgtccgattg tctagtgtct atgactgatt ttatgcgcct     720

gcgtcggtac tagttagcta actagctctg tatctggcgg acccgtggtg gaactgacga     780
```

-continued

```
gttcggaaca cccggccgca accctgggag acgtcccagg gacttcgggg gccgtttttg    840
tggcccgacc tgagtcctaa aatcccgatc gtttaggact ctttggtgca cccccctttag   900
aggagggata tgtggttctg gtaggagacg agaacctaaa acagttcccg cctccgtctg    960
aatttttgct ttcggtttgg gaccgaagcc gcgccgcgcg tcttgtctgc tgcagcatcg   1020
ttctgtgttg tctctgtctg actgtgtttc tgtatttgtc tgaaaatatg ggcccgggct   1080
agcctgttac cactccctta agtttgacct taggtcactg gaaagatgtc gagcggatcg   1140
ctcacaacca gtcggtagat gtcaagaaga gacgttgggt taccttctgc tctgcagaat   1200
ggccaacctt taacgtcgga tggccgcgag acggcacctt taaccgagac ctcatcaccc   1260
aggttaagat caaggtcttt tcacctggcc cgcatggaca cccagaccag gtggggtaca   1320
tcgtgacctg ggaagccttg gcttttgacc cccctccctg ggtcaagccc tttgtacacc   1380
ctaagcctcc gcctcctctt cctccatccg ccccgtctct ccccccttgaa cctcctcgtt   1440
cgaccccgcc tcgatcctcc ctttatccag ccctcactcc ttctctaggc gcccccatat   1500
ggccatatga gatcttatat ggggcacccc cgccccttgt aaacttccct gaccctgaca   1560
tgacaagagt tactaacagc ccctctctcc aagctcactt acaggctctc tacttagtcc   1620
agcacgaagt ctggagacct ctggcggcag cctaccaaga acaactggac cgaccggtgg   1680
tacctcaccc ttaccgagtc ggcgacacag tgtgggtccg ccgacaccag actaagaacc   1740
tagaacctcg ctggaaagga ccttacacag tcctgctgac caccccccacc gccctcaaag   1800
tagacggcat cgcagcttgg atacacgccg cccacgtgaa ggctgccgac cccgggggtg   1860
gaccatcctc tagactgcca tgctcgagat gctggaggga gtgcaggtgg agactattag   1920
ccccggagat ggcagaacat tccccaaaag aggacagact tgcgtcgtgc attatactgg   1980
aatgctggaa gacggcaaga aggtggacag cagccgggac cgaaacaagc ccttcaagtt   2040
catgctgggg aagcaggaag tgatccgggg ctgggaggaa ggagtcgcac agatgtcagt   2100
gggacagagg gccaaactga ctattagccc agactacgct tatggagcaa ccggccaccc   2160
cgggatcatt ccccctcatg ctacactggt cttcgatgtg gagctgctga agctggaaag   2220
cggaggagga tccggagtgg acgggtttgg agatgtggga gccctggaat ccctgcgggg   2280
caatgccgat ctggcttaca tcctgtctat ggagccttgc ggccactgtc tgatcattaa   2340
caatgtgaac ttctgcagag agagcgggct gcggaccaga acaggatcca atattgactg   2400
tgaaaagctg cggagaaggt tctctagtct gcactttatg gtcgaggtga aaggcgatct   2460
gaccgctaag aaaatggtgc tggccctgct ggaactggct cggcaggacc atggggcact   2520
ggattgctgc gtggtcgtga tcctgagtca cggctgccag gcttcacatc tgcagttccc   2580
tggggcagtc tatggaactg acggctgtcc agtcagcgtg gagaagatcg tgaacatctt   2640
caacggcacc tcttgcccaa gtctgggcgg gaagcccaaa ctgttcttta ttcaggcctg   2700
tggaggcgag cagaaagatc acggcttcga agtggctagc acctcccccg aggacgaatc   2760
acctggaagc aaccctgagc cagatgcaac cccccttccag gaaggcctga ggacatttga   2820
ccagctggat gccatctcaa gcctgcccac accttctgac attttcgtct cttacagtac   2880
tttccctgga tttgtgagct ggcgcgatcc aaagtcaggc agctggtacg tggagacact   2940
ggacgatatc tttgagcagt gggcccattc tgaagacctg cagagtctgc tgctgcgagt   3000
ggccaatgct gtctctgtga aggggatcta caaacagatg ccaggatgct tcaactttct   3060
gagaaagaaa ctgttcttta agacctccgc atctagggcc ccgcgggaag gtagagggag   3120
```

-continued

```
cctgctgaca tgtggcgatg tcgaggagaa tccgggacct atgggatgta gactgctgtg   3180
ctgtgctgtg ctgtgcctgc tgggggctgt gcctattgat accgaagtga ctcagactcc   3240
aaagcacctg gtcatgggca tgaccaacaa gaaaagcctg aaatgcgagc agcacatggg   3300
gcatagggcc atgtactggt ataagcagaa agctaagaaa ccccctgaac tgatgttcgt   3360
gtacagctat gagaagctgt ccatcaatga atccgtcccc tctcgcttca gtcccgagtg   3420
ccctaacagc tccctgctga atctgcacct gcatgctctg cagcctgaag actccgcact   3480
gtacctgtgc gcctctagtc acgggccagc ctcttacgag cagtattttg gacccggcac   3540
cagactgact gtgaccgaag atctgaagaa cgtcttccca cccgaggtgg cagtctttga   3600
accatctgag gccgaaatta gtcatactca gaaagccacc ctggtgtgcc tggctacagg   3660
cttctatccc gaccacgtgg agctgagttg gtgggtcaac ggcaaggaag tgcattcagg   3720
ggtctgcact gaccctcagc cactgaaaga gcagcctgct ctgaatgatt caaggtactg   3780
tctgtcaagc cggctgagag tgagcgccac tttttggcag aacccaagga atcacttccg   3840
ctgccaggtg cagttttatg gcctgagcga gaatgacgaa tggactcagg atcgcgctaa   3900
gccagtgacc cagatcgtct ccgcagaggc ctggggacga gcagactgtg gcttcacatc   3960
tgaaagttac cagcaggggg tgctgtctgc cacaatcctg tacgagattc tgctgggaaa   4020
ggccactctg tacgccgtgc tggtgagcgc cttagtctta atggccatgg tgaaaagaaa   4080
ggattccaga ggaggatccg gcgagggcag aggaagtctt ctaacatgcg gtgacgtgga   4140
ggagaatccc ggccctatga caagcatcag agccgtgttc atttttctgt ggctgcagct   4200
ggatctggtg aacggagaga atgtcgaaca gcatccttca actctgagcg tgcaggaggg   4260
cgattccgca gtcatcaagt gtacctactc agacagcgcc tccaattact ttccttggta   4320
taagcaggag ctggggaaag gaccacagct gatcattgat atcagaagca acgtgggcga   4380
aaagaaagac cagaggattg ctgtcacact gaataagact gcaaaacact tcagcctgca   4440
tattacagag actcagcccg aagactccgc cgtgtatttt tgcgccgctt ctaaggggtc   4500
ctctaacacc ggaaaactga tcttcggcca ggggaccaca ctgcaggtga agcctgacat   4560
tcagaatcca gatcccgccg tctaccagct gcgagactca aagagttcag ataaaagcgt   4620
gtgcctgttc accgactttg atagccagac aaacgtgtct cagagtaagg actccgacgt   4680
gtacatcacc gacaaatgcg tgctggatat gcgcagcatg gacttcaaga gcaacagcgc   4740
cgtggcatgg tccaacaagt ctgatttcgc ctgcgctaac gccttcaaca attctatcat   4800
tcccgaggat acattctttc ctagtccaga aagctcctgt gacgtgaagc tggtcgagaa   4860
aagtttcgaa accgatacaa acctgaattt tcagaatctg tccgtgatcg gcttccggat   4920
tctgctgctg aaagtggctg ggtttaatct gctgatgact ctgagactgt ggtcctcctg   4980
aacgcgtcat catcgatccg gattagtcca atttgttaaa gacaggatat cagtggtcca   5040
ggctctagtt ttgactcaac aatatcacca gctgaagcct atagagtacg agccatagat   5100
aaaataaaag attttattta gtctccagaa aaagggggga atgaaagacc ccacctgtag   5160
gtttggcaag ctagcttaag taacgccatt ttgcaaggca tggaaaaata cataactgag   5220
aatagagaag ttcagatcaa ggtcaggaac agatggaaca gctgaatatg ggccaaacag   5280
gatatctgtg gtaagcagtt cctgccccgg ctcagggcca agaacagatg gaacagctga   5340
atatgggcca aacaggatat ctgtggtaag cagttcctgc cccggctcag ggccaagaac   5400
agatggtccc cagatgcggt ccagccctca gcagtttcta gagaaccatc agatgtttcc   5460
agggtgcccc aaggacctga aatgaccctg tgccttattt gaactaacca atcagttcgc   5520
```

ttctcgcttc tgttcgcgcg cttctgctcc ccgagctcaa taaaagagcc cacaacccct 5580
cactcggggc gccagtcctc cgattgactg agtcgcccgg gtacccgtgt atccaataaa 5640
ccctcttgca gttgcatccg acttgtggtc tcgctgttcc ttgggagggt ctcctctgag 5700
tgattgacta cccgtcagcg ggggtctttc acacatgcag catgtatcaa aattaatttg 5760 gtttttttc ttaagtattt acattaaatg gccatagtac ttaaagttac attggcttcc 5820
ttgaaataaa catggagtat tcagaatgtg tcataaatat ttctaatttt aagatagtat 5880
ctccattggc tttctacttt ttcttttatt ttttttgtc ctctgtcttc catttgttgt 5940
tgttgttgtt tgtttgtttg tttgttggtt ggttggttaa tttttttta aagatcctac 6000 actatagttc aagctagact attagctact ctgtaaccca gggtgacctt gaagtcatgg 6060
gtagcctgct gttttagcct tcccacatct aagattacag gtatgagcta tcatttttgg 6120
tatattgatt gattgattga ttgatgtgtg tgtgtgtgat tgtgtttgtg tgtgtgactg 6180
tgaaaatgtg tgtatgggtg tgtgtgaatg tgtgtatgta tgtgtgtgtg tgagtgtgtg 6240
tgtgtgtgtg tgcatgtgtg tgtgtgtgac tgtgtctatg tgtatgactg tgtgtgtgtg 6300
tgtgtgtgtg tgtgtgtgtg tgtgtgtgtg tgtgttgtga aaaaatattc tatggtagtg 6360
agagccaacg ctccggctca ggtgtcaggt tggtttttga gacagagtct ttcacttagc 6420
ttggaattca ctggccgtcg ttttacaacg tcgtgactgg gaaaaccctg gcgttaccca 6480
acttaatcgc cttgcagcac atccccctt cgccagctgg cgtaatagcg aagaggcccg 6540
caccgatcgc ccttcccaac agttgcgcag cctgaatggc gaatggcgcc tgatgcggta 6600
ttttctcctt acgcatctgt gcggtatttc acaccgcata tggtgcactc tcagtacaat 6660
ctgctctgat gccgcatagt taagccagcc ccgacacccg ccaacacccg ctgacgcgcc 6720
ctgacgggct tgtctgctcc cggcatccgc ttacagacaa gctgtgaccg tctccgggag 6780
ctgcatgtgt cagaggtttt caccgtcatc accgaaacgc gcgatgacga aagggcctcg 6840
tgatacgcct atttttatag gttaatgtca tgataataat ggtttcttag acgtcaggtg 6900
gcacttttcg gggaaatgtg cgcggaaccc ctatttgttt atttttctaa atacattcaa 6960
atatgtatcc gctcatgaga caataaccct gataaatgct tcaataatat tgaaaaagga 7020
agagtatgag tattcaacat ttccgtgtcg cccttattcc cttttttgcg gcattttgcc 7080
ttcctgtttt tgctcaccca gaaacgctgg tgaaagtaaa agatgctgaa gatcagttgg 7140
gtgcacgagt gggttacatc gaactggatc tcaacagcgg taagatcctt gagagttttc 7200
gccccgaaga acgttttcca atgatgagca cttttaaagt tctgctatgt ggcgcggtat 7260
tatcccgtat tgacgccggg caagagcaac tcggtcgccg catacactat tctcagaatg 7320
acttggttga gtactcacca gtcacagaaa agcatcttac ggatggcatg acagtaagag 7380
aattatgcag tgctgccata accatgagtg ataacactgc ggccaactta cttctgacaa 7440
cgatcggagg accgaaggag ctaaccgctt ttttgcacaa catgggggat catgtaactc 7500
gccttgatcg ttgggaaccg gagctgaatg aagccatacc aaacgacgag cgtgacacca 7560
cgatgcctgt agcaatggca acaacgttgc gcaaactatt aactggcgaa ctacttactc 7620
tagcttcccg gcaacaatta atagactgga tggaggcgga taaagttgca ggaccacttc 7680
tgcgctcggc ccttccggct ggctggttta ttgctgataa atctggagcc ggtgagcgtg 7740
ggtctcgcgg tatcattgca gcactggggc cagatggtaa gccctcccgt atcgtagtta 7800
tctacacgac ggggagtcag gcaactatgg atgaacgaaa tagacagatc gctgagatag 7860
gtgcctcact gattaagcat tggtaactgt cagaccaagt ttactcatat atactttaga 7920
ttgatttaaa acttcatttt taatttaaaa ggatctaggt gaagatcctt tttgataatc 7980
tcatgaccaa aatcccttaa cgtgagtttt cgttccactg agcgtcagac cccgtagaaa 8040
agatcaaagg atcttcttga gatccttttt ttctgcgcgt aatctgctgc ttgcaaacaa 8100
aaaaaccacc gctaccagcg gtggtttgtt tgccggatca agagctacca actctttttc 8160
cgaaggtaac tggcttcagc agagcgcaga taccaaatac tgtccttcta gtgtagccgt 8220
agttaggcca ccacttcaag aactctgtag caccgcctac atacctcgct ctgctaatcc 8280
tgttaccagt ggctgctgcc agtggcgata agtcgtgtct taccgggttg gactcaagac 8340
gatagttacc ggataaggcg cagcggtcgg gctgaacggg gggttcgtgc acacagccca 8400
gcttggagcg aacgacctac accgaactga gatacctaca gcgtgagcat tgagaaagcg 8460
ccacgcttcc cgaagggaga aaggcggaca ggtatccggt aagcggcagg gtcggaacag 8520
gagagcgcac gagggagctt ccagggggaa acgcctggta tctttatagt cctgtcgggt 8580
ttcgccacct ctgacttgag cgtcgatttt tgtgatgctc gtcagggggg cggagcctat 8640
ggaaaaacgc cagcaacgcg gcctttttac ggttcctggc cttttgctgg ccttttgctc 8700
acatgttctt tcctgcgtta tcccctgatt ctgtggataa ccgtattacc gcctttgagt 8760
gagctgatac cgctcgccgc agccgaacga ccgagcgcag cgagtcagtg agcgaggaag 8820
cggaagagcg cccaatacgc aaaccgcctc tccccgcgcg ttggccgatt cattaatgca 8880
gctggcacga caggtttccc gactggaaag cgggcagtga gcgcaacgca attaatgtga 8940
gttagctcac tcattaggca ccccaggctt tacactttat gcttccggct cgtatgttgt 9000
gtggaattgt gagcggataa caatttcaca caggaaacag ctatgaccat gattacgcca 9060
agctttgctc ttaggagttt cctaatacat cccaaactca aatatataaa gcatttgact 9120
tgttctatgc cctagggggc ggggggaagc taagccagct ttttttaaca tttaaaatgt 9180
taattccatt ttaaatgcac agatgttttt atttcataag ggtttcaatg tgcatgaatg 9240
ctgcaatatt cctgttacca aagctagtat aaataaaaat agataaacgt ggaaattact 9300
tagagtttct gtcattaacg tttccttcct cagttgacaa cataaatgcg ctgctgagca 9360
agccagtttg catctgtcag gatcaatttc ccattatgcc agtcatatta attactagtc 9420
aattagttga tttttatttt tgacatatac atgtga 9456

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Ala Pro Ala Pro Thr Ala Val Val Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

-continued

Tyr Ala Leu Asn His Thr Leu Ser Val
1 5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Tyr Ala Leu Asn His Thr Leu Ser
1 5

<210> SEQ ID NO 121
<211> LENGTH: 16
<212> TYPE: PRT
<213> ORGANISM: Homo sapiens

<400> SEQUENCE: 121

Met Gly Ser Asn Lys Ser Lys Pro Lys Asp Ala Ser Gln Arg Arg Arg
1 5 10 15

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: Any amino acid

<400> SEQUENCE: 122

Met Gly Cys Xaa Cys
1 5

<210> SEQ ID NO 123
<211> LENGTH: 7
<212> TYPE: PRT
<213> ORGANISM: Homo sapiens

<400> SEQUENCE: 123

Thr Asp Pro Thr Arg Arg Phe
1 5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Ala Pro Ala Leu Pro Gly Pro Gln Phe
1 5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Ala Pro Ala Arg Pro Tyr Gln Gly Val
1 5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Leu Pro His Gln Pro Leu Ala Thr Tyr
1 5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Tyr Val Gln Pro Val Cys Pro Ser Tyr
1 5

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Ala Pro Ala Pro Ala Arg Pro Tyr Gln Gly Val
1 5 10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Thr Pro Ala Val Gly Pro Pro Leu
1 5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Gly Ser Gly Gly Gly Ser
1 5

<210> SEQ ID NO 131
<211> LENGTH: 8

-continued

<212> TYPE: PRT
<213> ORGANISM: Human herpesvirus 4

<400> SEQUENCE: 131

Arg Ala Lys Phe Lys Gln Leu Leu
1 5

<210> SEQ ID NO 132
<211> LENGTH: 9
<212> TYPE: PRT
<213> ORGANISM: Human herpesvirus 5

<400> SEQUENCE: 132

Asn Leu Val Pro Met Val Ala Thr Val
1 5

<210> SEQ ID NO 133
<211> LENGTH: 5
<212> TYPE: PRT
<213> ORGANISM: Homo sapiens

<400> SEQUENCE: 133

Gly Cys Phe Asn Phe
1 5

<210> SEQ ID NO 134
<211> LENGTH: 5
<212> TYPE: PRT
<213> ORGANISM: Homo sapiens

<400> SEQUENCE: 134

Ile Ser Ala Gln Thr
1 5

<210> SEQ ID NO 135
<211> LENGTH: 4
<212> TYPE: PRT
<213> ORGANISM: Homo sapiens

<400> SEQUENCE: 135

Ala Thr Pro Phe
1

<210> SEQ ID NO 136
<211> LENGTH: 4
<212> TYPE: PRT
<213> ORGANISM: Homo sapiens

<400> SEQUENCE: 136

Ala Val Pro Ile
1

<210> SEQ ID NO 137
<211> LENGTH: 5
<212> TYPE: PRT
<213> ORGANISM: Homo sapiens

<400> SEQUENCE: 137

Ala Ala Ala Ala Ala
1 5

<210> SEQ ID NO 138
<211> LENGTH: 5
<212> TYPE: PRT
<213> ORGANISM: Homo sapiens

<400> SEQUENCE: 138

Tyr Cys Ser Thr Leu
1 5

<210> SEQ ID NO 139
<211> LENGTH: 5
<212> TYPE: PRT
<213> ORGANISM: Homo sapiens

<400> SEQUENCE: 139

Cys Ile Val Ser Met
1 5

<210> SEQ ID NO 140
<211> LENGTH: 5
<212> TYPE: PRT
<213> ORGANISM: Homo sapiens

<400> SEQUENCE: 140

Gln Pro Thr Phe Thr
1 5

<210> SEQ ID NO 141
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Met Thr Ser Ile Arg Ala Val Phe Ile Phe Leu Trp Leu Gln Leu Asp
1 5 10 15

Leu Val Asn Gly Glu Asn Val Glu Gln His Pro Ser Thr Leu Ser Val
20 25 30

Gln Glu Gly Asp Ser Ala Val Ile Lys Cys Thr Tyr Ser Asp Ser Ala
35 40 45

Ser Asn Tyr Phe Pro Trp Tyr Lys Gln Glu Leu Gly Lys Gly Pro Gln
50 55 60

Leu Ile Ile Asp Ile Arg Ser Asn Val Gly Glu Lys Lys Asp Gln Arg
65 70 75 80

Ile Ala Val Thr Leu Asn Lys Thr Ala Lys His Phe Ser Leu His Ile
85 90 95

Thr Glu Thr Gln Pro Glu Asp Ser Ala Val Tyr Phe Cys Ala Ala Ser
100 105 110

Lys Gly Ser Ser Asn Thr Gly Lys Leu Ile Phe Gly Gln Gly Thr Thr
115 120 125

Leu Gln Val Lys Pro Asp Ile Gln Asn Pro Asp Pro Ala Val Tyr Gln
130 135 140

Leu Arg Asp Ser Lys Ser Ser Asp Lys Ser Val Cys Leu Phe Thr Asp
145 150 155 160

Phe Asp Ser Gln Thr Asn Val Ser Gln Ser Lys Asp Ser Asp Val Tyr
165 170 175

Ile Thr Asp Lys Thr Val Leu Asp Met Arg Ser Met Asp Phe Lys Ser
180 185 190

Asn Ser Ala Val Ala Trp Ser Asn Lys Ser Asp Phe Ala Cys Ala Asn
195 200 205

Ala Phe Asn Asn Ser Ile Ile Pro Glu Asp Thr Phe Phe Pro Ser Pro

```
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser


<210> SEQ ID NO 142
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser His Gly Pro Ala Ser Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
```

-continued

```
    290                 295                 300

Lys Arg Lys Asp Ser Arg Gly
305                 310
```